(12) United States Patent
Saunders et al.

(10) Patent No.: US 10,189,910 B2
(45) Date of Patent: *Jan. 29, 2019

(54) ANTI-DPEP3 ANTIBODIES AND METHODS OF USE

(71) Applicant: AbbVie Stemcentrx LLC, North Chicago, IL (US)

(72) Inventors: Laura Saunders, San Francisco, CA (US); Deepti Rokkam, Sunnyvale, CA (US); David Liu, San Francisco, CA (US); Mandy Boontanrart, San Francisco, CA (US)

(73) Assignee: AbbVie Stemcentrx LLC, North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,353

(22) Filed: Jun. 13, 2016

(65) Prior Publication Data

US 2017/0029530 A1 Feb. 2, 2017

Related U.S. Application Data

(63) Continuation of application No. PCT/US2014/070110, filed on Dec. 12, 2014.

(60) Provisional application No. 61/915,321, filed on Dec. 12, 2013.

(51) Int. Cl.
| | | |
|---|---|---|
| A61K 39/00 | (2006.01) | |
| C07K 16/00 | (2006.01) | |
| C07K 16/28 | (2006.01) | |
| C07K 16/40 | (2006.01) | |
| C07K 16/30 | (2006.01) | |
| A61K 31/551 | (2006.01) | |
| A61K 47/68 | (2017.01) | |

(52) U.S. Cl.
CPC ............ *C07K 16/40* (2013.01); *A61K 31/551* (2013.01); *A61K 47/6851* (2017.08); *C07K 16/30* (2013.01); *C12Y 304/13019* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/77* (2013.01)

(58) Field of Classification Search
None
See application file for complete search history.

(56) References Cited

U.S. PATENT DOCUMENTS

| | | |
|---|---|---|
| 5,191,066 A | 3/1993 | Bieniarz et al. |
| 5,648,237 A | 7/1997 | Carter |
| 6,362,331 B1 | 3/2002 | Kamal et al. |
| 6,376,217 B1 | 4/2002 | Better et al. |
| 6,753,165 B1 | 6/2004 | Cox et al. |
| 7,049,311 B1 | 5/2006 | Thurston et al. |
| 7,189,710 B2 | 3/2007 | Kamal et al. |
| 7,407,951 B2 | 8/2008 | Thurston et al. |
| 7,429,658 B2 | 9/2008 | Howard et al. |
| 7,557,099 B2 | 6/2009 | Howard et al. |
| 7,608,429 B2 | 10/2009 | Reilly et al. |
| 7,632,678 B2 | 12/2009 | Hansford et al. |
| 7,723,485 B2 | 5/2010 | Junutula et al. |
| 7,741,319 B2 | 6/2010 | Howard et al. |
| 7,837,980 B2 | 11/2010 | Alley et al. |
| 7,855,275 B2 | 12/2010 | Eigenbrot et al. |
| 8,008,443 B2 | 8/2011 | Dall' Acqua et al. |
| 8,034,808 B2 | 10/2011 | Delavault et al. |
| 8,053,562 B2 | 11/2011 | Humphreys |
| 8,163,736 B2 | 4/2012 | Gauzy et al. |
| 8,226,945 B2 | 7/2012 | Ebens, Jr. et al. |
| 8,507,654 B2 | 8/2013 | Baker et al. |
| 8,865,875 B2 | 10/2014 | Liu et al. |
| 2005/0152894 A1 | 7/2005 | Krummen et al. |
| 2006/0120959 A1 | 6/2006 | De Haen et al. |
| 2007/0292414 A1 | 12/2007 | Duntsch et al. |
| 2008/0138313 A1 | 6/2008 | Frankel |
| 2008/0175870 A1 | 7/2008 | Mather et al. |
| 2008/0220448 A1 | 9/2008 | Blincko et al. |
| 2008/0305044 A1 | 12/2008 | McDonagh et al. |
| 2009/0010945 A1 | 1/2009 | Alley et al. |
| 2010/0162416 A1 | 6/2010 | Krtolica et al. |
| 2010/0184119 A1 | 7/2010 | Bright et al. |
| 2010/0233165 A1 | 9/2010 | Liu et al. |
| 2010/0273160 A1 | 10/2010 | Donahoe et al. |
| 2010/0275280 A1 | 10/2010 | Clevers et al. |
| 2011/0020221 A1 | 1/2011 | Berman et al. |
| 2011/0033378 A1 | 2/2011 | Dimasi et al. |
| 2011/0256157 A1* | 10/2011 | Howard .............. C07D 487/04 424/181.1 |
| 2011/0301334 A1 | 12/2011 | Bhakta et al. |

(Continued)

FOREIGN PATENT DOCUMENTS

| | | |
|---|---|---|
| WO | WO 99/37779 | 1/1999 |
| WO | WO 2005/003171 | 1/2005 |

(Continued)

OTHER PUBLICATIONS

Padlan (Advances in Protein Chemistry, 1996, 49:57-133).*

(Continued)

*Primary Examiner* — Julie Wu

(74) *Attorney, Agent, or Firm* — Womble Bond Dickinson (US) LLP

(57) ABSTRACT

Provided herein are novel anti-DPEP3 antibodies and antibody drug conjugates (ADC), including derivatives thereof, and methods of using the same to treat proliferative disorders.

38 Claims, 51 Drawing Sheets

Specification includes a Sequence Listing.

(56) References Cited

U.S. PATENT DOCUMENTS

| | | | |
|---|---|---|---|
| 2012/0071634 | A1 | 3/2012 | Igawa et al. |
| 2012/0288498 | A1 | 11/2012 | Sooknanan et al. |
| 2013/0040362 | A1 | 2/2013 | Vogel et al. |
| 2013/0061340 | A1 | 3/2013 | Dylla et al. |
| 2013/0061342 | A1 | 3/2013 | Dylla et al. |
| 2013/0101581 | A1 | 4/2013 | Kuramochi et al. |
| 2013/0144041 | A1 | 6/2013 | Dillon et al. |
| 2013/0259806 | A1 | 10/2013 | Light et al. |
| 2013/0260385 | A1 | 10/2013 | Dylla et al. |
| 2013/0330350 | A1 | 12/2013 | Dimasi |
| 2014/0120581 | A1 | 5/2014 | Niwa et al. |
| 2014/0315743 | A1* | 10/2014 | Chapman ............ C12Q 1/6886 506/9 |
| 2014/0348839 | A1 | 11/2014 | Chowdhury et al. |
| 2015/0005477 | A1 | 1/2015 | Lowman et al. |
| 2015/0030636 | A1 | 1/2015 | Dylla et al. |
| 2015/0320879 | A1 | 11/2015 | Lyon et al. |

FOREIGN PATENT DOCUMENTS

| | | |
|---|---|---|
| WO | WO 2006/034488 | 3/2006 |
| WO | WO 2011/128650 | 10/2011 |
| WO | WO 2011/130613 | 10/2011 |
| WO | WO 2011/130616 | 10/2011 |
| WO | WO 2012/031280 | 3/2012 |
| WO | WO 2012/064733 | 5/2012 |
| WO | WO 2013/052108 | 4/2013 |
| WO | WO 2013/093809 | 6/2013 |
| WO | WO 2013/119964 | 8/2013 |
| WO | WO 2014/057074 | 4/2014 |
| WO | WO 2014/124316 | 8/2014 |
| WO | WO 2015/031698 | 3/2015 |
| WO | WO 2015/123265 | 8/2015 |
| WO | WO 2016/064749 | 4/2016 |

OTHER PUBLICATIONS

Corada (Blood, 2001; 97:1679-84).*
Berglund et al, Protein Science, 2008, 17:606-613.*
Kulkarni-Kale et al. Nucleic Acid Research, 2005, 33:W168-W171.*
Almagro & Fransson, Frontiers in Bioscience 2008; 13:1619-33.*
De Genst et al., Developmental and Comparative Immunology, 2006, 30:187-98.*
Ward et al. (Nature, 1989, 341:544-546).*
Barthelemy et al. (Journal of Biological Chemistry, 2008, 283:3639-3654).*
Choi et al., 2011, Molecular BioSystems, 2011, 7:3327-334.*
Griffiths et al. (The EMBO Journal, 1993, 12:725-734).*
Klimka et al., British Journal of Cancer, 2000, 83:252-260.*
Beiboer et al. (Journal of Molecular Biology, 2000, 296:833-849).*
Tzartos et al., Methods in Molecular Biology, 1996, 66:55-66.*
Berglund et al., "The epitope space of the human proteome," Protein Science (2008) 17:606-613.
Corada et al., "Monoclonal antibodies directed to different regions of vascular endothelial cadherin extracellular domain affect adhesion and clustering of the protein and modulate endothelial permeability," Blood (Mar. 15, 2001) 97:1679-84.
Kulkarni-Kale et al., "CEP: a conformational epitope prediction server," Nucleic Acids Res (2005) vol. 33, Web Server issue doi:10.1093/nar/gki460.
Padlan, "X-Ray Crystallography of Antibodies," Advances in Protein Chemistry (1996) 49:57-133.
Tzartos, "Epitope Mapping by Antibody Competition," Methods in Molecular Biology (1996) 66:55-66.
Office action dated Dec. 13, 2017, issued in Chilean application (No. 01432-2016).
Official action dated Mar. 26, 2018, issued in Colombian Application (No. 16-172.212).
Official action dated Feb. 15, 2018, issued in European application (No. 14870395.2).
Anti-DPEP3 Antibody (AAS55537C) product data sheet, Antibodyverify.com (2015), retrieved on May 6, 2015 from http://www.antibodyverify.com/anti-dpep3-antibody-aas55537c.html, pp. 1-2.
Anti-DPEP3 Antibody (HPA031870) product data sheet, Sigma-Aldrich (2015), retrieved on May 6, 2015 from http://www.sigmaaldrich.com/catalog/product/sigma/hpa031870?lang+en®ion+US#, pp. 1-2.
Boswell et al., "An integrated approach to identify normal tissue expression of targets for antibody-drug conjugates: case study of TENB2," British Journal of Pharmacology (2013) 168:445-457.
Chothia et al., "Structural Repertoire of the Human $V_H$ Segments," J Mol Biol (1992) 227:799-817.
Cook et al., "The human immunoglobulin $V_H$ repertoire," Immunol Today (1995) 16:237-242.
DPEP3 Antibody (NBP2-32395) product data sheet, Novusbio, Apr. 27, 2014, retrieved on May 6, 2015 from http://www.novusbio.com/PDFs2/NBP2-32395.pdf, pp. 1-5.
Dylla et al., "Colorectal Cancer Stem Cells are Enriched in Xenogeneic Tumors Following Chemotherapy," PLoS One (2008) 3(6):1-13.
Fazekas et al., "The Evaluation of Limiting Dilution Assays," J Immunol Methods (1982) 49(2):R11-23.
Habib et al., "Identification of Two Additional Members of the Membrane-Bound Dipeptidase Family," FASEB J (2003) 17(10):1313-1315.
Hoey et al., "DLL4 Blockade Inhibits Tumor Growth and Reduces Tumor-Initiating Cell Frequency," Cell Stem Cell (2009) 5(2):168-177.
Panowski, S., et al., "Site-specific Antibody Drug Conjugates for Cancer Therapy," MAbs (Jan.-Feb. 2014) 6(1):34-35.
Rodrigues, M. L., et al., "Engineering Fab' Fragments for Efficient F(ab)2 Formation in Escherichia coli and for Improved In Vivo Stability," The Journal of Immunology, Dec. 15, 1993, 151(12): 6954-6961.
Schulenburg et al., "Neoplastic Stem Cells: Current Concepts and Clinical Perspectives," Crit Rev Oncol Hematol (2010) 76(2):79-98.
Strop, P., et al., "Location Matters: Site of Conjugation Modulates Stability and Pharmacokinetics of Antibody Drug Conjugates," Chemistry & Biology, Feb. 21, 2013, 20:161-167.
Sun, M., et al., "Reduction-Alkylation Strategies for the Modification of Specific Monoclonal Antibody Disulfides," Bioconug. Chem. (2005) 16(5): 1282-1290.
Sussman, D., et al., Abstract 4634, "Engineered Cysteine Drug Conjugates Show Potency and Improved Safety," Cancer Research, Apr. 15, 2012, 72(8), Supp. 1.
Tomlinson et al., "The Repertoire of Human Germline $V_H$ Sequences Reveals About Fifty Groups of $V_H$ Segments with Different Hypervariable Loops," J Mol Biol (1992) 227:776-798.
Tomlinson et al., "The Structural Repertoire of the Human V Kappa Domain," EMBO J (1995) 14:4628-4638.
Umetsu, M., et al., "How Additives Influence the Refolding of Immunoglobulin-folded Proteins in a Stepwise Dialysis System: Spectroscopic Evidence for Highly Efficient Refolding of a Single-chain FV Fragment," J. Biol. Chem., Mar. 14, 2003, 278(11): 8979-8987.
Visvader et al., "Cancer Stem Cells in Solid Tumours: Accumulating Evidence and Unresolved Questions," Nat Rev Cancer (2008) 8(10):755-768.
Yoshitake et al., "Molecular characterization and expression of dipeptidase 3, a testis-specific membrane-bound dipeptidase: complex formation with TEX101, a germ-cell-specific antigen in the mouse testis," J Reprod Immunol (2011) 90(2):202-213.
Zhang et al., "Identification and Characterization of Ovarian Cancer-Initiating Cells from Primary Human Tumors," Cancer Res (2008) 68(11):4311-4320.
BC037243—Dipeptidase 3 [Homo sapiens].
BC051148—Dipeptidase 3 [Mus musculus].
BC085826—Dipeptidase 3 [Rattus norvegicus].
NM_022357—Dipeptidase 3, transcript variant 1 [Homo sapiens].
NM_001129758—Dipeptidase 3, transcript variant 2 [Homo sapiens].
NP_071750—Dipeptidase 2 precursor [Homo sapiens].
NP_071752.3—Dipeptidase 3 isoform a precursor [Homo sapiens].

(56) References Cited

OTHER PUBLICATIONS

NP_082236—Dipeptidase 3 precursor [Mus musculus].
NP_001008384—Dipeptidase 3 precursor [Rattus norvegicus].
NP_001123230—Dipeptidase 3 isoform b precursor [*Homo sapiens*].
NP_001180985—Dipeptidase 3 precursor [Macaca mulatta].
NP_001266956—Dipeptidase 3 precursor [Pan troglodytes].
Protein Data Bank (PDB) No. 1ITU—Renal dipeptidase [*Homo sapiens*] complexed with cilastatin.
UniProtKB/Swiss-Prot Q9H4B8.2—Dipeptidase 3 Precursor [*Homo sapiens*].
International Search Report dated Jun. 2, 2015, issued in PCT counterpart application (PCT/US2014/070110).
Written Opinion dated Jun. 2, 2015, issued in PCT counterpart application (PCT/US2014/070110).
Invitation to Pay Additional Fees dated Mar. 26, 2015, issued in PCT counterpart application (PCT/US2014/070110).

\* cited by examiner

Anti-DPEP3 Murine Antibody Characteristics

| Antibody | Isotype | Affinity (KD) | BIN | cDPEP3 Cross Reactive | rDPEP3 Cross Reactive | mDPEP3 Cross Reactive | hDPEP2 Cross Reactive |
|---|---|---|---|---|---|---|---|
| SC34.2 | IgG2b/k | +++ | B | YES | NO | NO | YES |
| SC34.3 | IgG2a/k | ++ | U | YES | NO | NO | NO |
| SC34.4 | IgG2b/k | ++ | B | YES | YES | NO | NO |
| SC34.5 | IgG1/k | +++ | A | NO | NO | NO | NO |
| SC34.6 | IgG1/k | +++ | A | NO | NO | NO | NO |
| SC34.7 | IgG1/k | ++ | A | YES | NO | NO | NO |
| SC34.8 | IgG2a/k | +++ | A | NO | NO | NO | NO |
| SC34.9 | IgG1/k | + | ND | NO | NO | NO | YES |
| SC34.10 | IgG1/k | ++ | C | NO | NO | NO | YES |
| SC34.11 | IgG2a/k | ++ | A | NO | NO | NO | NO |
| SC34.13 | IgG2a/k | ++ | A | YES | NO | NO | YES |
| SC34.14 | IgG1/k | +++ | A | NO | NO | NO | NO |
| SC34.15 | IgG1/k | ++ | A | YES | NO | NO | NO |
| SC34.16 | IgG1/k | +++ | A | NO | NO | NO | NO |
| SC34.18 | IgG2b/k | +++ | B | YES | NO | NO | NO |
| SC34.19 | IgG1/k | ++ | A | YES | NO | NO | NO |
| SC34.20 | IgG1/k | ++ | A | YES | NO | NO | NO |
| SC34.21 | IgG1/k | +++ | A | NO | NO | NO | NO |
| SC34.22 | IgG2a/k | ++ | A | NO | NO | NO | NO |
| SC34.24 | IgG1/k | +++ | A | YES | NO | NO | NO |

FIG. 4

Anti-DPEP3 Murine Antibody Characteristics

| Antibody | Isotype | Affinity (KD) | BIN | cDPEP3 Cross Reactive | rDPEP3 Cross Reactive | mDPEP3 Cross Reactive | hDPEP2 Cross Reactive |
|---|---|---|---|---|---|---|---|
| SC34.25 | IgG1/k | +++ | C | YES | NO | NO | NO |
| SC34.26 | IgG2b/k | + | A | NO | NO | NO | NO |
| SC34.27 | IgG1/k | +++ | A | YES | NO | NO | NO |
| SC34.28 | IgG1/k | ++ | A | NO | NO | NO | NO |
| SC34.29 | IgG2b/k | +++ | U | YES | NO | NO | NO |
| SC34.32 | IgG1/k | ++ | A | NO | NO | NO | NO |
| SC34.33 | IgG1/k | ++ | A | NO | NO | NO | NO |
| SC34.34 | IgG1/k | ++ | A | YES | NO | NO | NO |
| SC34.35 | IgG1/k | ++ | A | NO | NO | NO | NO |
| SC34.36 | IgG2a/k | ND | ND | YES | NO | NO | NO |
| SC34.37 | IgG1/k | + | ND | NO | NO | NO | NO |
| SC34.38 | IgG2b/k | +++ | A/B | NO | NO | NO | NO |
| SC34.39 | IgG2a/k | ++ | A | NO | NO | NO | NO |
| SC34.40 | IgG2a/k | ++ | A | NO | NO | NO | NO |
| SC34.41 | IgG1/k | + | A | NO | NO | NO | NO |
| SC34.43 | IgG1/k | +++ | C | YES | NO | NO | NO |
| SC34.44 | IgG1/k | +++ | A | NO | NO | NO | NO |
| SC34.45 | IgG1/k | +++ | C | YES | NO | NO | NO |
| SC34.46 | IgG1/k | +++ | A | YES | YES | YES | YES |
| SC34.47 | IgG2a/k | +++ | U | NO | NO | NO | NO |
| SC34.48 | IgG1/k | +++ | A | NO | NO | NO | YES |
| SC34.49 | IgG1/k | + | A | NO | NO | NO | NO |

FIG. 4 cont.

Anti-DPEP3 Murine Antibody Characteristics

| Antibody | Isotype | Affinity (KD) | BIN | cDPEP3 Cross Reactive | rDPEP3 Cross Reactive | mDPEP3 Cross Reactive | hDPEP2 Cross Reactive |
|---|---|---|---|---|---|---|---|
| SC34.50 | IgG2b/k | + | A/B | NO | NO | NO | NO |
| SC34.51 | IgG1/k | + | ND | NO | NO | NO | NO |
| SC34.52 | IgG2b/k | ++ | A/B | YES | NO | YES | YES |
| SC34.53 | IgG2b/k | ++ | B | NO | NO | NO | NO |
| SC34.54 | IgG2b/k | +++ | A | YES | NO | NO | NO |
| SC34.55 | IgG1/k | +++ | ND | NO | NO | NO | NO |
| SC34.56 | IgG1/k | ND | A | YES | NO | NO | NO |
| SC34.58 | IgG1/k | +++ | A | YES | NO | NO | NO |
| SC34.59 | IgG1/k | +++ | A | NO | NO | NO | NO |
| SC34.60 | IgG2b/k | ND | ND | NO | NO | NO | NO |
| SC34.61 | IgG1/k | + | A | NO | NO | NO | NO |
| SC34.62 | IgG2b/k | ND | ND | YES | YES | YES | YES |
| SC34.63 | IgG1/k | +++ | A | YES | NO | NO | NO |
| SC34.65 | IgG2a/k | +++ | A | NO | NO | NO | NO |
| SC34.66 | IgG2a/k | +++ | A | NO | NO | NO | NO |
| SC34.67 | IgG2a/k | +++ | ND | YES | NO | NO | NO |
| SC34.68 | IgG2a/k | +++ | A | NO | NO | NO | NO |
| SC34.69 | IgG1/k | + | ND | YES | NO | NO | NO |
| SC34.70 | IgG2b/k | + | ND | YES | YES | YES | YES |
| SC34.71 | IgG2a/k | +++ | U | NO | NO | NO | NO |
| SC34.72 | IgG2a/k | +++ | U | YES | NO | NO | NO |

FIG. 4 cont.

Anti-DPEP3 Murine Antibody Characteristics

| Antibody | Isotype | Affinity (KD) | BIN | cDPEP3 Cross Reactive | rDPEP3 Cross Reactive | mDPEP3 Cross Reactive | hDPEP2 Cross Reactive |
|---|---|---|---|---|---|---|---|
| SC34.73 | IgG1/k | +++ | A | NO | NO | NO | YES |
| SC34.74 | IgG1/k | + | A | YES | NO | NO | NO |
| SC34.75 | IgG1/k | ++ | A | YES | NO | NO | NO |
| SC34.76 | IgG1/k | +++ | C | YES | NO | NO | NO |
| SC34.77 | IgG1/k | ++ | C | NO | NO | NO | NO |
| SC34.78 | IgG1/k | + | ND | NO | NO | NO | NO |
| SC34.80 | IgG2a/k | ++ | A | YES | NO | NO | NO |
| SC34.81 | IgG1/k | +++ | A | NO | NO | NO | NO |
| SC34.83 | IgG2a/k | + | A | YES | YES | YES | NO |
| SC34.84 | IgG1/k | +++ | A | YES | NO | NO | NO |
| SC34.85 | IgG1/k | +++ | A | NO | NO | NO | NO |
| SC34.86 | IgG1/k | +++ | A | YES | YES | NO | NO |
| SC34.87 | IgG2a/k | ++ | U | NO | YES | NO | NO |
| SC34.88 | IgG1/k | + | A | NO | NO | NO | NO |
| SC34.89 | IgG1/k | +++ | A | YES | NO | NO | NO |
| SC34.90 | IgG2a/k | ++ | A | NO | NO | NO | NO |
| SC34.91 | IgG1/k | +++ | A | YES | NO | NO | NO |
| SC34.92 | IgG1/k | + | A | NO | NO | NO | NO |
| SC34.94 | IgG2a/k | ++ | D | NO | NO | NO | NO |
| SC34.95 | IgG1/k | +++ | A | YES | YES | NO | NO |
| SC34.96 | IgG1/k | +++ | ND | YES | NO | NO | NO |

FIG. 4 cont.

Anti-DPEP3 Murine Antibody Light Chain Variable Region Amino Acid Sequences

| Name | FR1 | CDRL1 | FR2 | CDRL2 | FR3 | CDRL3 | FR4 | SEQ ID NO |
|---|---|---|---|---|---|---|---|---|
| SC34.2 | DIQMTQTASSLSASLGDRVTISC | SASQGITNYLN | WYQQKPDGTVKLLIY | YTSRLHS | GVPSRFSGSGSGTDYSLTISNLEPEDIATYYC | QQYSKLPWT | FGGGTKLEIK | 21 |
| SC34.4 | DIVMSQSPSSLTVSVGEKVTMSC | KSSQSLLYSRNQKNYLA | WYQQKPGGQSPKLLIY | WASTRDS | GVPDRFTGTGSGTDFSLTISSVKTEDLAVYYC | HQHYRYPLT | FGAGTKLELK | 25 |
| SC34.5 | DIVMTQFPSSLAMSVGQKVTMNC | KSSQSLLNSSNQKNYLA | WFQQKPGGQSPKLLVY | FASTRES | GVPDRFLGSGSGTDFTLTISSVQAEDLADYFC | QQHYSTPFT | FGSGTKLEIK | 29 |
| SC34.6 | DIVMTQSPSSLAVSVGQNITMNC | KSSQSLLYNQKNYLA | WYQQKPGGQSPKLLVY | FASTRES | GVPDRFVGSGSGTDFTLTISNVQAEDLADYFC | QQHYTTPFT | FGSGTKLEIK | 33 |
| SC34.7 | DIVMSQSPSSLAVSVGEKVTMSC | KSSQSLLYSRYQKNYLA | WYQQKPGGQSPKLLIY | WASTRES | GVPDRFTGSGSGTDFTLTISSVKAEDLAVYYC | HQYVRYPLT | FGAGTKLEIK | 37 |
| SC34.11 | DIVMSQSPSSLAVSAGEKVTMSC | KSSQSLLNSRTRKNYLA | WYQQKPGGQSPKLLIY | WASTRES | GVPDRFTGSGSGTDFTLTISSVQAEDLAVYYC | KESYNLWT | FGGGTKLEIK | 41 |
| SC34.13 | DIVMSQSPSSLAVSVGEKVTLSC | KSSQSLLYSRYQKNYLA | WYQQKPGGQSPRLVIY | WASTRES | GVPDRFTGSGSGTDFTLTISSVKAEDLVVYC | QQYVRYPLT | FGSGTKLEIK | 45 |
| SC34.14 | DIQMTQAPASLSPSVGATVTITC | RTSEHIYSYLA | WYQQKQGKSPRLLVY | NAKTLAE | GVSSRFSGSGSGTQFSLQINSLQPEDFGNVYC | QHHYDTPYT | FGGGTKLEIK | 49 |
| SC34.16 | DIVMSQSPSSLAVSVGEKVTMSC | KSSQSLLYSRYQKNYLA | WYQQKPGGQSPKLLIY | WSSTRES | GVPDRFTGSGSGTDFTLTISSVKAEDLADYYC | QQYVRYPLT | FGAGTKLEIK | 53 |
| SC34.18 | DIVMTQSQKFMSTSVGDRVSITC | KASQNVRTAVG | WVQQKPGQSPKTLIY | LASNRHT | GVSDRFTGSGSGTDFTLTISNVQSEDLADYFC | LQHWNYPWT | FGGGTKLEIK | 57 |
| SC34.19 | DIVMSQSPSALAVSVGEKITMSC | KCSQSLLHSRDQKNYLA | WYQQKPGGQSPKLLIY | WASTRES | GVPDRFTGSGSGTDFTLTINTVKAEDLAVYYC | QQHYRYPLT | FGAGTKLEIK | 61 |
| SC34.20 | DIVMSQSPSSLTVSVGEKVTMSC | KSSQSLLYSTYQKNYLA | WFQQKPGGQSPKLLIY | WASTRES | GVPDRFTGSGSGTDFTLTISSVKAEDLAVYYC | QQYVRYPLT | FGAGTKLEIK | 65 |
| SC34.23 | QIVLTQSPAIMSASLGEEITLTC | SASSSVSYMH | WYQQKSGTSPKLLIY | STSNLAS | GVPSRFSGSGSGTFYSLTINTVEAEDAADYYC | HQWSSWT | FGGGTKLEIK | 69 |
| SC34.24 | DIVMSQSPSSLAVSVGEKVTMNC | KSSQSLLYSRYQKNYLA | WYQQKPGGQSPKLLIY | WASTRES | GVPDRFTGSGSGTDFTLTISSVKAEDLAVYYC | QQYVRYPLT | FGAGTKLEIK | 73 |
| SC34.25 | DIVMSQSPSSLAVSGGEKVTMSC | KSSQSLLYSRYQKNVVA | WVQQKPGGQSPKLLIY | WASTRES | GVPDRFTGSGSGTDFTLTISSVKAEDLAVYYC | QQYVRYPLT | FGAGTKLEIK | 77 |

FIG. 5A

Anti-DPEP3 Murine Antibody Light Chain Variable Region Amino Acid Sequences

| Name | FR1 | CDRL1 | FR2 | CDRL2 | FR3 | CDRL3 | FR4 | SEQ ID NO |
|---|---|---|---|---|---|---|---|---|
| SC34.26 | DVVLTQTPLTLSVTIGQPASISC | KSSQSLLYSNRRTYLN | WLLQRPGQSPKRLIY | LVSKLDS | GVPDRFTGSGSGTDFTLKISRVEAEDLGVYYC | VQGTHFPYT | FGTGTKLELK | 81 |
| SC34.27 | DIVMSQSPSSLAVSVGEKVTMSC | KSSQSLLYSRNQKNYLA | WYQQKPGQSPKLLIY | WASTRES | GVPDRFTGSGSGTDFTLTINSVKAEDLAVYYC | HQYVRYPLT | FGAGTKLELK | 85 |
| SC34.28 | QIVLTQSPAIMSASLGERVTMTC | TASSSVNSFYLH | WYQQKPGSSPKLWIH | STSNLAS | GVPGRFSGSGSGTSYSLTISSMEAEDAATYYC | HQYHRSPYT | FGGGTKLEIK | 89 |
| SC34.33 | QIVLTQSPAIMSASLGERVTMTC | TASSSVNSFYLH | WYQQKPGSSPKLWIH | STSNLAS | GVPGRFSGSGSGTSYSLTISSMEAEDAATYYC | HQYHRSPYT | FGGGTKLEIK | 93 |
| SC34.36 | DIQMTQTTSSLSASLGDRVTISC | RASQDISNYLN | WYQKPDGTVKLLIY | YTSRLHS | GVPSRFSGSGSGTDYSLTISNLEQEDIATYFC | QQGNTLPWT | FGGGTKLEIK | 97 |
| SC34.38 | DVVLTQTPLTLSVTIGQPASISC | KSSQSLLYSNRRTYLN | WLLQRPGQSPKRLIY | LVSKLDS | GVPDRFTGSGSGTDFTLKISRVEAEDLGVYYC | VQGTHFPFT | FGTGTKLELK | 101 |
| SC34.39 | QIVLTQSPAIMSASQGERVTMTC | TASSVSSNYLH | WYQQKPGSSPKLWIY | STSHLAS | GVPVRFSGSGSGTSYSLTISSMEAEDAATYYC | HQYHRSPYT | FGGGTKLEIK | 105 |
| SC34.40 | DIQMTQSPASLSASVGETVTMTC | RASENIYSNLA | WYQQKQGKSPQVLVY | AATNLAD | GVPSRFSGSESGTQFSLKINSLQPEDFGSYYC | QHFYGTPWT | FGGGTKLEIK | 109 |
| SC34.41 | DIQMIQSPSSMFASLGDRVSLSC | RASQGIRGNLD | WYQQKPGGTIKLLIY | STSNLNS | GVPSRFSGSGSGSDYSLTISSLESEDFADYYC | LQRDAYPYT | FGGGTKLEIK | 113 |
| SC34.46 | DIVMSQSPSSLAVSVGEKVTMSC | KSSQSLLYSKYQKNFLA | WYQQKPGQSPKLLIY | WASTRES | GVPDRFTGSGSGTDFTLTISNVKAEDLAVYYC | QQYVRYPLT | FGAGTTLELK | 117 |
| SC34.48 | DIQMTQAPASLSASVGETVTIC | RTSGHIYSYLA | WYQQKQGKSPQLLVY | NAKTLAE | GVSSRFSGSGSGTQFSLKITSLQPEDFGDYYC | QHHYDTPYT | FGGGTKLEIK | 121 |
| SC34.49 | DIQMTQSSSYLSVSLGGRVTITC | KASEHINNWLA | WYQQKPGNPPRLLIS | GATSLET | GVPSRFSGSGSGKDYTLSITGLQTEDIATYFC | QQYRSTPFT | FGSGTKLEIK | 125 |
| SC34.50 | DIQMTQSSSSFSVSLGDRVTITC | KASEDIYNRLA | WYQQKPGNAPRLLIS | GATSLET | GVPSRFSGSGSGKDYTLSITSLQTEDVATYYC | QQYWSTIFT | FGSGTKLEIK | 129 |
| SC34.53 | DVVLTQTPLTLSVTIGQPASISC | KSSQSLLYSNRRTYLN | WLLQRPGQSPKRLIY | LVSKLDS | GVPDRFTGSGSGTDFTLKITRVEAEDLGVYYC | VQGTHFPYT | FGTGTKLEIK | 133 |

FIG. 5A Cont.

Anti-DPEP3 Murine Antibody Light Chain Variable Region Amino Acid Sequences

| Name | FR1 | CDRL1 | FR2 | CDRL2 | FR3 | CDRL3 | FR4 | SEQ ID NO |
|---|---|---|---|---|---|---|---|---|
| SC34.58 | DIVMSQSPSSLAVSVGEKVTMSC | KSSQSLLYSRNQKNYLA | WYQQKPGQSPKLLIY | WASTRES | GVPDRFTGSGSGTDFTLTISSVKAEDLAVYYC | HQHYRYPLT | FGAGTKLELR | 137 |
| SC34.63 | DIVMSQSPSSLAVSVGEKVTMSC | KSSQSLLYSKYQKNYLA | WYQQKPGQSPKLLIY | WASTRES | GVPDRFTGSESGTDFTLTISSVKAEDLAVYYC | QQYVRYPLT | VGAGTKLELK | 141 |
| SC34.67 | DMVMSQSPSSLAVSVGEKVALSC | KSSQSLLHSRDQKNYLA | WYQQKPGQSPKLLIH | WASTRES | GVPARFTGSGSGTDFTLTISSVKAEDLAVYYC | QQSVRYPLT | FGAGTKLELK | 145 |
| SC34.71 | DIVMTQSQKFMSTSVGDRVSITC | KASQNVRTAVA | WYQQKPGQSPKTLIY | LASNRHT | GVPDRFTGSGSGTDFTLTISYVQSEDLADYFC | LQHLNYPWT | FGGGTKLEIK | 149 |
| SC34.76 | DIVMSQSPSSLAVSVGERVTMNC | KSSQSLFYSRYQKNYLA | WYQQKPGQSPKLLIY | WASTRES | GVPDRFTGSGSGTDFTLTISSVKAEDLAVYYC | QQYVRYPLT | FGAGTKLELK | 153 |
| SC34.78 | DINMTQSPATLSVTPGDRVSLSC | RASQSIGAYLH | WYQQKSHESPRLLIK | YVSQSIS | GIPSRFSGSGSGSDFTLSINSVEPEDVGVYYC | QNGHSFPLT | FGAGTKLELK | 157 |
| SC34.83 | QIVLIQSPAIMSASPGENVTMTC | SASSSVSYMH | WYQQKSGTSPKRMIY | DTSKLAS | GVPARFSGSGSGTSYSLTISMEAEDAATYYC | QQWNSYPPT | FGAGTKLELK | 161 |
| SC34.86 | DTVMSQSPSSLAVSVGEKVTLSC | KSSQSLLYSRYQKNYLA | WYQQKPGQSPKLLLY | WASTRES | GVPDRFTGSGSGTDFTLTISSVKAEDLAVYYC | QQHYRYPLT | FGAGTKLELK | 165 |
| SC34.87 | DIVMSQSPSSLAVSAGEKVTMSC | KSSQSLLNSRTRKNYLA | WYQQKPGQSPKLLIY | WASTRES | GVPGRFTGSGSGTDFTLTISSVQAEDLAVYYC | KQSYNLWT | FGGGTKLEIK | 169 |
| SC34.89 | DIVMSQSPSSLGVSVGEKVTLSC | KSSQSLFNKRDQKNYLA | WYQQKPGQSPKLLIY | WASTRES | GVPDRFTGSGSGTDFTLTIRSVKAEDLAVYYC | HQSYRYPLT | FGAGTKLELK | 173 |
| SC34.90 | QIVLTQSPAIMSASQGERVTMTC | TASSSVSSSYLH | WYQQKPGSSPKLMIY | STSNLAS | GVPVRFSGSGSGTSYSLTISMEAEDAATYYC | HQYHRSPYT | FGGGTKLEIK | 177 |
| SC34.91 | DIVMSQSPSSLAVSVGEKVTMSC | KSSQLLYSTVQKNYLA | WFQQKPGQSPKLLIY | WASTRES | GVPDRFTGSGSGTDFTLTISSVKAEDLAVYYC | QQYVRYPLT | FGAGTKLELK | 181 |
| SC34.95 | DIVLSQSPSSLAVSVGEKVTMSC | KSSQSLLNSRDRKNYLA | WCQQKPGQSPKVMIY | WASTRES | GVPDRFTGSGSGTDFTLTISSVKAEDLAVYYC | QQYSYPLT | VGAGTKLELK | 185 |

FIG. 5A Cont.

Anti-DPEP3 Humanized Antibody Light Chain Variable Region Amino Acid Sequences

| Name | FR1 | CDRL1 | FR2 | CDRL2 | FR3 | CDRL3 | FR4 | SEQ ID NO |
|---|---|---|---|---|---|---|---|---|
| hSC34.2 | DIQMTQSPSSLSASVGDRVTITC | SASQGITNYLN | WYQQKPGKAPKLLIY | YTSRLHS | GVPSRFSGSGSGTDFTLTISSLQPEDFATYYC | QQYSKLPWT | FGQGTKVEIK | 189 |
| hSC34.11 | DIQMTQSPSSLSASVGDRVTITC | KSSQSLLNSRTRKNYLA | WYQQKPGKVPKLLIY | WASTRES | GVPSRFSGSGSGTDFTLTISSLQPEDVATYYC | KESYNLWT | FGGGTKVEIK | 193 |
| hSC34.14 | DIQMTQSPSSLSASVGDRVTITC | RTSEHIYSYLA | WYQQKPGKAPKLLIY | NAKTLAE | GVPSRFSGSGSGTDFTLTISSLQPEDFATYYC | QHHYDTPYT | FGQGTKLEIK | 197 |
| hSC34.25 | DIVMTQSPDSLAVSLGERATINC | KSSQSLLYSRYQKNYVA | WYQQKPGQPPKLLIY | WASTRES | GVPDRFSGSGSGTDFTLTISSLQAEDVAVYYC | QQYYRYPLT | FGQGTKLEIK | 201 |
| hSC34.28 | EIVLTQSPATLSLSPGERATLSC | TASSSVNSFYLH | WYQQKPGLAPRLLIY | STSNLAS | GIPDRFSGSGSGTDFTLTISRLEPEDFAVYYC | HQVHRSPYT | FGQGTKLEIK | 205 |
| hSC34.38 | DVVMTQSPLSLPVTLGQPASISC | KSSQLLYSNRRTYLN | WFQQRPGQSPRRLIY | LVSKLDS | GVPDRFSGSGSGTDFTLKISRVEAEDVGVYYC | VQGTHFPFT | FGQGTKLEIK | 209 |
| hSC34.87 | DIVMTQSPDSLAVSLGERATINC | KSSQSLLNSRTRKNYLA | WYQQKPGQPPKLLIY | WASTRES | GVPDRFSGSGSGTDFTLTISSLQAEDVAVYYC | KQSYNLWT | FGGGTKLEIK | 213 |

FIG. 5A Cont.

Anti-DPEP3 Murine Antibody Heavy Chain Variable Region Amino Acid Sequences

| Name | FR1 | CDRH1 | FR2 | CDRH2 | FR3 | CDRH3 | FR4 | SEQ ID NO |
|---|---|---|---|---|---|---|---|---|
| SC34.2 | QIQLQQSGPELVKPGASVKISCKASGYTFT | DYYIN | WLKQRPGQGLEWIG | WIYPGSGPTKYNGKFRG | KATLTVDTSSSTVYMQLSSLTSEDSAVYFCAR | RGIYYYDGIYPNYFDY | WGQGTTLTVSS | 23 |
| SC34.4 | QVQLQQSGAELARPGASVKLSCKASGYTFT | SYGIN | WVKQRTGQGLEWIG | EIYPGSGNIYYNEKFKG | KAILTTDKSNTAYMQLSSLTSEDSAVYFCAR | VHDYGSWFPY | WAQGTLVTVSA | 27 |
| SC34.5 | EVQLQQSGPELVKPGASMKISCKASGYSFT | GYTMN | WVKQSHGKNLEWIG | LIYPYNDDTRYKQKFKG | KATLTVDKSSSTAYMELLSLTSEDSAVYYCTR | GYYGSPYFDV | WGAGTTVTVSS | 31 |
| SC34.6 | EVQLQQSGPELVKPGTSMKISCKASGYSFT | GYTMN | WVKQSHGKNLEWIG | LIYPYNDDTRYNRKFKG | KATLTVDKSSNTAYMELLSLTSVDSAVCYCAR | GSYGSPFFDV | WGAGTTVTVSS | 35 |
| SC34.7 | QVQVQQSGAELARPGASVKLSCKASGYTFT | SYGIN | WVKQRTGQGLEWIG | EIYPGSGNAYYNEKFKV | KAKLTTDNSSRTAYMQLINLTSEDSAVYFCAR | VHDYGSWFPY | WGQGTLVTVSA | 39 |
| SC34.11 | QVQLQQSGAELAKPGASVKMSCKASGYTFT | NYWMI | WVKQRPGQGLEWIG | YIDPTTDYTAYNQKFKD | KATVTADKSSSTAYMQLNSLTSEDSAVYYCAR | GGNVALDF | WGQGTSVTVSS | 43 |
| SC34.13 | QVQVQQSGAELARPGASVKLSCKASGYTFT | SYAIS | WVKQRTGQGLEWIG | EIYPGSGNTYVNGKFKG | KATLTTDKSSSTAYMQLSSLTSEDSAVYFCAR | VDDYGSWFPY | WGQGTLVTVSA | 47 |
| SC34.14 | EVQLQQSGPEMVKPGASVKISCKASGYIFT | DYYMH | WVKQSHGESLDWIG | RVNPKKGGTTVNQKFEG | KAILTVDKSSSTAYMDLNSLTSEDSAVVYCAM | GIYYSYDASFDY | WGQGTTLTVSS | 51 |
| SC34.16 | QVQLQQSGTELARPGASVKLSCKASEYTFT | SYAIT | WVRQRTGQGLEWIG | EIYPGSGNTYVNETFKG | KATLTSDKSSSTASMQLSSLTSEDSAVYFCAR | VHDYGSWFPY | WGQGTLVTVSA | 55 |
| SC34.18 | QVSLKESGGPGILQPSQTLSLTCSFSGFSLS | TSGMGVG | WIRQPSGKGLEWLA | NIWWDDSIYYNTALKS | RLTISKDTSKNQVFLKIASVDTADTATYSCAR | IESYYGNRAWFAY | WGQGTLVTVSA | 59 |
| SC34.19 | QVQLQQSGAELARPGASVKLSCKASGYTFT | SYAIT | WVKQRTGQGLEWIG | EIYPGSGNTFFNEKFKG | RATLTTDKSSSTAYMQLSSLTSEDSAVYFCAR | VHDYGSWFPY | WGQGTLVTVSA | 63 |
| SC34.20 | QVQLQQSGGSELARPGASVKLSCKASGYTFT | SYAIS | WVRQRTGQGLEWIG | EIYPESGNTDYNAQFKG | KATLTTDKSSSTAYMQLSSLTSEASAVYFCAR | VHDYGSWFPY | WGQGTLVTVSA | 67 |
| SC34.23 | EVQLQESGPSLVKPSQTLSLTCSVTGDSIT | SGSWN | WIRKFPGNKLEYMG | YINVSGGTYYNPSLKS | RISITRDTSKNHYYLQLNSVTTEDTATYYCGR | RLGSGGWFGY | WGQGTLVTVSA | 71 |
| SC34.24 | QVQLQQSGPELARPGASVKLSCKASEYTFT | SYAIT | WVKQRAGQGLEWIG | EIYPGSGDTYVNEKFKG | KATLTTDKSSSTAYMQLSSLTSEDSAVYFCAR | VHDYGSWFPY | WGQGTLVTVSA | 75 |
| SC34.25 | QVQLQQSGVELARPGASVKVSCKASGYTFT | SYAIS | WVKQRTGQGLEWIG | EIYPGSGETYVNEKFKG | KATLTTDKSSSTAYMHLSSLTSEDSAVYLCGR | VNDYGSWFPY | WGQGTLVTVSA | 79 |

FIG. 5B

Anti-DPEP3 Murine Antibody Heavy Chain Variable Region Amino Acid Sequences

| Name | FR1 | CDRH1 | FR2 | CDRH2 | FR3 | CDRH3 | FR4 | SEQ ID NO |
|---|---|---|---|---|---|---|---|---|
| SC34.26 | QVQLQQPGAELVKPGASVTLSCKASGYTFT | SYYIY | WVKQRPGEGLEWIG | EINPSNGGPNFNERFKN | KATLTVDKSSSTAYMQLSSLTSEDSAVYYCTR | GLLYYDYDRGFAY | WGQGTLVTVSA | 83 |
| SC34.27 | QVQLQQSGAELARPGASVKLSCKASGYTFR | SYGIN | WVKQRTGQGLEWIG | EIYPGRGDVYYNENFKG | KATLTTDKSSSTAYMQLSSLTSEDSAVFCAR | VHDYGSWFPY | WGQGTLVTVSA | 87 |
| SC34.28 | QVQLQQSGAELMKPGASVKISCKATGYTFS | SYWIE | WVKQRPGHGLEWIG | EILPGSGNTYYNERFKD | KATFTADTSSNTAYMQLSSLTSEDSAVYYCAR | RAAAYYSNPEWFAY | WGQGTLVTVSA | 91 |
| SC34.33 | QVQLQQSGAELMKPGASVKISCKATGYTFS | SYWIE | WVKQRPGHGLEWIG | EILPGSDKTYYNERFKD | KATFTADTSSNTAYMQLSSLTSEDSAVYYCTR | RAAAYYSNPEWFAY | WGQGTLVTVSA | 95 |
| SC34.36 | QVQLQQPGSVLVRPGASVKLSCKASGYTFT | SYWMH | WVKQRPGQGLEWIG | EISPTSGRPNYVNAKFKG | KATLTVDTSSSTAYVDLSSLTSEDSAVYYCAK | GEGYYGKAFDY | WGQGTTLTVSS | 99 |
| SC34.38 | QVQLQQPGAELVKPGASVTLSCKASGYTFT | SYYMY | WVKQRPGEGLEWIG | EINPSNGGANFNERFKN | KATLTVDKSSSTAYMQLSSLTSEDSAVFYCTR | GLLYYDYDRGFAY | WGQGTLVTVSA | 103 |
| SC34.39 | QVQLQQSGAELMKPGASVKISCKATGYTFS | NYWIE | WVKQRPGHGLEWIG | EILPGSDSTYFNEKFKG | KATFTADTSSNTAYMQLSSLTSEDSAVYYCTI | RSAAYYSNPEWFAY | WGQGTLVTVSA | 107 |
| SC34.40 | EVQLQESGPGLAKPSQTLSLTCSVTGYSIT | SDYWN | WIRKFPGNKLEYMG | YITYSGSTYYNPSLKS | RISITRDTSKNQYYLQLNSVTTEDTATYYCAR | ARVYYYDGRYGRAMDY | WGQGTSVTVSS | 111 |
| SC34.41 | EVKLVESGGGLVKPGGSLKLSCAASGFTFT | SYTMS | WVRQTPAKRLEWVA | TISTGGGNTYYPDIVKG | RFTISRDNARSTLYLQMSSLRSEDSAMYYCAR | RFYDGSYNYWYFDV | WGAGTTVTVSS | 115 |
| SC34.46 | QVQLQQSGTELARPGTSVKLSCKASGYTFR | SYAIS | WVRQRTGQGLEWIG | EIYPGSDKTYVNESLKG | KVTLTTDKCSSTANMQLTSLTSEDSAVVFCAR | VHDYGSWFPY | WGQGTLVTVSA | 119 |
| SC34.48 | EVQLQQSGLEMVKPGASVKISCKASGYIFT | DYYMH | WVKQSHGKSLDWIG | RVNPKKGGTTYNQKFEG | KATLTVDKSSSTAYMDLNSLTSEDSAVVYCAM | GIYFSYDASFDY | WGQGTTLTVSS | 123 |
| SC34.49 | EVQLQQSGPELVKPGSSVKISCKASGYIFT | DYHMN | WVKQSHGKSLEWIG | NINPYYGVSTYNQNLKG | TATLTVDKSSSTAYMELRGLTSEDSAVVYCVR | RAMDSPRFAY | WGQGTLVTVSA | 127 |
| SC34.50 | QVQLQQPGAELVRPGASVKLSCKASGYTFT | SYWIN | WVKQRPGQGLEWIG | NIFPSDSYTNVNQKFRD | KATLTVDKSSSTAYMQLSSPTSEDSAVVYCTI | RTYGNYFDY | WGQGTTLTVSS | 131 |
| SC34.53 | QVQLQQPGAELVKPGASVTLSCKASGYTFT | SYYIY | WVKQRPGEGLEWIG | EIDPSNGGPNFNDRFKN | KATLTVDKSSSTAYMQLSSLTSEDSAVYYCTR | GLLYYDYDRGFAY | WGQGTLVTVSA | 135 |

FIG. 5B Cont.

Anti-DPEP3 Murine Antibody Heavy Chain Variable Region Amino Acid Sequences

| Name | FR1 | CDRH1 | FR2 | CDRH2 | FR3 | CDRH3 | FR4 | SEQ ID NO |
|---|---|---|---|---|---|---|---|---|
| SC34.58 | QVQLQQSGAELARPGASVKLSCKASGYTFT | SYGVN | WVKQRTGQGLEWIG | EIYPGRGDVYYNDNFKG | KATLTTDKSSSTAYMQLSSLTSEDSAVYFCAR | VHDYGSWFPY | WGQGTLVTVSA | 139 |
| SC34.63 | QVQLQQSGVELARPGASVKLSCKASGYTFT | SYGID | WVKQRTGQGLEWIG | ETYPGRGDTYYNENFKG | KATLTTDKSSSTAFLQLSSLTSEDSAVYFCAR | VHDYGSWFPY | WGQGTLVTVSA | 143 |
| SC34.67 | QVQLQQSGAELARPGASVRLSCKASGYTFT | SYGIN | WVKQRTGQGLEWIG | EIYPGSGDSYYNKTFKG | KAILTTDKSSSTAYMQLSSLTPEDSAVYFCAR | VHDYGSWFPY | WGPGALVTVSA | 147 |
| SC34.71 | QVSLKESGPGILQPSQTLSLTCSFFGFSLS | TSSMGVG | WIRQPSGKGLEWLA | NIWWDNNKYYNAALKS | RLTISKDTSKNQVFLNIASVDTTDTATYYCAR | IESYYSNRAWFPY | WGRGTLVTVSA | 151 |
| SC34.76 | QVQLQQSGAELARPGASVKLSCKASGYTFT | SYAIN | WVKQRTGQGLEWIG | EVVPGSGNTYYNEKFKG | KAILTTDKSSSTGYMQLSNLTSEDSAVYFCAR | VHDYGSWFPY | WGQGTLVTVSA | 155 |
| SC34.78 | DVQLQESGRGLVKPSQSLSLTCTVTGYSLT | SDFAWN | WIRQFPGNKLEWMG | YIRYSGTTSYNPSLKS | RISITRDTSKNQFFLQLNSVTTEDTATYYCGY | GNYGYAMDY | WGQGTSVTVSS | 159 |
| SC34.83 | QVQLVKPGASVKLVKPGASVKISCKASGYAFS | HSWWN | WVKQRPGKGLEWIG | RIYPGDGDINYNGKFKG | KATLTADKSSSTAYMQLSSLTSEDSAVYFCAR | RGPSYNNYCFDY | WGQGTTLTVSS | 163 |
| SC34.86 | QVQLQQSGAELARPGASVKLSCKASGYTFT | SYTIT | WVKQRTGQGLEWIG | EIYPGSGNTYYNEKFKG | KATLTTDKSSSTAYMQLSSLTSEDSAVYFCAR | VHDYGSWFPY | WGQGTLVTVSA | 167 |
| SC34.87 | QVQLQQSGAELAKPGASVKMSCKASGYTFT | SYWML | WVKQRPGQGLEWIG | YIDPRNGYTEVNQKFKD | KATLTADKSSSTAYMQLSSLTSEDSAVYYCTR | GGNVAMDY | WGQGTSVTVSS | 171 |
| SC34.89 | QVQLQQSGAELARPGASVKLSCKASGYTFT | SYAIS | WVKQRTRQGLEWIG | EIYPGSGDIHYSGKFKG | KASLTTDKSSSTAYMQLSSLTSEDSAVYFCAR | VHDYGSWFPY | WGQGTLVTVSA | 175 |
| SC34.90 | QVQLQQSGAELMKPGASVKISCKATGYFS | YYWIE | WVKQRPGHGLEWIG | EILPGSDTTYYNEKFKG | KATFTADTSSNTAYMQLSSLTSEDSAVYYCTI | RRAAYYSNPEWFAY | WGQGTLVTVSA | 179 |
| SC34.91 | QVQLQQSGAELARPGASVKLSCKASGYTFR | SYAIS | WVKQRTGQGLEWIG | EIYPGSGDTYYNENFKG | KATLTTDKSSSTAYMQLSSLTSEDSAVYFCAR | VHDNGSWFPY | WGQGTLVTVSA | 183 |
| SC34.95 | QVQVKQSGAELARPGASVKLSCKASGYTFT | SYAIN | WLKQRTGQGLEWIG | EIYPGSGNTYYNESFKN | KATLTTDKSSTTAYMQLNSLTSEDSAVYFCAR | VHDYGSWFPY | WGQGTLVTVSA | 187 |

FIG. 5B Cont.

Anti-DPEP3 Humanized Antibody Heavy Chain Variable Region Amino Acid Sequences

| Name | FR1 | CDRH1 | FR2 | CDRH2 | FR3 | CDRH3 | FR4 | SEQ ID NO |
|---|---|---|---|---|---|---|---|---|
| hSC34.2 | EVQLVQSGAEVKKPGESLKISCKGSGYSFT | DYYIN | WVRQMPGKGLEWMG | WTYPGSGPTKYNGKFRG | QVTISADKSISTAYLQWSSLKASDTAMYYCAR | RGIYYDGIYPNYFDY | WGQGTTVTVSS | 191 |
| hSC34.11 | EVQLVQSGAEVKKPGESLKISCKGSGYSFT | NYWMI | WVRQMPGKGLEWMG | YIDPTTDYTAYNQKFKD | QVTISADKSISTAYLQWSSLKASDTAMYYCAR | GGNVALDF | WGQGTLVTVSS | 195 |
| hSC34.14 | QVQLVQSGAEVKKPGASVKVSCKASGYTFT | DYYMH | WVRQAPGQRLEWMG | RVNPKKGGTTVNQKFEG | RVTITRDTSASTAYMELSSLRSEDTAVYYCAM | GIYYSYDASFDY | WGQGTLVTVSS | 199 |
| hSC34.25 | QVQLVQSGAEVKKPGASVKVSCKASGYTFT | SYAIS | WVRQAPGQRLEWMG | EIYPGSGETYYNEKFKG | RVTITRDTSASTAYMELSSLRSEDTAVYYCAR | VNDYGSWFPY | WGQGTLVTVSS | 203 |
| hSC34.28 | QVQLVQSGAEVKKPGSSVKVSCKASGGTFS | SYWIE | WVRQAPGQGLEWMG | EILPGSGNTYYNERFKD | RVTITADESTSTAYMELSSLRSEDTAVYYCAR | RAAAYYSNPEWFAV | WGQGTLVTVSS | 207 |
| hSC34.38 | EVQLVQSGAEVKKPGESLKISCKGSGYSFT | SYMMY | WVRQMPGKGLEWMG | EINPSNGGANFNERFKN | QVTISADKSISTAYLQWSSLKASDTAMYYCTR | GLLYYDYDRGFAY | WGQGTLVTVSS | 211 |
| hSC34.87 | QVQLVQSGAEVKKPGASVKVSCKASGYTFT | SYWML | WVRQAPGQRLEWMG | YIDPRNGYTEYNQKFKD | RVTITRDTSASTAYMELSSLRSEDTAVYYCAR | GGNVAMDY | WGQGTLVTVSS | 215 |

FIG. 5B Cont.

Anti-DPEP3 Murine Antibody Variable Region Nucleic Acid Sequences

| Name | Chain | Nucleic Acid Sequence | SEQ ID NO |
|---|---|---|---|
| SC34.2 | Light Chain | GATATCCAGATGACACAGACTGCATCCTCCCTGTCTGCCTCTGTAGGAGACAGAGTCACCATCAGTTGCAGTGCAAGTCAGGGCATTAGCAGTGCATTAGCCAATTATTAAACTGGTATCAGCAGAAACCAGATGG AACTGTTAAACCTCCTGATCTATTACACATCAGTTTACACTGGAGTCCCATCAAGGTTCAGTGGCAGTGGGTCTGGGACAGATTATTCTCTCACCATCAGCAACCTGAACCTGAAGATATTG CCACTTACTATTGTCAGCAGTATAGTAAACTTCCGTGGACGTTCGGTGGAGGCACCAAGCTGGAAATCAAA | 20 |
| SC34.2 | Heavy Chain | CAGATCCAGCTGCAGCAGTCTGGACCTGAGCTGGTGAAGCCTGGGGCTTCAGTGAAGATATCTGCAAGGCTTCTGGCTACACCTTCACTGACTACTATATAAATTGGTTGAAGCAGAGGCCTGG ACAGGGACTTGAGTGGATTGGATGGATTTATCCTGGAAGCGGTCCTACTAAGTACAATGGGAAGTTCAAGGGCAAGGCCACATTGACTGTAGACACATCCTCCAGCACAGTCTACATGCAGCTCA GCAGCCTGACCTCTGAGGACTCTGCGGTCTATTTCTGTGCAAGACGGGGGATTTATTACTACGATGTATCTACCCAAATTACTTTGACTACTGGGGCCAAGGCACCACTCTCACAGTCTCCTCA | 22 |
| SC34.4 | Light Chain | GACATTGTGATGTCACAGTCTCCATCCTCCCTAACTGTGTCAGTTGGAGAGAAGGTTACTATGAGCTGCAAGTCCAGTCAGAGCCTTTTATATAGTCGCAATCAAAAGAACTACTTGGCTGGTA CCAGCAGAAACCAGGGCAGTCTCCTAAACTGCTGATTTACTGGGCATCCACTAGGGACTCTGGGGTCCCTGATCGCTTCACAGGCAGTGGATCTGGGACAGATTTCTCTCACCATCAGCAGTG TGAAAACTGAAGACCTGGCAGTTTATTACTGTCACCAACATTATAGGTATCCGTCACATTCGGTGCTGGGACCAAGCTGGAGCTGAAA | 24 |
| SC34.4 | Heavy Chain | CAGGTTCAGCTGCAGCAGTCTGGAGCTGAACTGGCAGGCCCAGGGGCCTCAGTGAAGCTGTCCTGTAAGGCTTCTGGATACACCTTCACAAGCTATGGTATAAACTGGGTGAAACAGAGAACTGG ACAGGGCCTTGAGTGATTGGAGAGATTTATCCTGGAAGTGGAAATATTTACTACAATGAGAAGTTTAAGGGCAAGGCCATACTACTGACTGTAGACAAATCCTCCAACAGCCTACTACGCAGCTCA GCAGCCTGACACTGAAGACTCTGAAGACTGCAGTCTATTTCTGTGCAAGAGTCCATATTACGGTTCCTTACTACTGGGCCCAAGGGACTCTGGTCACTGTCTCTGCA | 26 |
| SC34.5 | Light Chain | GACATTGTGATGACACAGTTTCCATCCTCCCTGGCTATGTCAGTGCAGGTCACTATGAACTGCAAGTCCAGTCAGAGCCTTTTAAATAGTAGTAATCAAAAGAACTATTTGGCCTGGTT CCAGCAGAAACCAGGACAGTCTCCTAAACTTCTGGTATACTTTGCATCCACTAGGGAATCCGGGGTCCCTGATCGCTTCATTGGCAGTGGATCTGGGACAGATTTCACTCTTACCATCAGCAGTG TGCAGGCTGAAGACCTGGCAGATTACTTCTGTCAGCAAGAATATAGCACTCCATTCACGTTCGGCTCGGGGACAAAATTGGAAATAAAA | 28 |
| SC34.5 | Heavy Chain | GAGGTCCAGCTGCAACAGTCTGGACCTGAGCTGGTGAAGCCTGGAGCTTCAATGAAGATATCTGCAAGGCTTCTGGTTACTCACTGGCTACACCATGAATTGGGTGAAGCAGAGCCATGG AAAGAACCTTGAGTGGATTGGACTTATTTATCCTTACAATGATGATCTTACTTACAATGAGAAGTTCAAGGGCAAGGCCACATTAACTGTAGACAAGTCATCCAGCACAGCCTACATGGAGCTCC TCAGTCTGACATCTGAGGACTCTGCAGTCTATTACTGTGCAAGAGGGTACTACGGTAGTACCTACGGGGCAGGGACAACGGTCACCGTCTCCTCA | 30 |
| SC34.6 | Light Chain | GACATTGTGATGACACAGTCTCCATCCTCCCTGGCTGTGTCAGTAGGAGACAGAGATATCACTGAACTGCAAGTCCAGTCAGAGCCTTTTATACAATCAAAAGAACTATTTGGCCTGGTACCAGCA GAAACCAGGACAGTCTCCTAAACTTCTGGATATCCTGGATCGCTTCACAGGCAGTGGATCTGGGACAGATTTCACTCTTACCATCAGCAATGTGCAGG CTGAAGACCTGGCAGATTACTTCTGTCAGCAACATTATACCACTCCATTCACGTTCGGCTCGGGGACAAAATTGGAAATTAAA | 32 |
| SC34.6 | Heavy Chain | GAGGTCCAGCTGCAACAGTCTGGACCTGAGCTGGTGAAGCCTGGAGCTTCAATGAAGACTTCATTCATTCACTGGCTACACCATGAATTGGGTGAAGCAGAGCCATGG AAAGAACCTTGAGTGGATTGGACTTATTTATCCTTACAATGATGATCTTACTTATACAACCGGAAGTTCAAGGGCAAGGCCACATTAACTGTAGACAAGTCATCCAACAGCCTACATGGAGCTCC TCAGTCTGACATCTGTGACATCTGCAGTCTGTTACTGTGCAAGAGGGTCCATTCTTCACTGCCGATGTCTGGGGTGCAGGGACCAACGGTCACCGTCTCCTCA | 34 |

FIG. 5C

Anti-DPEP3 Murine Antibody Variable Region Nucleic Acid Sequences

| Name | Chain | Nucleic Acid Sequence | SEQ ID NO |
|---|---|---|---|
| SC34.7 | Light Chain | GACATTGTGATGTCTCAGTCTCCATCCTCCCTAGCTGTGTCAGTTGGAGAGAAGGTTACTATGAGCTGCAAGTCCAGTCAGAGCCTTTTATATAGTCGCTATCAAAAGAACTACCTGGCTGGTA CCAGCAGAAACCAGGACAGTCTCCTAAACTGCTGATTTACTGGGCATCCACTAGGGAATCTGGGGTCCCTGATCGCTTCACAGGCAGTGGATCTGGGACAGATTTCACTCTCACCATCAGCAGTG TGAAGGCTGAAGACCTGGCAGTTTATTACTGTCAGCAATATTATAGGTATCCGCTCACGTTCGGTGCTGGGACCAAGCTGGAACTGAAA | 36 |
| SC34.7 | Heavy Chain | CAGGTTCAGGTGCAGCAGTCTGGAGCTGAATTGGCGAGGCCAGGGGCTTCAGTGAAGCTGTCCTGCAAGGCCTCTGGATACACCTTCACAAGCTATGGCATAAACTGGGTGAAGCAGAGAACTGG ACAGGGCCTTGAGTGGATTGGAGAGATTTATCCTGGAAGTGGTAACGCTTTACTATGAGAAGTTCAAGGGCAAGGCCACACTGACTGCAGACAAATCTTCCTCCAGCACAGCCTACATGCAGCTCA TCAACCTGACATCTGAGGATTCTGCAGTCTATTTCTGTGCAAGGGTCCATGATTACGGTTCCTTCTTTGGAGGGCTGGGCCAAGGGACTCTGGTCACTGTCTGCA | 38 |
| SC34.11 | Light Chain | GACATTGTGATGTCACAGTCTCCATCCTCCCTGGCTGTGTCAGCAGGAGAGAAGGTCACTATGAGCTGCAAATCCAGTCAGAGTCTGCTCAACAGTAGAACCCGAAAGAACTACTTGGCTTGGTA CCAGCAGAAGCCAGGACAGTCTCCTAAACTGCTGATCTACTGGGCATCCACTCGGGAATCTGGGGTCCCTGATCGCTTCACAGGCAGTGGATCTGGGACAGATTTCACTCTCACCATCAGCAGTG TGCAGGCTGAAGACCTGGCAGTTTATTACTGCAAGGAATCTTTATAATCTCTGGACTTTCGGTGGAGGCACCAAGCTGGAAATCAAA | 40 |
| SC34.11 | Heavy Chain | CAGGTCCAGCTTCAGCAGTCTGGGGCTGAACTGGCAAAACCTGGGGCTTCAGTGAAGATGTCCTGCAAGGCTTCTGGATACACATTTACTACCTTTACTACACTTTACTAATTATGGATGATCTGGGTAAACAGAGGCCTGG AACAGGCTGGAATGGATTGGATACATTGATCCCACCACTGACTATACTGCGTACAATGCAGAAGTTCAAGGACAAGGCCACAGTGACTGCAGACAAATCCTCCAGCACAGCCTACATGCAACTGA ACAGCCTGACATCTGAGGACTCTGCAGTCTATTTCTGTGCAAGAGGGGGAATGTGGCTTTGACTTTTTGGGGTCAAGGAACCTCAGTCACCGTCTCCTCA | 42 |
| SC34.13 | Light Chain | GACATTGTGATGTCACAGTCTCCATCCTCCCTAGCTGTGTCAGTTGGAGAGAAGGTTACTATGAGCTGCAAGTCCAGTCAGAGCCTTTTATATAGTAGGTATCAAAAGAACTATTTGGCCTGGTA CCAGCAGAAACCAGGGGCAGTCTCCTAGACTGGTAGTTTATTATTGTCAGCAATATTATAGGTATCCGCTCACGTTCGGTTCTGGGACCAAGCTGGAGCTGAAA | 44 |
| SC34.13 | Heavy Chain | CAGGTTCAGGTGCAGCAGTCTGGAGCTGAGCTGGTGAGGCCAGGGGCTTCAGTGAAGCTGTCCTGCAAGGCTTCTGGATACACCTTCACAAAGCTATGATATAAGCTGGGTGAAGCAGAGAACTGG ACAGGGCCTTGAGTGGATTGGAGAGATTTATCCTGGAAGTGGTAATACTACTACAATGGGAAGTTCAAGGGCAAGGCCACAGTGACTACAGACAAATCCTCCAGCACAGCCTACATGCAGCTCA GCAGCCTGACATCTGAGGACTCTGCAGTCTATTTCTGTGCAAGAGTCGATGATTACGGTTCCTTCTTTATTGGGCCAAGGGACTCTGGTCACTGTCTGCA | 46 |
| SC34.14 | Light Chain | GACATCCAGATGACTCAGGCTCCAGCCTCCCTATCTCATCTGTGGGAGCAACTGTCACCATCACATGTCGAACAAGTGAACAATATTACAGTTATTTAGCATGTATCAGCAGAAACAGGGAAA ATCTCCTGGTTATTGGTCTATAATGCAAAAACCTTAGCAGAAGGTGTCATCAAGGTTCAGTGCAGTGGATCAGGCACAGATTATTCTCTGCAGATCAACAGCCTGCAGCCTGAAGATTTTG GAAATTATTACTGTCAACATCATTATGATACTCCGTACACGTTCGGAGGGGGGACCAAGCTGGAAATAAAA | 48 |
| SC34.14 | Heavy Chain | GAGGTCCAACTGCAGCAGTCTGGACCTGAGCTGGTGAAGCCTGGGGCTTCAGTGAAGATATCCTGCAAGGCTTCTGGATACATATTCACTGACTACTACATGCACTGGGTGAAGCAGAGCCATGG AGAGAGCCTTGACTGGATTGGACGTGTTAATCCTACAACCAGAAGTTCGAGGGCAAGGCATATTGACTGTTGACAAGTCCTCCAGCACAGCCTACATGGACCTCA ACAGCCTGACATCTGAGGACTCTGCGGTCTATTACTGTGCAATGGGTATCTACTATAGTTACGACGCCTCCTTTGACTACTGGGGCCAAGGCACCACTCTCACAGTCTCCTCA | 50 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.16 | Light Chain | GACATTGTGATGTCACAGTCTCCATCCTCCCTAGCTGTGTCAGTTGGAGAGAAGGTTACTATGAGCTGCAAGTCCAGTCAGAGCCTTTTATATAGTAGATATCAAAGAATTACCTGGCTGGTACCAGCAGAAACCAGGGCAGTCTCCTAAACTGCTGATTTACTGGGCATCCACTCGGGAATCTGGGGTCCCTGATCGCTTCACAGGCAGTGGATCTGGGACAGATTTCACTCTCACCATCAGCAGTGTGAAGGCTGAAGACCTGGCAGATTATTACTGTCAGCAATATTATAGGTATCCACTCACGTTCGGTGCTGGGACCAAGCTGGAGCTGAAA | 52 |
| SC34.16 | Heavy Chain | CAGGTTCAGCTGCAGCAGTCTGGAACTGAGCTGGCGAGGCCAGGGGCTTCAGTGAAGCTGTCCTGCAAGGCTTCTGGATACACCTTCACAAGCTATGCTATAACCTGGGTGAGGCAGAGAACTGGACAGGGCCTTGAGTGGATTGGAGAGATTTATCCCGGAAGTGGTAATACTAACAATGAGACTTTCAAGGGCAAGGCCACACTGACTTCAGACACAATCTCCAGCACAGCCTCCATGCAGCTCAGCAGCCTGACATCTGAGGACTCTGCAGTCTATTTCTGTGCAAGAGTCCATGATTACGATTACGGTTCCTGGTTTGCTTACTGGGGCCAAGGGACTCTGGTCACTGTCTCTGCA | 54 |
| SC34.18 | Light Chain | GACATTGTGATGACCCAGTCTCAAAAATTCATGTCCACATCAGTAGGAGACAGGGTCAGTATCACCTGCAAGGCCAGTCAGAATGTTCGTACTGCTGTAGGCTGGTATCAACAGAAACAGGGCAGTCTCCTAAAACACTGATTTACTTGGCATCCAACCGGCACACTGGAGTCTCTGATCGCTTCACAGGCAGTGGATCTGGGACAGATTTCACTCTCACCATTAGTAGTGTGCAATCTGAAGACCTGGCAGATTATTTCTGTCTGCAACATTGGAATTATCCGTGGACGTTCGGTGGAGGCACCAAGCTGGAAATCAAA | 56 |
| SC34.18 | Heavy Chain | CAGGTTTCTCTGAAAGAGTCGGGCCTGGGATATTGCAGCCCTCAGTGACTTGTTCTTTCTCTGGGTTCACTGAGCACTCTGGTATGGGTAGGCTGATTGTCAGCCTTCAGGGAAGGGTCTGGAGTGGCTGGCCAACATTTGGTGGGATGATAGTATTACTATAACAGACGCCCTGAAGAGTCGGCTCACAATCTCCAAGAATACCTCCAAAACCAGGTCTTCCTCAAGATCGCCAGTGTGGACACTGCAGATACTGCCACATACTCCTGTGCTGCAGATAGAATCCTACTATGGTTACTGGGGCCAAGGGACTCTGGTCACTGTCTCTGCA | 58 |
| SC34.19 | Light Chain | GACATTGTGATGTCACAGTCTCCTTCCGCCCTAGCTGTGTCAGTTGGAGAGAAGATTACTATGAGCTGCAAGTGTAGTCAGAGCCTCTTACATAGTAGTGGATCGGATCAAAAGAACTACCTGGCCTGGTATCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTTCACTCTCACCATCAACAACTGTGAAGGCTGAAGACCTGGCAGATTATTACTGTCAGCAGTATTATTCTCAGATTCCGCTCACGTTCGGTGCTGGGACCAAGCTGGAGCTGAAA | 60 |
| SC34.19 | Heavy Chain | CAGGTTCAGCTGCAGCAGTCTGGAGCTGAGCTGGCGAGGCCAGGGGCTTCAGTGAAGCTGTCCTGCAAGGCTTCTGGATACACCTTCACAAGCTATGCTATAACCTGGGTGAAGCAGAGAACTGGACAGGGCCTTGAGTGGATTGGAGAGATTTATCCTTCAATGAGAAGTTCAAGGGCAGGGCCACACTGACTACAGACAAATCTCCAGCACAGCCTACATGCAGCTCAGCAGCCTGACATCTGAAGACTCTGCAGTCTATTTCTGTGTCCTAGAGTCCATGATTACGTTCTGTGTGCTGCAGATACTGGGGCCAAGGGACCACGGTCACCGTCTCCTCA | 62 |
| SC34.20 | Light Chain | GACATTGTGATGTCACAGTCTCACATCCTCCCTAACTGTGTCAGTTGGAGAGAAGGTTACTATGAGCTGCAAGTCCAGTCAGAGCCTTTTTATATAGTAGTACCTATCAAAGAACTACCTGGCCTGGTTCCAGCAGAAACCAGGGCAGTCTCCTAAACTGCTGATCTACTGGGCATCCACTAGGGAATCTGGGGTCCCTGATCGCTTCACAGGCAGTGGATCTGGGACAGATTTGGGACAGATTTCACTCTCACCATCAGCAGTGTGAAGGCTGAAGACCTGGCAGATTATTACTGTCAGAATGATTATAGTTATCCCTCACGTTCGGTGCTGGGACCAAGCTGGAAGCTGAAA | 64 |
| SC34.20 | Heavy Chain | CAGGTTCAGCTGCAGCAGTCTGGGCCTGAGCTGGCAAGGCCTGGGGCTTCAGTGAAGCTGTCCTGCAAGGCTTCTGGATACACCTTCTCAGAAGCTATGCTATAAGCTGGGTGAGGCAGAGAACTGGACAGGGCCTTGAGTGGATTGGAGAGATTATCCCAGAGCCACTGGATACCACTGGCACTGGCGAGTCCACGTTCAAGGGCAAGGCCACAGTCACTGACTACAGACACAATCTCCAGCACAGCCTACATGCAGCTCAGCAGCCTGACATCTGAAGACTCTGCAGTCTATTCTGTGCAAGAGTCCATGATTACGATTACAGCTTCCTTTCCTTACTGGGCCAAGGGACTCTGGTCACTGTCTCTGCA | 66 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.23 | Light Chain | CAAATTGTTCTCACCCAGTCTCCAGCAATCATGTCTGCATCTCTAGGGGAGGAGATCACCCTAACCTGCAGTGCCAGTCGAGTGTAAGTTACATGCACTGGTACCAGCAGAAGTCCGGCACTTCTCCCAAACTCTTGATTTATAGCACTTCCAAACTGGCTTCTGGAGTCCCTTCTCGCTTCAGTGGCAGTGGGTCTGGGACCTTTATTCTCTCACAATCAACACTGTGGAGGCTGAAGATGCTGCCGATTATTACTGCCATCAGTGAAGTAGTTGGACGTTCGGTGGAGGCACCAAGCTGGAAATCAAA | 68 |
| SC34.23 | Heavy Chain | GAGGTGCAGCTTCAGGAGTCAGGACCTAGCCTCGTGAAACCTTCTCAGACTCTCCTCCCTCACCTGTTCTGTCACCAGTGGTTCCTGGAACTGGATCCGGAAATTCCCAGGGAATAAACTTGAGTACATGGGATACATAAACTACATGTGTGCCACTTACTACAATCCATCTCTCAAAAGTCGAGACACATCCAAGAACCACTACTACCTGCAGTTGAATTCTGTGACTACTGAAGGACACAGCACCACATATTACTGTGAAGACAGCTGGGATGCGGGGGCTGGTTTGGTTTACTGGGGCCAAGGGACTCTGGTCACTGTCTCTGCA | 70 |
| SC34.24 | Light Chain | GACATTGTGATGTCACAGTCTCCATCCTCCCTAGCTGTGTCAGTTGGAGAGAAGGTTACTATGAACTGCAAGTCCAGTCAGAGCCTTTTATATAGTAGATATCAAAAGAACTACCTGGCCTGGTACCAGCAGAAACCAGGACAGTCTCCTAAACTGCTGATTTACTGGGCATCCACTAGGGAATCTGGGGTCCCTGATCGCTTCACAGGCAGTGGGTCTGGGACAGATTTCACTCTCACCATCAGCAGTGTGAAGGCTGAAGACCTGGCAGTTTATTACTGTCAGCAGTTTATTAGGTATCCGCTCACGTTCGGTGCTGGGACCAAGCTGGAGCTGAAA | 72 |
| SC34.24 | Heavy Chain | CAGGTTCAGCTGCAGCAGTCTGGACCTGAGCTGGTGAAGCCTGGGGCTTCAGTGAAGATATCTGCAAGGCTTCTGAATACACCTTCACAAGCTATGCTATAACCTGGGTGAAGCAGAGAGCTGGACAGGGCCTTGAGTGGATTGGAGAGATTTATCCTGGAAGTGGTGATACTTACTACAATGAGAAGTTCAAGGGCAAGGCCACACTGACTACAGACAAATCCTCCAGCACAGCCTACATGCAGCTCAGCAGCCTGACATCTGAGGACTCTGCAGTCTATTTCTGTGCAAGAGTCCATGATTACGGTTCCGTTTCCTTACTGGGGCCAAGGGACTCTGGTCACTGTCTCTGCA | 74 |
| SC34.25 | Light Chain | GACATAGTGATGTCACAGTCTCCATCCTCCCTAGCTGTGTCAGTTGGAGACAGGGTCACTATGAGCTGCAAGTCCAGTGAATATCTGTACACTGTGCTCCTGATACTGAGCTGTGGTGAAGCTGCAGGAGAAGGTCACTATGAGCTGCAAGTCCAGTGAATATCTGTACACTGTAGCTCAGTGGATCTGGGATCTGGGACAGATTTCACTCTCACCATCAGTAGTGTGAAGGCTGAAGACCTGGCAGCTTATTACTGTCAGCAGTTTATTAGGTATATTAGGTATCCGCTCACGTTCGGTGCTGGGACCAAGCTGGAGCTGAAA | 76 |
| SC34.25 | Heavy Chain | CAGGTGCAGCTGCAGCAGTCTGGAGTTGAGCTGGCGAGGCCAGGGGCTTCAGTGAAGCTGTCCTGCAAGGCTTCTGGATACACCTTCACAAGCTATGCTATAAGCTGGTGAAGCAGAGGAACTGGACAGGGCCTTGAGTGGATTATCCTGGAAGTGGTGAAACTTACTACAATGAGAAGTTCAAGGGCAAGGCCACACTGACTACAGACAAATCATCCAGTACAGCCTACATGCAGCTCAGCAGCCTGACATCTGAGGACTCTGCGGTCTATTACTGTGCAAGAGTCCTGCTCACGTTCGGTGCTGGGACCAAGCTGGAGCTGAAA | 78 |
| SC34.26 | Light Chain | GATGTTGTGCTGACCCAGACTCCACTCACTTTGTCGGTTACCATTGGACAACCAGCCTCTATCTCTTGCAAGTCAAGTCAGAGCCTCTTATATAGTAATAGAAGAACCTATTTGAATTGGTTATTACAGAGGCCAGGCCAGTCTCCAAAGCGCCTAATCTATCTGGTGTCTAAACTGGACTCTGGAGTCCCTGACAGGTTCAGTGGCAGTGGATCGGGACACAGATTTCACTGAACTGATCAGCAGAGATTTACACTGAAAATCAGCAGGGTGGAGGCTGAGGATCTGGGAGTTTATTACTGCTGGCAAGGTACACATTTTCCGTACACGTTCGGTGCCAAGGGACCAAGCTGGAAATCAAA | 80 |
| SC34.26 | Heavy Chain | CAGGTCCAACTGCAGCAGCCTGGGCTGAACTGGTGAAGCCTGGGGCTTCAGTGAAGGTCTCCTGCTACACCTTCACCAGCTACTATATCTACTGGGTGAAGCAGAGGCCTGGAGAAGGCCTTGAGTGGATTGGAGAGATTAATCCTAGCAATGGTCTTAACTTCAATGAGAAGTTCAAGAGCAAGGCCACACTGACTGTTGACAAATCCTCCAGCACAGCCTACATGCAACTCAGCAGCCTGACATCTGAGGACTCTGCGGTCTACTTCTGTACAAGAGGGGTTGCTTACTGGGGCCAAGGGACTCTGGTCACTGTCTCTGCA | 82 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.27 | Light Chain | GACATTGTGATGTCTCAGTCTCCATCCTCCCTAGCTGTGTCAGTTGGAGAGAAGGTTACTATGAGCTCAAGTCCAGTCAGAGCCTTTTATATAGTCGCAATCAAAAGAACTACCTGGCCTGGTACCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTTCACTCTCACCATTCAACAGTGTGAAGGCTGAAGACCTGGCAGTTTATTACTGTCACCAATATTATAGGTATCCGCTCACGTTCGGTGCTGGGACCAAGCTGGAACTGAAA | 84 |
| SC34.27 | Heavy Chain | CAGGTTCAGCTGCAGCAGTCTGGAGCTGAGCTGGCGAGGCCAGGGGCTTCAGTGAAGTTGTCTGCAAGGCTTCTGGATACACCTTCAGAAGTTATGGTATAAACTGGGTGAAGCAGAGAACTGGACAGGGCCTTGAGTGGATTGGAGAGATTTATCCTGGAAGAGGTGATGTTTACTACAATGAGAATTTCAAGGGCAAGGCCACACTGACTACAGACAAATCCTCCAGCACAGCCTACATGCAGCTCAGCAGCCTGACATCTGAGGACTCTGCAGTCTATTTCTGTGCAAGAGTCCATGATTACGGTTCCTGTTTTCCTTACTGGGGCCAAGGGACTCTGGTCACTGTCTCTGCA | 86 |
| SC34.28 | Light Chain | CAAATTGTTCTCACCCAGTCTCCAGCAATCATGTCTGCATCTCTAGGGGAACGGTCACCATGACCTGCAGCTCAAGTGTAAATTCCTTTTACTTGCACTGGTACCAGCAGAAGCCAGGATCCTCCCCAAACTCTGGATTCATAGCACATCCAACCTGGCTTCTGGAGTCCCTGGTTCGCTTCAGTGGCAGTGGGTCTGGGACCTCTTACTCTCTCACAATCAGCAGCATGGAGGCTGAAGATGCTGCCACTTATTACTGCCACCAGTATCGTTCCCCGTACACGTTCGGAGGGGGGACCAAGCTGGAAATAAAA | 88 |
| SC34.28 | Heavy Chain | CAGGTTCAGCTGCAGCAGTCTGGAGCTGAGCTGGTGAGGCCTGGGGCCTCAGTGAAGCTGTCCTGCAAGGCTACTGGCTACACATTCAGTAGCTACTGGATGAACTGGGTAAAGCAGAGGCCTGGACAGGGTCTTGAGTGGATTGGAAGGATTGATCCTAATGAATGGAAGTTACTACAATGAGAATTTCAAGAACAAGGCCACATTCACTGCAGATACATCTCCAACACAGCCTACATGCAACTCAGCAGCCTGACATCTGAAGACTCTGCCGTCTATTACTGTGCCAGGGACCGCTCCTATAGTAGTTACTTTGCTTACTGGGGCCAAGGGACTCTGGTCACTGTCTCTGCA | 90 |
| SC34.33 | Light Chain | CAAATTGTTCTCACCCAGTCTCCAGCAATCATGTCTGCATCTCTAGGGGAACGGTCACCATGTCGCATCTCTGATTCATAGACATCATCCAACCTGGCTTCTGGAGTCCCTGAGTTCTGCAGTGGGTCTGGGACCTCTTACTCTCTCACAATCAGCAGCATGGAGGCTGAAGATGCTGCCACTTATTACTGCCACCAGTATCATCGTTCCCCGTACACGTTCGGAGGGGGGACCAAGCTGGAAATAAAA | 92 |
| SC34.33 | Heavy Chain | CAGGTTCAGCTGCAGCAGTCTGGAGCTGAGCTGGTGAGGCCTGGGGCCTCAGTGAAGATATCCTCAGTGAAGGCTCTGGCTACACATTCAGTAGCTACTGGATGAACTGGGTAAAGCAGAGGCCTGGACAGGGTCTTGAGTGGATTGGAGAGATTTTACCTGGAAGTGATAAAACTTACTACAATGAGAAGTTCAAGGACAAGGCCACATTCACTGCAGATACATCTCCAACAACAGCCTACATGCAACTCAGCGAGCCTGACATCTGAAGACTCTGCCGTCTATTACTGTACAAGAAAGGGGCGCTCCTATAGTAGTAACCCCGAGTGGTTTGCTTACTGGGGCCAAGGGACTCTGGTCACTGTCTCTGCA | 94 |
| SC34.36 | Light Chain | GATATCCAGATGACACAGACTACATCCTCCCTGTCTGCTCTGTCTCTGGGAGACAGAGTCACCATCAGTTGCAGGGCAAGTCAGGACATTAGCAATTATTTAAACTGGTATCAGCAGAAACCAGATGGAACTGTTAAACTCCTGATCTACTACACATCAAGATTACACTGGAGTCCCATCAAGGTTCAGTGGCAGTGGGTCTGGAACAGATTATTCTCTCACCATTAGCAACCTGGAGCAAGGATGAAGATATTGCCACTTACTTTTGCCAACAGGGTAATACGCTTCCGTGGACGTTCGGTGGAGGCACCAAGCTGGAAATCAAA | 96 |
| SC34.36 | Heavy Chain | CAGGTCCAACTGCAGCAGCCTGGGGCTGAGCTGGTGAAGCCTGGGGCTTCAGTGAAGCTTGTCTGCACAGCTTCTGGCTACACCATTCACCAGCTACTGGATGCACTGGGTGAAGCAGAGGCCTGGACAAGGCCTTGAGTGGATTGGAGAGATTTCTCCTACTAGTGGTAGTACTAACTACAATGCGAAGTTCAAGGGCAAGGCCACACTGACTGTAGACACATCCTCCAGCACTGTGTACATGGAGCTCAGCAGCCTGACATCTGAGGACTCTGCGGTCTATTACTGTGCAAAAGGGAGGAGGCTACTACTGTGACTACTGGGGCCAAGGCACCACTCTCACAGTCTCCTCA | 98 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.38 | Light Chain | GATGTTGTGCTGACCCAGACTCCACTCACTTTGTCGGTTACCATTGGACAAACAGCCTCTCATCTCTTGCAGTCAAGTCAGAGCCTCTTATATAGTAATAGAAGAACCTATTTGAATTGGTTATT ACAGAGGCCAGGCCAGTCTCCAAAGCGCCTAATCTATCTGGTGTCTAAACTGGACTCTGGAGTCCCTGACAGGTTCACTGGCAGTGGATCGGGAACAGATTTTACACTGAAAATCAGCAGGGTGG AGGCTGAGGATTTTGGGAGTTTATTACTGCGTACAAGGTACACATTTTCCGTTCACGTTCGGTACTGGGACCAAGCTGGAGCTGAAA | 100 |
| SC34.38 | Heavy Chain | CAGGTCCAACTGCAGCAGCCTGGGGCTGAACTGGTGAAGCCTTGAAGGCTTCAGTGACATTGTCTTGGCTACACCTTCACCAGCTACTATATGTACTGGGTGAAGCAGAGGCCTGG AGAAGGCCTTGAGTGGATTGGAGAGATTAATCCTAGCAATGGTGTGCTAACTTCAATGAGAGATTCAAGAACAAGGCCACACTGACTGTTGACAAATCCTCCAGCACAGCCTACATGCAACTCA GCAGCCTGACATCTGAGGACTCTGCGGTCTTTACTGTACAAGAGGCTCTGCTTTACTGATTACGACAGGGGGTTGCTTACTGGGGCCAAGGGACTCTGGTCACTGTCTCTGCA | 102 |
| SC34.39 | Light Chain | CAAATTGTTCTCACCCAGTCTCCAGCAATCATGTCTGCATCTCAAGGGGAACGGGTCACCATGACCTGCAGTCTCCAGCTCAAGTGTAAGTTCCAATTACTTGCACTGGTACCAGCAGAAGCCAGG ATCCTCCCCCAAACTCTGGATTTATAGACATCCCACCTGGCTTCTGGAGTCCCTGCTCAGTGGCAGTGGGTCTGGGACCTCTTACTCTCTCACAATCAGCAGCATGGAGGCTGAAGATG CTGCCACCTATTACTGCCACCAGTATCATCGTTCCCCGTACACGTTCGGAGGGGGGACCAAGCTGGAAATCAAA | 104 |
| SC34.39 | Heavy Chain | CAGGTTCAACTGCAGCAGTCTGGAGCTGAGCTGATGAAGCCTGGGGCCTCAGTGAAGATATCCTGCAAGGCTACTGGCTACACATTCAGTAACTACTGGATAGAGTGGGTAAAGCAGAGGCCTGG ACATGGCCTTGAGTGGATTGGAGAGATTTTACCTGGAAGTGGTGATAGTACTTACTTGCTGAAAGTTCAAGGCAAGGGCCACATTCACTGCAGGCAAGGGCCACATACATCCTCCAACACAGCCTACATGCAACTCA GCAGCCTGACATCTGAGGACTCTGCCGTCTATTACTGTACAATAAGGTCGGCCGCTACTAGTAAGTAACCCCGAGTGGTTTGCTTACTGGGGCCAAGGGACTCTGGTCACTGTCTCTGCA | 106 |
| SC34.40 | Light Chain | GACATCCAGATGACTCAGTCTCCAGCCTCTCCAGCCTCTCTATCTGCATCTGTGGGAGAAAACTGTCACCATGACAAGTGTCACCATGACAAGTTCAGTGGCAGTGGGTCATCAAGGTTCAGTGGCATCATCAGCAGATGTTCAGCATGGAAGTGAATGCAAGGCACAAGTTCCTGAAGATCAACAGGGAAA ATCTCCAGGTCTGGTCTATGCTGCAACAAACTTAGCAGATGGTGCCATCAAGGTTCAGTGGCAGTGGATCGGGTGGGCAATCAACAGCCTGCAGCCTGAAGATTTTG GGAGTTATTACTGTCAACATTTATGGCTACCTCCGTGACGTTCGGTGAGGCCAAGCTGGAAATCAAA | 108 |
| SC34.40 | Heavy Chain | GAGGTGCAGCTTGCAGGAGTCAGGACCTCAGGGGCTCAGGGGTACATAACCTAGGTAGTTGCAAGTACATGCCACAACAGTCCAGATCTCGAAAGTCGAATCTCCAAAGTCGAATCTGGATCCGGAAATTCCCAGG GAATAAACTTGAGTACATGGGGCAGTACTAACCTACAGTGGTATAGTACTTACTACAATACATCTCCAAAGTCGAATCTGGAATCTCCAAAGAACACAGTCCTCCAAGAACCAGTATTACCTGCAGTTGAATT CTGTGACTACTGAGGACACAGCCACATATTACTGTGAAGAGGAGGGGTTTATTACTACGATGGTAGATACGGCCGCTATGGATACTGGGGTCAAGGAACCTCAGTCACCGTCTCCTCA | 110 |
| SC34.41 | Light Chain | GACATCCAGATGATTCAGTCTCCATCTCCATGTCTGCATCTGTCTGCAGTGGAGACAGAGTCAGTCAGTCTCTCTTGCCGCTCCATCTGCATCAGGGTAGTCAGGGCATTAGCACCTATTTAAATTGGTATCAGGCATTTAGCACCTATTTAAATTGGTATCAGCAGAAACCAGGTGG AACTATTTAAACTCCTGATCTACTCCACATCCAATTTAAATTCTGGTGTCCATCAAGGTTCAGTGGCAGTGGGTCTGGGTCAGATTATTCTCTCACCATCAGCAGCCTGAAGATCTCTCACCATCAGCAGCCTGAAGATTTTG CAGACTATTACTGTCTACAGCGTGATGCGTATCCGTACACGTTCGGAGGGGGGACCAAGCTGGAAATAAAA | 112 |
| SC34.41 | Heavy Chain | GAAGTGAAGCTGGTGGAGTCTGGGGGAGGCTTAGTGAAGCCTGGAGGGTCCTGAAACTCTCCTGTGCAGCCTCTGGATTCACTTTCACTAGCTATACCATGTCTTGGGTTCGTCAGACTCCGGC GAAGAGGCTGGAGTGGGTCGCAACATTAGTACTTGGTGGTGGTACTACTGGTCAACACCTATACCATGTCTTGGAAGTGAAGAAGCAGTCCAGGAGCCACCGTGATCCGTCGAGGAGCACCGTACCTCAGAGGACGCCGATTCACCATCTCCAGAGACAATGCCAAGAACACCCTGTACCTTCAAATGA GCAGCTGCAGCTGAGGTCTGAGGACTCGAGGACACGGCCATGTATTACTGTGCAAGACGATTCTACAACTACTGGTAGCTACAACTACTGTGATGTCGGGGAGCGCCAGGGACCACGGTCACCGTCTCCTCA | 114 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.46 | Light Chain | GACATTGTGATGTCACAGTCTCCATCCTCCCTAGCTGTGTCAGTTGGAGAGAAGGTTACTATGAGCTCAAGTCCAGTCAGAGCCTTTTATATAGTAGTAAATATCAAAAGAACTTCCTGGCTGGTA CCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTTCACTCTCACCATCAGCAATG TGAAGGCTGAAGACCTGGCAGTTTATTACTGTCAGCAGTTTATTAGGTATCCGCTCACGTTCGGTGCTGGGACCACGCTGGAGCTGAAA | 116 |
| SC34.46 | Heavy Chain | CAGGTTCAGCTGCAGCAGTCTGGAACTGAACTGGGCAGGACCTGGCGAGGCCAGGGACTTCAGTGAAGCTGTCCTGCAAGGCTTCTGGATACACCTTCAGAAGCTATGCTATAAGTTGGGTGAGACAGAGAACTGG ACAGGGCCTTGAGTGGATTGGAGAGATTTATCCTGGAAGTGATAAAACTTACTATAATGCAAGTCACCCTGACTACAGACAAATGTTCCAGCACAGCCAACATGCAGTCA CCAGCCTGACATCTGAGGACTCTGCAGTCTATTTCTGTGCAAGAGTCCATGATTACGGTTCGTGGTTTCCTTACTGGGGCCAAGGGACTCTGGTCACTGTCTCTGCA | 118 |
| SC34.48 | Light Chain | GACATCCAGATGACTCAGGCTCCAGCCTCCCTATCTGCATCTGTGGGAGAAACTGTCACCATCACATGTCGAACAAGTGGACATATTTACAGTTATTTAGCATGGTATCAGCAGAAACAGGGAAA ATCTCCTCAGTTATTGGTCTATAATGCAAAACCTTAGCAGAAGGTGTCATCAAGGTTCAGTGGCAGTGGATCAGGCACACAGTTTTCTCTGAAGATCACCAGCCTGCAGCCTGAAGATTTTG GAGATTATTACTGTCAACATCATTATGATACTCCGTACACGTTCGGAGGGGGGACCAAGCTGGAGATAAAA | 120 |
| SC34.48 | Heavy Chain | GAGGTCCAGCTGCAACAGTCTGGACTTGAGATGGTGAAGCCTGGGGCTTCAGTGAAGATATCCTGCAAGGCTTCTGGATACATATTCACTGACTACTACATGCACTGGGTGAAGCAGAGCCATGG AAAGAGCCTTGAGTGGATTGGACGTGTTAATCCTAAAAAAGGTGGTACTACCTACAACCAGAAGTTCAAGGGCAAGGCCACATTGACTGTTGACAAGTCCTCCAGCAAGTCTACATGGACCTCA ACAGCCTGACATCTGAGGACTCTGCGGTCTATTACTGCGCATATGACGCCTCCTTTGACTACTGGGGCCAAGGCACCACTCTCACAGTCTCTCA | 122 |
| SC34.49 | Light Chain | GACATCCAGATGACACAATCTTCATCCTCCTTTTCTGTATCTGTTGGAGAGCAGAGTCACCATTACTTGTCAAGGCAGTCAGAGTGAAAATTGGTTAGCCTGGTTTCAGCAGAAACCAGGAAA TCCTCCTAGGCTCTTAATATCTGGTGCAACCAGTTGGAAACTGGGGTCCCTTCAAGATTCAGTGGCAGTGGATCTGGAAAGGATTACACTCTCAGCATTACCAGTCTTCAGACTGAAGATATTG CTACTTATTATTCTGTCAACAGTATTGGAGTACTATATTCACGTTCGGCTCGGGGACAAAGTTGGAAATAAAA | 124 |
| SC34.49 | Heavy Chain | GAGGTCCAGCTGCAACAGTCTGGACCTGAGCTGGTGAAGCCTGGGTCTTCAGTGAAGATATCCTGTGAAGATACCATTCACTGACTACCACCATGAACTGGGTGAAGCAGAGCCATGG AAAGAGCCTTGAGTGGATTGGAAATATTAATCCTACTACGTGTACCTACAACCAGAACTTAAAGGGCACGGCCACATTACTGACTGTAGACAAGTCCTCCAGCACAGCCTACATGGAGCTCC GCGGCCTGACATCTGAGGACTCTGCAGTCTATTACTGTGCTATTACTGTAAGAAGGGCTATGGATTCCCCCCGGTTTGCTTACTGGGGCCAAGGGACTCTGGTCACTGTCTCTGCA | 126 |
| SC34.50 | Light Chain | GACATCCAGATGACACAATCTTCATCCTCCTTTTCTGTATCTCTAGGAGACAGAGTCACCATTACTTGCAAGGCAAGTGAGGACATATATAATGCGGTTAGCCTGGTATCAGCAGAAACCAGGAAA TGCTCCTAGGCTTCTTAATATCTGGTGCAACCAGTTGGAAACTGGGGTCCTTCAAGATTCAGTGGCAGTGGATCTGGAAAGGATTACACTCTCAGCATTACCAGTCTTCAGACTGAAGATGTTG CTACTTATTACTGTCAACAGTATTGGAGTACTATATTCACGTTCGGCTCGGGGACAAAGTTGGAAATAAAA | 128 |
| SC34.50 | Heavy Chain | CAGGTCCAACTGCAGCAGCCTGGGGCTGAGCTGGTGAAGCCTGGGGCTTCAGTGAAGCTGTCCTGCAAGGCTTCTGGCTACACCTTCACCAGCTACTGGATGAACTGGGTGAAACAGAGGCCTGG ACAAGGCCTTGAGTGGATCGGAAATATTTTTCCTCTGATAGTTATACTAACTACAATCAAAAGTTCAGGGACAAGGCCACATTGACTGTAGACAAATCCTCCAGCACAGCCTACATGCAGCTCA GCAGCCCGACATCTGAGGACTCTGCGGTCTATTACTGTGCGACTACTTTGACTACTGGGGCCAAGGGACCACGCTCACAGTCTCCTCA | 130 |

Anti-DPEP3 Murine Antibody Variable Region Nucleic Acid Sequences

| Name | Chain | Nucleic Acid Sequence | SEQ ID NO |
|---|---|---|---|
| SC34.53 | Light Chain | GATGTTGTGCTGACCCAGACTCCACTCACTTTGTCGGTTACCATTGGACAACCAGCCTCTATCTCTTGCAAGTCAAGTCAGAGCCTCTTATATAGTAATAGAAGAACCTATTTGAATTGGTTATT ACAGAGGCCAGGCCAGTCTCCAAAGCGCCTAATCTATCTGGTGTCTAAACTGGACTGGAGTCCCTGGAGTTCACTGGCAGTGGATCGGGAACAGATTTTACACTGAAAATCACCAGGGTGG AGGCTGAGGATTTGGGAGTTTATTACTGCTGGCAAGGTACACATTTTCCGTACACGTTCGGTACACGTTCGGAGGGACCAAGCTGGAGATCAAA | 132 |
| SC34.53 | Heavy Chain | CAGGTCCAACTGCAGCAGCCTGGGGCTGAACTGGTGAAGCCTGGGGCTTCAGTGAAGCTGTCTTGCAAGGCTTCTGGCTACACCTTCACCAGCTACTATATCTACTGGGTGAAGCAGAGGCCTGG AGAAGGCCTTGAGTGGATTGGAGAGATTGATCCTAGCAGATGGTCCTAACTTCAATGACAGATTCAAGAACAAGGCCACACTGACTGTTGACAAATCCTCAGCACAGCCTACATGCAACTCA GCAGCCTGACATCTGAGGACTCTGCGGTCTATTACTGTACAAGAGGCCTGCTCTACTATGTACAAGAGTCCAGTCTTACTGGGCCAAGGGACTCTGGTCACTGTCTCTGCA | 134 |
| SC34.58 | Light Chain | GACATTGTGATGTCTCAGTCTCCATCCTCCCTAGCTGTCTAGTTGGAGAGAAGGTTACTATGAGCTGCAAGTCCAGTCAGAGCCTTTATATAGTCGCAATCAAAAGAACTACCTGGCCTGGTA CCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTCACTCTCACCATCAGCAGTG TGAAGGCTGAAGACCTGGCAGTTTATTACTGCCAAGAACATTATAGGTATCCGCTCACGTTCGGTGCTGGGACCAAGCTGGAACTGAGA | 136 |
| SC34.58 | Heavy Chain | CAGGTTCAGCTGCAGCAGTCTGGAGCTGAGCTGGTGAGGCCTGGGGCCTCAGTGAAGATGTCCTGCAAGGCTTCAGTGAAGCTTCAGTGGATACACCTTCACAAGCTATGGTAAACTGGGTGAAACTGGGAAGCAGAGAACTGG ACAGGGCCTTGAGTGGATTGGAGAGATTTATCCTGGAAGAGGTGATGTTTACTACAGACAATTTCAAGGGCAAGGCCACACTGACTACAGACAAATCCTCAGCACAGCCTACATGCAGCTCA GCAGTCTGACATCTGAGGACTCTGCAGTCTATTCTGTGCAAGAGTCCTATTTCGTTCCTGGTTCCTTTACTGGGCCAAGGGACTCTGGTCACTGTCTCTGCA | 138 |
| SC34.63 | Light Chain | GACATTGTGATGTCACAGTCTCACGTCTCCATCCTCCCTAGCTGTCTGTCAGTTGCTGATTTACTGGGCATCCACTAAATTGCTGATTTACTGGGCATCCACTAGGGAATCTGGGGTCCCTGATCGCTTCACAGGCAGTGGATCTGAATCTGGGACAGATTTCACTCTCACCATCAGCAGTG CCAGCAGAAACCAGGGCAGTCTCCAGTTTATTACTGTCAACATATTATAGGTATCCGCTCACGTTCGGTGCTGGGACCAAGCTGGAGCTGAA TGAAGGCTGAAGACCTGGCAGTTTATTACTGTCAACATATTATAGGTATCCGCTCACGTTCGGTGCTGGGACCAAGCTGGAGCTGAA | 140 |
| SC34.63 | Heavy Chain | CAGGTTCAACTGCAGCAGTCTGGAGTTGAGCTGGTGGCGGAGGCCAGGGGCTTCAGTGAAGCTGTCCTGTAAGGCTTCTGGATACACCTTCACAAGCTATGTGATGTATTGATTGGGTGAAACAGAGAACTGG ACAGGGCCTTGAGTGGATTGGAGAGACTTATCCTGGAAGAGGTGATACTTACTACAATGAAAACTTCAAGGGCAAGGCCACACTGACTACAGACAAATCCTCAGCACAGCCTTCTTACAGCTCA GCAGCCTGACATCTGAGGACTCTGCAGTCTATTTCTGTGCAAGAGTCCATGATTACGGTTCCTGGTTTCCTTACTGGGGCCAAGGGACTCTGGTCACTGTCTCTGCA | 142 |
| SC34.67 | Light Chain | GACATTGTGATGTCACAGTCTCACGTCTCCATCCTCCCTAGCTGTCTGTCAGTTGGGGAGGAGAAGGTTGCTCTGCAGTCCAGTCAGAGCCTTTTACATAGTAGAGATCAAAAGAACTACCTGGCCTGGTA CCAGCAGAAACCAGGGCAGTCTCCTAAACTGCTGATTTACTGGGCATCCACTAGGGAATCTGGGGTCCCTGCTCGCTTCACAGGCAGTGGATCTGGGACAGATTTCACTCTCACCATCAGCAGTG TGAAGGCTGAAGACCTGGCAGTTTATTACTGTCAGCAATCTTATAGGTATCCGCTCACGTTCGGTGCTGGGACCAAGCTGGAGCTGAAA | 144 |
| SC34.67 | Heavy Chain | CAGGTTCAGCTGCAGCAGTCTGGAGCTGAGCTGGTGGCGGAGGCCTGGGGCTTCAGTGAAGCTTCTGGATACACCTTCACAAGCTATGTATAAACTGGGTGAAGCAGAGAACTGG ACAGGGCCTTGAGTGGATTGGGGAGATTTATCCTGGAAGTGGTGACAGTTACTACAATAAGACGTTCAAGGGCAAGGCCATATTGACTACAGACAAATCCTCAGCACAGCCTACATGCAGCTCA GCAGCCTGACACCTGAGGACTCTGCAGTCTATTTCTGTGCAAGAGTCCATGATTACGGTTCCTGGTTTCCTTACTGGGGCCAGGGGCTCTGGTCACTGTCTCTGCA | 146 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.71 | Light Chain | GACATTGTGATGACCCAGTCTCAAAAATTCATGTCCACATCAGTAGGAGACAGGGTCAGCATCACCTGCAAGGCCAGTCAGAATGTTCGTACTGCTGGTATCAACAGAAACAGGGCAGTCTCCTAAAACACTGATTTACTTGGCATCCAACCGGCACACTGGAGTCCCTGATCGCTTCACAGGCAGTGGGATCTGGGACGAGATTTCACTCTCACCATTAGCTATGTGCAATCTGAAGACCTGGCAGATTATTTCTGTCTGCAACATTTGAATTATCCGTGGACGTTCGGTGGAGGCACCAAGCTGGAAATCAAA | 148 |
| SC34.71 | Heavy Chain | CAGGTTTTCTCTGAAAGAGTCGGGCCTCGGGACTGGAGTGGCTGGCAAACATTTGGTGGGATAATACTATAAGCTCCAGCCCCTCAGTCTGACTTGTTCTTTCTTTGGGTTTTCACTGAGCACTTCTAGTATGGGTGTAGGGTGGATTCGTCAGCCTTCAGGGAAGGGTCTGGAGTGGCTGGCAAACATTTGGTGGGATAATACTATAAGCCGGCTCACAATCTCAAGGGATACCTCCAAAAACCAGGTTTTCCTCAACATGCCCAGTGTGGACACTACAGATCTGCCACACTACTGTGCTGAATAGAATCCTACTATAGTAGACTGGGCCGAGGGACTCTGGTCACTGTCTCTGCA | 150 |
| SC34.76 | Light Chain | GACATTGTGATGTCACAGTCTCCATCCTCCCTAGCTGTGTCAGTTGGAGAGAGGGTTACGATGAACTGCAAGTCCAGTCAGAGCCTTTTCTATAGTAGTCGCTATCAAAAGAACTACCTGGCTGGTACCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTTCACTCTCACCATCAGCAGTGTGCAGGCTGAAGACCTGGCAGTTTATTACTGTCAGCAATATTATAGGTATCCGCTCACGTTCGGTGCTGGGACCAAGCTGGAGCTGAAA | 152 |
| SC34.76 | Heavy Chain | CAGGTCAGCTCAGCAGTCTGGAGCTGAGCTGGGGCCTGGAGGGTAATACTATGGAGAGTTCAAGGGCAAGGCCATATGAACAGAACAAATCCTCAGCACAGGCTACATGCAGTCAACACCTTGAATACACCTTCAGTGGAGCTTCAGTGAAGCTGTCTCCTGCAAGGTAATGAGAAGTTCAAGGGCAAGGCCATATGAACAGAACAAATCCTCAGCACAGGCTACATGCAGTCAGCAACCTGACATCTGAGGACTCTGCAGTCTATTTCTGTGCAAGAGTCCATGATTACGGGTCCTGGTTTCCTTACTGGGGCCAAGGGACTCTGGTCACTGTCTCTGCA | 154 |
| SC34.78 | Light Chain | GACATTATGATGACTCAGTCTCCAGCCAGCTGTCTGTGACTCTCAAGGAGATAGAGTCTCTCTTTCTGCAGGGAGATCCCCTCCAGTTCAGTGGCAGTGGATCAGGGTCAGGTTCACTCTCAGTATCAACAGTGTGAACCTGAAGATGTTGGAGTTATTACTGTCAAAGCTTCTCATCAAATATGTTCCCAATCATCTCTGGGATCTGTGTCTCCAATCATCTGGGAATCTGGGCTGACGGTTCGGTGCTGGGACCAAGCTGGAGCTTAAA | 156 |
| SC34.78 | Heavy Chain | GATGTGCAGCTTCAGGAGTCGGGACGTGGCCTGGTGAAACCTTCACAGTCCCTGTCCCTCACCTGCACTGTCACTGGCTACTCCATCACTAGTAACTGGGAGTTGGATTGGCCTGGAAATAAGGCTACATAAGGCTACTAAATCCACATCTGGAACCACTACTGGCTACTCCATCAGTCAGCTGGAACATTGGGATCCGGGCAGTTTCCAGGAAACACAATGGAGTGGATAAGGCTACAGAACACTGGGAAGTCAAAAGGAGACACACAGTTCTTCCTGCAGTTGAATTCTGTGACAACTGAGGACACAGCCACATATTACTGTGCAAGGTATCGACAGTACTGGGGCTATGGGAACCTCAGTCACCGTCTCCTCA | 158 |
| SC34.83 | Light Chain | CAAATTGTTCTCATCCAGTCTCCAGCAATCATGTCTGCATCTCCAGGGGAGAATGTCACCATGACCTGCAGTTCAAGTCAAGTAAGTTACATGCACTGGTACCAGCAGAAGTCTGGCACCTCCCCAAAAGATGGATTTATGACACATCCAAACTGGCTTCTGGAGTCCCTGCTCGCTTCAGTGGCAGTGGGTCTGGGACCTCTTACTCTCTCACAATCAGCAGCATGGAGGCTGAAGATGCTGCCACTTATTATTGCCAGCAGTGGAATAGTTACCCACCCACGTTCGGTGCTGGGACCAAGCTGGAGCTGAAA | 160 |
| SC34.83 | Heavy Chain | CAGGTTCAGCTGCAGCAGTCTGGGGCTGAGCTGGAGAAGCCTGGCGCTTCAGTGAAGATATCCTGCAAGGCTTCTGGCTACGCATTCAGTGAATACACTATGCACTGGGTGAAGCAGAGCCATGGAAAGGGCCTTGAGTGGATTGGAGGTATTAATCCTAATAATGGTGGAGACTTATTACTATTTGCAGAAAGAGAAACTACTGACTGAGACAGCCAAATTCAAGGCCAAGGCCACACTGACTGTAGACAAGTCCTCCAGCACAGTCTACATGGAGCTCCGCAGCCTGACATCTGAGGACTCTGCGGTCTATTACTGTGCAAGAAGGGGCCCCTCTACTTCTGTGCTTATTGGGGGCCAAGGCACCACTCTCACAGTCTCCTCA | 162 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.86 | Light Chain | GACACTGTGATGTCACAGTCTCCATCTCCCTAGCGGTGTCAGTTGGAGAGAAGGTTACTCTGAGCTGCAAGTCCAGTCAGAGCCTTTTATATAGTAGTATCAAAAGAACTACCTGGCTGGTACCAGCAGAAACCAGGGCAGTCTCCTAAATGCTCTTTACTGGGCATCCACTAGGGAATCTGGGGTCCCTGACCGTCCACAGGGATCTGGGACGGATTTCACTCTCACCATCAGCAGTGTGAAGGCTGAAGACCTGGCAGTTTATTACTGTCAGCAACATTATTAGGTATCCGCTCACGTTCGGTGCTGGGACCAAGCTGGAGCTGAAA | 164 |
| SC34.86 | Heavy Chain | CAGGTTCAGCTGCAGCAGTCTGGAGCTGAGCTGGCGAGGCCAGGGGCTTCAGTGAAGCTGTCCTGTAAGGCTTCTGGATACACCTTCACAAGCTATATAACCTGGGTGAAGCAGAGAACTGGACAGGGCCTTGAGTGGATTGGAGAGATTTATCCTGGAAGTGGTAATACTACTAACATGAGAAGTTCAAGGGCAAGGCCACACTGACTACAGACAAATCTCCAGCACAGCCTACATGCAGCTCAGCAGCCTGACATCTGAGGACTCTGCAGTCTATTTCTGTGCAAGAGTCCATGATTACGGTTCCTGGTTTGCTTACTGGGGCCAAGGGACTCTGGTCACTGTCTCTGCA | 166 |
| SC34.87 | Light Chain | GACATTGTGATGTCACAGTCTCCATCCTCCCTGGCTGTGTCAGCAGGAGAAGGTCACTATGAGCTGCAAATCCAGTCTGTCTCAACAGTAGAACCCGAAAGAACTACTTGGCTTGGTACCAGCAGAAACCAGGGCAGTCTCCTAAACTGCTGATCTACTGGGCATCCACTAGGGAATCTGGGGTCCCTGATCGCTTCACAGGCAGTGGATCTGGGACAGGATTTTCACTCTCACCATCAGCAGTGTGCAGGCTGAAGACCTGGCAGTTTATTACTGCAAGCAATCTTATAATCTGTGGACGTTCGGTGGAGGCACCAAGCTGGAAATCAAA | 168 |
| SC34.87 | Heavy Chain | CAGGTCCAGCTTCAGCAGTCTGGGGCTGAACTGGCAAAACCTGGGGCCTCAGTGAAGATGTCCTGCAAGGCTTCTGGATACTGGATGCTCTGGGTAAAACAGAGGCCTGGACAGGGTCTGGAATGGATTGGATACATTGATCCTAGGAATGGTTATACTGAATACAATCAGAAGTTCAAGGACAAGGCCACATTGACTGCAGACAAATCTCCAGCACAGCCTACATGCAACTGAGCAGCCTGACATCTGAGGACTCTGCAGTCTATTACTGTACAAGAGGGGGAATGGTGGCTACTGGGGCCAAGGAACCTCAGTCACCGTCTCCTCA | 170 |
| SC34.89 | Light Chain | GACATTGTGATGTCACAGTCTCCATCCTCCCTAGGTGTGTCCGTTGGAGAGAAGGTTACGCTCAGAGCTTCAGTCAGAGCCTTTTTAATAAAAGAGATCAAAAGAACTACTTGGCCTGGTACCAAGAGAAACCAGGGCAGTCTCCTAAACTGCTGATTTATTACTGCACAATCTTATTACTGTCAAGGCAATCTTATAATCTGTGGACGTTCGGTGGAGGCACCAAGCTGGAAATCAAAGAATCTGGGGCGCCTGGGTCCTGACCGTCCACAGGCACAGCATCCTCAGCACAGCCTACATGCAGCTCAGCAGCCTGACATCTGAGGACTCTGCAGTCTATTTCTGTGCAAGAGTCCATGATTACGGTTCCTGGTTTGCTTACTGGGGCCAAGGGACTCTGGTCACTGTCTCTGCA | 172 |
| SC34.89 | Heavy Chain | CAGGTTCAGCTGCAGCAGTCTGGAGCTGAGCTGGCGAGGCCAGGGGCTTCAGTGAAGCTGTCCTGCAAGGCTTCTGGATACACCTTCACAAGCTATACTATAAGCTGGGTGAAACAGAGAACTAGACAGGGCCTTGAGTGGATTATCTGGAAGTTCACTACAGTGGAAGTGATATTCACGGATACCATGATCCCTCAGCCACTACAGACAAATCCTCAGCACAGCCTACATGCAGCTCAGCAGCCTGACATCTGAGGACTCTGCAGTCTATTTCTGTGCAAGAGTCCATGATTACGGTTCCTGGTTTGCTTACTGGGGCCAAGGGACTCTGGTCACTGTCTCTGCA | 174 |
| SC34.90 | Light Chain | CAAATTGTTCTCACCCAGTCTCCAGCAATCATGTCTGCATCTCAAGGGGAACGGTCACCATGACCTGCAGTGCCAGCTCAAGTGTAAGTTCCAGTTACTTGCACTGGTACCAGCAGAAGCCAGGATCCTCCCCCAAACTCTGGATTTATAGCACATCCAACCTGGCTTCAGGAGTCCCTGTTCGCTTCAGTGGCAGTGGGTCTGGGACCTCTTACTCTCTCACAATCAGCAGCATGGAGGCTGAAGATGCTGCCACTTATTACTGCCAGCAGTGGAGTAGTAATCCGTGCCCGTACACGTTCGGAGGGGGGACCAAGCTGGAAATTAAA | 176 |
| SC34.90 | Heavy Chain | CAGGTTCAGCTGCAGCAGTCTGGAGCTGGGCTGATGAAGCCTGGGGCCTCAGTGAAGATATCCTGCAAGGCTACTGGCTACACATTCAGTTACTACTGGATAGAGTGGGTAAAGCAGAGGCCTGGAACATGGCCTTGAGTGGATTGGAGAGATTTTACCTGGAAGTGGTAGTACTAACTACAATGAGAAGTTCAAGGGCAAGGCCACAACATTCACTGCAGATACATCCTCCAACAGCAGTGTTCTACTGTGCGGGCCAAGGGACCTCGGTCACTGTCTCTGCA | 178 |

FIG. 5C Cont.

Anti-DPEP3 Murine Antibody Variable Region Nucleic Acid Sequences

| Name | Chain | Nucleic Acid Sequence | SEQ ID NO |
|---|---|---|---|
| SC34.91 | Light Chain | GACATTGTGATGTCACAGTCTCCATCCTCCCTAGCTGTGTCAGTCGGAGAGAAGGTTACTATGAGCTGCAAGTCCAGTCAGAGCCTTTTATATAGTACCTATCAAAAGAACTACCTGGCTGGTT CCAGCAGAAACCAGGGCAGTCTCCTAAACTGCTGATTTACTGGGCATCCACTAGGGAATCTGGGGTCCCTGATCGCTTCACAGGCAGTGGATCTGGGACAGAGATTTCACTCTCACCATCAGCAGTG TGAAGGCTGAAGACCTGGCAGTTTATTACTGTCAGCAATATTATAGGTATCCGCTCACGTTCGGTCTGGGACCAAGCTGGAGCTGAAA | 180 |
| SC34.91 | Heavy Chain | CAGGTTCAGCTGCAGCAGTCTGGAGCTGAAGCTGGTGGCCCAGGGCTTCAGTGAAGCTGTCCTGCAAGGCTTTCTGGATACAACCTTCAGAAGCTATGCTATAAGCTGGGTGAAGCAGAGAACTGG ACAGGGCCTTGAGTGGATTGGAGAGATTTATCCTGGAAGTGGTGATACTTACTACAATGAGAACTTCAAGGGCAAGGCCACACTGACTGCAGACAAATCTTCCAGCACAGCCTACATGCAGCTCA GCAGCCTGACATCTGAGGACTCTGCAGTCTATTTCTGTGCAAGAGTCCATGATAACGGTTCCTGGTTTCCTTACTGGGGCCAAGGGACTCTGGTCACTGTCTCTGCA | 182 |
| SC34.95 | Light Chain | GACATTGTGCTGTCACAGTCTCCATCCTCCCTAGCTGTGTCAGTTGGAGAGAAGGTTACTATGAGCTGCAAGTCCAGTCAGAGCCTTTTAAATAGTAGGGATCGAAAGAACTATTTGGCCTGGTG CCAACAAAAACCAGGACAGTCTCCTAAAGTGATGATTTACTGGGCATCCACTAGGGAATCTGGGGTCCCTGATCGCTTCACAGGCAGTGGATCTGGGACAGATTTCACTCTCACCATCAGCAGTG TGAAGGCTGAAGACCTGGCAGTTTATTACTGTCAGCAATATTATAGCTATCCGCTCACGGTCCGGTGCCGGGACCAAGCTGGAGCTGAAA | 184 |
| SC34.95 | Heavy Chain | CAGGTTCAGGTTGAAGCAGTCTGGAGCTGGAGCCGGAGGCCAGGGCTTCAGTGAAGCTGTCCTGCAAGGCTTTCAGTGAAGCTGTCCTGCAAGGCTTCTGGATACAACCTTCACAAGCTATGCTATAAACTGGCTGAAGCAGAGAACTGG ACAGGGCCTTGAGTGGATTGGAGAGATTTATCCTGAAGTGTAATACTTACTACAATGAGAGCTTCAAAACAAGGCCACACTGACCACACAAGGCCACACTGACCGACAAGACCTCCACAGCCTACATGCAGCTCA ACAGCCTGACATCTGAGGACTCTGCAGTCTATTTCTGCGAAGAGTCCATGATTACGGTTCTTGGTTTCTTACTGGGGCCAAGGGACTCTGGTCACTGTCTCTGCA | 186 |

FIG. 5C Cont.

Anti-DPEP3 Humanized Antibody Variable Region Nucleic Acid Sequences

| Name | Chain | Nucleic Acid Sequence | SEQ ID NO |
|---|---|---|---|
| hSC34.2 | Light Chain | GACATCCAGATGACTCAGTCCCCATCCAGTCTCTCCGCCAGTCAAGCCTCTCCGCCAGTGTAGGCGATAGAGTGACTATTACCTGCTCTGCAAGCCAGGGCATCACAAATTATCTCAACTGGTACCAGCAGAAGCCC GGAAAAGCACCTAAACTTCTCATCTACTATACAAGCCGGCTCCACAGGGGTGCCTCCCGATTCTCTGGTAGCGATCCGGTACAGACTTCACACTCACATAAGCTCTCTCAGCCT GAGGATTTTGCTACCTACTATTGTCAGCAGTACTCTAAGCTCCCTGGACTTTTGGACAGGGACCAAGGTGGAGATCAAA | 188 |
| hSC34.2 | Heavy Chain | GAAGTTCAGCTTGTACAGAGCGGCGCCGGAGGTTAAGAAACCAGGGCAATCCTTGAAGATCTCCTGCAAAGGTTCCGGATACTCATTTACAGATTACTATATTAACTGGGTCAGACAGATG CCCGGCAAGGGTCTGGAGTGGATGGGTTGGACCATCCAGGGAGCGGTCCAACAAAGTATAATGGCAAATTTCGGGGCCAGGTTACCATATCTGCCGACAAGAGCATCTCCACAGCTAT CTCCAGTGGAGCTCTCGAAAGCATCCGATACAGCTATACTTGCGCTCGGCGCGGAATCTATTACTACGACGGCATCTACCCCAATTATTTTGACTACTGGGGCCAGGGTACCACC GTCACCGTCTCGAGC | 190 |
| hSC34.11 | Light Chain | GATATTCAAATGACCCAGTCTCCTCCTTGTTGTCGCTAGTCTGGGAGACCGAGTCACCATCACATGTAAGAGCAGTCAAAGTCTGCTCAACAGCCGTACCAGAAAAATTATCTTGCT TGGTACCAGCAAAAACCAGGGAAAGTTCCAAGGCCCCTAAGCTCCTGATCTACTGGGCATCCACCCGAGAATCCGGAGTCCCAGTCGGGTCCGGTCAGGAACAGATTTCACCTGACA ATCTCTTCACTGCAGCCTGAGGATGTGGCTACCTATTACTGTAAGGAGTCCTATAACCTCTGGACCTTCGGAGGTGCGACCAAGGTCGAGATCAAG | 192 |
| hSC34.11 | Heavy Chain | GAAGTGCAGCTCGTCCAGAGTGGCCTGAAGTCAAAAAGCCTGGGAGAGTTTGAAGATCTCCTGCAAAGGCAGCGGCTATAGCTTCACAAACTATTGGATGATTTGGGTCCGCCAGATG CCCGGCAAGGGCCTTGAGTGGATGGGATATATCGATCCAACACTGATTACACCGCATATAACCAGAAGTTCAAAGACCAGGTAACTATCTCAGCCGACAAAGTAAGCACCGCATAT CTTCAGTGGCTCATCACTGAAAGCTCCGACACCGCTATGTACTTCTGGAGGCAACGTGCCTCTCGACTTTTGGGGGCCAGGGGACTCTGGTTACCGTCTCGAGC | 194 |
| hSC34.14 | Light Chain | GATATCCAGATGACTCAGTCTCCCTCCCCTCTCTCTGCATCTGTCGGGAGACAGGGTGACTATTACTTGCCGCACCTCTGAGCATCTATCTACTCTTGCCTGGTACCAGCAAAGCCA GGAAAAGCTCTAAGCTGTTGATTTATAATGCAAAGACACTGCAAAGAGAGTGCCCTCCAAGGTTTAGCGGGTCCGGATCTGGTACAGACTTTACCCTCACCATCAGTAGCCTGCAACCC GAGGACTTTGCTACTTACTACTGTCAACACCACTATGATAACACATTCGGCCAGGGGACCAAAACTGGAGATTAAA | 196 |
| hSC34.14 | Heavy Chain | CAGGTGCAGCTGGTTCAGAGCGGGGCCGAGGTGAAAAAGCCTGGCGCATCTGTCAAGGTCTCTGTAAAGCCAGTGGATATACATTCGATAACAGCAGTGGATATACATTTACATGACATTCACTGACTATTACATGCATTCCGCCAGGCT CCAGGCCAGAGGCTGGAGTGGATGGGCGTGTCAACCCAAAGAAAAGGTGAACTACCTATATCAGAAGTTCAAAGGCCGGGTCACAATCACCAGAGACACTAGTGCCAGCACTGCATAT ATGGAACTCAGTAGCCTCCGCAGTAGGATAGCCTCTATTGTCTATATGGGAATTTACTACTCCTATGACCGCCTCCTTTGATTACTGGGGACAGGGAACCACTGTGACTGTGTCC TCC | 198 |
| hSC34.25 | Light Chain | GATATTGTGATGACACAGTCTCCCAGACACAGTCTCCCGATAGCCTGTCTGTTAGTCTCGGAGAACGTGCCACCATTAACTGCACAAGTCTAGTCAGTACTCAGAGATTTGTTGTACTCTCGATACCAGAAAAATTATGTGGCA TGGTACCAGCAGAAGCCAGGCCAGCCACCCAAACTCCTGATCTACTGGGCCTCAACCAGGGAAAAGCCGAGTGCCCAGATAGATTCAGCGGCAGTGGGTACCGATTTCACTCTCACA ATCAGCTTCACTGCAGCCTGAAGATGTGGCAGTGTATTATTGTCAGCAGTATCATATGTCCCCTGACCTTTGGACAGGGCACAAAGTTGGAAATCAAA | 200 |
| hSC34.25 | Heavy Chain | CAAGTACAGTTGGTGCAGAGCGGGGCTGAGGTGAAAAACCCGGCTACTCGGTACAGAAGGTTAGCTGCAAAGCCTCCGGTTACAGCATTTCACTCCTACGCCATTTCTTGGGTGCGCCAGGCA CCTGGCCAACGGCTTGAGTGGATGGGGAATCTACCCTGTTCCGGTGAGACTTATTACAATGAAAAGTTCAAGGAGAGGCGTCACTATCACCAGGGACGCTATGGATCGGATCTTGGTTCCCTTATTGGGACAGGGACCACCCTGGTTACAGTCTCTTCT | 202 |

FIG. 5C Cont.

Anti-DPEP3 Humanized Antibody Variable Region Nucleic Acid Sequences

| Name | Chain | Nucleic Acid Sequence | SEQ ID NO |
|---|---|---|---|
| hSC34.28 | Light Chain | GAAATAGTACTGACCCAGAGCCCGCTACACTCTCCTTGAGCCCTGGAGAGCGGGCAACACTCTCCTGCACAGCATCTTCCTTTACCTGCATTGGTACCAGCAGAAACCTGGGCTGGCTCCACGACTCCTCATTTATTCTACCTCTAATCTTGCTAGCGGGATCCCCGATCGGTTTCAGGCAGTGTAGCGGGACCGACTTCACCTTGACCATTTCCCGGCTGGAGCCTGAGGACTTCGCTGTATATTACTGCCATCAATACCATAGATCTCCCTATACCTTCGGCCAGGGGACCAAACTGGAGATTAAG | 204 |
| hSC34.28 | Heavy Chain | CAAGTGCAACTGGTGCAGTCCGGCGCTGAAGTCAAGAAACCCGGATCTTTCTGTGAAAGTGAGCTGTAAAGCATCCGGGGCACATTCAGCAGCTACTGGATCGGATGGGTGCCTCAGGCCCCCGGACAGGGACTGGAATGGATGGGTGAAATCTTGCCTGGTCCGGCAATACTTACTACAATGAGCGCTTCAAGGATCGAGTCACCATCACCGCTGATGAGTCAACCTCAACCTGCTACATGGAGCTGTCTTCTCTGCGATCTGAAGGACACAGCTGTATACTACTGTGCTAGACGGGCAGCCGGCTACTATTCTAACCCAGAGTGGTTCGCTTATTGGGGCCAAGGAACCCTGGTCACAGTGAGTTCT | 206 |
| hSC34.38 | Light Chain | GACGTCGTCATGACACAGTCCCCCCTGAGCCTCCCTGTGACTCTGGGTCAGCCAGCTTCCATCTCTTGCAAATCTAGCCAGTCCCTCTGTATAGTAACCGTGCACCTATCTGAACTGGTTTCAGCAGCGCCCAGGCCAAAGTCCCAGGCAGTTCATCTACCTGGTGTCTAAGTTGGATAGTGGAGTTCCCGATAGGTTTAGTGGATCCGGTTCTGGCACTGATTTCACACTGAAGATTAGTAGGGTCGAGGCAGAAGATGTGGGAGTGTATTACTGTGTGCAGGGGACACATTTTCCTTTTACCTTCGGCCAGGGCACCAAGCTGGAAATCAAG | 208 |
| hSC34.38 | Heavy Chain | GAGGTGCAGCTTGTCCAATCAGGGGCCGAAGTCAAGAAGCCTGGAGAATCTCTGAAGATCTCTTGTAAGGATCCGGTTATTCCTTCACTTCGTGAACAGATGTGGGTGAGACAGATGCCAGGCAAAGGCTTGGAATGGATGGGCGAGATCAACCCCAGCAATGGTGGGGCAACTTCAACGAGGATTCAAGAAACCAGGTTACTATCTCCGCAGACAAGAGCATATCAACCGCTTACCTTCAGTGGTCTTCCCTTAAGGCATCCGACACCGCTATGTACTACTGCACCCGAGGCCTGCTTTATTACGATTATGATAGAGGTTTTGCTTACTGGGGACAGGGAACATTGGTCACTGTGTCCAGT | 210 |
| hSC34.87 | Light Chain | GACATCGTGATGACCCAGTCTCCAGACTCCCTGGCTGTGTCTCTGGGCGAGAGGGCCACCATCAACTGCAAGTCCAGCCAGAGTTTATTAAACAGCCGCACCGTAAGAACTACTTAGCTTGGTACCAGCAGAAACCAGGACAGCCTCCTAAGCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAAGCAATCTTTATATCTGTGGACGTTCGGTGGAGGCACCAAGCTGGAAATCAAA | 212 |
| hSC34.87 | Heavy Chain | CAGGTCCAGCTTGTGCAGTCTGGGGCTGAGGTGAAGAAGCCTGGGGCTCAGTGAAGGTTTCCTGCAAGGCTTCTGGATACACCTTCACTAGCTATTGATGCTTTGGGTGCGCCAGGCCCCCGACAAAGGCTTGAGTGGATGGGATATCATCGACCCTAGAAATGGTTACACAGAAATAATCAGAAGTTCAAGGACAGAGTCACCATTACCAGGGACACATCCGGAGCAGCCTACATGGAGCTGAGCAGCCTGAGATCTGAAGACACGGCTGTGTATTACTGCGAGAGGGGGGAATGTGGCTATGGACTACTGGGGTCAAGGAACCCTAGTCACCGTCTCGAGT | 214 |

FIG. 5C Cont.

Anti-DPEP3 Humanized Full Length Amino Acid Sequences

| Name | Chain | Full Sequence | SEQ ID NO |
|---|---|---|---|
| hSC34.2 | Light Chain | DIQMTQSPSSLSASVGDRVTITCSASQGITNYLNWYQQKPGKAPKLLIYTSRLHSGVPSRFSGSGSGTDFTLTISSLQPEDFATYYCQQYSKLPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 216 |
| hSC34.2 | Heavy Chain | EVQLVQSGAEVKKPGESLKISCKGSGYSFTDYYINWVRQMPGKGGLEWMGWTVPGSGPTKYNGKFRGQVTISADKSISTAYLQWSSLKASDTAMYYCARRGYYYDGTYPNYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 217 |
| hSC34.11 | Light Chain | DIQMTQSPSSLSASVGDRVTITCKSSQSLLNSRTRKNYLAWYQQKPGPKVPKLLIYWASTRESGVPSRFSGSGSGTDFTLTISSLQPEDVATYYCKESYNLWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 218 |
| hSC34.11 | Heavy Chain | EVQLVQSGAEVKKPGESLKISCKGSGYSFTNVWMIWVRQMPGKGLEWMGVIDPTDYTAYNQKFKDQVTISADKSISTAYLQWSSLKASDTAMYYCARGGNVALDFWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 219 |
| hSC34.14 | Light Chain | DIQMTQSPSSLSASVGDRVTITCRTSEHIYSYLAWYQQKPGKAPKLLIYNAKTLAEGVPSRFSGSGSGTDFTLTISSLQPEDFATYYCQHHYDTPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 220 |
| hSC34.14 | Heavy Chain | QVQLVQSGAEVKKPGASVKVSCKASGYTFYNQKFEGRVTITRDTSASTAYMELSSLRSEDTAVYYCAMGIYYSYDASFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 221 |
| hSC34.25 | Light Chain | DIVMTQSPDSLAVSLGERATINCKSSQSLLYSRYQKNYVAWYQQKPGQPPKLLIYWASTRESGVPDRFSGSGSGTDFTLTISSLQAEDVAVYYCQQYRYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 222 |
| hSC34.25 | Heavy Chain | QVQLVQSGAEVKKPGASVKVSCKASGYTFTSYAISWVRQAPGQRLEWMGEIYPGSGETYYNEKFKGRVTITRDTSASTAYMELSSLRSEDTAVYYCARVNDYGSWFPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 223 |

CDRs of SC34.11 Light and Heavy Chain Variable Regions

Light Chain

Heavy Chain

CDRs of SC34.87 Light and Heavy Chain Variable Regions

Heavy Chain

Light Chain

US 10,189,910 B2

SEQUENCE LISTING

<160> NUMBER OF SEQ ID NOS: 273

<210> SEQ ID NO 1
<211> LENGTH: 107
<212> TYPE: PRT
<213> ORGANISM: Homo sapiens
<220> FEATURE:
<221> NAME/KEY: MISC_FEATURE
<223> OTHER INFORMATION: Kappa light chain (LC) constant region protein

<400> SEQUENCE: 1

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 2
<211> LENGTH: 329
<212> TYPE: PRT
<213> ORGANISM: Homo sapiens
<220> FEATURE:
<221> NAME/KEY: MISC_FEATURE
<223> OTHER INFORMATION: IgGI heavy chain (HC) constant region protein

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 3
<211> LENGTH: 453
<212> TYPE: PRT
<213> ORGANISM: Homo sapiens
<220> FEATURE:
<221> NAME/KEY: MISC_FEATURE
<223> OTHER INFORMATION: Human DPEP3  isoform a mature protein
      (UniProtKB /Swiss-Prot. Q9H4B8.2; residues 36-488)

<400> SEQUENCE: 3

Ala Glu Thr Thr Pro Gly Ala Pro Arg Ala Leu Ser Thr Leu Gly Ser
1               5                   10                  15

Pro Ser Leu Phe Thr Thr Pro Gly Val Pro Ser Ala Leu Thr Thr Pro
            20                  25                  30

Gly Leu Thr Thr Pro Gly Thr Pro Lys Thr Leu Asp Leu Arg Gly Arg
        35                  40                  45

Ala Gln Ala Leu Met Arg Ser Phe Pro Leu Val Asp Gly His Asn Asp
    50                  55                  60

Leu Pro Gln Val Leu Arg Gln Arg Tyr Lys Asn Val Leu Gln Asp Val
65                  70                  75                  80
```

```
Asn Leu Arg Asn Phe Ser His Gly Gln Thr Ser Leu Asp Arg Leu Arg
                 85                  90                  95

Asp Gly Leu Val Gly Ala Gln Phe Trp Ser Ala Ser Val Ser Cys Gln
            100                 105                 110

Ser Gln Asp Gln Thr Ala Val Arg Leu Ala Leu Glu Gln Ile Asp Leu
        115                 120                 125

Ile His Arg Met Cys Ala Ser Tyr Ser Glu Leu Glu Leu Val Thr Ser
130                 135                 140

Ala Glu Gly Leu Asn Ser Ser Gln Lys Leu Ala Cys Leu Ile Gly Val
145                 150                 155                 160

Glu Gly Gly His Ser Leu Asp Ser Ser Leu Ser Val Leu Arg Ser Phe
                165                 170                 175

Tyr Val Leu Gly Val Arg Tyr Leu Thr Leu Thr Phe Thr Cys Ser Thr
            180                 185                 190

Pro Trp Ala Glu Ser Ser Thr Lys Phe Arg His His Met Tyr Thr Asn
        195                 200                 205

Val Ser Gly Leu Thr Ser Phe Gly Glu Lys Val Glu Glu Leu Asn
    210                 215                 220

Arg Leu Gly Met Met Ile Asp Leu Ser Tyr Ala Ser Asp Thr Leu Ile
225                 230                 235                 240

Arg Arg Val Leu Glu Val Ser Gln Ala Pro Val Ile Phe Ser His Ser
                245                 250                 255

Ala Ala Arg Ala Val Cys Asp Asn Leu Leu Asn Val Pro Asp Ile
            260                 265                 270

Leu Gln Leu Leu Lys Lys Asn Gly Gly Ile Val Met Val Thr Leu Ser
        275                 280                 285

Met Gly Val Leu Gln Cys Asn Leu Leu Ala Asn Val Ser Thr Val Ala
290                 295                 300

Asp His Phe Asp His Ile Arg Ala Val Ile Gly Ser Glu Phe Ile Gly
305                 310                 315                 320

Ile Gly Gly Asn Tyr Asp Gly Thr Gly Arg Phe Pro Gln Gly Leu Glu
                325                 330                 335

Asp Val Ser Thr Tyr Pro Val Leu Ile Glu Glu Leu Leu Ser Arg Ser
            340                 345                 350

Trp Ser Glu Glu Glu Leu Gln Gly Val Leu Arg Gly Asn Leu Leu Arg
        355                 360                 365

Val Phe Arg Gln Val Glu Lys Val Arg Glu Glu Ser Arg Ala Gln Ser
370                 375                 380

Pro Val Glu Ala Glu Phe Pro Tyr Gly Gln Leu Ser Thr Ser Cys His
                385                 390                 395                 400

Ser His Leu Val Pro Gln Asn Gly His Gln Ala Thr His Leu Glu Val
            405                 410                 415

Thr Lys Gln Pro Thr Asn Arg Val Pro Trp Arg Ser Ser Asn Ala Ser
        420                 425                 430

Pro Tyr Leu Val Pro Gly Leu Val Ala Ala Thr Ile Pro Thr Phe
435                 440                 445

Thr Gln Trp Leu Cys
    450

<210> SEQ ID NO 4
<211> LENGTH: 488
<212> TYPE: PRT
<213> ORGANISM: Homo sapiens
<220> FEATURE:
<221> NAME/KEY: MISC_FEATURE
```

-continued

<223> OTHER INFORMATION: Human DPEP3 isoform a precursor
(UniProtKB/Swiss-Prot. Q9H4B8.2; residues 1-488)

<400> SEQUENCE: 4

```
Met Gln Pro Thr Gly Arg Glu Gly Ser Arg Ala Leu Ser Arg Arg Tyr
1               5                   10                  15

Leu Arg Arg Leu Leu Leu Leu Leu Leu Leu Leu Leu Arg Gln Pro
            20                  25                  30

Val Thr Arg Ala Glu Thr Thr Pro Gly Ala Pro Arg Ala Leu Ser Thr
            35                  40                  45

Leu Gly Ser Pro Ser Leu Phe Thr Thr Pro Gly Val Pro Ser Ala Leu
        50                  55                  60

Thr Thr Pro Gly Leu Thr Thr Pro Gly Thr Pro Lys Thr Leu Asp Leu
65                  70                  75                  80

Arg Gly Arg Ala Gln Ala Leu Met Arg Ser Phe Pro Leu Val Asp Gly
                85                  90                  95

His Asn Asp Leu Pro Gln Val Leu Arg Gln Arg Tyr Lys Asn Val Leu
            100                 105                 110

Gln Asp Val Asn Leu Arg Asn Phe Ser His Gly Gln Thr Ser Leu Asp
        115                 120                 125

Arg Leu Arg Asp Gly Leu Val Gly Ala Gln Phe Trp Ser Ala Ser Val
        130                 135                 140

Ser Cys Gln Ser Gln Asp Gln Thr Ala Val Arg Leu Ala Leu Glu Gln
145                 150                 155                 160

Ile Asp Leu Ile His Arg Met Cys Ala Ser Tyr Ser Glu Leu Glu Leu
                165                 170                 175

Val Thr Ser Ala Glu Gly Leu Asn Ser Ser Gln Lys Leu Ala Cys Leu
            180                 185                 190

Ile Gly Val Glu Gly Gly His Ser Leu Asp Ser Ser Leu Ser Val Leu
        195                 200                 205

Arg Ser Phe Tyr Val Leu Gly Val Arg Tyr Leu Thr Leu Thr Phe Thr
        210                 215                 220

Cys Ser Thr Pro Trp Ala Glu Ser Ser Thr Lys Phe Arg His His Met
225                 230                 235                 240

Tyr Thr Asn Val Ser Gly Leu Thr Ser Phe Gly Glu Lys Val Val Glu
                245                 250                 255

Glu Leu Asn Arg Leu Gly Met Met Ile Asp Leu Ser Tyr Ala Ser Asp
            260                 265                 270

Thr Leu Ile Arg Arg Val Leu Glu Val Ser Gln Ala Pro Val Ile Phe
        275                 280                 285

Ser His Ser Ala Ala Arg Ala Val Cys Asp Asn Leu Leu Asn Val Pro
        290                 295                 300

Asp Asp Ile Leu Gln Leu Leu Lys Lys Asn Gly Gly Ile Val Met Val
305                 310                 315                 320

Thr Leu Ser Met Gly Val Leu Gln Cys Asn Leu Leu Ala Asn Val Ser
                325                 330                 335

Thr Val Ala Asp His Phe Asp His Ile Arg Ala Val Ile Gly Ser Glu
            340                 345                 350

Phe Ile Gly Ile Gly Gly Asn Tyr Asp Gly Thr Gly Arg Phe Pro Gln
        355                 360                 365

Gly Leu Glu Asp Val Ser Thr Tyr Pro Val Leu Ile Glu Glu Leu Leu
    370                 375                 380

Ser Arg Ser Trp Ser Glu Glu Leu Gln Gly Val Leu Arg Gly Asn
385                 390                 395                 400
```

Leu Leu Arg Val Phe Arg Gln Val Glu Lys Val Arg Glu Glu Ser Arg
            405                 410                 415

Ala Gln Ser Pro Val Glu Ala Glu Phe Pro Tyr Gly Gln Leu Ser Thr
            420                 425                 430

Ser Cys His Ser His Leu Val Pro Gln Asn Gly His Gln Ala Thr His
            435                 440                 445

Leu Glu Val Thr Lys Gln Pro Thr Asn Arg Val Pro Trp Arg Ser Ser
        450                 455                 460

Asn Ala Ser Pro Tyr Leu Val Pro Gly Leu Val Ala Ala Thr Ile
465                 470                 475                 480

Pro Thr Phe Thr Gln Trp Leu Cys
            485

<210> SEQ ID NO 5
<211> LENGTH: 513
<212> TYPE: PRT
<213> ORGANISM: Homo sapiens
<220> FEATURE:
<221> NAME/KEY: MISC_FEATURE
<223> OTHER INFORMATION: Human DPEP3 isoform a precursor (GenBank
      Accession No. NP_071752.3)

<400> SEQUENCE: 5

Met Ile Arg Thr Pro Leu Ser Ala Ser Ala His Arg Leu Leu Leu Pro
1               5                   10                  15

Gly Ser Arg Gly Arg Pro Pro Arg Asn Met Gln Pro Thr Gly Arg Glu
            20                  25                  30

Gly Ser Arg Ala Leu Ser Arg Arg Tyr Leu Arg Arg Leu Leu Leu Leu
            35                  40                  45

Leu Leu Leu Leu Leu Leu Arg Gln Pro Val Thr Arg Ala Glu Thr Thr
        50                  55                  60

Pro Gly Ala Pro Arg Ala Leu Ser Thr Leu Gly Ser Pro Ser Leu Phe
65                  70                  75                  80

Thr Thr Pro Gly Val Pro Ser Ala Leu Thr Thr Pro Gly Leu Thr Thr
            85                  90                  95

Pro Gly Thr Pro Lys Thr Leu Asp Leu Arg Gly Arg Ala Gln Ala Leu
            100                 105                 110

Met Arg Ser Phe Pro Leu Val Asp Gly His Asn Asp Leu Pro Gln Val
            115                 120                 125

Leu Arg Gln Arg Tyr Lys Asn Val Leu Gln Asp Val Asn Leu Arg Asn
        130                 135                 140

Phe Ser His Gly Gln Thr Ser Leu Asp Arg Leu Arg Asp Gly Leu Val
145                 150                 155                 160

Gly Ala Gln Phe Trp Ser Ala Ser Val Ser Cys Gln Ser Gln Asp Gln
            165                 170                 175

Thr Ala Val Arg Leu Ala Leu Glu Gln Ile Asp Leu Ile His Arg Met
            180                 185                 190

Cys Ala Ser Tyr Ser Glu Leu Glu Leu Val Thr Ser Ala Glu Gly Leu
            195                 200                 205

Asn Ser Ser Gln Lys Leu Ala Cys Leu Ile Gly Val Glu Gly Gly His
        210                 215                 220

Ser Leu Asp Ser Ser Leu Ser Val Leu Arg Ser Phe Tyr Val Leu Gly
225                 230                 235                 240

Val Arg Tyr Leu Thr Leu Thr Phe Thr Cys Ser Thr Pro Trp Ala Glu
            245                 250                 255

Ser Ser Thr Lys Phe Arg His His Met Tyr Thr Asn Val Ser Gly Leu
            260                 265                 270

Thr Ser Phe Gly Glu Lys Val Val Glu Glu Leu Asn Arg Leu Gly Met
        275                 280                 285

Met Ile Asp Leu Ser Tyr Ala Ser Asp Thr Leu Ile Arg Arg Val Leu
    290                 295                 300

Glu Val Ser Gln Ala Pro Val Ile Phe Ser His Ser Ala Ala Arg Ala
305                 310                 315                 320

Val Cys Asp Asn Leu Leu Asn Val Pro Asp Asp Ile Leu Gln Leu Leu
                325                 330                 335

Lys Lys Asn Gly Gly Ile Val Met Val Thr Leu Ser Met Gly Val Leu
            340                 345                 350

Gln Cys Asn Leu Leu Ala Asn Val Ser Thr Val Ala Asp His Phe Asp
        355                 360                 365

His Ile Arg Ala Val Ile Gly Ser Glu Phe Ile Gly Ile Gly Gly Asn
    370                 375                 380

Tyr Asp Gly Thr Gly Arg Phe Pro Gln Gly Leu Glu Asp Val Ser Thr
385                 390                 395                 400

Tyr Pro Val Leu Ile Glu Glu Leu Leu Ser Arg Ser Trp Ser Glu Glu
                405                 410                 415

Glu Leu Gln Gly Val Leu Arg Gly Asn Leu Leu Arg Val Phe Arg Gln
            420                 425                 430

Val Glu Lys Val Arg Glu Glu Ser Arg Ala Gln Ser Pro Val Glu Ala
        435                 440                 445

Glu Phe Pro Tyr Gly Gln Leu Ser Thr Ser Cys His Ser His Leu Val
450                 455                 460

Pro Gln Asn Gly His Gln Ala Thr His Leu Glu Val Thr Lys Gln Pro
465                 470                 475                 480

Thr Asn Arg Val Pro Trp Arg Ser Ser Asn Ala Ser Pro Tyr Leu Val
                485                 490                 495

Pro Gly Leu Val Ala Ala Ala Thr Ile Pro Thr Phe Thr Gln Trp Leu
            500                 505                 510

Cys

<210> SEQ ID NO 6
<211> LENGTH: 1724
<212> TYPE: DNA
<213> ORGANISM: Homo sapiens
<220> FEATURE:
<221> NAME/KEY: misc_feature
<223> OTHER INFORMATION: Human DPEP3 cDNA clone (GenBank Accession No.
      BC037243)

<400> SEQUENCE: 6
gtcgtcatga tccggacccc attgtcggcc tctgcccatc gcctgctcct cccaggctcc      60
cgcggccgac cccgcgcaa catgcagccc acgggccgcg agggttcccg cgcgctcagc     120
cggcggtatc tgcggcgtct gctgctcctg ctactgctgc tgctgctgcg gcagcccgta     180
acccgcgcgg agaccacgcc gggcgccccc agagccctct ccacgctggg ctcccccagc     240
ctcttcacca cgccgggtgt ccccagcgcc ctcactaccc caggcctcac tacgccaggc     300 accccaaaa ccctggacct tcggggtcgc gcgcaggccc tgatgcggag tttcccactc     360
gtggacggcc acaatgacct gccccaggtc ctgagacagc gttacaagaa tgtgcttcag     420
gatgttaact gcgaaaattt cagccatggt cagaccagcc tggacaggct tagagacggc     480
ctcgtgggtg cccagttctg gtcagcctcc gtctcatgcc agtcccagga ccagactgcc     540

```
gtgcgcctcg ccctggagca gattgacctc attcaccgca tgtgtgcctc ctactctgaa    600
ctcgagcttg tgacctcagc tgaaggtctg aacagctctc aaaagctggc ctgcctcatt    660
ggcgtggagg gtggtcactc actggacagc agcctctctg tgctgcgcag tttctatgtg    720
ctgggggtgc gctacctgac acttaccttc acctgcagta caccatgggc agagagttcc    780
accaagttca gacaccacat gtacaccaac gtcagcggat tgacaagctt tggtgagaaa    840
gtagtagagg agttgaaccg cctgggcatg atgatagatt tgtcctatgc atcggacacc    900
ttgataagaa gggtcctgga agtgtctcag gctcctgtga tcttctccca ctcagctgcc    960
agagctgtgt gtgacaattt gttgaatgtt cccgatgata tcctgcagct tctgaagaag   1020
aacggtggca tcgtgatggt gacactgtcc atggggtgc tgcagtgcaa cctgcttgct    1080
aacgtgtcca ctgtggcaga tcactttgac acatcaggg cagtcattgg atctgagttc    1140
atcgggattg gtggaaatta tgacgggact ggccggttcc ctcagggct ggaggatgtg    1200 tccacatacc cagtcctgat agaggagttg ctgagtcgta gctggagcga ggaagagctt   1260
caaggtgtcc ttcgtggaaa cctgctgcgg gtcttcagac aagtggaaaa ggtgagagag   1320
gagagcaggg cgcagagccc cgtggaggct gagtttccat atgggcaact gagcacatcc   1380
tgccactccc acctcgtgcc tcagaatgga caccaggcta ctcatctgga ggtgaccaag   1440
cagccaacca atcgggtccc ctggaggtcc tcaaatgcct ccccatacct tgttccaggc   1500
cttgtggctg ctgccaccat cccaaccttc acccagtggc tctgctgaca cagtcggtcc   1560
ccgcagaggt cactgtggca aagcctcaca aagcccctc tcctagttca ttcacaagca   1620
tatgctgaga ataaacatgt tacacatgga aaaaaaaaa aaaaaaaaa aaaaaaaaa     1680 aaaaaaaaaa aaaaaaaaaa aaaaaaaaaa aaaaaaaaaa aaaa                   1724
```

<210> SEQ ID NO 7
<211> LENGTH: 486
<212> TYPE: PRT
<213> ORGANISM: Homo sapiens
<220> FEATURE:
<221> NAME/KEY: MISC_FEATURE
<223> OTHER INFORMATION: Human DPEP2 protein (GenBank Accession No.
    NP_071750)

<400> SEQUENCE: 7

```
Met Gln Pro Ser Gly Leu Glu Gly Pro Gly Thr Phe Gly Arg Trp Pro
1               5                   10                  15

Leu Leu Ser Leu Leu Leu Leu Leu Leu Leu Gln Pro Val Thr Cys
            20                  25                  30

Ala Tyr Thr Thr Pro Gly Pro Pro Arg Ala Leu Thr Thr Leu Gly Ala
        35                  40                  45

Pro Arg Ala His Thr Met Pro Gly Thr Tyr Ala Pro Ser Thr Thr Leu
    50                  55                  60

Ser Ser Pro Ser Thr Gln Gly Leu Gln Glu Gln Ala Arg Ala Leu Met
65                  70                  75                  80

Arg Asp Phe Pro Leu Val Asp Gly His Asn Asp Leu Pro Leu Val Leu
                85                  90                  95

Arg Gln Val Tyr Gln Lys Gly Leu Gln Asp Val Asn Leu Arg Asn Phe
            100                 105                 110

Ser Tyr Gly Gln Thr Ser Leu Asp Arg Leu Arg Asp Gly Leu Val Gly
        115                 120                 125

Ala Gln Phe Trp Ser Ala Tyr Val Pro Cys Gln Thr Gln Asp Arg Asp
    130                 135                 140
```

```
Ala Leu Arg Leu Thr Leu Glu Gln Ile Asp Leu Ile Arg Arg Met Cys
145                 150                 155                 160

Ala Ser Tyr Ser Glu Leu Glu Leu Val Thr Ser Ala Lys Ala Leu Asn
            165                 170                 175

Asp Thr Gln Lys Leu Ala Cys Leu Ile Gly Val Glu Gly Gly His Ser
        180                 185                 190

Leu Asp Asn Ser Leu Ser Ile Leu Arg Thr Phe Tyr Met Leu Gly Val
            195                 200                 205

Arg Tyr Leu Thr Leu Thr His Thr Cys Asn Thr Pro Trp Ala Glu Ser
        210                 215                 220

Ser Ala Lys Gly Val His Ser Phe Tyr Asn Asn Ile Ser Gly Leu Thr
225                 230                 235                 240

Asp Phe Gly Glu Lys Val Val Ala Glu Met Asn Arg Leu Gly Met Met
            245                 250                 255

Val Asp Leu Ser His Val Ser Asp Ala Val Ala Arg Arg Ala Leu Glu
        260                 265                 270

Val Ser Gln Ala Pro Val Ile Phe Ser His Ser Ala Ala Arg Gly Val
        275                 280                 285

Cys Asn Ser Ala Arg Asn Val Pro Asp Ile Leu Gln Leu Leu Lys
290                 295                 300

Lys Asn Gly Gly Val Val Met Val Ser Leu Ser Met Gly Val Ile Gln
305                 310                 315                 320

Cys Asn Pro Ser Ala Asn Val Ser Thr Val Ala Asp His Phe Asp His
            325                 330                 335

Ile Lys Ala Val Ile Gly Ser Lys Phe Ile Gly Ile Gly Gly Asp Tyr
            340                 345                 350

Asp Gly Ala Gly Lys Phe Pro Gln Gly Leu Glu Asp Val Ser Thr Tyr
            355                 360                 365

Pro Val Leu Ile Glu Glu Leu Leu Ser Arg Gly Trp Ser Glu Glu Glu
        370                 375                 380

Leu Gln Gly Val Leu Arg Gly Asn Leu Leu Arg Val Phe Arg Gln Val
385                 390                 395                 400

Glu Lys Val Gln Glu Glu Asn Lys Trp Gln Ser Pro Leu Glu Asp Lys
                405                 410                 415

Phe Pro Asp Glu Gln Leu Ser Ser Ser Cys His Ser Asp Leu Ser Arg
            420                 425                 430

Leu Arg Gln Arg Gln Ser Leu Thr Ser Gly Gln Glu Leu Thr Glu Ile
        435                 440                 445

Pro Ile His Trp Thr Ala Lys Leu Pro Ala Lys Trp Ser Val Ser Glu
        450                 455                 460

Ser Ser Pro His Met Ala Pro Val Leu Ala Val Val Ala Thr Phe Pro
465                 470                 475                 480

Val Leu Ile Leu Trp Leu
            485

<210> SEQ ID NO 8
<211> LENGTH: 493
<212> TYPE: PRT
<213> ORGANISM: Mus musculus
<220> FEATURE:
<221> NAME/KEY: MISC_FEATURE
<223> OTHER INFORMATION: Mouse DPEP3 protein (GenBank Accession No.
      NP_082236)

<400> SEQUENCE: 8
```

```
Met Gln Pro Ala Gly Leu Glu Gly Pro Arg Ala Leu Gly Leu Arg Pro
1               5                   10                  15

Leu Gly His Arg Leu Ser Leu Leu Gly Val Leu Leu Leu Val Pro Ser
            20                  25                  30

Leu Trp Val Thr Cys Thr Leu Thr Thr Pro Ser Pro Ser Ser Ala Pro
            35                  40                  45

Thr Thr Pro Glu Ala Ser Asn Ala Thr Thr Ala Pro Gly Ile Pro Asn
        50                  55                  60

Asp Thr Ala Thr Ser Gly Val Thr Ser Asp Pro Arg Leu Arg Glu Gln
65                  70                  75                  80

Ala Leu Ala Leu Met Arg Asp Phe Pro Leu Val Asp Gly His Asn Asp
                85                  90                  95

Leu Pro Leu Leu Leu Arg Glu Leu Phe Gln Asn Gln Leu Gln Asp Val
            100                 105                 110

Asn Leu Arg Asn Phe Thr Arg Gly Gln Thr Asn Leu Asp Arg Leu Arg
            115                 120                 125

Asp Gly Leu Val Gly Ala Gln Phe Trp Ser Ala Tyr Ile Pro Cys Gln
        130                 135                 140

Thr Gln Asp Arg Asp Ala Val Arg Leu Ala Leu Glu Gln Ile Asp Leu
145                 150                 155                 160

Ile Arg Arg Met Cys Ser Ala Tyr Pro Glu Leu Glu Leu Val Thr Ser
                165                 170                 175

Ala Asp Gly Leu Asn Asn Thr Gln Lys Leu Ala Cys Leu Ile Gly Val
            180                 185                 190

Glu Gly Gly His Ser Leu Asp Thr Ser Leu Ala Val Leu Arg Ser Phe
        195                 200                 205

Tyr Glu Leu Gly Val Arg Tyr Leu Thr Leu Thr Phe Thr Cys Ser Thr
210                 215                 220

Pro Trp Ala Glu Ser Ala Thr Lys Phe Arg His His Phe Tyr Thr Asn
225                 230                 235                 240

Ile Ser Gly Leu Thr Ser Phe Gly Glu Lys Val Val Glu Glu Met Asn
            245                 250                 255

Arg Leu Gly Met Met Ile Asp Leu Ser His Ala Ser Asp Thr Leu Val
        260                 265                 270

Lys Gln Thr Leu Glu Val Ser Gln Ala Pro Val Ile Phe Ser His Ser
            275                 280                 285

Ala Ala Arg Ser Val Cys Asp Asn Leu Leu Asn Ile Pro Asp Asp Ile
        290                 295                 300

Leu Gln Leu Leu Lys Lys Asn Gly Gly Ile Val Met Val Thr Leu Ser
305                 310                 315                 320

Met Gly Val Leu Gln Cys Ser Leu Phe Ala Asn Val Ser Thr Val Ala
            325                 330                 335

Asp His Phe Asp His Ile Arg Thr Val Ile Gly Ser Glu Phe Ile Gly
        340                 345                 350

Ile Gly Gly Ser Tyr Asp Gly Ser Gly Arg Phe Pro Gln Gly Leu Glu
            355                 360                 365

Asp Val Ser Thr Tyr Pro Val Leu Ile Glu Glu Leu Leu Ser Arg Gly
        370                 375                 380

Trp Asp Glu Arg Glu Leu Gln Gly Val Leu Arg Gly Asn Leu Leu Arg
385                 390                 395                 400

Val Phe Arg Gln Val Glu Gln Val Arg Glu Lys Ser Leu Gly Gln Ser
            405                 410                 415

Pro Val Glu Val Lys Phe Pro Glu Arg Gln Gln Ser Asn Thr Cys His
```

|      |     |     |     | 420 |     |     |     | 425 |     |     |     | 430 |     |     |
| ---- | --- | --- | --- | --- | --- | --- | --- | --- | --- | --- | --- | --- | --- | --- |
| Ser  | His | Leu | Leu | Pro | Gln | Pro | Gln | Glu | Asp | Gln | His | Gln | Asp | Thr | His |
|      |     |     | 435 |     |     |     | 440 |     |     |     | 445 |     |     |     |

Leu Lys Val Thr Lys Leu Pro Asn Ile Leu Gln Arg Ala Ser Lys Ala
    450            455            460

Pro Pro His Pro Leu Pro Gly Leu Met Ala Thr Leu Thr Ser Leu Ala
465            470            475            480

Leu Ile Leu Trp Leu Cys Cys Ser Gly His Arg Ala Val
           485             490

<210> SEQ ID NO 9
<211> LENGTH: 1726
<212> TYPE: DNA
<213> ORGANISM: Mus musculus
<220> FEATURE:
<221> NAME/KEY: misc_feature
<223> OTHER INFORMATION: Mouse DPEP3 cDNA clone (GenBank Accession No. BC051148)

<400> SEQUENCE: 9

| | |
|---|---|
| gttgcgcagc agggtgactg gaagcccttc caagcgaggc cacgtcctag ggaccctgaa | 60 |
| tcgaaggtcc gaacccattg tcgccctctg ccctatccct gcccttctca agcgctcttg | 120 |
| tgaccaagac tgagcaccat gcagcccgcg ggtcttgagg tccacgcgc gctcggcctg | 180 |
| cggcctctgg ggcaccggct gtccctgctg ggggtgttac ttctagttcc gtctctgtgg | 240 |
| gtaacctgca ccctgactac tccgagcccc tccagtgctc cgacaacacc ggaagcctcc | 300 |
| aatgccacga ccgctccagg cattcctaat gacacggcca cgtcaggtgt gaccagtgac | 360 |
| cctcgccttc gagagcaagc actggctctg atgcgagact cccacttgt ggatggccac | 420 |
| aacgacctgc tctgctctt gagagaactt ttccagaacc agctgcagga tgtgaatctg | 480 |
| cgcaatttca cccgtggcca gaccaacctg ataggctca gggacggcct tgtgggtgcc | 540 |
| cagttctggt cagcctacat cccgtgccaa acccaggacc gggatgccgt acgcctagcc | 600 |
| ctggagcaga ttgatctcat tcgtcgcatg tgctctgctt accctgagct ggagctggtg | 660 |
| acctcagctg atggtctgaa taacactcag aagctggcct gcctcattgg tgtagagggt | 720 |
| ggtcactcac tggacaccag cctcgctgtg ttgcgcagtt tctatgagct aggagtgcgc | 780 |
| tacctgactc ttaccttcac ctgcagcaca ccgtgggcag aaagcgccac aaaattcaga | 840 |
| caccatttct acaccaacat tagtgggttg acaagctttg gtgagaaagt agtggaagaa | 900 |
| atgaaccgtc tggcatgat gatagacttg tcccacgcct cggacacctt agtgaagcag | 960 |
| accctggagg tgtctcaggc tcctgtgatc ttctcacact cggcggctag atcggtgtgt | 1020 |
| gacaatttgc tgaatattcc tgatgacata ttgcaacttc tgaagaagaa cggtggcatc | 1080 |
| gtgatggtga cactatccat gggggtgcta cagtgcagtc tgtttgctaa cgtgtccact | 1140 |
| gtagcagatc atttttgacca catcaggaca gtcattggat ctgagttcat tgggatcggt | 1200 |
| ggaagctatg acgggtctgg aaggttccct cagggactgg aggatgtatc tacataccca | 1260 |
| gtgctgatag aggagttgct gagtcgcggt tgggatgaac gagagcttca aggtgtcctt | 1320 |
| cgaggaaacc tgcttcgggt cttcagacaa gtggaacagg tgagagagaa aagccttggg | 1380 |
| cagagccctg tggaggtcaa gtttccagag aggcagcaga gcaacacctg ccactcccac | 1440 |
| ctgctgcctc agcctcagga ggaccaacac caggatacac acctgaaggt gacaaagctg | 1500 |
| ccaaacatcc tccagagagc ctcaaaagcc cctcccacc ccttgccagg cctcatggct | 1560 |
| acgctcacct ccctagccct catcctttgg ctatgttgct ctggccacag ggcagtttag | 1620 |

```
caaaacccac aaagttcccc tcctcattgc tgagacccca gcttatgttg agaataaata   1680
cctgaaacat cacgacaaaa aaaaaaaaaa aaaaaaaaaa aaaaaa               1726
```

<210> SEQ ID NO 10
<211> LENGTH: 488
<212> TYPE: PRT
<213> ORGANISM: Rattus norvegicus
<220> FEATURE:
<221> NAME/KEY: MISC_FEATURE
<223> OTHER INFORMATION: Rat DPEP3 protein (GenBank Accession No.
      NP_001008384)

<400> SEQUENCE: 10

```
Met Gln Pro Thr Gly Pro Glu Gly Pro Arg Ala Leu Ser Leu Arg Pro
1               5                   10                  15

Leu Gly His Arg Leu Ser Leu Leu Gly Val Leu Leu Ile Ile Pro Ser
            20                  25                  30

Leu Trp Val Thr Cys Asn Gln Thr Thr Pro Ser Leu Ser Ser Ala Pro
        35                  40                  45

Thr Ser Pro Gly Ala Ser Ser Ala Met Thr Thr Pro Gly Ile Pro Asn
    50                  55                  60

Asp Thr Thr Thr Ser Gly Val Thr Ser Asp Pro Arg Leu Arg Glu Gln
65                  70                  75                  80

Ala Leu Ala Leu Met Arg Asp Phe Pro Leu Val Asp Gly His Asn Asp
                85                  90                  95

Leu Pro Leu Leu Leu Arg Glu Leu Phe Gln Asn Lys Leu Gln Asp Val
            100                 105                 110

Asn Leu His Asn Phe Thr Arg Gly Gln Thr Ser Leu Asp Arg Leu Arg
        115                 120                 125

Asp Gly Leu Val Gly Ala Gln Phe Trp Ser Ala Tyr Ile Pro Cys Gln
    130                 135                 140

Thr Gln Asp Arg Asp Ala Val Arg Val Ala Leu Glu Gln Ile Asp Leu
145                 150                 155                 160

Ile Arg Arg Met Cys Ser Ala Tyr Pro Glu Leu Glu Leu Val Thr Ser
                165                 170                 175

Ala Asp Gly Leu Asn Ser Thr Gln Lys Leu Ala Cys Leu Ile Gly Leu
            180                 185                 190

Glu Gly Gly His Ser Leu Asp Thr Ser Leu Ala Val Leu Arg Ser Phe
        195                 200                 205

Tyr Glu Leu Gly Val Arg Tyr Leu Thr Leu Thr Phe Thr Cys Ser Thr
    210                 215                 220

Pro Trp Ala Glu Ser Ala Thr Lys Phe Arg His His Phe Tyr Thr Asn
225                 230                 235                 240

Ile Ser Gly Leu Thr Ser Phe Gly Glu Lys Val Val Glu Glu Met Asn
                245                 250                 255

Arg Ile Gly Met Met Ile Asp Leu Ser His Ala Ser Asp Thr Leu Val
            260                 265                 270

Lys Gln Thr Leu Glu Ala Ser Arg Ala Pro Val Ile Phe Ser His Ser
        275                 280                 285

Ala Ala Arg Ser Val Cys Asp Asn Leu Leu Asn Val Pro Asp Asp Ile
    290                 295                 300

Leu Gln Leu Leu Lys Lys Asn Gly Gly Ile Val Met Val Thr Leu Ser
305                 310                 315                 320

Met Gly Val Leu Gln Cys Ser Leu Leu Ala Asn Val Ser Thr Val Ala
                325                 330                 335
```

```
Asp His Phe Asp His Ile Arg Thr Val Ile Gly Ser Glu Phe Ile Gly
                340                 345                 350

Ile Gly Gly Ser Tyr Asp Gly Ser Gly Arg Phe Pro Gln Gly Leu Glu
            355                 360                 365

Asp Val Ser Thr Tyr Pro Val Leu Leu Glu Glu Leu Leu Arg Arg Gly
    370                 375                 380

Trp Gly Glu Gln Glu Leu Gln Gly Val Leu Arg Gly Asn Leu Leu Arg
385                 390                 395                 400

Val Phe Arg Gln Val Glu Gln Val Arg Glu Lys Ser Leu Gly Gln Ser
                405                 410                 415

Pro Val Glu Val Val Phe Pro Glu Arg Gln Gln Ser Ser Thr Cys His
            420                 425                 430

Ser His Leu Leu Pro Gln Ser Gln Asp Ala His Leu Lys Val Thr Lys
        435                 440                 445

Leu Pro Ser Ser Gln Val Leu Gln Arg Ala Ser Lys Ala Pro Pro Cys
    450                 455                 460

Pro Leu Leu Gly Leu Val Ala Ala Val Thr Ser Pro Ala Phe Thr Leu
465                 470                 475                 480

Trp Leu Cys Cys Ser Gly His Arg
                485

<210> SEQ ID NO 11
<211> LENGTH: 1692
<212> TYPE: DNA
<213> ORGANISM: Rattus norvegicus
<220> FEATURE:
<221> NAME/KEY: misc_feature
<223> OTHER INFORMATION: Rat DPEP3 cDNA clone (GenBank Accession No.
      BC085826)

<400> SEQUENCE: 11
gcccttacaa gcaaggcgac gtcctagggt accctgaatc gaaggtccga acccccattgt      60 caccctctgc cctatccctg cccttctcag gcttttgtga ccaagactga gcaacatgca     120
acccacgggt cctgagggtc cacgcgcgct cagcttgagg cctctggggc accggctatc     180
cctgttgggg gtgttactta taattccgtc actatgggta acctgcaacc agactactcc     240
gagcctctcc agtgctccga cctcaccggg agcctccagt gccatgacca ctccaggcat     300
tcctaatgac acaactacgt caggcgtgac cagtgaccct cgccttcgag agcaagcact     360
ggccctgatg cgagacttcc cacttgtgga tggccacaac gacctgcctc tgctcctgag     420 agaactttc cagaacaagc tgcaggatgt gaatctgcac aatttcaccc gtggccagac     480
cagcctggat aggctcaggg atggccttgt gggtgcccag ttctggtcag cctacatccc     540
atgccaaacc caggatcggg atgccgtgcg cgtagccctg gagcagattg acctcatccg     600
acgcatgtgt tctgcttacc ggagttggga gcttgtgacc tcagctgatg gtctgaatag     660
cactcagaag ctggcctgcc tcattggact agagggtggt cactcactgg acaccagcct     720
cgctgtgctg cgcagtttct acgagctagg agtccgctac ctgacactta ccttcacgtg     780
cagcacaccc tgggcagaaa gtgccacgaa attcagacac catttctaca ccaacatcag     840 cggggttgaca gctttggag agaaagtagt ggaagaaatg aaccgcatag gtatgatgat     900
agatttgtcc cacgcctcag acaccttagt gaagcaaacc ctggaggcgt ctcgggctcc     960
tgtgatcttc tcccattcag cggctagatc agtgtgtgac aacttgctga atgttcctga    1020
tgacatactg cagcttctga agaagaatgg tggcattgtg atggtgacac tgtccatggg    1080
```

```
ggtgctgcag tgcagtctgc ttgctaatgt gtccactgta gcagatcatt ttgaccacat    1140
caggacagtc attggatctg aattcattgg gattggtgga agctatgatg ggtctggaag    1200
gttccctcag gggctggagg atgtgtctac atacccagtg ctcttagagg agttgctgag    1260
acgaggctgg ggtgaacaag agcttcaagg tgtccttcga ggaaacctgc ttcgggtctt    1320
cagacaagtg aacaggtga gagaaaaaag ccttgggcag agccctgtgg aggtcgtgtt    1380
cccagagagg caacagagca gcacctgcca ctcccacctg ctgcctcagt ctcaggacgc    1440
acacttgaag gtgaccaagc tgccaagtag ccaggtgctc cagagggcct ccaaagcccc    1500
gccatgcccc ttgctaggcc tcgtggctgc tgtcacctcc ccagccttca cccttttggct   1560 ttgttgctct ggccacaggt gagtttagca aaacccacac cgttcccctc ctcactgccc    1620
aggccccagc ttatgttaag aataaatacc tgaaacacca ggaaaaaaaa aaaaaaaaaa    1680
aaaaaaaaaa aa                                                        1692
```

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

```
<210> SEQ ID NO 20
<211> LENGTH: 321
<212> TYPE: DNA
<213> ORGANISM: Mus musculus
<220> FEATURE:
<221> NAME/KEY: misc_feature
<223> OTHER INFORMATION: SC34.2 Light Chain Variable Region

<400> SEQUENCE: 20
gatatccaga tgacacagac tgcatcctcc ctgtctgcct ctctgggaga cagagtcacc        60
atcagttgca gtgcaagtca gggcattacc aattatttaa actggtatca gcagaaacca       120
gatggaactg ttaaactcct gatctattac acatcacgtt tacactcagg agtcccatca       180
aggttcagtg gcagtgggtc tgggacagat tattctctca ccatcagcaa cctggaacct       240
gaagatattg ccacttacta ttgtcagcag tatagtaaac ttccgtggac gttcggtgga       300
ggcaccaagc tggaaatcaa a                                                 321

<210> SEQ ID NO 21
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.2 Light Chain Variable Region

<400> SEQUENCE: 21

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Thr Pro Ser Arg Phe Ser Gly
    50                  55                  60

Ser Gly Ser Gly Lys Asp Tyr Thr Leu Ser Ile Thr Ser Leu Arg Thr
65                  70                  75                  80

Glu Asp Ala Ala Thr Tyr Tyr Cys Gln Gln Tyr Trp Ser Thr Pro Leu
                85                  90                  95

Thr Phe Gly Thr Gly Thr Lys Leu Glu Leu Lys
            100                 105

<210> SEQ ID NO 22
<211> LENGTH: 375
<212> TYPE: DNA
<213> ORGANISM: Mus musculus
<220> FEATURE:
<221> NAME/KEY: misc_feature
<223> OTHER INFORMATION: SC34.2 Heavy Chain Variable Region

<400> SEQUENCE: 22
cagatccagc tgcagcagtc tggacctgag ctggtgaagc ctggggcttc agtgaagata        60
tcctgcaagg cttctggcta caccttcact gactactata aaattggtt gaagcagagg        120 cctggacagg gacttgagtg gattggatgg acttatcctg aagcggtcc tactaagtac        180 aatgggaagt tcaggggcaa ggccacattg actgtagaca catcctccag cacagtctac       240
atgcagctca gcagcctgac ctctgaggac tctgcggtct atttctgtgc aagacggggg       300
atttattact acgatggtat ctacccaaat tactttgact actggggcca aggcaccact       360
ctcacagtct cctca                                                        375
```

<210> SEQ ID NO 23
<211> LENGTH: 127
<212> TYPE: PRT
<213> ORGANISM: Mus musculus
<220> FEATURE:
<221> NAME/KEY: MISC_FEATURE
<223> OTHER INFORMATION: SC34.2 Heavy Chain Variable Region

<400> SEQUENCE: 23

```
Glu Val Gln Ile Gln Leu Gln Gln Ser Gly Pro Glu Leu Val Lys Pro
1               5                   10                  15

Gly Ala Ser Val Lys Ile Ser Cys Lys Ala Ser Gly Tyr Thr Phe Thr
            20                  25                  30

Asp Tyr Tyr Ile Asn Trp Leu Lys Gln Arg Pro Gly Gln Gly Leu Glu
        35                  40                  45

Trp Ile Gly Trp Thr Tyr Pro Gly Ser Gly Pro Thr Lys Tyr Asn Gly
    50                  55                  60

Lys Phe Arg Gly Lys Ala Thr Leu Thr Val Asp Thr Ser Ser Ser Thr
65                  70                  75                  80

Val Tyr Met Gln Leu Ser Ser Leu Thr Ser Glu Asp Ser Ala Val Tyr
                85                  90                  95

Phe Cys Ala Arg Arg Gly Ile Tyr Tyr Tyr Asp Gly Ile Tyr Pro Asn
            100                 105                 110

Tyr Phe Asp Tyr Trp Gly Gln Gly Thr Thr Leu Thr Val Ser Ser
        115                 120                 125
```

<210> SEQ ID NO 24
<211> LENGTH: 340
<212> TYPE: DNA
<213> ORGANISM: Mus musculus
<220> FEATURE:
<221> NAME/KEY: misc_feature
<223> OTHER INFORMATION: SC34.4 Light Chain Variable Region

<400> SEQUENCE: 24

```
ggacattgtg atgtcacagt ctccatcctc cctaactgtg tcagttggag agaaggttac      60
tatgagctgc aagtccagtc agagcctttt atatagtcgc aatcaaaaga actacttggc     120
ctggtaccag cagaaaccag ggcagtctcc taaactgctg atttactggg catccactag     180
ggactctggg gtccctgatc gcttcacagg cactggatct gggacagatt tctctctcac     240
catcagcagt gtgaaaactg aagacctggc agtttattac tgtcaccaac attataggta     300
tccgctcaca ttcggtgctg ggaccaagct ggagctgaaa                            340
```

<210> SEQ ID NO 25
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.4 Light Chain Variable Region

<400> SEQUENCE: 25

```
Asp Ile Val Met Ser Gln Ser Pro Ser Ser Leu Thr Val Ser Val Gly
1               5                   10                  15

Glu Lys Val Thr Met Ser Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Asp Ser Gly Val
```

```
                    50                  55                  60
Pro Asp Arg Phe Thr Gly Thr Gly Ser Gly Thr Asp Phe Ser Leu Thr
 65                  70                  75                  80

Ile Ser Ser Val Lys Thr Glu Asp Leu Ala Val Tyr Tyr Cys His Gln
                 85                  90                  95

His Tyr Arg Tyr Pro Leu Thr Phe Gly Ala Gly Thr Lys Leu Glu Leu
                100                 105                 110

Lys

<210> SEQ ID NO 26
<211> LENGTH: 357
<212> TYPE: DNA
<213> ORGANISM: Mus musculus
<220> FEATURE:
<221> NAME/KEY: misc_feature
<223> OTHER INFORMATION: SC34.4 Heavy Chain Variable Region

<400> SEQUENCE: 26
caggttcagc tgcagcagtc tggagctgaa ctggcgaggc caggggcctc agtgaagctg      60
tcctgtaagg cttctggata caccttcaca agctatggta aaactgggt gaaacagaga      120 actggacagg gccttgagtg gattggagag atttatcctg gaagtggaaa tatttactac     180
aatgagaagt ttaagggcaa ggccatactg actactgata atcctccaa cacagcctac      240 atgcagctca gcagcctgac atctgaagac tctgcagtct atttctgtgc aagagtccat     300
gattacggtt cctggtttcc ttactgggcc caagggactc tggtcactgt ctctgca       357

<210> SEQ ID NO 27
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.4 Heavy Chain Variable Region

<400> SEQUENCE: 27

Gln Val Gln Leu Gln Gln Ser Gly Ala Glu Leu Ala Arg Pro Gly Ala
  1               5                  10                  15

Ser Val Lys Leu Ser Cys Lys Ala Ser Gly Tyr Thr Phe Thr Ser Tyr
                 20                  25                  30

Gly Ile Asn Trp Val Lys Gln Arg Thr Gly Gln Gly Leu Glu Trp Ile
             35                  40                  45

Gly Glu Ile Tyr Pro Gly Ser Gly Asn Ile Tyr Tyr Asn Glu Lys Phe
         50                  55                  60

Lys Gly Lys Ala Ile Leu Thr Thr Asp Lys Ser Ser Asn Thr Ala Tyr
 65                  70                  75                  80

Met Gln Leu Ser Ser Leu Thr Ser Glu Asp Ser Ala Val Tyr Phe Cys
                 85                  90                  95

Ala Arg Val His Asp Tyr Gly Ser Trp Phe Pro Tyr Trp Ala Gln Gly
                100                 105                 110

Thr Leu Val Thr Val Ser Ala
        115

<210> SEQ ID NO 28
<211> LENGTH: 339
<212> TYPE: DNA
<213> ORGANISM: Mus musculus
<220> FEATURE:
<221> NAME/KEY: misc_feature
<223> OTHER INFORMATION: SC34.5 Light Chain Variable Region
```

<400> SEQUENCE: 28

```
gacattgtga tgacacagtt tccatcctcc ctggctatgt cagtaggaca gaaggtcact      60
atgaactgca agtccagtca gagcctttta aatagtagta atcaaaagaa ctatttggcc     120
tggttccagc agaaaccagg acagtctcct aaacttctgg tatactttgc atccactagg    180
gaatctgggg tccctgatcg cttcttaggc agtggatctg ggacagattt cactcttacc    240
atcagcagtg tgcaggctga agacctggca gattacttct gtcagcaaca ttatagcact    300
ccattcacgt tcggctcggg gacaaaattg gaaataaaa                            339
```

<210> SEQ ID NO 29
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.5 Light Chain Variable Region

<400> SEQUENCE: 29

```
Asp Ile Val Met Thr Gln Phe Pro Ser Ser Leu Ala Met Ser Val Gly
1               5                   10                  15
Gln Lys Val Thr Met Asn Cys Lys Ser Ser Gln Ser Leu Leu Asn Ser
            20                  25                  30
Ser Asn Gln Lys Asn Tyr Leu Ala Trp Phe Gln Gln Lys Pro Gly Gln
        35                  40                  45
Ser Pro Lys Leu Leu Val Tyr Phe Ala Ser Thr Arg Glu Ser Gly Val
    50                  55                  60
Pro Asp Arg Phe Leu Gly Ser Gly Ser Gly Thr Asp Phe Thr Leu Thr
65                  70                  75                  80
Ile Ser Ser Val Gln Ala Glu Asp Leu Ala Asp Tyr Phe Cys Gln Gln
                85                  90                  95
His Tyr Ser Thr Pro Phe Thr Phe Gly Ser Gly Thr Lys Leu Glu Ile
            100                 105                 110
Lys
```

<210> SEQ ID NO 30
<211> LENGTH: 357
<212> TYPE: DNA
<213> ORGANISM: Mus musculus
<220> FEATURE:
<221> NAME/KEY: misc_feature
<223> OTHER INFORMATION: SC34.5 Heavy Chain Variable Region

<400> SEQUENCE: 30

```
gaggtccagc tgcaacagtc tggacctgag ctggtgaagc ctggagcttc aatgaagata     60
tcctgcaagg cttctggtta tcattcact ggctacacca tgaattgggt gaagcagagc    120
catggaaaga accttgagtg gattggactt atttatcctt acaatgatga tactaggtac    180
aaacagaagt tcaagggcaa ggccacatta actgtagaca gtcatccag cacagcctac    240
atggagctcc tcagtctgac atctgaggac tctgcagtct attactgtac aagagggtac    300
tacggtagtc cgtacttcga tgtctggggc gcagggacaa cggtcaccgt ctcctca      357
```

<210> SEQ ID NO 31
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.5 Heavy Chain Variable Region

<400> SEQUENCE: 31

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Tyr Pro Tyr Asn Asp Asp Thr Arg Tyr Lys Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Thr Arg Gly Tyr Tyr Gly Ser Pro Tyr Phe Asp Val Trp Gly Ala Gly
            100                 105                 110

Thr Thr Val Thr Val Ser Ser
            115

<210> SEQ ID NO 32
<211> LENGTH: 333
<212> TYPE: DNA
<213> ORGANISM: Mus musculus
<220> FEATURE:
<221> NAME/KEY: misc_feature
<223> OTHER INFORMATION: SC34.6 Light Chain Variable Region

<400> SEQUENCE: 32
gacattgtga tgacacagtc tccatcctcc ctggctgtgt cagtaggaca gaatatcact      60
atgaactgca agtccagtca gagcctttta tacaatcaaa agaactattt ggcctggtac     120
cagcagaaac caggacagtc tcctaaactt ctggtatact ttgcatccac tagggaatct     180
ggggtccctg atcgcttcgt aggcagtgga tctgggacag atttcactct taccatcagc     240
aatgtgcagg ctgaagacct ggcagattac ttctgtcagc aacattatac cactccattc     300
acgttcggct cggggacaaa attggaaatt aaa                                  333

<210> SEQ ID NO 33
<211> LENGTH: 111
<212> TYPE: PRT
<213> ORGANISM: Mus musculus
<220> FEATURE:
<221> NAME/KEY: MISC_FEATURE
<223> OTHER INFORMATION: SC34.6 Light Chain Variable Region

<400> SEQUENCE: 33

Asp Ile Val Met Thr Gln Ser Pro Ser Ser Leu Ala Val Ser Val Gly
1               5                   10                  15

Gln Asn Ile Thr Met Asn Cys Lys Ser Ser Gln Ser Leu Leu Tyr Asn
            20                  25                  30

Gln Lys Asn Tyr Leu Ala Trp Tyr Gln Gln Lys Pro Gly Gln Ser Pro
        35                  40                  45

Lys Leu Leu Val Tyr Phe Ala Ser Thr Arg Glu Ser Gly Val Pro Asp
    50                  55                  60

Arg Phe Val Gly Ser Gly Ser Gly Thr Asp Phe Thr Leu Thr Ile Ser
65                  70                  75                  80

Asn Val Gln Ala Glu Asp Leu Ala Asp Tyr Phe Cys Gln Gln His Tyr
                85                  90                  95

Thr Thr Pro Phe Thr Phe Gly Ser Gly Thr Lys Leu Glu Ile Lys
            100                 105                 110

<210> SEQ ID NO 34
<211> LENGTH: 357
<212> TYPE: DNA
<213> ORGANISM: Mus musculus
<220> FEATURE:
<221> NAME/KEY: misc_feature
<223> OTHER INFORMATION: SC34.6 Heavy Chain Variable Region

<400> SEQUENCE: 34
gaggtccagc tgcaacagtc tggacctgag ctggtgaagc ctggaacttc aatgaagata     60
tcctgcaagg cttctggtta ctcattcact ggctacacca tgaattgggt gaagcagagc    120
catggaaaga accttgagtg gattggactt atttatcctt acaatgatga ctactaggtac   180 aaccggaagt tcaagggcaa ggccacatta actgtagaca agtcatccaa cacagcctac    240
atggagctcc tcagtctgac atctgtggac tctgcagtct gttactgtgc aagagggtcc    300
tacggtagtc cattcttcga tgtctggggc gcaggacaa cggtcaccgt ctcctca       357

<210> SEQ ID NO 35
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.6 Heavy Chain Variable Region

<400> SEQUENCE: 35

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Tyr Pro Tyr Asn Asp Asp Thr Arg Tyr Asn Arg Lys Phe
    50                  55                  60

Lys Gly Lys Ala Thr Leu Thr Val Asp Lys Ser Ser Asn Thr Ala Tyr
65                  70                  75                  80

Met Glu Leu Leu Ser Leu Thr Ser Val Asp Ser Ala Val Cys Tyr Cys
                85                  90                  95

Ala Arg Gly Ser Tyr Gly Ser Pro Phe Phe Asp Val Trp Gly Ala Gly
            100                 105                 110

Thr Thr Val Thr Val Ser Ser
        115

<210> SEQ ID NO 36
<211> LENGTH: 339
<212> TYPE: DNA
<213> ORGANISM: Mus musculus
<220> FEATURE:
<221> NAME/KEY: misc_feature
<223> OTHER INFORMATION: SC34.7 Light Chain Variable Region

<400> SEQUENCE: 36
gacattgtga tgtctcagtc tccatcctcc ctagctgtgt cagttggaga aaggttact     60 atgagctgca gtccagtca gagccttta tatagtcgct atcaaaagaa ctacctggcc    120
tggtaccagc agaaaccagg acagtctcct aaactgctga tttactgggc atccactagg   180

```
gaatctgggg tccctgatcg cttcacaggc agtggatctg ggacagattt cactctcacc    240
atcagcagtg tgaaggctga agacctggca gtttattact gtcaccaata ttataggtat    300
ccgctcacgt tcggtgctgg gaccaagctg gaactgaaa                           339
```

<210> SEQ ID NO 37
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.7 Light Chain Variable Region

<400> SEQUENCE: 37

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Arg Tyr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Arg Tyr Pro Leu Thr Phe Gly Ala Gly Thr Lys Leu Glu Leu
            100                 105                 110

Lys
```

<210> SEQ ID NO 38
<211> LENGTH: 357
<212> TYPE: DNA
<213> ORGANISM: Mus musculus
<220> FEATURE:
<221> NAME/KEY: misc_feature
<223> OTHER INFORMATION: SC34.7 Heavy Chain Variable Region

<400> SEQUENCE: 38

```
caggttcagg tgcagcagtc tggagctgaa ttggcgaggc caggggcttc agtgaagctg    60
tcctgcaagg cctctggata caccttcaca agctatggca taaactgggt gaagcagaga    120
actggacagg ccttgagtg gattggagag atttatcctg gaagtggtaa cgcttactat    180
aatgagaagt tcaaggtcaa ggccaaactg actacagaca attcctccag acagcctac    240 atgcagctca tcaacctgac atctgaggat tctgcagtct atttctgtgc aagggtccat    300
gattacggtt cctggtttcc ttactggggc caagggactc tggtcactgt ctctgca      357
```

<210> SEQ ID NO 39
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.7 Heavy Chain Variable Region

<400> SEQUENCE: 39

```
Gln Val Gln Val Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30
```

Gly Ile Asn Trp Val Lys Gln Arg Thr Gly Gln Gly Leu Glu Trp Ile
         35                  40                  45

Gly Glu Ile Tyr Pro Gly Ser Gly Asn Ala Tyr Tyr Asn Glu Lys Phe
     50                  55                  60

Lys Val Lys Ala Lys Leu Thr Thr Asp Asn Ser Ser Arg Thr Ala Tyr
 65              70                  75                  80

Met Gln Leu Ile Asn Leu Thr Ser Glu Asp Ser Ala Val Tyr Phe Cys
                 85                  90                  95

Ala Arg Val His Asp Tyr Gly Ser Trp Phe Pro Tyr Trp Gly Gln Gly
             100                 105                 110

Thr Leu Val Thr Val Ser Ala
         115

<210> SEQ ID NO 40
<211> LENGTH: 336
<212> TYPE: DNA
<213> ORGANISM: Mus musculus
<220> FEATURE:
<221> NAME/KEY: misc_feature
<223> OTHER INFORMATION: SC34.11 Light Chain Variable Region

<400> SEQUENCE: 40
gacattgtga tgtcacagtc tccatcctcc ctggctgtgt cagcaggaga gaaggtcact     60
atgagctgca atccagtca gagtctgctc aacagtagaa cccgaaagaa ctacttggct    120
tggtaccagc agaagccagg acagtctcct aaactgctga tctactgggc atccactcgg    180
gaatctgggg tccctgatcg cttcacaggc agtggatctg ggacagattt cactctcacc    240
atcagcagtg tgcaggctga agacctggca gtttattact gcaaggaatc ttataatctc    300
tggactttcg gtggaggcac caagctggaa atcaaa                              336

<210> SEQ ID NO 41
<211> LENGTH: 112
<212> TYPE: PRT
<213> ORGANISM: Mus musculus
<220> FEATURE:
<221> NAME/KEY: MISC_FEATURE
<223> OTHER INFORMATION: SC34.11 Light Chain Variable Region

<400> SEQUENCE: 41

Asp Ile Val Met Ser Gln Ser Pro Ser Ser Leu Ala Val Ser Ala Gly
  1               5                  10                  15

Glu Lys Val Thr Met Ser Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65              70                  75                  80

Ile Ser Ser Val Gln Ala Glu Asp Leu Ala Val Tyr Tyr Cys Lys Glu
                 85                  90                  95

Ser Tyr Asn Leu Trp Thr Phe Gly Gly Gly Thr Lys Leu Glu Ile Lys
             100                 105                 110

<210> SEQ ID NO 42
<211> LENGTH: 351
<212> TYPE: DNA
<213> ORGANISM: Mus musculus
<220> FEATURE:
<221> NAME/KEY: misc_feature
<223> OTHER INFORMATION: SC34.11 Heavy Chain Variable Region

<400> SEQUENCE: 42

```
caggtccagc ttcagcagtc tggggctgaa ctggcaaaac ctggggcctc agtgaagatg      60
tcctgcaagg cttctggcta cacctttact aactattgga tgatctgggt aaaacagagg     120
cctggacagg gtctggaatg gattggatac attgatccca ccactgacta tactgcgtac     180
aatcagaagt tcaaggacaa ggccacagtg actgcagaca atcctccag cacagcctac      240
atgcaactga cagcctgac atctgaggac tctgcagtct attactgtgc aagaggggg      300
aatgtggctt tggactttg gggtcaagga acctcagtca ccgtctcctc a              351
```

<210> SEQ ID NO 43
<211> LENGTH: 117
<212> TYPE: PRT
<213> ORGANISM: Mus musculus
<220> FEATURE:
<221> NAME/KEY: MISC_FEATURE
<223> OTHER INFORMATION: SC34.11 Heavy Chain Variable Region

<400> SEQUENCE: 43

```
Gln Val Gln Leu Gln Gln Ser Gly Ala Glu Leu Ala Lys Pro Gly Ala
 1               5                  10                  15
Ser Val Lys Met Ser Cys Lys Ala Ser Gly Tyr Thr Phe Thr Asn Tyr
             20                  25                  30
Trp Met Ile Trp Val Lys Gln Arg Pro Gly Gln Gly Leu Glu Trp Ile
         35                  40                  45
Gly Tyr Ile Asp Pro Thr Thr Asp Tyr Thr Ala Tyr Asn Gln Lys Phe
     50                  55                  60
Lys Asp Lys Ala Thr Val Thr Ala Asp Lys Ser Ser Thr Ala Tyr
 65                  70                  75                  80
Met Gln Leu Asn Ser Leu Thr Ser Glu Asp Ser Ala Val Tyr Tyr Cys
                 85                  90                  95
Ala Arg Gly Gly Asn Val Ala Leu Asp Phe Trp Gly Gln Gly Thr Ser
            100                 105                 110
Val Thr Val Ser Ser
        115
```

<210> SEQ ID NO 44
<211> LENGTH: 339
<212> TYPE: DNA
<213> ORGANISM: Mus musculus
<220> FEATURE:
<221> NAME/KEY: misc_feature
<223> OTHER INFORMATION: SC34.13 Light Chain Variable Region

<400> SEQUENCE: 44

```
gacattgtga tgtcacagtc tccatcctcc ctagctgtgt cagttggaga gaaggttact      60
ctgagctgca gtccagtca gagcctttta tatagtaggg atcaaaagaa ctatttggcc     120
tggtaccagc agaaaccagg gcagtctcct agactggtga tttactgggc atctactagg     180
gaatctgggg tccctgatcg cttcacaggc agtggatctg gacagattt cactctcacc     240
atcagcagtg tgaaggctga agacctggta gtttattatt gtcagcaata ttataggtat     300
ccgctcacgt tcggttctgg gaccaagctg gagctgaaa                            339
```

<210> SEQ ID NO 45
<211> LENGTH: 113

```
<212> TYPE: PRT
<213> ORGANISM: Mus musculus
<220> FEATURE:
<221> NAME/KEY: MISC_FEATURE
<223> OTHER INFORMATION: SC34.13 Light Chain Variable Region

<400> SEQUENCE: 45

Asp Ile Val Met Ser Gln Ser Pro Ser Ser Leu Ala Val Ser Val Gly
1               5                   10                  15

Glu Lys Val Thr Leu Ser Cys Lys Ser Ser Gln Ser Leu Leu Tyr Ser
            20                  25                  30

Arg Tyr Gln Lys Asn Tyr Leu Ala Trp Tyr Gln Gln Lys Pro Gly Gln
        35                  40                  45

Ser Pro Arg Leu Val Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Val Val Tyr Tyr Cys Gln Gln
                85                  90                  95

Tyr Tyr Arg Tyr Pro Leu Thr Phe Gly Ser Gly Thr Lys Leu Glu Leu
            100                 105                 110

Lys

<210> SEQ ID NO 46
<211> LENGTH: 357
<212> TYPE: DNA
<213> ORGANISM: Mus musculus
<220> FEATURE:
<221> NAME/KEY: misc_feature
<223> OTHER INFORMATION: SC34.13 Heavy Chain Variable Region

<400> SEQUENCE: 46
caggttcagg tgcagcagtc tggagctgag ctggcgaggc caggggcttc agtgaagctg      60
tcctgcaagg cttctggata caccttcaca agctatgcta taagctgggt gaagcagaga     120
actggacagg gccttgagtg gattggagag atttatcctg gaagtggtaa tacttactac     180
aatgggaagt tcaagggcaa ggccacactg actacagaca atcctccag cacagcctac      240 atgcagctca gcagcctgac atctgaggac tctgcagtct atttctgtgc aagagtcgat     300
gattacggtt cctggtttcc ttattggggc caagggactc tggtcactgt gtctgca        357

<210> SEQ ID NO 47
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.13 Heavy Chain Variable Region

<400> SEQUENCE: 47

Gln Val Gln Val Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Ala Ile Ser Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Gly Lys Phe
    50                  55                  60

Lys Gly Lys Ala Thr Leu Thr Thr Asp Lys Ser Ser Ser Thr Ala Tyr
65                  70                  75                  80
```

```
Met Gln Leu Ser Ser Leu Thr Ser Glu Asp Ser Ala Val Tyr Phe Cys
                85                  90                  95

Ala Arg Val Asp Asp Tyr Gly Ser Trp Phe Pro Tyr Trp Gly Gln Gly
            100                 105                 110

Thr Leu Val Thr Val Ser Ala
        115
```

```
<210> SEQ ID NO 48
<211> LENGTH: 321
<212> TYPE: DNA
<213> ORGANISM: Mus musculus
<220> FEATURE:
<221> NAME/KEY: misc_feature
<223> OTHER INFORMATION: SC34.14 Light Chain Variable Region

<400> SEQUENCE: 48
gacatccaga tgactcaggc tccagcctcc ctatctccat ctgtgggagc aactgtcacc      60
atcacatgtc gaacaagtga acatatttac agttatttag catggtatca gcagaaacag     120
ggaaaatctc ctcggttatt ggtctataat gcaaaaacct agcagaaagg tgtgtcatca     180
aggttcagtg gcagtggatc aggcacacag ttttctctgc agatcaacag cctgcagcct     240
gaagattttg gaaattatta ctgtcaacat cattatgata ctccgtacac gttcggaggg     300
gggaccaagc tggaaataaa a                                                321
```

```
<210> SEQ ID NO 49
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.14 Light Chain Variable Region

<400> SEQUENCE: 49

Asp Ile Gln Met Thr Gln Ala Pro Ala Ser Leu Ser Pro Ser Val Gly
1               5                   10                  15

Ala Thr Val Thr Ile Thr Cys Arg Thr Ser Glu His Ile Tyr Ser Tyr
            20                  25                  30

Leu Ala Trp Tyr Gln Gln Lys Gln Gly Lys Ser Pro Arg Leu Leu Val
        35                  40                  45

Tyr Asn Ala Lys Thr Leu Ala Glu Gly Val Ser Ser Arg Phe Ser Gly
    50                  55                  60

Ser Gly Ser Gly Thr Gln Phe Ser Leu Gln Ile Asn Ser Leu Gln Pro
65                  70                  75                  80

Glu Asp Phe Gly Asn Tyr Tyr Cys Gln His His Tyr Asp Thr Pro Tyr
                85                  90                  95

Thr Phe Gly Gly Gly Thr Lys Leu Glu Ile Lys
            100                 105
```

```
<210> SEQ ID NO 50
<211> LENGTH: 363
<212> TYPE: DNA
<213> ORGANISM: Mus musculus
<220> FEATURE:
<221> NAME/KEY: misc_feature
<223> OTHER INFORMATION: SC34.14 Heavy Chain Variable Region

<400> SEQUENCE: 50
gaggtccaac tgcagcagtc tggacctgag atggtgaagc ctggggcttc agtgaagata      60
tcctgcaagg cttctggata catattcact gactactaca tgcactgggt gaagcagagc     120
```

```
catggagaga gccttgactg gattggacgt gttaatccta aaaaaggtgg tactacctac      180
aaccagaagt tcgagggcaa ggccatattg actgttgaca gtcctccag cacagcctac       240 atggacctca acagcctgac atctgaggac tctgcggtct attactgtgc aatgggtatc      300
tactatagtt acgacgcctc ctttgactac tggggccaag gcaccactct cacagtctcc      360
tca                                                                    363
```

```
<210> SEQ ID NO 51
<211> LENGTH: 122
<212> TYPE: PRT
<213> ORGANISM: Mus musculus
<220> FEATURE:
<221> NAME/KEY: MISC_FEATURE
<223> OTHER INFORMATION: SC34.14 Heavy Chain Variable Region

<400> SEQUENCE: 51
```

Glu Val Gln Leu Gln Gln Ser Gly Pro Glu Met Val Lys Pro Gly
1               5                   10                  15

Ala Ser Val Lys Ile Ser Cys Lys Ala Ser Gly Tyr Ile Phe Thr Asp
            20                  25                  30

Tyr Tyr Met His Trp Val Lys Gln Ser His Gly Glu Ser Leu Asp Trp
        35                  40                  45

Ile Gly Arg Val Asn Pro Lys Lys Gly Gly Thr Thr Tyr Asn Gln Lys
    50                  55                  60

Phe Glu Gly Lys Ala Ile Leu Thr Val Asp Lys Ser Ser Ser Thr Ala
65                  70                  75                  80

Tyr Met Asp Leu Asn Ser Leu Thr Ser Glu Asp Ser Ala Val Tyr Tyr
                85                  90                  95

Cys Ala Met Gly Ile Tyr Tyr Ser Tyr Asp Ala Ser Phe Asp Tyr Trp
            100                 105                 110

Gly Gln Gly Thr Thr Leu Thr Val Ser Ser
        115                 120

```
<210> SEQ ID NO 52
<211> LENGTH: 339
<212> TYPE: DNA
<213> ORGANISM: Mus musculus
<220> FEATURE:
<221> NAME/KEY: misc_feature
<223> OTHER INFORMATION: SC34.16 Light Chain Variable Region

<400> SEQUENCE: 52
gacattgtga tgtcacagtc tccatcctcc ctagctgtgt cagttggaga aaggttact       60 atgagctgca gtccagtca gagccttta tatagtagat atcaaagaa ttacctggcc        120 tggtaccagc agaaaccagg gcagtctcct aaactgctga tttactggtc atccactcgg     180
gaatctgggg tccctgatcg cttcacaggc agtggatctg ggacagattt cactctcacc     240
atcagcagtg tgaaggctga agacctggca gattattact gtcagcaata ttataggtat    300
ccactcacgt tcggtgctgg gaccaagctg gagctgaaa                            339
```

```
<210> SEQ ID NO 53
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.16 Light Chain Variable Region

<400> SEQUENCE: 53
```

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Arg Tyr Gln Lys Asn Tyr Leu Ala Trp Tyr Gln Lys Pro Gly Gln
            35                  40                  45

Ser Pro Lys Leu Leu Ile Tyr Trp Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Asp Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys

<210> SEQ ID NO 54
<211> LENGTH: 357
<212> TYPE: DNA
<213> ORGANISM: Mus musculus
<220> FEATURE:
<221> NAME/KEY: misc_feature
<223> OTHER INFORMATION: SC34.16 Heavy Chain Variable Region

<400> SEQUENCE: 54
caggttcagc tgcagcagtc tggaactgag ctggcgaggc caggggcttc agtgaagctg      60
tcctgcaagg cttctgaata ccttcaca agctatgcta taacctgggt gaggcagaga      120
actggacagg ccttgagtg gattggagag atttatcccg gaagtggtaa tacttactac      180
aatgagactt tcaagggcaa ggccacactg acttcagaca atcctccag cacagcctcc      240 atgcagctca gcagcctgac atctgaggac tctgcagtct atttctgtgc aagagtccat      300
gattacggtt cctggtttcc ttactggggc caagggactc tggtcactgt ctctgca      357

<210> SEQ ID NO 55
<211> LENGTH: 120
<212> TYPE: PRT
<213> ORGANISM: Mus musculus
<220> FEATURE:
<221> NAME/KEY: MISC_FEATURE
<223> OTHER INFORMATION: SC34.16 Heavy Chain Variable Region

<400> SEQUENCE: 55

Glu Gln Val Gln Leu Gln Ser Gly Thr Glu Leu Ala Arg Pro Gly
1               5                   10                  15

Ala Ser Val Lys Leu Ser Cys Lys Ala Ser Gly Tyr Thr Phe Thr Ser
                20                  25                  30

Tyr Ala Ile Thr Trp Val Arg Gln Arg Thr Gly Gln Gly Leu Glu Trp
            35                  40                  45

Ile Gly Glu Ile Tyr Pro Gly Ser Gly Asn Thr Tyr Tyr Asn Glu Thr
50                  55                  60

Phe Lys Gly Lys Ala Thr Leu Thr Ser Asp Lys Ser Ser Thr Ala
65                  70                  75                  80

Ser Met Gln Leu Ser Ser Leu Thr Ser Glu Asp Ser Ala Val Tyr Phe
                85                  90                  95

Cys Ala Arg Val His Asp Tyr Gly Ser Trp Phe Pro Tyr Trp Gly Gln
            100                 105                 110
```

```
Gly Thr Leu Val Thr Val Ser Ala
        115                 120

<210> SEQ ID NO 56
<211> LENGTH: 321
<212> TYPE: DNA
<213> ORGANISM: Mus musculus
<220> FEATURE:
<221> NAME/KEY: misc_feature
<223> OTHER INFORMATION: SC34.18 Light Chain Variable Region

<400> SEQUENCE: 56
gacattgtga tgacccagtc tcaaaaattc atgtccacat cagtaggaga cagggtcagc      60
gtcgcctgca aggccggtca gaatgtgggt actagtgtag cctggtatca acagaaacca     120
ggacattctc ctaaatcact gatttactcg gcatcctacc ggtacagtgg agtccctaat     180
cgcttcacag gcagtggatc tgggacagat ttcactctca ccatcagcaa tgtgcagtct     240
gaagacttgg cagactattt ctgtcagcaa tatatcacct atccgtacac gttcggaggg     300
gggaccaagc tggaaataat a                                              321

<210> SEQ ID NO 57
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.18 Light Chain Variable Region

<400> SEQUENCE: 57

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Gly Trp Tyr Gln Gln Lys Pro Gly Gln Ser Pro Lys Thr Leu Ile
        35                  40                  45

Tyr Leu Ala Ser Asn Arg His Thr Gly Val Ser Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Trp
                85                  90                  95

Thr Phe Gly Gly Gly Thr Lys Leu Glu Ile Lys
            100                 105

<210> SEQ ID NO 58
<211> LENGTH: 369
<212> TYPE: DNA
<213> ORGANISM: Mus musculus
<220> FEATURE:
<221> NAME/KEY: misc_feature
<223> OTHER INFORMATION: SC34.18 Heavy Chain Variable Region

<400> SEQUENCE: 58
caggtttctc tgaaagagtc gggccctggg atattgcagc cctcccagac cctcagtctg      60
acttgttctt tctctgggtt ttcactgagc acttctggta tgggtgtagg ctggattcgt     120
cagccttcag ggaagggtct ggagtggctg gccaacattt ggtgggatga tagtatttac     180
tataacacag ccctgaagag tcggctcaca atctccaagg atacctccaa aaaccaggtc     240
ttcctcaaga tcgccagtgt ggacactgca gatactgcca catactcctg tgctcgaata     300
```

```
gaatcctact atggtaaccg ggcctggttt gcttactggg gccaagggac tctggtcact      360
gtctctgca                                                              369
```

<210> SEQ ID NO 59
<211> LENGTH: 123
<212> TYPE: PRT
<213> ORGANISM: Mus musculus
<220> FEATURE:
<221> NAME/KEY: MISC_FEATURE
<223> OTHER INFORMATION: SC34.18 Heavy Chain Variable Region

<400> SEQUENCE: 59

```
Gln Val Ser Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Ser Ile Tyr Tyr Asn Thr Ala
    50                  55                  60

Leu Lys Ser Arg Leu Thr Ile Ser Lys Asp Thr Ser Lys Asn Gln Val
65                  70                  75                  80

Phe Leu Lys Ile Ala Ser Val Asp Thr Ala Asp Thr Ala Thr Tyr Ser
                85                  90                  95

Cys Ala Arg Ile Glu Ser Tyr Tyr Gly Asn Arg Ala Trp Phe Ala Tyr
            100                 105                 110

Trp Gly Gln Gly Thr Leu Val Thr Val Ser Ala
        115                 120
```

<210> SEQ ID NO 60
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.19 Light Chain Variable Region

<400> SEQUENCE: 60

```
gacattgtga tgtcacagtc tccttccgcc ctagctgtgt cagttggaga agattact       60 atgagctgca agtgtagtca gagcctctta catagtcgcg atcaaaagaa ctacctggcc    120
tggtatcagc agaaaccagg gcagtctccc aaactgctga tttactgggc atccactagg    180
gaatctgggg tccctgatcg cttcacaggc agtggatctg ggacagattt cactctcacc    240
atcaacactg tgaaggctga agacctggca gtttattact gtcagcaaca ttataggtat    300
ccgctcacgt tcggtgctgg gaccaagctg gagctgaaa                           339
```

<210> SEQ ID NO 61
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.19 Light Chain Variable Region

<400> SEQUENCE: 61

```
Asp Ile Val Met Ser Gln Ser Pro Ser Ala Leu Ala Val Ser Val Gly
1               5                   10                  15

Glu Lys Ile Thr Met Ser Cys Lys Cys Ser Gln Ser Leu Leu His Ser
            20                  25                  30
```

Arg Asp Gln Lys Asn Tyr Leu Ala Trp Tyr Gln Gln Lys Pro Gly Gln
                35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Asn Thr Val Lys Ala Glu Asp Leu Ala Val Tyr Tyr Cys Gln Gln
                 85                  90                  95

His Tyr Arg Tyr Pro Leu Thr Phe Gly Ala Gly Thr Lys Leu Glu Leu
            100                 105                 110

Lys

<210> SEQ ID NO 62
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.19 Heavy Chain Variable Region

<400> SEQUENCE: 62
caggttcagc tgcagcagtc tggagctgag ctggcgaggc caggggcttc agtgaagctg      60
tcctgcaagg cttctggata caccttcaca agctatgcta taacctgggt gaagcagaga     120
actggacagg gccttgagtg gattggagag atttatcctg gaagtggtaa tactttcttc     180
aatgagaagt tcaagggcag ggccacactg actacagaca atcctccag cacagcctac      240 atgcagctca gcagcctgac atctgaggac tctgcagtct atttctgtgc tagagtccat     300
gattacggtt cctggtttcc ttactggggc caagggactc tggtcactgt ctctgca        357

<210> SEQ ID NO 63
<211> LENGTH: 120
<212> TYPE: PRT
<213> ORGANISM: Mus musculus
<220> FEATURE:
<221> NAME/KEY: MISC_FEATURE
<223> OTHER INFORMATION: SC34.19 Heavy Chain Variable Region

<400> SEQUENCE: 63

Gln Gln Val Gln Leu Gln Gln Ser Gly Ala Glu Leu Ala Arg Pro Gly
 1               5                  10                  15

Ala Ser Val Lys Leu Ser Cys Lys Ala Ser Gly Tyr Thr Phe Thr Ser
                 20                  25                  30

Tyr Ala Ile Thr Trp Val Lys Gln Arg Thr Gly Gln Gly Leu Glu Trp
             35                  40                  45

Ile Gly Glu Ile Tyr Pro Gly Ser Gly Asn Thr Phe Phe Asn Glu Lys
 50                  55                  60

Phe Lys Gly Arg Ala Thr Leu Thr Thr Asp Lys Ser Ser Ser Thr Ala
 65                  70                  75                  80

Tyr Met Gln Leu Ser Ser Leu Ser Glu Asp Ser Ala Val Tyr Phe
                 85                  90                  95

Cys Ala Arg Val His Asp Tyr Gly Ser Trp Phe Pro Tyr Trp Gly Gln
            100                 105                 110

Gly Thr Leu Val Thr Val Ser Ala
            115                 120

<210> SEQ ID NO 64
<211> LENGTH: 339
<212> TYPE: DNA

```
<213> ORGANISM: Mus musculus
<220> FEATURE:
<221> NAME/KEY: MISC_FEATURE
<223> OTHER INFORMATION: SC34.20 Light Chain Variable Region

<400> SEQUENCE: 64
gacattgtga tgtcacagtc tccatcctcc ctaactgtgt cagttggaga gaaggttact    60
atgagctgca agtccagtca gagccttttta tatagtacct atcaaaagaa ctacctggcc   120
tggttccagc agaaaccagg gcagtctcct aaactgctga tttactgggc atccactagg   180
gaatctgggg tccctgatcg cttcacaggc agtggatctg ggacagattt cactctcacc   240
atcagcagtg tgaaggctga agacctggca gtttattact gtcagcaata ttataggtat   300
ccgctcacgt tcggtgctgg gaccaagctg gagctgaaa                          339

<210> SEQ ID NO 65
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.20 Light Chain Variable Region

<400> SEQUENCE: 65

Asp Ile Val Met Ser Gln Ser Pro Ser Ser Leu Thr Val Ser Val Gly
1               5                   10                  15

Glu Lys Val Thr Met Ser Cys Lys Ser Ser Gln Ser Leu Leu Tyr Ser
            20                  25                  30

Thr Tyr Gln Lys Asn Tyr Leu Ala Trp Phe Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys

<210> SEQ ID NO 66
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.20 Heavy Chain Variable Region

<400> SEQUENCE: 66
caggttcagc tgcagcagtc tggatctgaa ctggcgaggc caggggcttc agtgaagctg    60
tcctgcaagg cttctggata caccttcaga agctatgcta taagctgggt gaggcagaga   120
actggacagg gccttgagtg gattggagag atttatcctg aaagtggtaa tactgactac   180
aatgcgcagt tcaagggcaa ggccacactg actacagaca atcctccag cacagcctac   240 atgcagctca gcagcctgac atctgaggcc tctgcagtct atttctgtgc aagagtccat   300
gattacggtt cctggtttcc ttactggggc caagggactc tggtcactgt ctctgca      357

<210> SEQ ID NO 67
<211> LENGTH: 119
```

<212> TYPE: PRT
<213> ORGANISM: Mus musculus
<220> FEATURE:
<221> NAME/KEY: MISC_FEATURE
<223> OTHER INFORMATION: SC34.20 Heavy Chain Variable Region

<400> SEQUENCE: 67

Gln Val Gln Leu Gln Gln Ser Gly Ser Glu Leu Ala Arg Pro Gly Ala
1               5                   10                  15

Ser Val Lys Leu Ser Cys Lys Ala Ser Gly Tyr Thr Phe Arg Ser Tyr
            20                  25                  30

Ala Ile Ser Trp Val Arg Gln Arg Thr Gly Gln Gly Leu Glu Trp Ile
        35                  40                  45

Gly Glu Ile Tyr Pro Glu Ser Gly Asn Thr Asp Tyr Asn Ala Gln Phe
    50                  55                  60

Lys Gly Lys Ala Thr Leu Thr Thr Asp Lys Ser Ser Thr Ala Tyr
65                  70                  75                  80

Met Gln Leu Ser Ser Leu Thr Ser Glu Ala Ser Ala Val Tyr Phe Cys
                85                  90                  95

Ala Arg Val His Asp Tyr Gly Ser Trp Phe Pro Tyr Trp Gly Gln Gly
            100                 105                 110

Thr Leu Val Thr Val Ser Ala
        115

<210> SEQ ID NO 68
<211> LENGTH: 312
<212> TYPE: DNA
<213> ORGANISM: Mus musculus
<220> FEATURE:
<221> NAME/KEY: MISC_FEATURE
<223> OTHER INFORMATION: SC34.23 Light Chain Variable Region

<400> SEQUENCE: 68
caaattgttc tcacccagtc tccagcaatc atgtctgcat ctctagggga ggagatcacc      60
ctaacctgca gtgccagctc gagtgtaagt tacatgcact ggtaccagca gaagtccggc     120
acttctccca aactcttgat ttatagcact tccaacctgg cttctggagt ccctctcgc     180
ttcagtggca gtgggtctgg gaccttttat tctctcacaa tcaacactgt ggaggctgaa     240
gatgctgccg attattactg ccatcagtgg agtagttgga cgttcggtgg aggcaccaag     300
ctggaaatca aa                                                        312

<210> SEQ ID NO 69
<211> LENGTH: 104
<212> TYPE: PRT
<213> ORGANISM: Mus musculus
<220> FEATURE:
<221> NAME/KEY: MISC_FEATURE
<223> OTHER INFORMATION: SC34.23 Light Chain Variable Region

<400> SEQUENCE: 69

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Asn Thr Val Glu Ala Glu

```
                65                  70                  75                  80
Asp Ala Ala Asp Tyr Tyr Cys His Gln Trp Ser Ser Trp Thr Phe Gly
                    85                  90                  95

Gly Gly Thr Lys Leu Glu Ile Lys
            100

<210> SEQ ID NO 70
<211> LENGTH: 354
<212> TYPE: DNA
<213> ORGANISM: Mus musculus
<220> FEATURE:
<221> NAME/KEY: MISC_FEATURE
<223> OTHER INFORMATION: SC34.23 Heavy Chain Variable Region

<400> SEQUENCE: 70
gaggtgcagc ttcaggagtc aggacctagc ctcgtgaaac cttctcagac tctgtccctc     60
acctgttctg tcactggcga ctccatcacc agtggttcct ggaactggat ccggaaattc    120
ccagggaata acttgagta catgggatac ataaactaca gtggtggcac ttactacaat    180
ccatctctca aaagtcgaat ctccatcact cgagacacat ccaagaacca ctactacctg    240
cagttgaatt ctgtgactac tgaggacaca gccacatatt actgtggaag acgactggga    300
tcggggggct ggtttggtta ctggggccaa gggactctgg tcactgtctc tgca          354

<210> SEQ ID NO 71
<211> LENGTH: 118
<212> TYPE: PRT
<213> ORGANISM: Mus musculus
<220> FEATURE:
<221> NAME/KEY: MISC_FEATURE
<223> OTHER INFORMATION: SC34.23 Heavy Chain Variable Region

<400> SEQUENCE: 71

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Ser Trp Asn Trp Ile Arg Lys Phe Pro Gly Asn Lys Leu Glu Tyr Met
        35                  40                  45

Gly Tyr Ile Asn Tyr Ser Gly Gly Thr Tyr Tyr Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Asn Ser Val Thr Thr Glu Asp Thr Ala Thr Tyr Tyr Cys Gly
                85                  90                  95

Arg Arg Leu Gly Ser Gly Gly Trp Phe Gly Tyr Trp Gly Gln Gly Thr
            100                 105                 110

Leu Val Thr Val Ser Ala
        115

<210> SEQ ID NO 72
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.24 Light Chain Variable Region

<400> SEQUENCE: 72
gacattgtga tgtcacagtc tccatcctcc ctagctgtgt cagttggaga gaaggttact     60
```

```
atgaactgca agtccagtca gagccttta tatagtagat atcaaaagaa ctacctggcc    120
tggtaccagc agaaaccagg acagtctcct aaactgctga tttactgggc atccactagg    180
gaatctgggg tccctgatcg cttcacaggc agtgggtctg gacagattt cactctcacc    240 atcagcagtg tgaaggctga agacctggca gtttattact gtcagcaata ttataggtat    300
ccgctcacgt tcggtgctgg gaccaagctg gagctgaaa                           339
```

```
<210> SEQ ID NO 73
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.24 Light Chain Variable Region

<400> SEQUENCE: 73
```

```
Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Leu Tyr Ser
            20                  25                  30

Arg Tyr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys
```

```
<210> SEQ ID NO 74
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.24 Heavy Chain Variable Region

<400> SEQUENCE: 74
```

```
caggttcagc tgcagcagtc tggacctgag ctggcgaggc caggggcttc agtgaagctg    60
tcctgcaagg cttctgaata caccttcaca agctatgcta taacctgggt gaagcagaga    120
gctggacagg gccttgagtg gattgggag atttatcctg gaagtggtga tacttactac    180
aatgagaagt tcaagggcaa ggccacactg actacagaca atcctccag cacagcctac    240 atgcagctca gcagcctgac atctgaggac tctgcagtct atttctgtgc aagagtccat    300
gattacggtt cctggtttcc ttactgggc caagggactc tggtcactgt ctctgca       357
```

```
<210> SEQ ID NO 75
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.24 Heavy Chain Variable Region

<400> SEQUENCE: 75
```

Gln Val Gln Leu Gln Gln Ser Gly Pro Glu Leu Ala Arg Pro Gly Ala

```
1               5                   10                  15
Ser Val Lys Leu Ser Cys Lys Ala Ser Glu Tyr Thr Phe Thr Ser Tyr
                20                  25                  30

Ala Ile Thr Trp Val Lys Gln Arg Ala Gly Gln Gly Leu Glu Trp Ile
                35                  40                  45

Gly Glu Ile Tyr Pro Gly Ser Gly Asp Thr Tyr Tyr Asn Glu Lys Phe
                50                  55                  60

Lys Gly Lys Ala Thr Leu Thr Thr Asp Lys Ser Ser Ser Thr Ala Tyr
 65                 70                  75                  80

Met Gln Leu Ser Ser Leu Thr Ser Glu Asp Ser Ala Val Tyr Phe Cys
                85                  90                  95

Ala Arg Val His Asp Tyr Gly Ser Trp Phe Pro Tyr Trp Gly Gln Gly
                100                 105                 110

Thr Leu Val Thr Val Ser Ala
                115

<210> SEQ ID NO 76
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.25 Light Chain Variable Region

<400> SEQUENCE: 76
gacatagtga tgtcacagtc tccatcctcc ctagctgtgt caggtggaga gaaggtcact     60
atgagctgca gtccagtca gagccttta tatagtaggt atcaaaagaa ctacgtggcc      120
tggtaccagc agaaaccagg gcagtctcct aaactgctga tttactgggc atccactagg    180
gaatctgggg tccctgatcg cttcacaggc agtggatctg ggacagattt cactctcacc    240
atcagtagtg tgaaggctga agacctggca gtttattact gtcagcaata ttataggtat   300
ccgctcacgt tcggtgctgg gaccaagctg gagctgaaa                           339

<210> SEQ ID NO 77
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.25 Light Chain Variable Region

<400> SEQUENCE: 77

Asp Ile Val Met Ser Gln Ser Pro Ser Ser Leu Ala Val Ser Gly Gly
 1              5                   10                  15

Glu Lys Val Thr Met Ser Cys Lys Ser Ser Gln Ser Leu Leu Tyr Ser
                20                  25                  30

Arg Tyr Gln Lys Asn Tyr Val Ala Trp Tyr Gln Gln Lys Pro Gly Gln
                35                  40                  45

Ser Pro Lys Leu Leu Ile Tyr Trp Ala Ser Thr Arg Glu Ser Gly Val
                50                  55                  60

Pro Asp Arg Phe Thr Gly Ser Gly Ser Gly Thr Asp Phe Thr Leu Thr
 65                 70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Phe Gly Ala Gly Thr Lys Leu Glu Leu
                100                 105                 110

Lys
```

<210> SEQ ID NO 78
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.25 Heavy Chain Variable Region

<400> SEQUENCE: 78

```
caggtgcagc tgcagcagtc tggagttgag ctggcgaggc caggggcttc agtgaaggtg      60
tcctgcaagg cttctggata caccttcaca agctatgcta taagctgggt gaagcagaga     120
actggacagg gccttgagtg gattggagag atttatcctg gaagtggtga aacttactac     180
aatgagaagt tcaagggcaa ggccacactg actacagaca aatcatccag tacggcctac     240
atgcacctca gcagcctgac atctgaggac tctgcagtct atttatgtgg aagagtcaat     300
gattacggtt cctggtttcc ttactggggc caagggactc tggtcactgt ctctgca       357
```

<210> SEQ ID NO 79
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.25 Heavy Chain Variable Region

<400> SEQUENCE: 79

```
Gln Val Gln Leu Gln Gln Ser Gly Val Glu Leu Ala Arg Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Lys Gln Arg Thr Gly Gln Gly Leu Glu Trp Ile
        35                  40                  45

Gly Glu Ile Tyr Pro Gly Ser Gly Glu Thr Tyr Tyr Asn Glu Lys Phe
    50                  55                  60

Lys Gly Lys Ala Thr Leu Thr Thr Asp Lys Ser Ser Ser Thr Ala Tyr
65                  70                  75                  80

Met His Leu Ser Ser Leu Thr Ser Glu Asp Ser Ala Val Tyr Leu Cys
                85                  90                  95

Gly Arg Val Asn Asp Tyr Gly Ser Trp Phe Pro Tyr Trp Gly Gln Gly
            100                 105                 110

Thr Leu Val Thr Val Ser Ala
        115
```

<210> SEQ ID NO 80
<211> LENGTH: 336
<212> TYPE: DNA
<213> ORGANISM: Mus musculus
<220> FEATURE:
<221> NAME/KEY: MISC_FEATURE
<223> OTHER INFORMATION: SC34.26 Light Chain Variable Region

<400> SEQUENCE: 80

```
gatgttgtgc tgacccagac tccactcact ttgtcggtta ccattggaca accagcctct      60
atctcttgca agtcaagtca gagcctctta tatagtaata agaaccta tttgaattgg       120 ttattacaga ggccaggcca gtctccaaag cgcctaatct atctggtgtc taaactggac     180
tctggagtcc ctgacaggtt cactggcagt ggatcgggaa cagattttac actgaaaatc     240
agcagggtgg aggctgagga tttgggagtt tattactgcg tacaaggtac acatttccg      300
```

```
tacacgttcg gtactgggac caagctggag ctgaaa                              336
```

<210> SEQ ID NO 81
<211> LENGTH: 112
<212> TYPE: PRT
<213> ORGANISM: Mus musculus
<220> FEATURE:
<221> NAME/KEY: MISC_FEATURE
<223> OTHER INFORMATION: SC34.26 Light Chain Variable Region

<400> SEQUENCE: 81

```
Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Arg Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Tyr Thr Phe Gly Thr Gly Thr Lys Leu Glu Leu Lys
            100                 105                 110
```

<210> SEQ ID NO 82
<211> LENGTH: 366
<212> TYPE: DNA
<213> ORGANISM: Mus musculus
<220> FEATURE:
<221> NAME/KEY: MISC_FEATURE
<223> OTHER INFORMATION: SC34.26 Heavy Chain Variable Region

<400> SEQUENCE: 82

```
caggtccaac tgcagcagcc tggggctgaa ctggtgaagc ctggggcttc agtgacattg    60
tcttgcaagg cttctggcta cacctttacc agctactata tctactgggt gaagcagagg   120
cctggagaag gccttgagtg gattggagag attaatccta gcaatggtgg tcctaacttc   180
aatgagagat caagaacaa ggccacactg actgttgaca atcctccag cacagcctac    240 atgcaactca gcagcctgac atctgaggac tctgcggtct attactgtac aagaggcctg   300
ctctactatg attacgacag ggggtttgct tactggggcc aagggactct ggtcactgtc   360
tctgca                                                               366
```

<210> SEQ ID NO 83
<211> LENGTH: 122
<212> TYPE: PRT
<213> ORGANISM: Mus musculus
<220> FEATURE:
<221> NAME/KEY: MISC_FEATURE
<223> OTHER INFORMATION: SC34.26 Heavy Chain Variable Region

<400> SEQUENCE: 83

```
Gln Val Gln Leu Gln Gln Pro Gly Ala Glu Leu Val Lys Pro Gly Ala
1               5                   10                  15

Ser Val Thr Leu Ser Cys Lys Ala Ser Gly Tyr Thr Phe Thr Ser Tyr
            20                  25                  30

Tyr Ile Tyr Trp Val Lys Gln Arg Pro Gly Glu Gly Leu Glu Trp Ile
        35                  40                  45
```

Gly Glu Ile Asn Pro Ser Asn Gly Pro Asn Phe Asn Glu Arg Phe
        50                  55                  60

Lys Asn Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gly Leu Leu Tyr Tyr Asp Tyr Asp Arg Gly Phe Ala Tyr Trp
            100                 105                 110

Gly Gln Gly Thr Leu Val Thr Val Ser Ala
            115                 120

<210> SEQ ID NO 84
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.27 Light Chain Variable Region

<400> SEQUENCE: 84
gacattgtga tgtctcagtc tccatcctcc ctagctgtgt cagttggaga gaaggttact      60
atgagctgca agtccagtca gagccttta tatagtcgca atcaaaagaa ctacctggcc     120
tggtaccagc agaaaccagg gcagtctcct aaactgctga tttactgggc atccactagg    180
gaatctgggg tccctgatcg cttcacaggc agtggatctg ggacagattt cactctcacc    240
atcaacagtg tgaaggctga agacctggca gtttattact gtcaccaata ttataggtat    300
ccgctcacgt tcggtgctgg gaccaagctg gaactgaaa                           339

<210> SEQ ID NO 85
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.27 Light Chain Variable Region

<400> SEQUENCE: 85

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
             20                  25                  30

Arg Asn Gln Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Asn Ser Val Lys Ala Glu Asp Leu Ala Val Tyr Tyr Cys His Gln
                 85                  90                  95

Tyr Tyr Arg Tyr Pro Leu Thr Phe Gly Ala Gly Thr Lys Leu Glu Leu
            100                 105                 110

Lys

<210> SEQ ID NO 86
<211> LENGTH: 357
<212> TYPE: DNA
<213> ORGANISM: Mus musculus
<220> FEATURE:

<221> NAME/KEY: MISC_FEATURE
<223> OTHER INFORMATION: SC34.27 Heavy Chain Variable Region

<400> SEQUENCE: 86

```
caggttcagc tgcagcagtc tggagctgag ctggcgaggc caggggcttc agtgaagttg      60
tcctgcaagg cttctggata caccttcaga agttatggta taaactgggt gaagcagaga     120
actggacagg ccttgagtg gattggagag atttatcctg gaagaggtga tgtttactac     180
aatgagaatt tcaagggcaa ggccacactg actacagaca atcctccag cacagcctac     240 atgcagctca gcagcctgac atctgaggac tctgcagtct atttctgtgc aagagtccat     300
gattacggtt cctggtttcc ttactggggc caagggactc tggtcactgt ctctgca       357
```

<210> SEQ ID NO 87
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.27 Heavy Chain Variable Region

<400> SEQUENCE: 87

```
Gln Val Gln Leu Gln Gln Ser Gly Ala Glu Leu Ala Arg Pro Gly Ala
1               5                  10                  15

Ser Val Lys Leu Ser Cys Lys Ala Ser Gly Tyr Thr Phe Arg Ser Tyr
            20                  25                  30

Gly Ile Asn Trp Val Lys Gln Arg Thr Gly Gln Gly Leu Glu Trp Ile
        35                  40                  45

Gly Glu Ile Tyr Pro Gly Arg Gly Asp Val Tyr Tyr Asn Glu Asn Phe
    50                  55                  60

Lys Gly Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val His Asp Tyr Gly Ser Trp Phe Pro Tyr Trp Gly Gln Gly
            100                 105                 110

Thr Leu Val Thr Val Ser Ala
        115
```

<210> SEQ ID NO 88
<211> LENGTH: 324
<212> TYPE: DNA
<213> ORGANISM: Mus musculus
<220> FEATURE:
<221> NAME/KEY: MISC_FEATURE
<223> OTHER INFORMATION: SC34.28 Light Chain Variable Region

<400> SEQUENCE: 88

```
caaattgttc tcacccagtc tccagcaatc atgtctgcat ctctagggga acgggtcacc      60
atgacctgca ctgccagctc aagtgtaaat tccttttact tgcactggta ccagcagaag     120
ccaggatcct cccccaaact ctggattcat agcacatcca acctggcttc tggagtccca     180
ggtcgcttca gtggcagtgg gtctgggacc tcttactctc tcacaatcag cagcatggag     240
gctgaagatg ctgccactta ttactgccac cagtatcatc gttccccgta cacgttcgga     300 gggggggacca agctggaaat aaaa                                           324
```

<210> SEQ ID NO 89
<211> LENGTH: 108
<212> TYPE: PRT

```
<213> ORGANISM: Mus musculus
<220> FEATURE:
<221> NAME/KEY: MISC_FEATURE
<223> OTHER INFORMATION: SC34.28 Light Chain Variable Region

<400> SEQUENCE: 89
```

| Gln | Ile | Val | Leu | Thr | Gln | Ser | Pro | Ala | Ile | Met | Ser | Ala | Ser | Leu | Gly |
|---|---|---|---|---|---|---|---|---|---|---|---|---|---|---|---|
| 1 | | | | 5 | | | | | 10 | | | | | 15 | |

| Glu | Arg | Val | Thr | Met | Thr | Cys | Thr | Ala | Ser | Ser | Ser | Val | Asn | Ser | Phe |
|---|---|---|---|---|---|---|---|---|---|---|---|---|---|---|---|
| | | | 20 | | | | | 25 | | | | | 30 | | |

| Tyr | Leu | His | Trp | Tyr | Gln | Gln | Lys | Pro | Gly | Ser | Ser | Pro | Lys | Leu | Trp |
|---|---|---|---|---|---|---|---|---|---|---|---|---|---|---|---|
| | | 35 | | | | | 40 | | | | | 45 | | | |

| Ile | His | Ser | Thr | Ser | Asn | Leu | Ala | Ser | Gly | Val | Pro | Gly | Arg | Phe | Ser |
|---|---|---|---|---|---|---|---|---|---|---|---|---|---|---|---|
| | 50 | | | | | 55 | | | | | 60 | | | | |

| Gly | Ser | Gly | Ser | Gly | Thr | Ser | Tyr | Ser | Leu | Thr | Ile | Ser | Ser | Met | Glu |
|---|---|---|---|---|---|---|---|---|---|---|---|---|---|---|---|
| 65 | | | | | 70 | | | | | 75 | | | | | 80 |

| Ala | Glu | Asp | Ala | Ala | Thr | Tyr | Tyr | Cys | His | Gln | Tyr | His | Arg | Ser | Pro |
|---|---|---|---|---|---|---|---|---|---|---|---|---|---|---|---|
| | | | | 85 | | | | | 90 | | | | | 95 | |

| Tyr | Thr | Phe | Gly | Gly | Gly | Thr | Lys | Leu | Glu | Ile | Lys |
|---|---|---|---|---|---|---|---|---|---|---|---|
| | | | 100 | | | | | 105 | | | |

```
<210> SEQ ID NO 90
<211> LENGTH: 369
<212> TYPE: DNA
<213> ORGANISM: Mus musculus
<220> FEATURE:
<221> NAME/KEY: MISC_FEATURE
<223> OTHER INFORMATION: SC34.28 Heavy Chain Variable Region

<400> SEQUENCE: 90
caggttcagc tgcagcagtc tggagctgag ctgatgaagc ctggggcctc agtgaagata      60
tcctgcaagg ctactggcta cacattcagt agctactgga tagagtgggt aaagcagagg     120
cctggacatg gccttgagtg gattggagag atttttacctg aagtggtaa tacttactac     180 aatgagagat caaggacaa ggccacattc actgcagata catcctccaa cacagcctac     240
atgcaactca gcagcctgac atctgaagac tctgccgtct attactgtgc aagaagggcg     300
gccgcctact atagtaaccc cgagtggttt gcttactggg gccaagggac tctggtcact     360
gtctctgca                                                              369

<210> SEQ ID NO 91
<211> LENGTH: 123
<212> TYPE: PRT
<213> ORGANISM: Mus musculus
<220> FEATURE:
<221> NAME/KEY: MISC_FEATURE
<223> OTHER INFORMATION: SC34.28 Heavy Chain Variable Region

<400> SEQUENCE: 91
```

| Gln | Val | Gln | Leu | Gln | Gln | Ser | Gly | Ala | Glu | Leu | Met | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Ile | Ser | Cys | Lys | Ala | Thr | Gly | Tyr | Thr | Phe | Ser | Ser | Tyr |
|---|---|---|---|---|---|---|---|---|---|---|---|---|---|---|---|
| | | | 20 | | | | | 25 | | | | | 30 | | |

| Trp | Ile | Glu | Trp | Val | Lys | Gln | Arg | Pro | Gly | His | Gly | Leu | Glu | Trp | Ile |
|---|---|---|---|---|---|---|---|---|---|---|---|---|---|---|---|
| | | 35 | | | | | 40 | | | | | 45 | | | |

| Gly | Glu | Ile | Leu | Pro | Gly | Ser | Gly | Asn | Thr | Tyr | Tyr | Asn | Glu | Arg | Phe |
|---|---|---|---|---|---|---|---|---|---|---|---|---|---|---|---|
| | 50 | | | | | 55 | | | | | 60 | | | | |

| Lys | Asp | Lys | Ala | Thr | Phe | Thr | Ala | Asp | Thr | Ser | Ser | Asn | Thr | Ala | Tyr |
|---|---|---|---|---|---|---|---|---|---|---|---|---|---|---|---|
| 65 | | | | | 70 | | | | | 75 | | | | | 80 |

```
Met Gln Leu Ser Ser Leu Thr Ser Glu Asp Ser Ala Val Tyr Tyr Cys
                85                  90                  95

Ala Arg Arg Ala Ala Tyr Tyr Ser Asn Pro Glu Trp Phe Ala Tyr
            100                 105                 110

Trp Gly Gln Gly Thr Leu Val Thr Val Ser Ala
        115                 120
```

<210> SEQ ID NO 92
<211> LENGTH: 324
<212> TYPE: DNA
<213> ORGANISM: Mus musculus
<220> FEATURE:
<221> NAME/KEY: MISC_FEATURE
<223> OTHER INFORMATION: SC34.33 Light Chain Variable Region

<400> SEQUENCE: 92

```
caaattgttc tcacccagtc tccagcaatc atgtctgcat ctctagggga acgggtcacc      60
atgacctgca ctgccagctc aagtgtaaat tcctttttact tacactggta ccagcagaag    120
ccaggatcct cccccaaact ctggattcat agcacatcca acctggcttc tggagtccca    180
ggtcgcttca gtggcagtgg gtctgggacc tcttactctc tcacaatcag cagcatggag    240
gctgaagatg ctgccactta ttactgccac cagtatcatc gttccccgta cacgttcgga    300 gggggggacca agctggaaat aaaa                                          324
```

<210> SEQ ID NO 93
<211> LENGTH: 108
<212> TYPE: PRT
<213> ORGANISM: Mus musculus
<220> FEATURE:
<221> NAME/KEY: MISC_FEATURE
<223> OTHER INFORMATION: SC34.33 Light Chain Variable Region

<400> SEQUENCE: 93

```
Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Asn Ser Phe
            20                  25                  30

Tyr Leu His Trp Tyr Gln Gln Lys Pro Gly Ser Ser Pro Lys Leu Trp
        35                  40                  45

Ile His Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Tyr Thr Phe Gly Gly Gly Thr Lys Leu Glu Ile Lys
            100                 105
```

<210> SEQ ID NO 94
<211> LENGTH: 369
<212> TYPE: DNA
<213> ORGANISM: Mus musculus
<220> FEATURE:
<221> NAME/KEY: MISC_FEATURE
<223> OTHER INFORMATION: SC34.33 Heavy Chain Variable Region

<400> SEQUENCE: 94

```
caggttcagc tgcagcagtc tggagctgag ctgatgaagc ctggggcctc agtgaagata     60
tcctgcaagg ctactggcta cacattcagt agctactgga tagagtgggt aaagcagagg    120
```

```
cctggacatg gccttgagtg gattggagag attttacctg gaagtgataa aacttactac    180
aatgagaggt tcaaggacaa ggccacattc acggcagata catcctccaa cacagcctac    240
atgcaactca gcagcctgac atctgaagac tctgccgtct attactgtac aagaagggcg    300
gccgcctact atagtaaccc cgagtggttt gcttactggg gccaagggac tctggtcact    360
gtctctgca                                                            369

<210> SEQ ID NO 95
<211> LENGTH: 124
<212> TYPE: PRT
<213> ORGANISM: Mus musculus
<220> FEATURE:
<221> NAME/KEY: MISC_FEATURE
<223> OTHER INFORMATION: SC34.33 Heavy Chain Variable Region

<400> SEQUENCE: 95

Glu Gln Val Gln Leu Gln Gln Ser Gly Ala Glu Leu Met Lys Pro Gly
1               5                   10                  15

Ala Ser Val Lys Ile Ser Cys Lys Ala Thr Gly Tyr Thr Phe Ser Ser
            20                  25                  30

Tyr Trp Ile Glu Trp Val Lys Gln Arg Pro Gly His Gly Leu Glu Trp
        35                  40                  45

Ile Gly Glu Ile Leu Pro Gly Ser Asp Lys Thr Tyr Tyr Asn Glu Arg
    50                  55                  60

Phe Lys Asp Lys Ala Thr Phe Thr Ala Asp Thr Ser Ser Asn Thr Ala
65                  70                  75                  80

Tyr Met Gln Leu Ser Ser Leu Thr Ser Glu Asp Ser Ala Val Tyr Tyr
                85                  90                  95

Cys Thr Arg Arg Ala Ala Ala Tyr Tyr Ser Asn Pro Glu Trp Phe Ala
            100                 105                 110

Tyr Trp Gly Gln Gly Thr Leu Val Thr Val Ser Ala
        115                 120

<210> SEQ ID NO 96
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.36 Light Chain Variable Region

<400> SEQUENCE: 96
gatatccaga tgacacagac tacatcctcc ctgtctgcct ctctgggaga cagagtcacc     60
atcagttgca gggcaagtca ggacattagc aattatttaa actggtatca gcagaaacca    120
gatggaactg ttaaactcct gatctactac acatcaagat acactcagg agtcccatca     180 aggttcagtg gcagtgggtc tggaacagat tattctctca ccattagcaa cctggagcaa    240
gaggatattg ccacttactt tgccagcag ggtaatacgc ttccgtggac gttcggtgga     300
ggcaccaagc tggaaatcaa a                                              321

<210> SEQ ID NO 97
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.36 Light Chain Variable Region

<400> SEQUENCE: 97
```

-continued

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
                35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 98
<211> LENGTH: 360
<212> TYPE: DNA
<213> ORGANISM: Mus musculus
<220> FEATURE:
<221> NAME/KEY: MISC_FEATURE
<223> OTHER INFORMATION: SC34.36 Heavy Chain Variable Region

<400> SEQUENCE: 98

```
caggtccaac tgcagcagcc tgggtctgtg ctggtgaggc ctggagcttc agtgaagctg     60
tcctgcaagg cttctggcta cacattcacc agctactgga tgcactgggt gaagcagagg    120
cctggacaag ccttgagtg gattggagag atttctccta ctagtggtag gcctaactac    180
aatgcgaagt tcaagggcaa ggccacactg actgttgaca tcctccag cacagcctac     240
gtggatctca gcagcctgac atctgaggac tctgcggtct attactgtgc aaaggggag    300
ggctactatg gtaaagcctt tgactactgg ggccaaggca ccactctcac agtctcctca   360
```

<210> SEQ ID NO 99
<211> LENGTH: 120
<212> TYPE: PRT
<213> ORGANISM: Mus musculus
<220> FEATURE:
<221> NAME/KEY: MISC_FEATURE
<223> OTHER INFORMATION: SC34.36 Heavy Chain Variable Region

<400> SEQUENCE: 99

```
Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
                35                  40                  45

Gly Glu Ile Ser Pro Thr Ser Gly Arg Pro Asn Tyr Asn Ala Lys Phe
    50                  55                  60

Lys Gly Lys Ala Thr Leu Thr Val Asp Thr Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Lys Gly Glu Gly Tyr Tyr Gly Lys Ala Phe Asp Tyr Trp Gly Gln
            100                 105                 110

Gly Thr Thr Leu Thr Val Ser Ser
            115                 120
```

<210> SEQ ID NO 100
<211> LENGTH: 336
<212> TYPE: DNA
<213> ORGANISM: Mus musculus
<220> FEATURE:
<221> NAME/KEY: MISC_FEATURE
<223> OTHER INFORMATION: SC34.38 Light Chain Variable Region

<400> SEQUENCE: 100

| | | |
|---|---|---|
| gatgttgtgc tgacccagac tccactcact tgtcggtta ccattggaca accagcctct | 60 |
| atctcttgca agtcaagtca gagcctctta tatagtaata aagaaccta tttgaattgg | 120 |
| ttattacaga ggccaggcca gtctccaaag cgcctaatct atctggtgtc taaactggac | 180 |
| tctggagtcc ctgacaggtt cactggcagt ggatcgggaa cagattttac actgaaaatc | 240 |
| agcagggtgg aggctgagga tttgggagtt tattactgcg tacaaggtac acattttccg | 300 |
| ttcacgttcg gtactgggac caagctggag ctgaaa | 336 |

<210> SEQ ID NO 101
<211> LENGTH: 112
<212> TYPE: PRT
<213> ORGANISM: Mus musculus
<220> FEATURE:
<221> NAME/KEY: MISC_FEATURE
<223> OTHER INFORMATION: SC34.38 Light Chain Variable Region

<400> SEQUENCE: 101

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Arg Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Thr Gly Thr Lys Leu Glu Leu Lys
            100                 105                 110

<210> SEQ ID NO 102
<211> LENGTH: 366
<212> TYPE: DNA
<213> ORGANISM: Mus musculus
<220> FEATURE:
<221> NAME/KEY: MISC_FEATURE
<223> OTHER INFORMATION: SC34.38 Heavy Chain Variable Region

<400> SEQUENCE: 102

| | | |
|---|---|---|
| caggtccaac tgcagcagcc tggggctgaa ctggtgaagc ctggggcttc agtgacattg | 60 |
| tcttgcaagg cttctggcta caccttcacc agctactata tgtactgggt gaagcagagg | 120 |
| cctggagaag gccttgagtg gattggagag attaatccta gcaatggtgg tgctaacttc | 180 |
| aatgagagat tcaagaacaa ggccacactg actgttgaca atcctccag cacagcctac | 240 |
| atgcaactca gcagcctgac atctgaggac tctgcggtct tttactgtac aagaggcctg | 300 |
| ctctactatg attacgacag ggggtttgct tactggggcc aagggactct ggtcactgtc | 360 |
| tctgca | 366 |

<210> SEQ ID NO 103
<211> LENGTH: 122
<212> TYPE: PRT
<213> ORGANISM: Mus musculus
<220> FEATURE:
<221> NAME/KEY: MISC_FEATURE
<223> OTHER INFORMATION: SC34.38 Heavy Chain Variable Region

<400> SEQUENCE: 103

Gln Val Gln Leu Gln Gln Pro Gly Ala Glu Leu Val Lys Pro Gly Ala
1               5                   10                  15

Ser Val Thr Leu Ser Cys Lys Ala Ser Gly Tyr Thr Phe Thr Ser Tyr
            20                  25                  30

Tyr Met Tyr Trp Val Lys Gln Arg Pro Gly Glu Gly Leu Glu Trp Ile
        35                  40                  45

Gly Glu Ile Asn Pro Ser Asn Gly Gly Ala Asn Phe Asn Glu Arg Phe
    50                  55                  60

Lys Asn Lys Ala Thr Leu Thr Val Asp Lys Ser Ser Thr Ala Tyr
65                  70                  75                  80

Met Gln Leu Ser Ser Leu Thr Ser Glu Asp Ser Ala Val Phe Tyr Cys
                85                  90                  95

Thr Arg Gly Leu Leu Tyr Tyr Asp Tyr Asp Arg Gly Phe Ala Tyr Trp
            100                 105                 110

Gly Gln Gly Thr Leu Val Thr Val Ser Ala
        115                 120

<210> SEQ ID NO 104
<211> LENGTH: 324
<212> TYPE: DNA
<213> ORGANISM: Mus musculus
<220> FEATURE:
<221> NAME/KEY: MISC_FEATURE
<223> OTHER INFORMATION: SC34.39 Light Chain Variable Region

<400> SEQUENCE: 104
caaattgttc tcacccagtc tccagcaatc atgtctgcat ctcaagggga acgggtcacc      60
atgacctgca ctgccagctc aagtgtaagt tccaattact tgcactggta ccagcagaag    120
ccaggatcct cccccaaact ctggatttat agcacatccc acctggcttc tggagtccca    180
gttcgcttca gtggcagtgg gtctgggacc tcttactctc tcacaatcag cagcatggag    240
gctgaagatg ctgccaccta ttactgccac cagtatcatc gttccccgta cacgttcgga    300
gggggaccaa gctggaaaat caaa                                             324

<210> SEQ ID NO 105
<211> LENGTH: 108
<212> TYPE: PRT
<213> ORGANISM: Mus musculus
<220> FEATURE:
<221> NAME/KEY: MISC_FEATURE
<223> OTHER INFORMATION: SC34.39 Light Chain Variable Region

<400> SEQUENCE: 105

Gln Ile Val Leu Thr Gln Ser Pro Ala Ile Met Ser Ala Ser Gln Gly
1               5                   10                  15

Glu Arg Val Thr Met Thr Cys Thr Ala Ser Ser Ser Val Ser Ser Asn
            20                  25                  30

Tyr Leu His Trp Tyr Gln Gln Lys Pro Gly Ser Ser Pro Lys Leu Trp
        35                  40                  45

Ile Tyr Ser Thr Ser His Leu Ala Ser Gly Val Pro Val Arg Phe Ser
            50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                85                  90                  95

Tyr Thr Phe Gly Gly Gly Thr Lys Leu Glu Ile Lys
            100                 105

<210> SEQ ID NO 106
<211> LENGTH: 369
<212> TYPE: DNA
<213> ORGANISM: Mus musculus
<220> FEATURE:
<221> NAME/KEY: MISC_FEATURE
<223> OTHER INFORMATION: SC34.39 Heavy Chain Variable Region

<400> SEQUENCE: 106
caggttcaac tgcagcagtc tggagctgag ctgatgaagc ctggggcctc agtgaagata     60
tcctgcaagg ctactggcta cacattcagt aactactgga tagagtgggt aaagcagagg    120
cctggacatg gccttgagtg gattggagag atttttacctg gaagtgatag tacttacttc   180
aatgagaagt tcaagggcaa ggccacattc actgcagata catcctccaa cacagcctac    240
atgcaactca gcagcctgac atctgaggac tctgccgtct attactgtac aataaggtcg    300
gccgcctact atagtaaccc cgagtggttt gcttactggg gccaagggac tctggtcact    360
gtctctgca                                                            369

<210> SEQ ID NO 107
<211> LENGTH: 123
<212> TYPE: PRT
<213> ORGANISM: Mus musculus
<220> FEATURE:
<221> NAME/KEY: MISC_FEATURE
<223> OTHER INFORMATION: SC34.39 Heavy Chain Variable Region

<400> SEQUENCE: 107

Gln Val Gln Leu Gln Gln Ser Gly Ala Glu Leu Met Lys Pro Gly Ala
 1               5                  10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Ser Thr Tyr Phe Asn Glu Lys Phe
 50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                85                  90                  95

Thr Ile Arg Ser Ala Ala Tyr Tyr Ser Asn Pro Glu Trp Phe Ala Tyr
            100                 105                 110

Trp Gly Gln Gly Thr Leu Val Thr Val Ser Ala
        115                 120

<210> SEQ ID NO 108
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.40 Light Chain Variable Region

<400> SEQUENCE: 108

```
gacatccaga tgactcagtc tccagcctcc ctatctgcat ctgtgggaga aactgtcacc    60
atgacatgtc gagcaagtga gaatatttac agtaatttag catggtatca gcagaaacag   120
ggaaaatctc ctcaggtcct ggtctatgct gcaacaaact tagcagatgg tgtgccatca   180
aggttcagtg gcagtgaatc aggcacacag ttttctctga agatcaacag cctgcagcct   240
gaagattttg ggagttatta ctgtcaacat ttttatggta ctccgtggac gttcggtgga   300
ggcaccaagc tggaaatcaa a                                              321
```

<210> SEQ ID NO 109
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.40 Light Chain Variable Region

<400> SEQUENCE: 109

```
Asp Ile Gln Met Thr Gln Ser Pro Ala Ser Leu Ser Ala Ser Val Gly
1               5                   10                  15
Glu Thr Val Thr Met Thr Cys Arg Ala Ser Glu Asn Ile Tyr Ser Asn
            20                  25                  30
Leu Ala Trp Tyr Gln Gln Lys Gln Gly Lys Ser Pro Gln Val Leu Val
        35                  40                  45
Tyr Ala Ala Thr Asn Leu Ala Asp Gly Val Pro Ser Arg Phe Ser Gly
    50                  55                  60
Ser Glu Ser Gly Thr Gln Phe Ser Leu Lys Ile Asn Ser Leu Gln Pro
65                  70                  75                  80
Glu Asp Phe Gly Ser Tyr Tyr Cys Gln His Phe Tyr Gly Thr Pro Trp
                85                  90                  95
Thr Phe Gly Gly Gly Thr Lys Leu Glu Ile Lys
            100                 105
```

<210> SEQ ID NO 110
<211> LENGTH: 372
<212> TYPE: DNA
<213> ORGANISM: Mus musculus
<220> FEATURE:
<221> NAME/KEY: MISC_FEATURE
<223> OTHER INFORMATION: SC34.40 Heavy Chain Variable Region

<400> SEQUENCE: 110

```
gaggtgcagc ttcaggagtc aggacctggc ctggcaaaac cttctcagac tctgtccctc    60
acctgttctg tcactggcta ctccatcacc agtgattact ggaactggat ccggaaattc   120
ccagggaata acttgagta catggggtac ataacctaca gtggtagtac ttactacaat   180
ccatctctca aaagtcgaat ctccatcact gagacacat ccaagaacca gtattacctg   240
cagttgaatt ctgtgactac tgaggacaca gccacatatt actgtgcaag agcgagggtt   300
tattactacg atggtagata cggccgcgct atggactact ggggtcaagg aacctcagtc   360
accgtctcct ca                                                        372
```

<210> SEQ ID NO 111
<211> LENGTH: 124
<212> TYPE: PRT
<213> ORGANISM: Mus musculus
<220> FEATURE:

<221> NAME/KEY: MISC_FEATURE
<223> OTHER INFORMATION: SC34.40 Heavy Chain Variable Region

<400> SEQUENCE: 111

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Thr Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Ala Arg Val Tyr Tyr Tyr Asp Gly Arg Tyr Gly Arg Ala Met Asp
            100                 105                 110

Tyr Trp Gly Gln Gly Thr Ser Val Thr Val Ser Ser
            115                 120

<210> SEQ ID NO 112
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.41 Light Chain Variable Region

<400> SEQUENCE: 112
gacatccaga tgattcagtc tccatcgtcc atgtttgcct ctctgggaga cagagtcagt      60
ctctcttgtc gggctagtca gggcattaga ggtaatttag actggtatca gcagaaacca     120
ggtggaacta ttaaactcct gatctactcc acatccaatt taaattctgg tgtcccatca     180
aggttcagtg gcagtgggtc tgggtcagat tattctctca ccatcagcag cctagagtct     240
gaagattttg cagactatta ctgtctacag cgtgatgcgt atccgtacac gttcggaggg     300
gggaccaagc tggaaataaa a                                                321

<210> SEQ ID NO 113
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.41 Light Chain Variable Region

<400> SEQUENCE: 113

Asp Ile Gln Met Ile Gln Ser Pro Ser Ser Met Phe Ala Ser Leu Gly
1               5                   10                  15

Asp Arg Val Ser Leu Ser Cys Arg Ala Ser Gln Gly Ile Arg Gly Asn
            20                  25                  30

Leu Asp Trp Tyr Gln Gln Lys Pro Gly Gly Thr Ile Lys Leu Leu Ile
        35                  40                  45

Tyr Ser Thr Ser Asn Leu Asn Ser Gly Val Pro Ser Arg Phe Ser Gly
    50                  55                  60

Ser Gly Ser Gly Ser Asp Tyr Ser Leu Thr Ile Ser Ser Leu Glu Ser
65                  70                  75                  80

Glu Asp Phe Ala Asp Tyr Tyr Cys Leu Gln Arg Asp Ala Tyr Pro Tyr

```
                    85                  90                  95
Thr Phe Gly Gly Gly Thr Lys Leu Glu Ile Lys
            100                 105

<210> SEQ ID NO 114
<211> LENGTH: 369
<212> TYPE: DNA
<213> ORGANISM: Mus musculus
<220> FEATURE:
<221> NAME/KEY: MISC_FEATURE
<223> OTHER INFORMATION: SC34.41 Heavy Chain Variable Region

<400> SEQUENCE: 114
gaagtgaagc tggtggagtc tgggggaggc ttagtgaagc ctggagggtc cctgaaactc      60
tcctgtgcag cctctggatt cactttcact agctatacca tgtcttgggt tcgtcagact     120
ccggcgaaga ggctggagtg gtcgcaacc attagtactg gtggtggtaa cacctactat      180
ccagacattg tgaagggccg attcaccatc tccagagaca tgccaggag cacccctgtac    240 cttcaaatga gcagtctgag gtctgaggac tcggccatgt attactgtgc aagacgattc    300
tacgatggta gctacaacta ctggtacttc gatgtctggg gcgcaggac cacggtcacc    360 gtctcctca                                                             369

<210> SEQ ID NO 115
<211> LENGTH: 123
<212> TYPE: PRT
<213> ORGANISM: Mus musculus
<220> FEATURE:
<221> NAME/KEY: MISC_FEATURE
<223> OTHER INFORMATION: SC34.41 Heavy Chain Variable Region

<400> SEQUENCE: 115

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Ser Tyr
            20                  25                  30

Thr Met Ser Trp Val Arg Gln Thr Pro Ala Lys Arg Leu Glu Trp Val
        35                  40                  45

Ala Thr Ile Ser Thr Gly Gly Gly Asn Thr Tyr Tyr Pro Asp Ile Val
    50                  55                  60

Lys Gly Arg Phe Thr Ile Ser Arg Asp Asn Ala Arg Ser Thr Leu Tyr
65                  70                  75                  80

Leu Gln Met Ser Ser Leu Arg Ser Glu Asp Ser Ala Met Tyr Tyr Cys
                85                  90                  95

Ala Arg Arg Phe Tyr Asp Gly Ser Tyr Asn Tyr Trp Tyr Phe Asp Val
            100                 105                 110

Trp Gly Ala Gly Thr Thr Val Thr Val Ser Ser
        115                 120

<210> SEQ ID NO 116
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.46 Light Chain Variable Region

<400> SEQUENCE: 116
gacattgtga tgtcacagtc tccatcctcc ctagctgtgt cagttggaga gaaggttact      60
atgagctgca agtccagtca gagccttttta tatagtaaat atcaaaagaa cttcctggcc    120
```

```
tggtaccagc agaaaccagg gcagtctcct aaactgctga tttactgggc atccactagg      180
gaatctgggg tccctgatcg cttcacaggc agtggatctg ggacagattt cactctcacc      240
atcagcaatg tgaaggctga agacctggca gtttattact gtcagcagta ttataggtat      300
ccgctcacgt tcggtgctgg gaccacgctg gagctgaaa                            339
```

<210> SEQ ID NO 117
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.46 Light Chain Variable Region

<400> SEQUENCE: 117

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Lys Tyr Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Val Lys Ala Glu Asp Leu Ala Val Tyr Tyr Cys Gln Gln
                85                  90                  95

Tyr Tyr Arg Tyr Pro Leu Thr Phe Gly Ala Gly Thr Thr Leu Glu Leu
            100                 105                 110

Lys
```

<210> SEQ ID NO 118
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.46 Heavy Chain Variable Region

<400> SEQUENCE: 118

```
caggttcagc tgcagcagtc tggaactgaa ctggcgaggc cagggacttc agtgaagctg      60
tcctgcaagg cttctggata caccttcaga agctatgcta taagttgggt gagacagaga     120
actggacagg gccttgagtg gattggagag atttatcctg gaagtgataa aacttactat     180
aatgaaagct taagggcaa ggtcaccctg actacagaca atgttccag cacagccaac      240 atgcagctca ccagcctgac atctgaggac tctgcagtct atttctgtgc aagagtccat     300
gattacggtt cctggtttcc ttactggggc caagggactc tggtcactgt ctctgca        357
```

<210> SEQ ID NO 119
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.46 Heavy Chain Variable Region

<400> SEQUENCE: 119

```
Gln Val Gln Leu Gln Gln Ser Gly Thr Glu Leu Ala Arg Pro Gly Thr
1               5                   10                  15
```

Ser Val Lys Leu Ser Cys Lys Ala Ser Gly Tyr Thr Phe Arg Ser Tyr
    20                  25                  30

Ala Ile Ser Trp Val Arg Gln Arg Thr Gly Gln Gly Leu Glu Trp Ile
        35                  40                  45

Gly Glu Ile Tyr Pro Gly Ser Asp Lys Thr Tyr Tyr Asn Glu Ser Leu
50                      55                  60

Lys Gly Lys Val Thr Leu Thr Thr Asp Lys Cys Ser Ser Thr Ala Asn
65                  70                  75                  80

Met Gln Leu Thr Ser Leu Thr Ser Glu Asp Ser Ala Val Tyr Phe Cys
                85                  90                  95

Ala Arg Val His Asp Tyr Gly Ser Trp Phe Pro Tyr Trp Gly Gln Gly
                100                 105                 110

Thr Leu Val Thr Val Ser Ala
        115

<210> SEQ ID NO 120
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.48 Light Chain Variable Region

<400> SEQUENCE: 120
gacatccaga tgactcaggc tccagcctcc ctatctgcat ctgtgggaga aactgtcacc      60
atcacatgtc gaacaagtgg acatatttac agttatttag catggtatca gcagaaacag     120
ggaaaatctc ctcagttatt ggtctataat gcaaaaacct tagcagaagg tgtgtcatca     180
aggttcagtg gcagtggatc aggcacacag ttttctctga agatcaccag cctgcagcct     240
gaagattttg gagattatta ctgtcaacat cattatgata ctccgtacac gttcggaggg     300
gggaccaagc tggagataaa a                                               321

<210> SEQ ID NO 121
<211> LENGTH: 109
<212> TYPE: PRT
<213> ORGANISM: Mus musculus
<220> FEATURE:
<221> NAME/KEY: MISC_FEATURE
<223> OTHER INFORMATION: SC34.48 Light Chain Variable Region

<400> SEQUENCE: 121

Glu Val Asp Ile Gln Met Thr Gln Ala Pro Ala Ser Leu Ser Ala Ser
1               5                   10                  15

Val Gly Glu Thr Val Thr Ile Thr Cys Arg Thr Ser Gly His Ile Tyr
            20                  25                  30

Ser Tyr Leu Ala Trp Tyr Gln Gln Lys Gln Gly Lys Ser Pro Gln Leu
        35                  40                  45

Leu Val Tyr Asn Ala Lys Thr Leu Ala Glu Gly Val Ser Ser Arg Phe
    50                  55                  60

Ser Gly Ser Gly Ser Gly Thr Gln Phe Ser Leu Lys Ile Thr Ser Leu
65                  70                  75                  80

Gln Pro Glu Asp Phe Gly Asp Tyr Tyr Cys Gln His His Tyr Asp Thr
                85                  90                  95

Pro Tyr Thr Phe Gly Gly Gly Thr Lys Leu Glu Ile Lys
            100                 105

<210> SEQ ID NO 122

```
<211> LENGTH: 363
<212> TYPE: DNA
<213> ORGANISM: Mus musculus
<220> FEATURE:
<221> NAME/KEY: MISC_FEATURE
<223> OTHER INFORMATION: SC34.48 Heavy Chain Variable Region

<400> SEQUENCE: 122
gaggtccagc tgcaacagtc tggacttgag atggtgaagc ctggggcttc agtgaagata    60
tcctgcaagg cttctggata catattcact gactactaca tgcactgggt gaagcagagc   120
catggaaaga gccttgactg gattggacgt gttaatccta aaaaaggtgg tactacctac   180
aaccagaagt tcgagggcaa ggccacattg actgttgaca gtcctccag cacagcctac    240 atggacctca acagcctgac atctgaggac tctgcggtct attactgtgc aatgggtatc   300
tactttagtt acgacgcctc ctttgactac tggggccaag gcaccactct cacagtctcc   360
tca                                                                  363

<210> SEQ ID NO 123
<211> LENGTH: 121
<212> TYPE: PRT
<213> ORGANISM: Mus musculus
<220> FEATURE:
<221> NAME/KEY: MISC_FEATURE
<223> OTHER INFORMATION: SC34.48 Heavy Chain Variable Region

<400> SEQUENCE: 123

Glu Val Gln Leu Gln Gln Ser Gly Leu Glu Met Val Lys Pro Gly Ala
1               5                   10                  15

Ser Val Lys Ile Ser Cys Lys Ala Ser Gly Tyr Ile Phe Thr Asp Tyr
            20                  25                  30

Tyr Met His Trp Val Lys Gln Ser His Gly Lys Ser Leu Asp Trp Ile
        35                  40                  45

Gly Arg Val Asn Pro Lys Lys Gly Gly Thr Thr Tyr Asn Gln Lys Phe
    50                  55                  60

Glu Gly Lys Ala Thr Leu Thr Val Asp Lys Ser Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Met Gly Ile Tyr Phe Ser Tyr Asp Ala Ser Phe Asp Tyr Trp Gly
            100                 105                 110

Gln Gly Thr Thr Leu Thr Val Ser Ser
        115                 120

<210> SEQ ID NO 124
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.49 Light Chain Variable Region

<400> SEQUENCE: 124
gacatccaga tgacacaatc ttcatcctac ttgtctgtat ctctaggagg cagagtcacc    60
attacttgca aggcaagtga acacattaat aattggttag cctggtatca gcagaaacca   120
ggaaatcctc ctaggctctt aatatctggt gcaaccagtt tggaaactgg ggttccttca   180
agattcagtg gcagtggatc tggaaaggat tacactctca gcattaccgg tcttcagact   240
gaagatattg ctacttattt ctgtcaacag tatcggagta ctccattcac gttcggctcg   300
```

```
gggacaaagt tggaaataaa a                                              321
```

<210> SEQ ID NO 125
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.49 Light Chain Variable Region

<400> SEQUENCE: 125

```
Asp Ile Gln Met Thr Gln Ser Ser Tyr Leu Ser Val Ser Leu Gly
1               5                   10                  15

Gly Arg Val Thr Ile Thr Cys Lys Ala Ser Glu His Ile Asn Asn Trp
            20                  25                  30

Leu Ala Trp Tyr Gln Gln Lys Pro Gly Asn Pro Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Gly Leu Gln Thr
65                  70                  75                  80

Glu Asp Ile Ala Thr Tyr Phe Cys Gln Gln Tyr Arg Ser Thr Pro Phe
                85                  90                  95

Thr Phe Gly Ser Gly Thr Lys Leu Glu Ile Lys
            100                 105
```

<210> SEQ ID NO 126
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.49 Heavy Chain Variable Region

<400> SEQUENCE: 126

```
gaggtccagc tgcaacagtc tggacctgag ctggtgaagc ctgggtcttc agtgaagata    60
tcctgtaagg cttctggata cacattcact gactaccaca tgaactgggt gaagcagagc   120
catggaaaga gccttgagtg gattggaaat attaatcctt actatggtgt tagtacctac   180
aaccagaact taaagggcac ggccacattg actgtagaca gtcctccag cacagcctac    240 atggagctcc gcggcctgac atctgaggac tctgcagtct attactgtgt aagaagggct   300
atggattccc ccggtttgc ttactggggc caagggactc tggtcactgt ctctgca      357
```

<210> SEQ ID NO 127
<211> LENGTH: 120
<212> TYPE: PRT
<213> ORGANISM: Mus musculus
<220> FEATURE:
<221> NAME/KEY: MISC_FEATURE
<223> OTHER INFORMATION: SC34.49 Heavy Chain Variable Region

<400> SEQUENCE: 127

```
Gln Glu Val Gln Leu Gln Gln Ser Gly Pro Glu Leu Val Lys Pro Gly
1               5                   10                  15

Ser Ser Val Lys Ile Ser Cys Lys Ala Ser Gly Tyr Thr Phe Thr Asp
            20                  25                  30

Tyr His Met Asn Trp Val Lys Gln Ser His Gly Lys Ser Leu Glu Trp
        35                  40                  45

Ile Gly Asn Ile Asn Pro Tyr Tyr Gly Val Ser Thr Tyr Asn Gln Asn
    50                  55                  60
```

Leu Lys Gly Thr Ala Thr Leu Thr Val Asp Lys Ser Ser Thr Ala
65                  70                  75                  80

Tyr Met Glu Leu Arg Gly Leu Thr Ser Glu Asp Ser Ala Val Tyr Tyr
            85                  90                  95

Cys Val Arg Arg Ala Met Asp Ser Pro Arg Phe Ala Tyr Trp Gly Gln
            100                 105                 110

Gly Thr Leu Val Thr Val Ser Ala
        115                 120

<210> SEQ ID NO 128
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.50 Light Chain Variable Region

<400> SEQUENCE: 128
gacatccaga tgacacaatc ttcatcctcc ttttctgtat ctctaggaga cagagtcacc     60
attacttgca aggcaagtga ggacatatat aatcggttag cctggtatca gcagaaacca    120
ggaaatgctc ctaggctctt aatatctggt gcgaccagtt tggaaactgg ggttccttca    180
agattcagtg gcagtggatc tggaaaggat tacactctca gcattaccag tcttcagact    240
gaagatgttg ctacttatta ctgtcaacag tattggagta ctatattcac gttcggctcg    300
gggacaaagt tggaaataaa a                                              321

<210> SEQ ID NO 129
<211> LENGTH: 108
<212> TYPE: PRT
<213> ORGANISM: Mus musculus
<220> FEATURE:
<221> NAME/KEY: MISC_FEATURE
<223> OTHER INFORMATION: SC34.50 Light Chain Variable Region

<400> SEQUENCE: 129

Gln Asp Ile Gln Met Thr Gln Ser Ser Ser Phe Ser Val Ser Leu
1               5                   10                  15

Gly Asp Arg Val Thr Ile Thr Cys Lys Ala Ser Glu Asp Ile Tyr Asn
            20                  25                  30

Arg Leu Ala Trp Tyr Gln Gln Lys Pro Gly Asn Ala Pro Arg Leu Leu
        35                  40                  45

Ile Ser Gly Ala Thr Ser Leu Glu Thr Gly Val Pro Ser Arg Phe Ser
50                  55                  60

Gly Ser Gly Ser Gly Lys Asp Tyr Thr Leu Ser Ile Thr Ser Leu Gln
65                  70                  75                  80

Thr Glu Asp Val Ala Thr Tyr Tyr Cys Gln Gln Tyr Trp Ser Thr Ile
            85                  90                  95

Phe Thr Phe Gly Ser Gly Thr Lys Leu Glu Ile Lys
            100                 105

<210> SEQ ID NO 130
<211> LENGTH: 354
<212> TYPE: DNA
<213> ORGANISM: Mus musculus
<220> FEATURE:
<221> NAME/KEY: MISC_FEATURE
<223> OTHER INFORMATION: SC34.50 Heavy Chain Variable Region

<400> SEQUENCE: 130

```
caggtccaac tgcagcagcc tggggctgag ctggtgaggc ctggggcttc agtgaagctg    60
tcctgcaagg cttctggcta caccttcacc agctactgga taaactgggt gaaacagagg   120
cctggacaag gccttgagtg gatcggaaat attttccctt ctgatagtta ctaactac    180 aatcaaaagt tcaggacaa ggccacattg actgtagaca atcctccag cacagcctac    240 atgcagctca gcagcccgac atctgaggac tctgcggtct attactgtac aatccgtacc   300
tatggtaact actttgacta ctggggccaa ggcaccactc tcacagtctc ctca          354
```

```
<210> SEQ ID NO 131
<211> LENGTH: 118
<212> TYPE: PRT
<213> ORGANISM: Mus musculus
<220> FEATURE:
<221> NAME/KEY: MISC_FEATURE
<223> OTHER INFORMATION: SC34.50 Heavy Chain Variable Region

<400> SEQUENCE: 131
```

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Phe Pro Ser Asp Ser Tyr Thr Asn Tyr Asn Gln Lys Phe
    50                  55                  60

Arg Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Ile Arg Thr Tyr Gly Asn Tyr Phe Asp Tyr Trp Gly Gln Gly Thr
            100                 105                 110

Thr Leu Thr Val Ser Ser
        115

```
<210> SEQ ID NO 132
<211> LENGTH: 336
<212> TYPE: DNA
<213> ORGANISM: Mus musculus
<220> FEATURE:
<221> NAME/KEY: MISC_FEATURE
<223> OTHER INFORMATION: SC34.53 Light Chain Variable Region

<400> SEQUENCE: 132
gatgttgtgc tgacccagac tccactcact ttgtcggtta ccattggaca accagcctct    60
atctcttgca gtcaagtca gagcctctta tatagtaata agaaaccta tttgaattgg    120 ttattacaga ggccaggcca gtctccaaag cgcctaatct atctggtgtc taaactggac   180
tctggagtcc ctgacaggtt cactggcagt ggatcgggaa cagatttac actgaaaatc    240 accagggtgg aggctgagga tttgggagtt tattactgcg tacaaggtac acattttccg   300
tacacgttcg gtactgggac caagctggag atcaaa                              336
```

```
<210> SEQ ID NO 133
<211> LENGTH: 112
<212> TYPE: PRT
<213> ORGANISM: Mus musculus
<220> FEATURE:
<221> NAME/KEY: MISC_FEATURE
<223> OTHER INFORMATION: SC34.53 Light Chain Variable Region
```

<400> SEQUENCE: 133

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Arg Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Thr Arg Val Glu Ala Glu Asp Leu Gly Val Tyr Tyr Cys Val Gln Gly
                85                  90                  95

Thr His Phe Pro Tyr Thr Phe Gly Thr Gly Thr Lys Leu Glu Ile Lys
            100                 105                 110

<210> SEQ ID NO 134
<211> LENGTH: 366
<212> TYPE: DNA
<213> ORGANISM: Mus musculus
<220> FEATURE:
<221> NAME/KEY: MISC_FEATURE
<223> OTHER INFORMATION: SC34.53 Heavy Chain Variable Region

<400> SEQUENCE: 134
caggtccaac tgcagcagcc tggggctgaa ctggtgaagc ctggggcttc agtgacattg      60
tcttgcaagg cttctggcta ccttcacc agctactata tctactgggt gaagcagagg      120
cctggagaag gccttgagtg gattggagag attgatccta gcaatggtgg tcctaacttc      180
aatgacagat tcaagaacaa ggccacactg actgttgaca atcctccag cacagcctac      240 atgcaactca gcagcctgac atctgaggac tctgcggtct attactgtac aagaggcctg      300
ctctactatg attacgacag ggggtttgct tactggggcc aagggactct ggtcactgtc      360
tctgca                                                                 366

<210> SEQ ID NO 135
<211> LENGTH: 123
<212> TYPE: PRT
<213> ORGANISM: Mus musculus
<220> FEATURE:
<221> NAME/KEY: MISC_FEATURE
<223> OTHER INFORMATION: SC34.53 Heavy Chain Variable Region

<400> SEQUENCE: 135

Glu Gln Val Gln Leu Gln Gln Pro Gly Ala Glu Leu Val Lys Pro Gly
1               5                   10                  15

Ala Ser Val Thr Leu Ser Cys Lys Ala Ser Gly Tyr Thr Phe Thr Ser
            20                  25                  30

Tyr Tyr Ile Tyr Trp Val Lys Gln Arg Pro Gly Glu Gly Leu Glu Trp
        35                  40                  45

Ile Gly Glu Ile Asp Pro Ser Asn Gly Gly Pro Asn Phe Asn Asp Arg
    50                  55                  60

Phe Lys Asn Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Thr Arg Gly Leu Leu Tyr Tyr Asp Tyr Asp Arg Gly Phe Ala Tyr
            100                 105                 110

Trp Gly Gln Gly Thr Leu Val Thr Val Ser Ala
        115                  120

<210> SEQ ID NO 136
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.58 Light Chain Variable Region

<400> SEQUENCE: 136

```
gacattgtga tgtctcagtc tccatcctcc ctagctgtgt cagttggaga aaggttact      60 atgagctgca agtccagtca gagccttta tatagtcgca atcaaaagaa ctacctggcc     120
tggtaccagc agaaaccagg gcagtctcct aaactgctga tttactgggc atccactagg    180
gaatctgggg tccctgatcg cttcacaggc agtggatctg gacagattt cactctcacc     240 atcagcagtg tgaaggctga agacctggca gtttattact gtcaccaaca ttataggtat    300
ccgctcacgt tcggtgctgg gaccaagctg gaactgaga                            339
```

<210> SEQ ID NO 137
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.58 Light Chain Variable Region

<400> SEQUENCE: 137

Asp Ile Val Met Ser Gln Ser Pro Ser Ser Leu Ala Val Ser Val Gly
1              5                  10               15

Glu Lys Val Thr Met Ser Cys Lys Ser Ser Gln Ser Leu Leu Tyr Ser
          20                  25                  30

Arg Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65              70                  75                  80

Ile Ser Ser Val Lys Ala Glu Asp Leu Ala Val Tyr Tyr Cys His Gln
             85                  90                  95

His Tyr Arg Tyr Pro Leu Thr Phe Gly Ala Gly Thr Lys Leu Glu Leu
             100                105              110

Arg

<210> SEQ ID NO 138
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.58 Heavy Chain Variable Region

<400> SEQUENCE: 138

```
caggttcagc tgcagcagtc tggagctgag ctggcgaggc caggggcttc agtgaagctg      60
tcctgcaagg cttctggata caccttcaca agctatggtg taaactgggt gaagcagaga    120
actggacagg gccttgagtg gattggagag atttatcctg gaagaggtga tgtttactac    180
aatgacaatt tcaagggcaa ggccacactg actacagaca atcctccag cacagcctac     240
```

```
atgcagctca gcagtctgac atctgaggac tctgcagtct atttctgtgc aagagtccat    300
gattacggtt cctggtttcc ttactggggc caagggactc tggtcactgt ctctgca      357
```

<210> SEQ ID NO 139
<211> LENGTH: 120
<212> TYPE: PRT
<213> ORGANISM: Mus musculus
<220> FEATURE:
<221> NAME/KEY: MISC_FEATURE
<223> OTHER INFORMATION: SC34.58 Heavy Chain Variable Region

<400> SEQUENCE: 139

Glu Gln Val Gln Leu Gln Gln Ser Gly Ala Glu Leu Ala Arg Pro Gly
1               5                   10                  15

Ala Ser Val Lys Leu Ser Cys Lys Ala Ser Gly Tyr Thr Phe Thr Ser
            20                  25                  30

Tyr Gly Val Asn Trp Val Lys Gln Arg Thr Gly Gln Gly Leu Glu Trp
        35                  40                  45

Ile Gly Glu Ile Tyr Pro Gly Arg Gly Asp Val Tyr Tyr Asn Asp Asn
    50                  55                  60

Phe Lys Gly Lys Ala Thr Leu Thr Thr Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Val His Asp Tyr Gly Ser Trp Phe Pro Tyr Trp Gly Gln
            100                 105                 110

Gly Thr Leu Val Thr Val Ser Ala
        115                 120

<210> SEQ ID NO 140
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.63 Light Chain Variable Region

<400> SEQUENCE: 140

```
gacattgtga tgtcacagtc tccatcctcc ctagctgtgt cagttggaga gaaggttact    60
atgagctgca gtccagtca gagccttttta tatagtaaat atcaaaagaa ctacttggcc   120
tggtaccagc agaaaccagg gcagtctcct aaattgctga tttactgggc atccactagg   180
gaatctgggg tccctgatcg cttcacaggc agtgaatctg ggacagattt cactctcacc   240
atcagcagtg tgaaggctga agacctggca gtttattact gtcaacaata ttataggtat   300
ccgctcacgg tcggagctgg gaccaagctg gagctgaaa                          339
```

<210> SEQ ID NO 141
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.63 Light Chain Variable Region

<400> SEQUENCE: 141

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Lys Tyr Gln Lys Asn Tyr Leu Ala Trp Tyr Gln Gln Lys Pro Gly Gln
                35                  40                  45

Ser Pro Lys Leu Leu Ile Tyr Trp Ala Ser Thr Arg Glu Ser Gly Val
    50                  55                  60

Pro Asp Arg Phe Thr Gly Ser Glu Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Val Gly Ala Gly Thr Lys Leu Glu Leu
            100                 105                 110

Lys

<210> SEQ ID NO 142
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.63 Heavy Chain Variable Region

<400> SEQUENCE: 142
caggttcaac tgcagcagtc tggagttgag ctggcgaggc caggggcttc agtgaagctg      60
tcctgtaagg cttctggata caccttcaca agctatggta ttgattgggt gaaacagaga     120
actggacagg gccttgagtg gattggagag acttatcctg gaagaggtga tacttactac     180
aatgaaaact tcaagggcaa ggccacactg actacagaca atcctccag cacagccttc      240 ttacagctca gcagcctgac atctgaggac tctgcagtct atttctgtgc aagagtccat     300
gattacggtt cctggtttcc ttactggggc caagggactc tggtcactgt ctctgca        357

<210> SEQ ID NO 143
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.63 Heavy Chain Variable Region

<400> SEQUENCE: 143

Gln Val Gln Leu Gln Gln Ser Gly Val Glu Leu Ala Arg Pro Gly Ala
1               5                   10                  15

Ser Val Lys Leu Ser Cys Lys Ala Ser Gly Tyr Thr Phe Thr Ser Tyr
                20                  25                  30

Gly Ile Asp Trp Val Lys Gln Arg Thr Gly Gln Gly Leu Glu Trp Ile
            35                  40                  45

Gly Glu Thr Tyr Pro Gly Arg Gly Asp Thr Tyr Tyr Asn Glu Asn Phe
    50                  55                  60

Lys Gly Lys Ala Thr Leu Thr Thr Asp Lys Ser Ser Ser Thr Ala Phe
65                  70                  75                  80

Leu Gln Leu Ser Ser Leu Thr Ser Glu Asp Ser Ala Val Tyr Phe Cys
                85                  90                  95

Ala Arg Val His Asp Tyr Gly Ser Trp Phe Pro Tyr Trp Gly Gln Gly
            100                 105                 110

Thr Leu Val Thr Val Ser Ala
        115

<210> SEQ ID NO 144
<211> LENGTH: 339

```
<212> TYPE: DNA
<213> ORGANISM: Mus musculus
<220> FEATURE:
<221> NAME/KEY: MISC_FEATURE
<223> OTHER INFORMATION: SC34.67 Light Chain Variable Region

<400> SEQUENCE: 144
gacatggtga tgtcacagtc tccatcctcc ctagctgtgt cagttgggga gaaggttgct    60
ctgagctgca agtccagtca gagccttta catagtagag atcaaaagaa ctacctggcc   120
tggtaccagc agaaaccagg gcagtctcct aaactgctga ttcactgggc atccactagg   180
gaatctgggg tccctgctcg cttcacaggc agtggatctg ggacagattt cactctcacc   240
atcagcagtg tgaaggctga agacctggca gtttattact gtcagcaatc ttataggtat   300
ccgctcacgt tcggtgctgg gaccaagctg gagctgaaa                          339

<210> SEQ ID NO 145
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.67 Light Chain Variable Region

<400> SEQUENCE: 145

Asp Met Val Met Ser Gln Ser Pro Ser Ser Leu Ala Val Ser Val Gly
1               5                   10                  15

Glu Lys Val Ala Leu Ser Cys Lys Ser Ser Gln Ser Leu Leu His Ser
            20                  25                  30

Arg Asp Gln Lys Asn Tyr Leu Ala Trp Tyr Gln Gln Lys Pro Gly Gln
        35                  40                  45

Ser Pro Lys Leu Leu Ile His Trp Ala Ser Thr Arg Glu Ser Gly Val
    50                  55                  60

Pro Ala Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Ser Tyr Arg Tyr Pro Leu Thr Phe Gly Ala Gly Thr Lys Leu Glu Leu
            100                 105                 110

Lys

<210> SEQ ID NO 146
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.67 Heavy Chain Variable Region

<400> SEQUENCE: 146
caggttcagc tgcagcagtc tggagctgag ctggcgaggc caggggcttc agtgagactg    60
tcctgcaagg cttctggata caccttcaca agctatggta aaactgggt gaagcagaga   120 actggacagg gccttgagtg gattgggag atttatcctg gaagtggtga cagttactac   180
aataagacgt tcaagggcaa ggccatattg actacagaca atcctccag cacagcctac   240 atgcagctca gcagcctgac acctgaggac tctgcagtct atttctgtgc aagagtccat   300
gattacggtt cctggtttcc ttactgggggc ccaggggctc tggtcactgt ctctgca    357

<210> SEQ ID NO 147
```

```
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.67 Heavy Chain Variable Region

<400> SEQUENCE: 147

Gln Val Gln Leu Gln Gln Ser Gly Ala Glu Leu Ala Arg Pro Gly Ala
1               5                   10                  15

Ser Val Arg Leu Ser Cys Lys Ala Ser Gly Tyr Thr Phe Thr Ser Tyr
            20                  25                  30

Gly Ile Asn Trp Val Lys Gln Arg Thr Gly Gln Gly Leu Glu Trp Ile
        35                  40                  45

Gly Glu Ile Tyr Pro Gly Ser Gly Asp Ser Tyr Asn Lys Thr Phe
    50                  55                  60

Lys Gly Lys Ala Ile Leu Thr Thr Asp Lys Ser Ser Thr Ala Tyr
65                  70                  75                  80

Met Gln Leu Ser Ser Leu Thr Pro Glu Asp Ser Ala Val Tyr Phe Cys
                85                  90                  95

Ala Arg Val His Asp Tyr Gly Ser Trp Phe Pro Tyr Trp Gly Pro Gly
            100                 105                 110

Ala Leu Val Thr Val Ser Ala
        115

<210> SEQ ID NO 148
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.71 Light Chain Variable Region

<400> SEQUENCE: 148
gacattgtga tgacccagtc tcaaaaattc atgtccacat cagtaggaga cagggtcagc     60
atcacctgca aggccagtca gaatgttcgt actgctgtag cctggtatca acagaaacca    120
gggcagtctc ctaaaacact gatttacttg gcatccaacc ggcacactgg agtccctgat    180
cgcttcacag gcagtggatc tgggacagat ttcactctca ccattagcta tgtgcaatct    240
gaagacctgg cagattattt ctgtctgcaa catttgaatt atccgtggac gttcggtgga    300
ggcaccaagc tggaaatcaa a                                              321

<210> SEQ ID NO 149
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.71 Light Chain Variable Region

<400> SEQUENCE: 149

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Thr Leu Ile
        35                  40                  45

Tyr Leu Ala Ser Asn Arg His Thr Gly Val Pro Asp Arg Phe Thr Gly
    50                  55                  60
```

```
Ser Gly Ser Gly Thr Asp Phe Thr Leu Thr Ile Ser Tyr Val Gln Ser
 65                  70                  75                  80

Glu Asp Leu Ala Asp Tyr Phe Cys Leu Gln His Leu Asn Tyr Pro Trp
                 85                  90                  95

Thr Phe Gly Gly Gly Thr Lys Leu Glu Ile Lys
            100                 105
```

<210> SEQ ID NO 150
<211> LENGTH: 369
<212> TYPE: DNA
<213> ORGANISM: Mus musculus
<220> FEATURE:
<221> NAME/KEY: MISC_FEATURE
<223> OTHER INFORMATION: SC34.71 Heavy Chain Variable Region

<400> SEQUENCE: 150

```
caggtttctc tgaaagagtc gggccctggg atattgcagc cctcccagac cctcagtctg     60
acttgttctt tctttgggtt ttcactgagc acttctagta tgggtgtagg gtggattcgt    120
cagccttcag ggaagggtct ggagtggctg gcaaacattt ggtgggataa taataaatac    180
tataacgcag ccctgaagag ccggctcaca atctccaagg atacctccaa aaaccaggtt    240
ttcctcaaca tcgccagtgt ggacactaca gatactgcca catactactg tgctcgaata    300
gaatcctact atagtaatcg ggcctggttt ccttactggg gccgagggac tctggtcact    360
gtctctgca                                                            369
```

<210> SEQ ID NO 151
<211> LENGTH: 123
<212> TYPE: PRT
<213> ORGANISM: Mus musculus
<220> FEATURE:
<221> NAME/KEY: MISC_FEATURE
<223> OTHER INFORMATION: SC34.71 Heavy Chain Variable Region

<400> SEQUENCE: 151

```
Gln Val Ser Leu Lys Glu Ser Gly Pro Gly Ile Leu Gln Pro Ser Gln
 1               5                  10                  15

Thr Leu Ser Leu Thr Cys Ser Phe Phe Gly Phe Ser Leu Ser Thr Ser
             20                  25                  30

Ser Met Gly Val Gly Trp Ile Arg Gln Pro Ser Gly Lys Gly Leu Glu
         35                  40                  45

Trp Leu Ala Asn Ile Trp Trp Asp Asn Asn Lys Tyr Tyr Asn Ala Ala
 50                  55                  60

Leu Lys Ser Arg Leu Thr Ile Ser Lys Asp Thr Ser Lys Asn Gln Val
 65                  70                  75                  80

Phe Leu Asn Ile Ala Ser Val Asp Thr Thr Asp Thr Ala Thr Tyr Tyr
                 85                  90                  95

Cys Ala Arg Ile Glu Ser Tyr Tyr Ser Asn Arg Ala Trp Phe Pro Tyr
            100                 105                 110

Trp Gly Arg Gly Thr Leu Val Thr Val Ser Ala
            115                 120
```

<210> SEQ ID NO 152
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.76 Light Chain Variable Region

<400> SEQUENCE: 152

```
gacattgtga tgtcacagtc tccatcctcc ctagctgtgt cagttggaga gagggttacg    60
atgaactgca agtccagtca gagccttttc tatagtcgct atcaaaagaa ctacctggcc   120
tggtaccagc agaaaccagg gcagtctcct aaactgctga tttactgggc atccactagg   180
gaatctgggg tccctgatcg cttcacaggc agtggatctg ggacagattt cactctcacc   240
atcagcagtg tgaaggctga agacctggca gtttattact gtcagcaata ttataggtat   300
ccgctcacgt tcggtgctgg gaccaagctg gagctgaaa                          339
```

<210> SEQ ID NO 153
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.76 Light Chain Variable Region

<400> SEQUENCE: 153

```
Asp Ile Val Met Ser Gln Ser Pro Ser Ser Leu Ala Val Ser Val Gly
1               5                   10                  15

Glu Arg Val Thr Met Asn Cys Lys Ser Ser Gln Ser Leu Phe Tyr Ser
            20                  25                  30

Arg Tyr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys
```

<210> SEQ ID NO 154
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.76 Heavy Chain Variable Region

<400> SEQUENCE: 154

```
caggttcagc tgcagcagtc tggagctgag ctggcgaggc caggggcttc agtgaagctg    60
tcctgcaaga cttctgaata caccttcaca agctatgcaa taaactgggt gaagcagaga   120
actggacagg gccttgagtg gattggagag gtttatcctg aagtggtaa tacttattac   180 aatgagaagt tcaagggcaa ggccatactg acgacagaca atcctccag cacaggctac   240 atgcagctca gcaacctgac atctgaggac tctgcagtct atttctgtgc aagagtccat   300
gattacgggt cctggtttcc ttactggggc caagggactc tggtcactgt ctctgca     357
```

<210> SEQ ID NO 155
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.76 Heavy Chain Variable Region

<400> SEQUENCE: 155

```
Gln Val Gln Leu Gln Gln Ser Gly Ala Glu Leu Ala Arg Pro Gly Ala
1               5                   10                  15
Ser Val Lys Leu Ser Cys Lys Thr Ser Glu Tyr Thr Phe Thr Ser Tyr
            20                  25                  30
Ala Ile Asn Trp Val Lys Gln Arg Thr Gly Gln Gly Leu Glu Trp Ile
        35                  40                  45
Gly Glu Val Tyr Pro Gly Ser Gly Asn Thr Tyr Tyr Asn Glu Lys Phe
    50                  55                  60
Lys Gly Lys Ala Ile Leu Thr Thr Asp Lys Ser Ser Thr Gly Tyr
65                  70                  75                  80
Met Gln Leu Ser Asn Leu Thr Ser Glu Asp Ser Ala Val Tyr Phe Cys
                85                  90                  95
Ala Arg Val His Asp Tyr Gly Ser Trp Phe Pro Tyr Trp Gly Gln Gly
            100                 105                 110
Thr Leu Val Thr Val Ser Ala
        115
```

<210> SEQ ID NO 156
<211> LENGTH: 321
<212> TYPE: DNA
<213> ORGANISM: Mus musculus
<220> FEATURE:
<221> NAME/KEY: MISC_FEATURE
<223> OTHER INFORMATION: SC34.78 Light Chain Variable Region

<400> SEQUENCE: 156

```
gacattatga tgactcagtc tccagccacg ctgtctgtga ctccaggaga tagagtctct    60
ctttcctgca gggccagcca gagtattggc gcctacttac actggtatca acaaaaatca   120
catgagtctc caaggcttct catcaaatat gtttcccaat ccatctctgg atcccctcc    180
aggttcagtg gcagtggatc agggtcagat ttcactctca gtatcaacag tgtggaacct   240
gaagatgttg gagtgtatta ctgtcaaaat ggtcacagct ttccgctcac gttcggtgct   300
gggaccaagc tggagcttaa a                                             321
```

<210> SEQ ID NO 157
<211> LENGTH: 107
<212> TYPE: PRT
<213> ORGANISM: Mus musculus
<220> FEATURE:
<221> NAME/KEY: MISC_FEATURE
<223> OTHER INFORMATION: SC34.78 Light Chain Variable Region

<400> SEQUENCE: 157

```
Asp Ile Met Met Thr Gln Ser Pro Ala Thr Leu Ser Val Thr Pro Gly
1               5                   10                  15
Asp Arg Val Ser Leu Ser Cys Arg Ala Ser Gln Ser Ile Gly Ala Tyr
            20                  25                  30
Leu His Trp Tyr Gln Gln Lys Ser His Glu Ser Pro Arg Leu Leu Ile
        35                  40                  45
Lys Tyr Val Ser Gln Ser Ile Ser Gly Ile Pro Ser Arg Phe Ser Gly
    50                  55                  60
Ser Gly Ser Gly Ser Asp Phe Thr Leu Ser Ile Asn Ser Val Glu Pro
65                  70                  75                  80
Glu Asp Val Gly Val Tyr Tyr Cys Gln Asn Gly His Ser Phe Pro Leu
                85                  90                  95
Thr Phe Gly Ala Gly Thr Lys Leu Glu Leu Lys
        100                 105
```

```
                100             105
```

<210> SEQ ID NO 158
<211> LENGTH: 354
<212> TYPE: DNA
<213> ORGANISM: Mus musculus
<220> FEATURE:
<221> NAME/KEY: MISC_FEATURE
<223> OTHER INFORMATION: SC34.78 Heavy Chain Variable Region

<400> SEQUENCE: 158

```
gatgtgcagc ttcaggagtc gggacgtggc ctggtgaaac cttctcagtc tctgtccctc      60
acctgcactg tcactggcta ctcactcacc agtgattttg cctggaactg gatccggcag     120
tttccaggaa acaaactgga gtggatgggc tacataaggt acagtggtac cactagctac     180
aatccatctc tcaaaagtcg aatctctatc actcgagaca catccaagaa ccagttcttc     240
ctgcagttga attctgtgac aactgaggac acagccacat attactgtgg ctatggtaac     300
tacgggtatg ctatggacta ctggggtcaa ggaacctcag tcaccgtctc ctca           354
```

<210> SEQ ID NO 159
<211> LENGTH: 118
<212> TYPE: PRT
<213> ORGANISM: Mus musculus
<220> FEATURE:
<221> NAME/KEY: MISC_FEATURE
<223> OTHER INFORMATION: SC34.78 Heavy Chain Variable Region

<400> SEQUENCE: 159

```
Asp Val Gln Leu Gln Glu Ser Gly Arg Gly Leu Val Lys Pro Ser Gln
1               5                   10                  15

Ser Leu Ser Leu Thr Cys Thr Val Thr Gly Tyr Ser Leu Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Arg Tyr Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Gly Tyr Gly Asn Tyr Gly Tyr Ala Met Asp Tyr Trp Gly Gln Gly Thr
            100                 105                 110

Ser Val Thr Val Ser Ser
        115
```

<210> SEQ ID NO 160
<211> LENGTH: 318
<212> TYPE: DNA
<213> ORGANISM: Mus musculus
<220> FEATURE:
<221> NAME/KEY: MISC_FEATURE
<223> OTHER INFORMATION: SC34.83 Light Chain Variable Region

<400> SEQUENCE: 160

```
caaattgttc tcatccagtc tccagcaatc atgtctgcat ctccagggga gaatgtcacc      60
atgacctgca gtgccagttc aagtgtaagt tacatgcact ggtaccagca gaagtctggc     120
acctccccca aaagatggat ttatgacaca tccaaactgg cttctggagt ccctgctcgc     180
ttcagtggca gtgggtctgg gacctcttac tctctcacaa tcagcagcat ggaggctgaa     240
```

```
gatgctgcca cttattattg ccagcagtgg aatagttacc cacccacgtt cggtgctggg    300
accaagctgg agctgaaa                                                  318
```

<210> SEQ ID NO 161
<211> LENGTH: 106
<212> TYPE: PRT
<213> ORGANISM: Mus musculus
<220> FEATURE:
<221> NAME/KEY: MISC_FEATURE
<223> OTHER INFORMATION: SC34.83 Light Chain Variable Region

<400> SEQUENCE: 161

```
Gln Ile Val Leu Ile Gln Ser Pro Ala Ile Met Ser Ala Ser Pro Gly
 1               5                  10                  15

Glu Asn Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                 70                  75                  80

Asp Ala Ala Thr Tyr Tyr Cys Gln Gln Trp Asn Ser Tyr Pro Pro Thr
                85                  90                  95

Phe Gly Ala Gly Thr Lys Leu Glu Leu Lys
            100                 105
```

<210> SEQ ID NO 162
<211> LENGTH: 363
<212> TYPE: DNA
<213> ORGANISM: Mus musculus
<220> FEATURE:
<221> NAME/KEY: MISC_FEATURE
<223> OTHER INFORMATION: SC34.83 Heavy Chain Variable Region

<400> SEQUENCE: 162

```
caggttcagc tgcagcagtc tggggctgag ctggtgaagc ctggggcctc agtgaagata    60
tcctgcaaag cttctggcta cgcattcagt cactcctgga tgaactgggt gaagcagagg   120
cctggaaagg gtcttgagtg gattggacgg atttatcctg agatggaga tattaattat    180 aatgggaagt tcaagggcaa agccacactg actcagaca gtcctccag cacagcctac     240 atgcaactca gcagcctgac atctgaggac tctgcggtct acttctgtgc aagaaggggc   300
ccctcctata taattactg ttttgactat tggggccaag gcaccactct cacagtctcc    360
tca                                                                  363
```

<210> SEQ ID NO 163
<211> LENGTH: 121
<212> TYPE: PRT
<213> ORGANISM: Mus musculus
<220> FEATURE:
<221> NAME/KEY: MISC_FEATURE
<223> OTHER INFORMATION: SC34.83 Heavy Chain Variable Region

<400> SEQUENCE: 163

```
Gln Val Gln Leu Gln Gln Ser Gly Ala Glu Leu Val Lys Pro Gly Ala
 1               5                  10                  15

Ser Val Lys Ile Ser Cys Lys Ala Ser Gly Tyr Ala Phe Ser His Ser
                20                  25                  30

Trp Met Asn Trp Val Lys Gln Arg Pro Gly Lys Gly Leu Glu Trp Ile
```

```
                35                  40                  45
Gly Arg Ile Tyr Pro Gly Asp Gly Asp Ile Asn Tyr Asn Gly Lys Phe
        50                  55                  60
Lys Gly Lys Ala Thr Leu Thr Ala Asp Lys Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Arg Gly Pro Ser Tyr Asn Asn Tyr Cys Phe Asp Tyr Trp Gly
            100                 105                 110
Gln Gly Thr Thr Leu Thr Val Ser Ser
            115                 120

<210> SEQ ID NO 164
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.86 Light Chain Variable Region

<400> SEQUENCE: 164
gacactgtga tgtcacagtc tccatcctcc ctagcggtgt cagttggaga aaaggttact      60
ctgagctgca agtccagtca gagccttttta tatagtaggt atcaaaagaa ctacctggcc    120
tggtaccagc agaaaccagg gcagtctcct aaattgctgc tttactgggc atccactagg    180
gaatctgggg tccctgaccg cttcacaggc agtggatctg ggacagattt cactctcacc    240
atcagcagtg tgaaggctga agacctggca gtttattact gtcagcaaca ttataggtat    300
ccgctcacgt tcggtgctgg gaccaagctg gagctgaaa                           339

<210> SEQ ID NO 165
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.86 Light Chain Variable Region

<400> SEQUENCE: 165

Asp Thr Val Met Ser Gln Ser Pro Ser Ser Leu Ala Val Ser Val Gly
1               5                   10                  15
Glu Lys Val Thr Leu Ser Cys Lys Ser Ser Gln Ser Leu Leu Tyr Ser
                20                  25                  30
Arg Tyr Gln Lys Asn Tyr Leu Ala Trp Tyr Gln Gln Lys Pro Gly Gln
            35                  40                  45
Ser Pro Lys Leu Leu Leu Tyr Trp Ala Ser Thr Arg Glu Ser Gly Val
        50                  55                  60
Pro Asp Arg Phe Thr Gly Ser Gly Ser Gly Thr Asp Phe Thr Leu Thr
65                  70                  75                  80
Ile Ser Ser Val Lys Ala Glu Asp Leu Ala Val Tyr Tyr Cys Gln Gln
                85                  90                  95
His Tyr Arg Tyr Pro Leu Thr Phe Gly Ala Gly Thr Lys Leu Glu Leu
            100                 105                 110
Lys

<210> SEQ ID NO 166
<211> LENGTH: 357
<212> TYPE: DNA
<213> ORGANISM: Mus musculus
```

<220> FEATURE:
<221> NAME/KEY: MISC_FEATURE
<223> OTHER INFORMATION: SC34.86 Heavy Chain Variable Region

<400> SEQUENCE: 166

```
caggttcagc tgcagcagtc tggagctgag ctggcgaggc caggggcttc agtgaagctg      60
tcctgtaagg cttctggata caccttcaca agctatacta taacctgggt gaagcagaga     120
actggacagg gccttgagtg gattggagag atttatcctg gaagtggtaa tacttactac     180
aatgagaagt tcaagggcaa ggccacactg actacagaca atcctccag cacagcctac     240
atgcagctca gcagcctgac atctgaggac tctgcagtct atttctgtgc aagagtccat     300
gattacggtt cctggtttcc ttactgggc caagggactc tggtcactgt ctctgca        357
```

<210> SEQ ID NO 167
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.86 Heavy Chain Variable Region

<400> SEQUENCE: 167

Gln Val Gln Leu Gln Gln Ser Gly Ala Glu Leu Ala Arg Pro Gly Ala
1               5                  10                  15

Ser Val Lys Leu Ser Cys Lys Ala Ser Gly Tyr Thr Phe Thr Ser Tyr
            20                  25                  30

Thr Ile Thr Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Val His Asp Tyr Gly Ser Trp Phe Pro Tyr Trp Gly Gln Gly
            100                 105                 110

Thr Leu Val Thr Val Ser Ala
        115

<210> SEQ ID NO 168
<211> LENGTH: 336
<212> TYPE: DNA
<213> ORGANISM: Mus musculus
<220> FEATURE:
<221> NAME/KEY: MISC_FEATURE
<223> OTHER INFORMATION: SC34.87 Light Chain Variable Region

<400> SEQUENCE: 168

```
gacattgtga tgtcacagtc tccatcctcc ctggctgtgt cagcaggaga gaaggtcact      60
atgagctgca aatccagtca gagtctgctc aacagtagaa cccgaaagaa ctacttggct     120
tggtaccagc agaaaccagg gcagtctcct aaactgctga tctactgggc atccactagg     180
gaatctgggg tccctggtcg cttcacaggc agtggatctg ggacagattt cactctcacc     240
atcagcagtg tgcaggctga agacctggca gtttattact gcaagcaatc ttataatctg     300
tggacgttcg gtggaggcac caagctggaa atcaaa                              336
```

<210> SEQ ID NO 169
<211> LENGTH: 112

```
<212> TYPE: PRT
<213> ORGANISM: Mus musculus
<220> FEATURE:
<221> NAME/KEY: MISC_FEATURE
<223> OTHER INFORMATION: SC34.87 Light Chain Variable Region

<400> SEQUENCE: 169
```

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Gly Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

```
<210> SEQ ID NO 170
<211> LENGTH: 351
<212> TYPE: DNA
<213> ORGANISM: Mus musculus
<220> FEATURE:
<221> NAME/KEY: MISC_FEATURE
<223> OTHER INFORMATION: SC34.87 Heavy Chain Variable Region

<400> SEQUENCE: 170
```
caggtccagc ttcagcagtc tggggctgaa ctggcaaaac ctggggcctc agtgaagatg    60
tcctgcaagg cttctggcta caccttact agctactgga tgctctgggt aaaacagagg    120
cctggacagg gtctggaatg gattggatac attgatccta ggaatggtta tactgaatac    180
aatcagaagt tcaaggacaa ggccacattg actgcagaca atcctccag cacagcctac     240 atgcaactga gcagcctgac atctgaggac tctgcagtct attactgtac aagagggggg    300
aatgtggcta tggactactg gggtcaagga acctcagtca ccgtctcctc a             351

```
<210> SEQ ID NO 171
<211> LENGTH: 117
<212> TYPE: PRT
<213> ORGANISM: Mus musculus
<220> FEATURE:
<221> NAME/KEY: MISC_FEATURE
<223> OTHER INFORMATION: SC34.87 Heavy Chain Variable Region

<400> SEQUENCE: 171
```

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met Leu Trp Val Lys Gln Arg Pro Gly Gln Gly Leu Glu Trp Ile
        35                  40                  45

Gly Tyr Ile Asp Pro Arg Asn Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys

```
                    85                  90                  95
Thr Arg Gly Gly Asn Val Ala Met Asp Tyr Trp Gly Gln Gly Thr Ser
                100                 105                 110
Val Thr Val Ser Ser
        115

<210> SEQ ID NO 172
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.89 Light Chain Variable Region

<400> SEQUENCE: 172
gacattgtga tgtcacagtc tccatcctcc ctaggtgtgt ccgttggaga gaaggttacg    60
ctgagctgca agtccagtca gagccttttt aataaaagag atcaaaagaa ctacctggcc   120
tggtaccaac agaaaccagg gcagtctcct aaactgctga tttactgggc atccactagg   180
gaatctgggg tccctgatcg cttcacgggc agtggatctg gacagattt cattctcacc   240 atcaggagtg tgaaggctga agacctggca gtttattact gtcaccaatc ttataggtat   300
ccgctcacgt tcggcgctgg gaccaagctg gagctgaaa                         339

<210> SEQ ID NO 173
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.89 Light Chain Variable Region

<400> SEQUENCE: 173

Asp Ile Val Met Ser Gln Ser Pro Ser Ser Leu Gly Val Ser Val Gly
1               5                   10                  15
Glu Lys Val Thr Leu Ser Cys Lys Ser Ser Gln Ser Leu Phe Asn Lys
            20                  25                  30
Arg Asp Gln Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Ile Leu Thr
65                  70                  75                  80
Ile Arg Ser Val Lys Ala Glu Asp Leu Ala Val Tyr Tyr Cys His Gln
                85                  90                  95
Ser Tyr Arg Tyr Pro Leu Thr Phe Gly Ala Gly Thr Lys Leu Glu Leu
                100                 105                 110
Lys

<210> SEQ ID NO 174
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.89 Heavy Chain Variable Region

<400> SEQUENCE: 174
caggttcagc tgcagcagtc tggagctgag ctggcgaggc caggggcttc agtgaagctg    60
tcctgcaagg cttctggata caccttcaca agctatgcta taagctgggt gaaacagaga   120
```

```
actagacagg gccttgagtg gattggagag atttatcctg gaagtggtga tattcactac      180
agtgggaagt tcaagggcaa ggcctcactg actacagaca atcctccag cacagcctac       240 atgcagctca gcagcctgac atctgaggac tctgcagtct atttctgtgc aagagtccat      300
gattacggtt cctggtttcc ttactggggc caagggactc tggtcactgt ctctgca        357

<210> SEQ ID NO 175
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.89 Heavy Chain Variable Region

<400> SEQUENCE: 175

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Ala Ile Ser Trp Val Lys Gln Arg Thr Arg Gln Gly Leu Glu Trp Ile
        35                  40                  45

Gly Glu Ile Tyr Pro Gly Ser Gly Asp Ile His Tyr Ser Gly Lys Phe
    50                  55                  60

Lys Gly Lys Ala Ser Leu Thr Thr Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val His Asp Tyr Gly Ser Trp Phe Pro Tyr Trp Gly Gln Gly
            100                 105                 110

Thr Leu Val Thr Val Ser Ala
        115

<210> SEQ ID NO 176
<211> LENGTH: 324
<212> TYPE: DNA
<213> ORGANISM: Mus musculus
<220> FEATURE:
<221> NAME/KEY: MISC_FEATURE
<223> OTHER INFORMATION: SC34.90 Light Chain Variable Region

<400> SEQUENCE: 176
caaattgttc tcacccagtc tccagcaatc atgtctgcat ctcaagggga acgggtcacc      60
atgacctgca ctgccagctc aagtgtaagt tccagttact tgcactggta ccagcagaag     120
ccaggatcct cccccaaact ctggatttat agcacatcca acctggcttc tggagtccca     180
gttcgcttca gtggcagtgg gtctgggacc tcttactctc tcacaatcag cagcatggag     240
gctgaagatg ctgccaccta ttactgccac cagtatcatc gttccccgta cacgttcgga     300
gggggaccca agctggaaat taaa                                            324

<210> SEQ ID NO 177
<211> LENGTH: 108
<212> TYPE: PRT
<213> ORGANISM: Mus musculus
<220> FEATURE:
<221> NAME/KEY: MISC_FEATURE
<223> OTHER INFORMATION: SC34.90 Light Chain Variable Region

<400> SEQUENCE: 177

Gln Ile Val Leu Thr Gln Ser Pro Ala Ile Met Ser Ala Ser Gln Gly
```

```
1               5                   10                  15
Glu Arg Val Thr Met Thr Cys Thr Ala Ser Ser Ser Val Ser Ser
            20                  25                  30
Tyr Leu His Trp Tyr Gln Gln Lys Pro Gly Ser Ser Pro Lys Leu Trp
            35                  40                  45
Ile Tyr Ser Thr Ser Asn Leu Ala Ser Gly Val Pro Val Arg Phe Ser
    50                  55                  60
Gly Ser Gly Ser Gly Thr Ser Tyr Ser Leu Thr Ile Ser Ser Met Glu
65                  70                  75                  80
Ala Glu Asp Ala Ala Thr Tyr Tyr Cys His Gln Tyr His Arg Ser Pro
                85                  90                  95
Tyr Thr Phe Gly Gly Gly Thr Lys Leu Glu Ile Lys
            100                 105
```

```
<210> SEQ ID NO 178
<211> LENGTH: 369
<212> TYPE: DNA
<213> ORGANISM: Mus musculus
<220> FEATURE:
<221> NAME/KEY: MISC_FEATURE
<223> OTHER INFORMATION: SC34.90 Heavy Chain Variable Region

<400> SEQUENCE: 178
caggttcagc tgcagcagtc tggagctgag ctgatgaagc ctggggcctc agtgaagata      60
tcctgcaagg ctactggcta cacattcagt tactactgga tagagtgggt aaagcagagg     120
cctggacatg gccttgagtg gattggagag atttttacctg gaagtgatac cacttactac   180
aatgagaagt tcaagggcaa ggccacattc actgcagata tcctccaa cacagcctac      240 atgcaactca gcagcctgac atctgaggac tctgccgtct attactgtac aataaggagg    300
gccgcctact atagtaaccc cgagtggttt gcttactggg gccaagggac tctggtcact    360
gtctctgca                                                            369
```

```
<210> SEQ ID NO 179
<211> LENGTH: 123
<212> TYPE: PRT
<213> ORGANISM: Mus musculus
<220> FEATURE:
<221> NAME/KEY: MISC_FEATURE
<223> OTHER INFORMATION: SC34.90 Heavy Chain Variable Region

<400> SEQUENCE: 179

Gln Val Gln Leu Gln Gln Ser Gly Ala Glu Leu Met Lys Pro Gly Ala
1               5                   10                  15
Ser Val Lys Ile Ser Cys Lys Ala Thr Gly Tyr Thr Phe Ser Tyr Tyr
            20                  25                  30
Trp Ile Glu Trp Val Lys Gln Arg Pro Gly His Gly Leu Glu Trp Ile
            35                  40                  45
Gly Glu Ile Leu Pro Gly Ser Asp Thr Thr Tyr Tyr Asn Glu Lys Phe
    50                  55                  60
Lys Gly Lys Ala Thr Phe Thr Ala Asp Thr Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Thr Ile Arg Arg Ala Ala Tyr Tyr Ser Asn Pro Glu Trp Phe Ala Tyr
            100                 105                 110
Trp Gly Gln Gly Thr Leu Val Thr Val Ser Ala
            115                 120
```

<210> SEQ ID NO 180
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.91 Light Chain Variable Region

<400> SEQUENCE: 180

```
gacattgtga tgtcacagtc tccatcctcc ctagctgtgt cagttggaga aaaggttact    60
atgagctgca agtccagtca gagccttta tatagtacct atcaaaagaa ctacctggcc   120
tggttccagc agaaaccagg gcagtctcct aaactgctga tttactgggc atccactagg   180
gaatctgggg tccctgatcg cttcacaggc agtggatctg gacagattt cactctcacc   240 atcagcagtg tgaaggctga agacctggca gtttattact gtcagcaata ttataggtat   300
ccgctcacgt tcggtgctgg gaccaagctg gagctgaaa                          339
```

<210> SEQ ID NO 181
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.91 Light Chain Variable Region

<400> SEQUENCE: 181

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Thr Tyr Gln Lys Asn Tyr Leu Ala Trp Phe Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys
```

<210> SEQ ID NO 182
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.91 Heavy Chain Variable Region

<400> SEQUENCE: 182

```
caggttcagc tgcagcagtc tggagctgag ctggcgaggc caggggcttc agtgaagctg    60
tcctgcaagg cttctggata caccttcaga agctatgcta taagctgggt gaagcagaga   120
actggacagg gccttgagtg gattggagag atttatcctg aagtggtga tacttactac   180 aatgagaact tcaagggcaa ggccacactg actacagaca aatcctccag cacagcctac   240
atgcagctca gcagcctgac atctgaggac tctgcagtct atttctgtgc aagagtccat   300
```

```
gataacggtt cctggtttcc ttactggggc caagggactc tggtcactgt ctctgca       357
```

<210> SEQ ID NO 183
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.91 Heavy Chain Variable Region

<400> SEQUENCE: 183

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Arg Ser Tyr
            20                  25                  30

Ala Ile Ser Trp Val Lys Gln Arg Thr Gly Gln Gly Leu Glu Trp Ile
        35                  40                  45

Gly Glu Ile Tyr Pro Gly Ser Gly Asp Thr Tyr Tyr Asn Glu Asn Phe
    50                  55                  60

Lys Gly Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val His Asp Asn Gly Ser Trp Phe Pro Tyr Trp Gly Gln Gly
            100                 105                 110

Thr Leu Val Thr Val Ser Ala
        115
```

<210> SEQ ID NO 184
<211> LENGTH: 339
<212> TYPE: DNA
<213> ORGANISM: Mus musculus
<220> FEATURE:
<221> NAME/KEY: MISC_FEATURE
<223> OTHER INFORMATION: SC34.95 Light Chain Variable Region

<400> SEQUENCE: 184

```
gacattgtgc tgtcacagtc tccatcctcc ctagctgtgt cagttggaga gaaggttact    60
atgagctgca agtccagtca gagccttta  aatagtaggg atcgaaagaa ctatttggcc   120
tggtgccaac aaaaaccagg acagtctcct aaagtgatga tttactgggc atccactagg   180
gaatctgggg tccctgatcg cttcacaggc agtggatctg gacagatttt cactctcacc   240
atcagcagtg tgaaggctga agacctggca gtttattact gtcagcaata ttatagctat   300
ccgctcacgg tcggtgccgg gaccaagctg gagctgaaa                          339
```

<210> SEQ ID NO 185
<211> LENGTH: 113
<212> TYPE: PRT
<213> ORGANISM: Mus musculus
<220> FEATURE:
<221> NAME/KEY: MISC_FEATURE
<223> OTHER INFORMATION: SC34.95 Light Chain Variable Region

<400> SEQUENCE: 185

```
Asp Ile Val Leu Ser Gln Ser Pro Ser Ser Leu Ala Val Ser Val Gly
1               5                   10                  15

Glu Lys Val Thr Met Ser Cys Lys Ser Ser Gln Ser Leu Leu Asn Ser
            20                  25                  30

Arg Asp Arg Lys Asn Tyr Leu Ala Trp Cys Gln Gln Lys Pro Gly Gln
        35                  40                  45
```

```
Ser Pro Lys Val Met Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Lys Ala Glu Asp Leu Ala Val Tyr Tyr Cys Gln Gln
                85                  90                  95
Tyr Tyr Ser Tyr Pro Leu Thr Val Gly Ala Gly Thr Lys Leu Glu Leu
                100                 105                 110
Lys
```

```
<210> SEQ ID NO 186
<211> LENGTH: 357
<212> TYPE: DNA
<213> ORGANISM: Mus musculus
<220> FEATURE:
<221> NAME/KEY: MISC_FEATURE
<223> OTHER INFORMATION: SC34.95 Heavy Chain Variable Region

<400> SEQUENCE: 186
caggttcagg tgaagcagtc tggagctgag ctggcgaggc caggggcttc agtgaagctg      60
tcctgcaagg cttctggata caccttcaca agctatgcta taaactggct gaagcagaga    120
actggacagg gccttgagtg gattggagag atttatcctg gaagtggtaa tacttactac    180
aatgagagct caaaaacaa ggccacactg accacagaca gtcctccac acagcctac    240 atgcagctca acagcctgac atctgaggac tctgcagtct atttctgcgc aagagtccat    300
gattacggtt cttggtttcc ttactggggc caagggactc tggtcactgt ctctgca       357
```

```
<210> SEQ ID NO 187
<211> LENGTH: 119
<212> TYPE: PRT
<213> ORGANISM: Mus musculus
<220> FEATURE:
<221> NAME/KEY: MISC_FEATURE
<223> OTHER INFORMATION: SC34.95 Heavy Chain Variable Region

<400> SEQUENCE: 187

Gln Val Gln Val Lys Gln Ser Gly Ala Glu Leu Ala Arg Pro Gly Ala
1               5                   10                  15
Ser Val Lys Leu Ser Cys Lys Ala Ser Gly Tyr Thr Phe Thr Ser Tyr
                20                  25                  30
Ala Ile Asn Trp Leu Lys Gln Arg Thr Gly Gln Gly Leu Glu Trp Ile
            35                  40                  45
Gly Glu Ile Tyr Pro Gly Ser Gly Asn Thr Tyr Tyr Asn Glu Ser Phe
    50                  55                  60
Lys Asn Lys Ala Thr Leu Thr Thr Asp Lys Ser Ser Thr Thr Ala Tyr
65                  70                  75                  80
Met Gln Leu Asn Ser Leu Thr Ser Glu Asp Ser Ala Val Tyr Phe Cys
                85                  90                  95
Ala Arg Val His Asp Tyr Gly Ser Trp Phe Pro Tyr Trp Gly Gln Gly
                100                 105                 110
Thr Leu Val Thr Val Ser Ala
        115
```

```
<210> SEQ ID NO 188
<211> LENGTH: 321
<212> TYPE: DNA
<213> ORGANISM: Artificial Sequence
<220> FEATURE:
```

<223> OTHER INFORMATION: hSC34.2 Light Chain Variable Region

<400> SEQUENCE: 188

| | |
|---|---|
| gacatccaga tgactcagtc cccatcaagc ctctccgcca gtgtaggcga tagagtgact | 60 |
| attacctgct ctgcaagcca gggcatcaca aattatctca actggtacca gcagaagccc | 120 |
| ggaaaagcac ctaaacttct catctactat acaagccggc tccacagcgg cgtgccctcc | 180 |
| cgattctctg gtagcggatc cggtacagac ttcacactca caataagctc tctccagcct | 240 |
| gaggattttg ctacctacta ttgtcagcag tactctaagc tcccctggac ttttggacag | 300 |
| gggaccaagg tggagatcaa a | 321 |

<210> SEQ ID NO 189
<211> LENGTH: 107
<212> TYPE: PRT
<213> ORGANISM: Artificial Sequence
<220> FEATURE:
<223> OTHER INFORMATION: hSC34.2 Light Chain Variable Region

<400> SEQUENCE: 189

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Gly Ile Thr Asn Tyr
            20                  25                  30
Leu Asn Trp Tyr Gln Gln Lys Pro Gly Lys Ala Pro Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Lys Leu Pro Trp
                85                  90                  95
Thr Phe Gly Gln Gly Thr Lys Val Glu Ile Lys
            100                 105

<210> SEQ ID NO 190
<211> LENGTH: 375
<212> TYPE: DNA
<213> ORGANISM: Artificial Sequence
<220> FEATURE:
<223> OTHER INFORMATION: hSC34.2 Heavy Chain Variable Region

<400> SEQUENCE: 190

| | |
|---|---|
| gaagttcagc ttgtacagag cggcgccgag gttaagaaac caggcgaatc cttgaagatc | 60 |
| tcctgcaaag gttccggata ctcatttaca gattactata ttaactgggt cagacagatg | 120 |
| cccggcaagg gtctggagtg gatgggttgg acctatccag ggagcggtcc aacaaagtat | 180 |
| aatggcaaat tcggggcca ggttaccata tctgccgaca agagcatctc cacagcatat | 240 |
| ctccagtgga gctctctgaa agcatccgat acagctatgt actattgcgc tcggcgcgga | 300 |
| atctattact acgacggcat ctaccccaat tattttgact actggggcca gggtaccacc | 360 |
| gtcaccgtct cgagc | 375 |

<210> SEQ ID NO 191
<211> LENGTH: 125
<212> TYPE: PRT
<213> ORGANISM: Artificial Sequence
<220> FEATURE:
<223> OTHER INFORMATION: hSC34.2 Heavy Chain Variable Region -continued

<400> SEQUENCE: 191

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Asn Trp Val Arg Gln Met Pro Gly Lys Gly Leu Glu Trp Met
        35                  40                  45

Gly Trp Thr Tyr Pro Gly Ser Gly Pro Thr Lys Tyr Asn Gly Lys Phe
    50                  55                  60

Arg Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Ile Tyr Tyr Asp Gly Ile Tyr Pro Asn Tyr Phe
            100                 105                 110

Asp Tyr Trp Gly Gln Gly Thr Thr Val Thr Val Ser Ser
        115                 120                 125

<210> SEQ ID NO 192
<211> LENGTH: 336
<212> TYPE: DNA
<213> ORGANISM: Artificial Sequence
<220> FEATURE:
<223> OTHER INFORMATION: hSC34.11 Light Chain Variable Region

<400> SEQUENCE: 192
gatattcaaa tgacccagtc tccttctagt ttgtccgcta gtgtgggaga ccgagtcacc        60
atcacatgta agagcagtca agtctgctg aacagccgta ccagaaaaaa ttatcttgct       120
tggtaccagc aaaaaccagg gaaagttcca agctgcttta tctactgggc ttctacccga       180
gaatccggag tgcccagtcg gttcagtggg tccggttcag gaacagattt caccctgaca       240
atctcttcac tgcagcctga ggatgtggct acctattact gtaaggagtc ctataacctc       300
tggaccttcg gaggtggcac caaagtcgag atcaag                                 336

<210> SEQ ID NO 193
<211> LENGTH: 112
<212> TYPE: PRT
<213> ORGANISM: Artificial Sequence
<220> FEATURE:
<223> OTHER INFORMATION: hSC34.11 Light Chain Variable Region

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Thr Arg Lys Asn Tyr Leu Ala Trp Tyr Gln Gln Lys Pro Gly Lys
        35                  40                  45

Val Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Lys Glu
                85                  90                  95

Ser Tyr Asn Leu Trp Thr Phe Gly Gly Gly Thr Lys Val Glu Ile Lys
            100                 105                 110

<210> SEQ ID NO 194
<211> LENGTH: 351
<212> TYPE: DNA
<213> ORGANISM: Artificial Sequence
<220> FEATURE:
<223> OTHER INFORMATION: hSC34.11 Heavy Chain Variable Region

<400> SEQUENCE: 194

```
gaagtgcagc tcgtccagag tggcgctgaa gtcaaaaagc ctggggagag tttgaagatc      60
tcctgcaaag gcagcggcta tagcttcaca aactattgga tgatttgggt ccgccagatg     120
cccggcaagg gccttgagtg gatgggatat atcgatccaa ccactgatta caccgcatat     180
aaccagaagt tcaaagacca ggtaactatc tcagccgaca aaagtataag caccgcatat     240
cttcagtggt catcactgaa agcctccgac accgctatgt actattgcgc tcgtggaggc     300
aacgtggctc tcgacttttg ggggcagggg actctggtta ccgtctcgag c              351
```

<210> SEQ ID NO 195
<211> LENGTH: 117
<212> TYPE: PRT
<213> ORGANISM: Artificial Sequence
<220> FEATURE:
<223> OTHER INFORMATION: hSC34.11 Heavy Chain Variable Region

<400> SEQUENCE: 195

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Met Ile Trp Val Arg Gln Met Pro Gly Lys Gly Leu Glu Trp Met
        35                  40                  45

Gly Tyr Ile Asp Pro Thr Thr Asp Tyr Thr Ala Tyr Asn Gln Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Val Ala Leu Asp Phe Trp Gly Gln Gly Thr Leu
            100                 105                 110

Val Thr Val Ser Ser
        115
```

<210> SEQ ID NO 196
<211> LENGTH: 321
<212> TYPE: DNA
<213> ORGANISM: Artificial Sequence
<220> FEATURE:
<223> OTHER INFORMATION: hSC34.14 Light Chain Variable Region

<400> SEQUENCE: 196

```
gatatccaga tgactcagtc cccctcctct ctctctgcat ctgtcgggga cagggtgact      60
attacttgcc gcacctctga gcatatctac tcttaccttg cctggtacca gcaaaagcca     120
ggaaaagctc ctaagctgtt gatttataat gcaaagacac tggccgaagg agtgccctcc     180
aggtttagcg ggtccggatc tggtacagac tttaccctca ccatcagtag cctgcaaccc     240
gaggactttg ctacttacta ctgtcaacac cactatgata ccccatacac attcggccag     300
gggacaaaac tggagattaa a                                                321
```

-continued

<210> SEQ ID NO 197
<211> LENGTH: 107
<212> TYPE: PRT
<213> ORGANISM: Artificial Sequence
<220> FEATURE:
<223> OTHER INFORMATION: hSC34.14 Light Chain Variable Region

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu His Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Thr Pro Tyr
                85                  90                  95

Thr Phe Gly Gln Gly Thr Lys Leu Glu Ile Lys
            100                 105

<210> SEQ ID NO 198
<211> LENGTH: 363
<212> TYPE: DNA
<213> ORGANISM: Artificial Sequence
<220> FEATURE:
<223> OTHER INFORMATION: hSC34.14 Heavy Chain Variable Region

<400> SEQUENCE: 198
caggtgcagc tcgttcagag cggggccgag gtgaaaaagc ctggcgcatc tgtcaaggtc      60
tcctgtaaag ccagtggata cattcact gactattaca tgcattgggt ccgccaggct      120
ccaggccaga ggctggagtg gatgggccgt gtcaacccaa agaaaggtgg aactacctat     180
aatcagaagt tcgaaggccg ggtcacaatc accagagaca ctagtgccag cactgcatat     240
atggaactca gtagcctccg cagtgaggat accgctgtgt actattgtgc tatgggaatt     300
tactactcct atgacgcctc ctttgattac tggggacagg gaaccactgt gactgtgtcc     360
tcc                                                                   363

<210> SEQ ID NO 199
<211> LENGTH: 121
<212> TYPE: PRT
<213> ORGANISM: Artificial Sequence
<220> FEATURE:
<223> OTHER INFORMATION: hSC34.14 Heavy Chain Variable Region

<400> SEQUENCE: 199

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Arg Leu Glu Trp Met
        35                  40                  45

Gly Arg Val Asn Pro Lys Lys Gly Gly Thr Thr Tyr Asn Gln Lys Phe
    50                  55                  60

Glu Gly Arg Val Thr Ile Thr Arg Asp Thr Ser Ala Ser Thr Ala Tyr
65                  70                  75                  80

```
Met Glu Leu Ser Ser Leu Arg Ser Glu Asp Thr Ala Val Tyr Tyr Cys
             85                  90                  95

Ala Met Gly Ile Tyr Tyr Ser Tyr Asp Ala Ser Phe Asp Tyr Trp Gly
            100                 105                 110

Gln Gly Thr Thr Val Thr Val Ser Ser
        115                 120

<210> SEQ ID NO 200
<211> LENGTH: 339
<212> TYPE: DNA
<213> ORGANISM: Artificial Sequence
<220> FEATURE:
<223> OTHER INFORMATION: hSC34.25 Light Chain Variable Region

<400> SEQUENCE: 200
gatattgtga tgacacagtc tcccgatagc cttgctgtta gtctcggaga acgtgccacc      60
attaactgca agtctagtca gagtttgttg tactctcgat accagaaaaa ttatgtggca    120
tggtaccagc agaagccagg ccagccacca aaactcctga tctactgggc ctcaaccagg    180
gaaagcggag tgccagatag attcagcggc agtgggtcag gtaccgattt cactctcaca    240
atcagctcac tgcaagctga ggatgtggca gtgtattatt gtcagcagta ctatcgctat    300
cccctgacct ttggacaggg cacaaagttg gaaatcaaa                           339

<210> SEQ ID NO 201
<211> LENGTH: 113
<212> TYPE: PRT
<213> ORGANISM: Artificial Sequence
<220> FEATURE:
<223> OTHER INFORMATION: hSC34.25 Light Chain Variable Region

<400> SEQUENCE: 201

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Leu Leu Tyr Ser
            20                  25                  30

Arg Tyr Gln Lys Asn Tyr Val Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Tyr Pro Leu Thr Phe Gly Gln Gly Thr Lys Leu Glu Ile
            100                 105                 110

Lys

<210> SEQ ID NO 202
<211> LENGTH: 357
<212> TYPE: DNA
<213> ORGANISM: Artificial Sequence
<220> FEATURE:
<223> OTHER INFORMATION: hSC34.25 Heavy Chain Variable Region

<400> SEQUENCE: 202
caagtacagt tggtgcagag cggggctgag gtgaaaaaac ccggcgctag cgtgaaggtt      60
agctgcaaag cctccggtta cacatttaca tcctacgcca tttcttgggt gcgccaggca    120
cctggccaac ggcttgagtg gatgggcgaa atctaccctg gttccggtga gacttattac    180
```

```
aatgaaaagt tcaagggacg cgtcactatc accagggaca ccagcgcaag caccgcttat    240
atggagctgt cctctcttag atctgaagac actgctgtct actactgtgc aagggtgaac    300
gactatggat cttggttccc ttattgggga cagggcaccc tggttacagt ctcttct       357
```

<210> SEQ ID NO 203
<211> LENGTH: 119
<212> TYPE: PRT
<213> ORGANISM: Artificial Sequence
<220> FEATURE:
<223> OTHER INFORMATION: hSC34.25 Heavy Chain Variable Region

<400> SEQUENCE: 203

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Arg Leu Glu Trp Met
        35                  40                  45

Gly Glu Ile Tyr Pro Gly Ser Gly Glu Thr Tyr Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Asp Tyr Gly Ser Trp Phe Pro Tyr Trp Gly Gln Gly
            100                 105                 110

Thr Leu Val Thr Val Ser Ser
        115
```

<210> SEQ ID NO 204
<211> LENGTH: 324
<212> TYPE: DNA
<213> ORGANISM: Artificial Sequence
<220> FEATURE:
<223> OTHER INFORMATION: hSC34.28 Light Chain Variable Region

<400> SEQUENCE: 204

```
gaaatagtac tgacccagag ccccgctaca ctctccttga gccctggaga gcgggcaaca    60
ctctcctgca cagcatcttc cagcgtcaat tccttttacc tgcattggta ccagcagaaa    120
cctgggctgg ctccacgact cctcatttat tctacctcta atcttgctag cgggatcccc    180
gatcggtttt caggcagtgg tagcgggacc gacttcacct tgaccatttc ccggctggag    240
cctgaggact cgctgtgtata ttactgccat caataccata gatctcccta ccttcggc     300 caggggacca aactggagat taag                                            324
```

<210> SEQ ID NO 205
<211> LENGTH: 108
<212> TYPE: PRT
<213> ORGANISM: Artificial Sequence
<220> FEATURE:
<223> OTHER INFORMATION: hSC34.28 Light Chain Variable Region

<400> SEQUENCE: 205

```
Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Asn Ser Phe
            20                  25                  30
```

Tyr Leu His Trp Tyr Gln Gln Lys Pro Gly Leu Ala Pro Arg Leu Leu
             35                  40                  45

Ile Tyr Ser Thr Ser Asn Leu Ala Ser Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys His Gln Tyr His Arg Ser Pro
                 85                  90                  95

Tyr Thr Phe Gly Gln Gly Thr Lys Leu Glu Ile Lys
            100                 105

<210> SEQ ID NO 206
<211> LENGTH: 369
<212> TYPE: DNA
<213> ORGANISM: Artificial Sequence
<220> FEATURE:
<223> OTHER INFORMATION: hSC34.28 Heavy Chain Variable Region

<400> SEQUENCE: 206
caagtgcaac tggtgcagtc cggcgctgaa gtgaaaaaac ccggatcttc tgtgaaagtg      60
agctgtaaag catccggggg cacattcagc agctactgga tcgaatgggt cgtcaggcc     120 cccggacagg gactggaatg gatgggtgaa atcttgcctg gttccggcaa tacttactac    180
aatgagcgct tcaaggatcg agtcaccatc accgctgatg agtcaacctc aactgcttac    240
atggagctgt cttccctgcg atctgaggac acagctgtat actactgtgc tagacgggca    300
gccgcttact attctaaccc agagtggttc gcttattggg gccaaggaac cctggtcaca    360
gtgagttct                                                            369

<210> SEQ ID NO 207
<211> LENGTH: 123
<212> TYPE: PRT
<213> ORGANISM: Artificial Sequence
<220> FEATURE:
<223> OTHER INFORMATION: hSC34.28 Heavy Chain Variable Region

<400> SEQUENCE: 207

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Trp Ile Glu Trp Val Arg Gln Ala Pro Gly Gln Gly Leu Glu Trp Met
         35                  40                  45

Gly Glu Ile Leu Pro Gly Ser Gly Asn Thr Tyr Tyr Asn Glu Arg Phe
 50                  55                  60

Lys Asp Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Ala Ala Ala Tyr Tyr Ser Asn Pro Glu Trp Phe Ala Tyr
            100                 105                 110

Trp Gly Gln Gly Thr Leu Val Thr Val Ser Ser
        115                 120

<210> SEQ ID NO 208
<211> LENGTH: 336
<212> TYPE: DNA
<213> ORGANISM: Artificial Sequence
<220> FEATURE:

<223> OTHER INFORMATION: hSC34.38 Light Chain Variable Region

<400> SEQUENCE: 208

```
gacgtcgtca tgacacagtc cccctgagc ctccctgtga ctctgggtca gccagcttcc      60
atctcttgca atctagcca gtccctcctg tatagtaacc gtcgcaccta tctgaactgg    120
tttcagcagc gcccaggcca agtcccagg cggctcatct acctggtgtc taagttggat    180
agtggagttc cgataggtt tagtggatcc ggttctggca ctgatttcac actgaagatt    240
agtagggtcg aggcagaaga tgtgggagtg tattactgtg tgcaggggac acattttcct    300
tttaccttcg gccagggcac caagctggaa atcaag                              336
```

<210> SEQ ID NO 209
<211> LENGTH: 112
<212> TYPE: PRT
<213> ORGANISM: Artificial Sequence
<220> FEATURE:
<223> OTHER INFORMATION: hSC34.38 Light Chain Variable Region

<400> SEQUENCE: 209

Asp Val Val Met Thr Gln Ser Pro Leu Ser Leu Pro Val Thr Leu Gly
1               5                   10                  15
Gln Pro Ala Ser Ile Ser Cys Lys Ser Ser Gln Ser Leu Leu Tyr Ser
            20                  25                  30
Asn Arg Arg Thr Tyr Leu Asn Trp Phe Gln Gln Arg Pro Gly Gln Ser
        35                  40                  45
Pro Arg Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Val Gln Gly
                85                  90                  95
Thr His Phe Pro Phe Thr Phe Gly Gln Gly Thr Lys Leu Glu Ile Lys
            100                 105                 110

<210> SEQ ID NO 210
<211> LENGTH: 366
<212> TYPE: DNA
<213> ORGANISM: Artificial Sequence
<220> FEATURE:
<223> OTHER INFORMATION: hSC34.38 Heavy Chain Variable Region

<400> SEQUENCE: 210

```
gaggtgcagc ttgtccaatc aggggccgaa gtcaagaaac tggagaatc tctgaagata    60
tcttgtaagg gatccggtta ttccttcact tcctattaca tgtactgggt gagacagatg   120
ccaggcaaag gcttggaatg gatgggcgag atcaacccca gcaatggtgg ggccaacttc   180
aacgagagat tcaagaacca ggttactatc tccgcagaca gagcatatc aaccgcttac   240
cttcagtggt cttcccttaa ggcatccgac accgctatgt actactgcac ccgaggcctg   300
ctttattacg attatgatag aggttttgct tactgggac agggaacatt ggtcactgtg   360
tccagt                                                               366
```

<210> SEQ ID NO 211
<211> LENGTH: 122
<212> TYPE: PRT
<213> ORGANISM: Artificial Sequence
<220> FEATURE:
<223> OTHER INFORMATION: hSC34.38 Heavy Chain Variable Region

<400> SEQUENCE: 211

| Glu | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |

| Ser | Leu | Lys | Ile | Ser | Cys | Lys | Gly | Ser | Gly | Tyr | Ser | Phe | Thr | Ser | Tyr |
|---|---|---|---|---|---|---|---|---|---|---|---|---|---|---|---|
| | | | 20 | | | | | 25 | | | | | 30 | | |

| Tyr | Met | Tyr | Trp | Val | Arg | Gln | Met | Pro | Gly | Lys | Gly | Leu | Glu | Trp | Met |
|---|---|---|---|---|---|---|---|---|---|---|---|---|---|---|---|
| | | 35 | | | | | 40 | | | | | 45 | | | |

| Gly | Glu | Ile | Asn | Pro | Ser | Asn | Gly | Gly | Ala | Asn | Phe | Asn | Glu | Arg | Phe |
|---|---|---|---|---|---|---|---|---|---|---|---|---|---|---|---|
| 50 | | | | | 55 | | | | | 60 | | | | | |

| Lys | Asn | Gln | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Leu | Gln | Trp | Ser | Ser | Leu | Lys | Ala | Ser | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Thr | Arg | Gly | Leu | Leu | Tyr | Tyr | Asp | Tyr | Asp | Arg | Gly | Phe | Ala | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Leu | Val | Thr | Val | Ser | Ser |
|---|---|---|---|---|---|---|---|---|---|
| | | | 115 | | | | 120 | | |

<210> SEQ ID NO 212
<211> LENGTH: 336
<212> TYPE: DNA
<213> ORGANISM: Artificial Sequence
<220> FEATURE:
<223> OTHER INFORMATION: hSC34.87 Light Chain Variable Region

<400> SEQUENCE: 212

```
gacatcgtga tgacccagtc tccagactcc ctggctgtgt ctctgggcga gagggccacc      60
atcaactgca gtccagcca gagtttatta aacagccgca cccgtaagaa ctacttagct     120
tggtaccagc agaaaccagg acagcctcct aagctgctca tttactgggc atctaccccgg    180
gaatccgggg tccctgaccg attcagtggc agcgggtctg ggacagattt cactctcacc     240
atcagcagcc tgcaggctga agatgtggca gtttattact gtaagcaatc ttataatctg     300
tggacgttcg gtggaggcac caagctggaa atcaaa                               336
```

<210> SEQ ID NO 213
<211> LENGTH: 112
<212> TYPE: PRT
<213> ORGANISM: Artificial Sequence
<220> FEATURE:
<223> OTHER INFORMATION: hSC34.87 Light Chain Variable Region

<400> SEQUENCE: 213

| Asp | Ile | Val | Met | Thr | Gln | Ser | Pro | Asp | Ser | Leu | Ala | Val | Ser | Leu | Gly |
|---|---|---|---|---|---|---|---|---|---|---|---|---|---|---|---|
| 1 | | | | 5 | | | | | 10 | | | | | 15 | |

| Glu | Arg | Ala | Thr | Ile | Asn | Cys | Lys | Ser | Ser | Gln | Ser | Leu | Leu | Asn | Ser |
|---|---|---|---|---|---|---|---|---|---|---|---|---|---|---|---|
| | | | 20 | | | | | 25 | | | | | 30 | | |

| Arg | Thr | Arg | Lys | Asn | Tyr | Leu | Ala | Trp | Tyr | Gln | Gln | Lys | Pro | Gly | Gln |
|---|---|---|---|---|---|---|---|---|---|---|---|---|---|---|---|
| | | 35 | | | | | 40 | | | | | 45 | | | |

| Pro | Pro | Lys | Leu | Leu | Ile | Tyr | Trp | Ala | Ser | Thr | Arg | Glu | Ser | Gly | Val |
|---|---|---|---|---|---|---|---|---|---|---|---|---|---|---|---|
| | 50 | | | | | 55 | | | | | 60 | | | | |

| Pro | Asp | Arg | Phe | Ser | Gly | Ser | Gly | Ser | Gly | Thr | Asp | Phe | Thr | Leu | Thr |
|---|---|---|---|---|---|---|---|---|---|---|---|---|---|---|---|
| 65 | | | | | 70 | | | | | 75 | | | | | 80 |

| Ile | Ser | Ser | Leu | Gln | Ala | Glu | Asp | Val | Ala | Val | Tyr | Tyr | Cys | Lys | Gln |
|---|---|---|---|---|---|---|---|---|---|---|---|---|---|---|---|
| | | | | 85 | | | | | 90 | | | | | 95 | |

| Ser | Tyr | Asn | Leu | Trp | Thr | Phe | Gly | Gly | Gly | Thr | Lys | Leu | Glu | Ile | Lys |
|---|---|---|---|---|---|---|---|---|---|---|---|---|---|---|---|
| | | | 100 | | | | | 105 | | | | | 110 | | |

<210> SEQ ID NO 214
<211> LENGTH: 351
<212> TYPE: DNA
<213> ORGANISM: Artificial Sequence
<220> FEATURE:
<223> OTHER INFORMATION: hSC34.87 Heavy Chain Variable Region

<400> SEQUENCE: 214

```
caggtccagc ttgtgcagtc tggggctgag gtgaagaagc ctggggcctc agtgaaggtt      60
tcctgcaagg cttctggata caccttcact agctattgga tgctttgggt gcgccaggcc     120
cccggacaaa ggcttgagtg gatgggatac atcgaccctc gaaatggtta cacagaatat     180
aatcagaagt tcaaggacag agtcaccatt accaggaca catccgcgag cacagcctac     240
atggagctga gcagcctgag atctgaagac acggctgtgt attactgtgc gagaggggggg     300
aatgtggcta tggactactg gggtcaagga accctagtca ccgtctcgag t              351
```

<210> SEQ ID NO 215
<211> LENGTH: 117
<212> TYPE: PRT
<213> ORGANISM: Artificial Sequence
<220> FEATURE:
<223> OTHER INFORMATION: hSC34.87 Heavy Chain Variable Region

<400> SEQUENCE: 215

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Leu Trp Val Arg Gln Ala Pro Gly Gln Arg Leu Glu Trp Met
        35                  40                  45

Gly Tyr Ile Asp Pro Arg Asn Gly Tyr Thr Glu Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Val Ala Met Asp Tyr Trp Gly Gln Gly Thr Leu
            100                 105                 110

Val Thr Val Ser Ser
        115

<210> SEQ ID NO 216
<211> LENGTH: 214
<212> TYPE: PRT
<213> ORGANISM: Artificial Sequence
<220> FEATURE:
<223> OTHER INFORMATION: hSC34.2 Light Chain

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro

```
            65                   70                  75                  80
Glu Asp Phe Ala Thr Tyr Tyr Cys Gln Gln Tyr Ser Lys Leu Pro Trp
                     85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 217
<211> LENGTH: 454
<212> TYPE: PRT
<213> ORGANISM: Artificial Sequence
<220> FEATURE:
<223> OTHER INFORMATION: hSC34.2 Heavy Chain

<400> SEQUENCE: 217

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Ile Asn Trp Val Arg Gln Met Pro Gly Lys Gly Leu Glu Trp Met
            35                  40                  45

Gly Trp Thr Tyr Pro Gly Ser Gly Pro Thr Lys Tyr Asn Gly Lys Phe
    50                  55                  60

Arg Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Ile Tyr Tyr Tyr Asp Gly Ile Tyr Pro Asn Tyr Phe
            100                 105                 110

Asp Tyr Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
```

```
                210                 215                 220
Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly
            450

<210> SEQ ID NO 218
<211> LENGTH: 219
<212> TYPE: PRT
<213> ORGANISM: Artificial Sequence
<220> FEATURE:
<223> OTHER INFORMATION: hSC34.11 Light Chain

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Arg Thr Arg Lys Asn Tyr Leu Ala Trp Tyr Gln Gln Lys Pro Gly Lys
            35                  40                  45

Val Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Lys Glu
                85                  90                  95

Ser Tyr Asn Leu Trp Thr Phe Gly Gly Gly Thr Lys Val Glu Ile Lys
                100                 105                 110

Arg Thr Val Ala Ala Pro Ser Val Phe Ile Phe Pro Pro Ser Asp Glu
```

```
              115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 219
<211> LENGTH: 446
<212> TYPE: PRT
<213> ORGANISM: Artificial Sequence
<220> FEATURE:
<223> OTHER INFORMATION: hSC34.11 Heavy Chain

<400> SEQUENCE: 219

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Met Ile Trp Val Arg Gln Met Pro Gly Lys Gly Leu Glu Trp Met
        35                  40                  45

Gly Tyr Ile Asp Pro Thr Thr Asp Tyr Thr Ala Tyr Asn Gln Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Val Ala Leu Asp Phe Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

```
            260                 265                 270
Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 220
<211> LENGTH: 214
<212> TYPE: PRT
<213> ORGANISM: Artificial Sequence
<220> FEATURE:
<223> OTHER INFORMATION: hSC34.14 Light Chain

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu His Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                    180                 185                 190
Ala Cys Glu Val Thr His Gln Gly Leu Ser Ser Pro Val Thr Lys Ser
            195                 200                 205

Phe Asn Arg Gly Glu Cys
        210

<210> SEQ ID NO 221
<211> LENGTH: 450
<212> TYPE: PRT
<213> ORGANISM: Artificial Sequence
<220> FEATURE:
<223> OTHER INFORMATION: hSC34.14 Heavy Chain

<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Arg Leu Glu Trp Met
        35                  40                  45

Gly Arg Val Asn Pro Lys Lys Gly Gly Thr Thr Tyr Asn Gln Lys Phe
50                  55                  60

Glu Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Met Gly Ile Tyr Tyr Ser Tyr Asp Ala Ser Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                    325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly
    450

<210> SEQ ID NO 222
<211> LENGTH: 220
<212> TYPE: PRT
<213> ORGANISM: Artificial Sequence
<220> FEATURE:
<223> OTHER INFORMATION: hSC34.25 Light Chain

<400> SEQUENCE: 222

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Tyr Ser
                20                  25                  30
Arg Tyr Gln Lys Asn Tyr Val Ala Trp Tyr Gln Gln Lys Pro Gly Gln
            35                  40                  45
Pro Pro Lys Leu Leu Ile Tyr Trp Ala Ser Thr Arg Glu Ser Gly Val
        50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Arg Tyr Pro Leu Thr Phe Gly Gln Gly Thr Lys Leu Glu Ile
                100                 105                 110
Lys Arg Thr Val Ala Ala Pro Ser Val Phe Ile Phe Pro Pro Ser Asp
            115                 120                 125
Glu Gln Leu Lys Ser Gly Thr Ala Ser Val Val Cys Leu Leu Asn Asn
        130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220
```

```
<210> SEQ ID NO 223
<211> LENGTH: 448
<212> TYPE: PRT
<213> ORGANISM: Artificial Sequence
<220> FEATURE:
<223> OTHER INFORMATION: hSC34.25 Heavy Chain

<400> SEQUENCE: 223
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Ala | Ile | Ser | Trp | Val | Arg | Gln | Ala | Pro | Gly | Gln | Arg | Leu | Glu | Trp | Met |
| | | | 35 | | | | | 40 | | | | | 45 | | |
| Gly | Glu | Ile | Tyr | Pro | Gly | Ser | Gly | Glu | Thr | Tyr | Tyr | Asn | Glu | Lys | Phe |
| 50 | | | | | 55 | | | | | 60 | | | | | |
| Lys | Gly | Arg | Val | Thr | Ile | Thr | Arg | Asp | Thr | Ser | Ala | Ser | Thr | Ala | Tyr |
| 65 | | | | 70 | | | | | 75 | | | | | 80 | |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Val | Asn | Asp | Tyr | Gly | Ser | Trp | Phe | Pro | Tyr | Trp | Gly | Gln | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| 130 | | | | | 135 | | | | | 140 | | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Lys | Val | Glu | Pro | Lys | Ser | Cys | Asp | Lys |
| 210 | | | | | 215 | | | | | 220 | | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Asn | Ser | Thr | Tyr | Arg | Val |
| 290 | | | | | 295 | | | | | 300 | | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | | 355 | | | | | 360 | | | | | 365 | | |
| Cys | Leu | Val | Lys | Gly | Phe | Tyr | Pro | Ser | Asp | Ile | Ala | Val | Glu | Trp | Glu |

```
                370                 375                 380
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445
```

<210> SEQ ID NO 224
<211> LENGTH: 215
<212> TYPE: PRT
<213> ORGANISM: Artificial Sequence
<220> FEATURE:
<223> OTHER INFORMATION: hSC34.28 Light Chain

<400> SEQUENCE: 224

```
Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Asn Ser Phe
                20                  25                  30

Tyr Leu His Trp Tyr Gln Gln Lys Pro Gly Leu Ala Pro Arg Leu Leu
            35                  40                  45

Ile Tyr Ser Thr Ser Asn Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 225
<211> LENGTH: 452
<212> TYPE: PRT
<213> ORGANISM: Artificial Sequence
<220> FEATURE:
<223> OTHER INFORMATION: hSC34.28 Heavy Chain

<400> SEQUENCE: 225

```
Gln Val Gln Leu Val Gln Ser Gly Ala Glu Val Lys Lys Pro Gly Ser
1               5                   10                  15
```

-continued

Ser Val Lys Val Ser Cys Lys Ala Ser Gly Thr Phe Ser Ser Tyr
            20                  25                  30
Trp Ile Glu Trp Val Arg Gln Ala Pro Gly Gln Gly Leu Glu Trp Met
 35                  40                  45
Gly Glu Ile Leu Pro Gly Ser Gly Asn Thr Tyr Tyr Asn Glu Arg Phe
 50                  55                  60
Lys Asp Arg Val Thr Ile Thr Ala Asp Glu Ser Thr Ser Thr Ala Tyr
65                   70                  75                  80
Met Glu Leu Ser Ser Leu Arg Ser Glu Asp Thr Ala Val Tyr Tyr Cys
                85                  90                  95
Ala Arg Arg Ala Ala Ala Tyr Tyr Ser Asn Pro Glu Trp Phe Ala Tyr
                100                 105                 110
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
            355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser

-continued

```
             435                 440                 445
Leu Ser Pro Gly
    450

<210> SEQ ID NO 226
<211> LENGTH: 452
<212> TYPE: PRT
<213> ORGANISM: Artificial Sequence
<220> FEATURE:
<223> OTHER INFORMATION: hSC34.28ss1 Heavy Chain

<400> SEQUENCE: 226

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Asn Thr Tyr Tyr Asn Glu Arg Phe
    50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Ala Ala Tyr Tyr Ser Asn Pro Glu Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Ser Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
```

```
                    340                 345                 350
Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 227
<211> LENGTH: 219
<212> TYPE: PRT
<213> ORGANISM: Artificial Sequence
<220> FEATURE:
<223> OTHER INFORMATION: hSC34.38 Light Chain

<400> SEQUENCE: 227

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Arg Arg Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 228
<211> LENGTH: 451
<212> TYPE: PRT
```

<213> ORGANISM: Artificial Sequence
<220> FEATURE:
<223> OTHER INFORMATION: hSC34.38 Heavy Chain

<400> SEQUENCE: 228

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Tyr Met Tyr Trp Val Arg Gln Met Pro Gly Lys Gly Leu Glu Trp Met
        35                  40                  45

Gly Glu Ile Asn Pro Ser Asn Gly Gly Ala Asn Phe Asn Glu Arg Phe
    50                  55                  60

Lys Asn Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Leu Leu Tyr Asp Tyr Asp Arg Gly Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

385             390             395             400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
        450

<210> SEQ ID NO 229
<211> LENGTH: 219
<212> TYPE: PRT
<213> ORGANISM: Artificial Sequence
<220> FEATURE:
<223> OTHER INFORMATION: hSC34.87 Light Chain

<400> SEQUENCE: 229

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 230
<211> LENGTH: 446
<212> TYPE: PRT
<213> ORGANISM: Artificial Sequence
<220> FEATURE:
<223> OTHER INFORMATION: hSC34.87 Heavy Chain

<400> SEQUENCE: 230

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
             20                  25                  30

Trp Met Leu Trp Val Arg Gln Ala Pro Gly Gln Arg Leu Glu Trp Met
         35                  40                  45

Gly Tyr Ile Asp Pro Arg Asn Gly Tyr Thr Glu Tyr Asn Gln Lys Phe
     50                  55                  60

Lys Asp Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Asn Val Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
```

<210> SEQ ID NO 231

<400> SEQUENCE: 231

000

<210> SEQ ID NO 232
<211> LENGTH: 11
<212> TYPE: PRT
<213> ORGANISM: Artificial Sequence
<220> FEATURE:
<223> OTHER INFORMATION: hSC34.2 CDRL1

<400> SEQUENCE: 232

Ser Ala Ser Gln Gly Ile Thr Asn Tyr Leu Asn
1               5                   10

<210> SEQ ID NO 233
<211> LENGTH: 7
<212> TYPE: PRT
<213> ORGANISM: Artificial Sequence
<220> FEATURE:
<223> OTHER INFORMATION: hSC34.2 CDRL2

<400> SEQUENCE: 233

Tyr Thr Ser Arg Leu His Ser
1               5

<210> SEQ ID NO 234
<211> LENGTH: 9
<212> TYPE: PRT
<213> ORGANISM: Artificial Sequence
<220> FEATURE:
<223> OTHER INFORMATION: hSC34.2 CDRL3

<400> SEQUENCE: 234

Gln Gln Tyr Ser Lys Leu Pro Trp Thr
1               5

<210> SEQ ID NO 235
<211> LENGTH: 5
<212> TYPE: PRT
<213> ORGANISM: Artificial Sequence
<220> FEATURE:
<223> OTHER INFORMATION: hSC34.2 CDRH1

<400> SEQUENCE: 235

Asp Tyr Tyr Ile Asn
1               5

<210> SEQ ID NO 236
<211> LENGTH: 17
<212> TYPE: PRT
<213> ORGANISM: Artificial Sequence
<220> FEATURE:
<223> OTHER INFORMATION: hSC34.2 CDRH2

<400> SEQUENCE: 236

Trp Thr Tyr Pro Gly Ser Gly Pro Thr Lys Tyr Asn Gly Lys Phe Arg
1               5                   10                  15

Gly

<210> SEQ ID NO 237
<211> LENGTH: 16

```
<212> TYPE: PRT
<213> ORGANISM: Artificial Sequence
<220> FEATURE:
<223> OTHER INFORMATION: hSC34.2 CDRH3

<400> SEQUENCE: 237

Arg Gly Ile Tyr Tyr Asp Gly Ile Tyr Pro Asn Tyr Phe Asp Tyr
1               5                   10                  15

<210> SEQ ID NO 238
<211> LENGTH: 17
<212> TYPE: PRT
<213> ORGANISM: Artificial Sequence
<220> FEATURE:
<223> OTHER INFORMATION: hSC34.11 CDRL1

<400> SEQUENCE: 238

Lys Ser Ser Gln Ser Leu Leu Asn Ser Arg Thr Arg Lys Asn Tyr Leu
1               5                   10                  15
Ala

<210> SEQ ID NO 239
<211> LENGTH: 7
<212> TYPE: PRT
<213> ORGANISM: Artificial Sequence
<220> FEATURE:
<223> OTHER INFORMATION: hSC34.11 CDRL2

<400> SEQUENCE: 239

Trp Ala Ser Thr Arg Glu Ser
1               5

<210> SEQ ID NO 240
<211> LENGTH: 8
<212> TYPE: PRT
<213> ORGANISM: Artificial Sequence
<220> FEATURE:
<223> OTHER INFORMATION: hSC34.11 CDRL3

<400> SEQUENCE: 240

Lys Glu Ser Tyr Asn Leu Trp Thr
1               5

<210> SEQ ID NO 241
<211> LENGTH: 5
<212> TYPE: PRT
<213> ORGANISM: Artificial Sequence
<220> FEATURE:
<223> OTHER INFORMATION: hSC34.11 CDRH1

<400> SEQUENCE: 241

Asn Tyr Trp Met Ile
1               5

<210> SEQ ID NO 242
<211> LENGTH: 17
<212> TYPE: PRT
<213> ORGANISM: Artificial Sequence
<220> FEATURE:
<223> OTHER INFORMATION: hSC34.11 CDRH2

<400> SEQUENCE: 242

Tyr Ile Asp Pro Thr Thr Asp Tyr Thr Ala Tyr Asn Gln Lys Phe Lys
1               5                   10                  15
Asp
```

```
<210> SEQ ID NO 243
<211> LENGTH: 8
<212> TYPE: PRT
<213> ORGANISM: Artificial Sequence
<220> FEATURE:
<223> OTHER INFORMATION: hSC34.11 CDRH3

<400> SEQUENCE: 243

Gly Gly Asn Val Ala Leu Asp Phe
1               5

<210> SEQ ID NO 244
<211> LENGTH: 11
<212> TYPE: PRT
<213> ORGANISM: Artificial Sequence
<220> FEATURE:
<223> OTHER INFORMATION: hSC34.14 CDRL1

<400> SEQUENCE: 244

Arg Thr Ser Glu His Ile Tyr Ser Tyr Leu Ala
1               5                   10

<210> SEQ ID NO 245
<211> LENGTH: 7
<212> TYPE: PRT
<213> ORGANISM: Artificial Sequence
<220> FEATURE:
<223> OTHER INFORMATION: hSC34.14 CDRL2

<400> SEQUENCE: 245

Asn Ala Lys Thr Leu Ala Glu
1               5

<210> SEQ ID NO 246
<211> LENGTH: 9
<212> TYPE: PRT
<213> ORGANISM: Artificial Sequence
<220> FEATURE:
<223> OTHER INFORMATION: hSC34.14 CDRL3

<400> SEQUENCE: 246

Gln His His Tyr Asp Thr Pro Tyr Thr
1               5

<210> SEQ ID NO 247
<211> LENGTH: 5
<212> TYPE: PRT
<213> ORGANISM: Artificial Sequence
<220> FEATURE:
<223> OTHER INFORMATION: hSC34.14 CDRH1

<400> SEQUENCE: 247

Asp Tyr Tyr Met His
1               5

<210> SEQ ID NO 248
<211> LENGTH: 17
<212> TYPE: PRT
<213> ORGANISM: Artificial Sequence
<220> FEATURE:
<223> OTHER INFORMATION: hSC34.14 CDRH2

<400> SEQUENCE: 248

Arg Val Asn Pro Lys Lys Gly Gly Thr Thr Tyr Asn Gln Lys Phe Glu
1               5                   10                  15

Gly
```

```
<210> SEQ ID NO 249
<211> LENGTH: 12
<212> TYPE: PRT
<213> ORGANISM: Artificial Sequence
<220> FEATURE:
<223> OTHER INFORMATION: hSC34.14 CDRH3

<400> SEQUENCE: 249

Gly Ile Tyr Tyr Ser Tyr Asp Ala Ser Phe Asp Tyr
1               5                   10

<210> SEQ ID NO 250
<211> LENGTH: 17
<212> TYPE: PRT
<213> ORGANISM: Artificial Sequence
<220> FEATURE:
<223> OTHER INFORMATION: hSC34.25 CDRL1

<400> SEQUENCE: 250

Lys Ser Ser Gln Ser Leu Leu Tyr Ser Arg Tyr Gln Lys Asn Tyr Val
1               5                   10                  15

Ala

<210> SEQ ID NO 251
<211> LENGTH: 7
<212> TYPE: PRT
<213> ORGANISM: Artificial Sequence
<220> FEATURE:
<223> OTHER INFORMATION: hSC34.25 CDRL2

<400> SEQUENCE: 251

Trp Ala Ser Thr Arg Glu Ser
1               5

<210> SEQ ID NO 252
<211> LENGTH: 9
<212> TYPE: PRT
<213> ORGANISM: Artificial Sequence
<220> FEATURE:
<223> OTHER INFORMATION: hSC34.25 CDRL3

<400> SEQUENCE: 252

Gln Gln Tyr Tyr Arg Tyr Pro Leu Thr
1               5

<210> SEQ ID NO 253
<211> LENGTH: 5
<212> TYPE: PRT
<213> ORGANISM: Artificial Sequence
<220> FEATURE:
<223> OTHER INFORMATION: hSC34.25 CDRH1

<400> SEQUENCE: 253

Ser Tyr Ala Ile Ser
1               5

<210> SEQ ID NO 254
<211> LENGTH: 17
<212> TYPE: PRT
<213> ORGANISM: Artificial Sequence
<220> FEATURE:
<223> OTHER INFORMATION: hSC34.25 CDRH2

<400> SEQUENCE: 254

Glu Ile Tyr Pro Gly Ser Gly Glu Thr Tyr Tyr Asn Glu Lys Phe Lys
```

1               5                   10                  15

Gly

<210> SEQ ID NO 255
<211> LENGTH: 10
<212> TYPE: PRT
<213> ORGANISM: Artificial Sequence
<220> FEATURE:
<223> OTHER INFORMATION: hSC34.25 CDRH3

<400> SEQUENCE: 255

Val Asn Asp Tyr Gly Ser Trp Phe Pro Tyr
1               5                   10

<210> SEQ ID NO 256
<211> LENGTH: 12
<212> TYPE: PRT
<213> ORGANISM: Artificial Sequence
<220> FEATURE:
<223> OTHER INFORMATION: hSC34.28 and hSC34.28ss1 CDRL1

<400> SEQUENCE: 256

Thr Ala Ser Ser Ser Val Asn Ser Phe Tyr Leu His
1               5                   10

<210> SEQ ID NO 257
<211> LENGTH: 7
<212> TYPE: PRT
<213> ORGANISM: Artificial Sequence
<220> FEATURE:
<223> OTHER INFORMATION: hSC34.28 and hSC34.28ss1 CDRL2

<400> SEQUENCE: 257

Ser Thr Ser Asn Leu Ala Ser
1               5

<210> SEQ ID NO 258
<211> LENGTH: 9
<212> TYPE: PRT
<213> ORGANISM: Artificial Sequence
<220> FEATURE:
<223> OTHER INFORMATION: hSC34.28 and hSC34.28ss1 CDRL3

<400> SEQUENCE: 258

His Gln Tyr His Arg Ser Pro Tyr Thr
1               5

<210> SEQ ID NO 259
<211> LENGTH: 5
<212> TYPE: PRT
<213> ORGANISM: Artificial Sequence
<220> FEATURE:
<223> OTHER INFORMATION: hSC34.28 and hSC34.28ss1 CDRH1

<400> SEQUENCE: 259

Ser Tyr Trp Ile Glu
1               5

<210> SEQ ID NO 260
<211> LENGTH: 17
<212> TYPE: PRT
<213> ORGANISM: Artificial Sequence
<220> FEATURE:
<223> OTHER INFORMATION: hSC34.28 and hSC34.28ss1 CDRH2

<400> SEQUENCE: 260

```
Glu Ile Leu Pro Gly Ser Gly Asn Thr Tyr Tyr Asn Glu Arg Phe Lys
1               5                   10                  15
Asp
```

<210> SEQ ID NO 261
<211> LENGTH: 14
<212> TYPE: PRT
<213> ORGANISM: Artificial Sequence
<220> FEATURE:
<223> OTHER INFORMATION: hSC34.28 and hSC34.28ss1 CDRH3

<400> SEQUENCE: 261

```
Arg Ala Ala Ala Tyr Tyr Ser Asn Pro Glu Trp Phe Ala Tyr
1               5                   10
```

<210> SEQ ID NO 262
<211> LENGTH: 16
<212> TYPE: PRT
<213> ORGANISM: Artificial Sequence
<220> FEATURE:
<223> OTHER INFORMATION: hSC34.38 CDRL1

<400> SEQUENCE: 262

```
Lys Ser Ser Gln Ser Leu Leu Tyr Ser Asn Arg Arg Thr Tyr Leu Asn
1               5                   10                  15
```

<210> SEQ ID NO 263
<211> LENGTH: 7
<212> TYPE: PRT
<213> ORGANISM: Artificial Sequence
<220> FEATURE:
<223> OTHER INFORMATION: hSC34.38 CDRL2

<400> SEQUENCE: 263

```
Leu Val Ser Lys Leu Asp Ser
1               5
```

<210> SEQ ID NO 264
<211> LENGTH: 9
<212> TYPE: PRT
<213> ORGANISM: Artificial Sequence
<220> FEATURE:
<223> OTHER INFORMATION: hSC34.38 CDRL3

<400> SEQUENCE: 264

```
Val Gln Gly Thr His Phe Pro Phe Thr
1               5
```

<210> SEQ ID NO 265
<211> LENGTH: 5
<212> TYPE: PRT
<213> ORGANISM: Artificial Sequence
<220> FEATURE:
<223> OTHER INFORMATION: hSC34.38 CDRH1

<400> SEQUENCE: 265

```
Ser Tyr Tyr Met Tyr
1               5
```

<210> SEQ ID NO 266
<211> LENGTH: 17
<212> TYPE: PRT
<213> ORGANISM: Artificial Sequence
<220> FEATURE:
<223> OTHER INFORMATION: hSC34.38 CDRH2

<400> SEQUENCE: 266

-continued

Glu Ile Asn Pro Ser Asn Gly Gly Ala Asn Phe Asn Glu Arg Phe Lys
1               5                   10                  15
Asn

<210> SEQ ID NO 267
<211> LENGTH: 13
<212> TYPE: PRT
<213> ORGANISM: Artificial Sequence
<220> FEATURE:
<223> OTHER INFORMATION: hSC34.38 CDRH3

<400> SEQUENCE: 267

Gly Leu Leu Tyr Tyr Asp Tyr Asp Arg Gly Phe Ala Tyr
1               5                   10

<210> SEQ ID NO 268
<211> LENGTH: 17
<212> TYPE: PRT
<213> ORGANISM: Artificial Sequence
<220> FEATURE:
<223> OTHER INFORMATION: hSC34.87 CDRL1

<400> SEQUENCE: 268

Lys Ser Ser Gln Ser Leu Leu Asn Ser Arg Thr Arg Lys Asn Tyr Leu
1               5                   10                  15
Ala

<210> SEQ ID NO 269
<211> LENGTH: 7
<212> TYPE: PRT
<213> ORGANISM: Artificial Sequence
<220> FEATURE:
<223> OTHER INFORMATION: hSC34.87 CDRL2

<400> SEQUENCE: 269

Trp Ala Ser Thr Arg Glu Ser
1               5

<210> SEQ ID NO 270
<211> LENGTH: 8
<212> TYPE: PRT
<213> ORGANISM: Artificial Sequence
<220> FEATURE:
<223> OTHER INFORMATION: hSC34.87 CDRL3

<400> SEQUENCE: 270

Lys Gln Ser Tyr Asn Leu Trp Thr
1               5

<210> SEQ ID NO 271
<211> LENGTH: 5
<212> TYPE: PRT
<213> ORGANISM: Artificial Sequence
<220> FEATURE:
<223> OTHER INFORMATION: hSC34.87 CDRH1

<400> SEQUENCE: 271

Ser Tyr Trp Met Leu
1               5

<210> SEQ ID NO 272
<211> LENGTH: 17
<212> TYPE: PRT
<213> ORGANISM: Artificial Sequence
<220> FEATURE:

-continued

```
<223> OTHER INFORMATION: hSC34.87 CDRH2

<400> SEQUENCE: 272

Tyr Ile Asp Pro Arg Asn Gly Tyr Thr Glu Tyr Asn Gln Lys Phe Lys
1               5                   10                  15

Asp

<210> SEQ ID NO 273
<211> LENGTH: 8
<212> TYPE: PRT
<213> ORGANISM: Artificial Sequence
<220> FEATURE:
<223> OTHER INFORMATION: hSC34.87 CDRH3

<400> SEQUENCE: 273

Gly Gly Asn Val Ala Met Asp Tyr
1               5
```

ANTI-DPEP3 ANTIBODIES AND METHODS OF USE

CROSS REFERENCED APPLICATIONS

This application claims the benefit of U.S. Provisional Application No. 61/915,321 filed on Dec. 12, 2013, which is incorporated herein by reference in its entirety.

SEQUENCE LISTING

This application contains a sequence listing which has been submitted in ASCII format via EFS-Web and is hereby incorporated by reference in its entirety. Said ASCII copy, created on Dec. 11, 2014, is named sc3401pct_S69697_1050WO_SEQL_121114.txt and is 264,346 bytes in size.

FIELD OF THE INVENTION

This application generally relates to novel anti-DPEP3 antibodies or immunoreactive fragments thereof and compositions, including antibody drug conjugates, comprising the same for the treatment, diagnosis or prophylaxis of cancer and any recurrence or metastasis thereof.

Selected embodiments of the invention provide for the use of such anti-DPEP3 antibodies or antibody drug conjugates for the treatment of cancer comprising a reduction in tumorigenic cell frequency.

BACKGROUND OF THE INVENTION

Differentiation and proliferation of stem cells and progenitor cells are normal ongoing processes that act in concert to support tissue growth during organogenesis, cell repair and cell replacement. The system is tightly regulated to ensure that only appropriate signals are generated based on the needs of the organism. Cell proliferation and differentiation normally occur only as necessary for the replacement of damaged or dying cells or for growth. However, disruption of these processes can be triggered by many factors including the under- or overabundance of various signaling chemicals, the presence of altered microenvironments, genetic mutations or a combination thereof. Disruption of normal cellular proliferation and/or differentiation can lead to various disorders including proliferative diseases such as cancer.

Conventional therapeutic treatments for cancer include chemotherapy, radiotherapy and immunotherapy. Often these treatments are ineffective and surgical resection may not provide a viable clinical alternative. Limitations in the current standard of care are particularly evident in those cases where patients undergo first line treatments and subsequently relapse. In such cases refractory tumors, often aggressive and incurable, frequently arise. The overall survival rates for many solid tumors have remained largely unchanged over the years due, at least in part, to the failure of existing therapies to prevent relapse, tumor recurrence and metastasis. There remains therefore a great need to develop more targeted and potent therapies for proliferative disorders. The current invention addresses this need.

SUMMARY OF THE INVENTION

In a broad aspect the present invention provides isolated antibodies which specifically bind to human DPEP3 protein. In certain embodiments the DPEP3 protein is expressed on tumor initiating cells. In other embodiments the antibodies of the invention bind to DPEP3 and compete for binding with an antibody that binds to an epitope on DPEP3.

In particular aspects of the invention, the antibodies of the invention bind to an epitope in a DPEP3 protein, wherein the epitope comprises three or more residues selected from the group consisting of E217, R242, Q248, Q372, K375, and E379 of SEQ ID NO: 3. For example, such an epitope can comprise (1) R242, Q248, Q372; (2) R242, Q248, K375 (3) R242, Q248, E379; (4) R242, Q372, K375; (5) R242, Q372, E379; (6) R242, K375, E379; (7) Q248, Q372, K375; (8) Q248, Q372, E379; (9) Q248, K375, E379; (10) Q372, K375, E379; (11) R242, Q248, Q372, K375; (12) R242, Q248, Q372, E379; (13) R242, Q248, K375, E379; (14) R242, Q372, K375, E379; (15) Q248, Q372, K375, E379; (16) R242, Q248, Q372, K375, E379; (17) E217, R242, Q248; (18) E217, R242, Q372; (19) E217, R242, K375; (20) E217, R242, E379; (21) E217, Q248, Q372; (22) E217, Q248, K375; (23) E217, Q248, E379; (24) E217, Q372, K375; (25) E217, K375, E379; (26) E217, Q372, E379; (27) E217, R242, Q248, Q372; (28) E217, R242, Q248, E379; (29) E217, Q248, Q372, K375; (30) E217, R242, Q372, K375; (31) E217, R242, Q248, K375; (32) E217, Q372, K375, E379; (33) E217, Q248, K375, E379; (34) E217, Q248, Q372, E379; (35) E217, R242, K375, E379; (36) E217, R242, Q372, E379; (37) E217, Q248, Q372, K375, E379; (38) E217, R242, Q372, K375, E379; (39) E217, R242, Q248, K375, E379; (40) E217, R242, Q248, Q372, E379; or (41) E217, R242, Q248, Q372, K375; or (42) E217, R242, Q248, Q372, K375 E379.

In other particular aspects of the invention, the antibodies of the invention bind to an epitope in a DPEP3 protein, wherein the epitope comprises three or more residues selected from the group consisting of R46, R48, R54, and S55 of SEQ ID NO: 3. For example, such an epitope can comprise (1) R46, R48, R54; (2) R46, R48, S55; (3) R46, R54, S55; (4) R48, R54, S55; or (5) R46, R48, R54, S55.

In other particular aspects of the invention, the antibodies of the invention bind to an epitope in a DPEP3 protein, wherein the epitope comprises three or more residues selected from the group consisting of Q248, S380, S384, and V386 of SEQ ID NO: 3. For example, such an epitope can comprise (1) S380, S384, V386; (2) S380, S384, Q248; (3) S380, V386, Q248; (4) S384, V386, Q248; or (5) S380, S384, V386, Q248.

In other particular aspects of the invention the antibody binds specifically to DPEP3 and competes for binding with an antibody comprising: a light chain variable region (VL) of SEQ ID NO: 21 and a heavy chain variable region (VH) of SEQ ID NO: 23; or a VL of SEQ ID NO: 25 and a VH of SEQ ID NO: 27; or a VL of SEQ ID NO: 29 and a VH of SEQ ID NO: 31; or a VL of SEQ ID NO: 33 and a VH of SEQ ID NO: 35; or a VL of SEQ ID NO: 37 and a VH of SEQ ID NO: 39; or a VL of SEQ ID NO: 41 and a VH of SEQ ID NO: 43; or a VL of SEQ ID NO: 45 and a VH of SEQ ID NO: 47; or a VL of SEQ ID NO: 49 and a VH of SEQ ID NO: 51; or a VL of SEQ ID NO: 53 and a VH of SEQ ID NO: 55; or a VL of SEQ ID NO: 57 and a VH of SEQ ID NO: 59; or a VL of SEQ ID NO: 61 and a VH of SEQ ID NO: 63; or a VL of SEQ ID NO: 65 and a VH of SEQ ID NO: 67; or a VL of SEQ ID NO: 69 and a VH of SEQ ID NO: 71; or a VL of SEQ ID NO: 73 and a VH of SEQ ID NO: 75; or a VL of SEQ ID NO: 77 and a VH of SEQ ID NO: 79; or a VL of SEQ ID NO: 81 and a VH of SEQ ID NO: 83; or a VL of SEQ ID NO: 85 and a VH of SEQ ID NO: 87; or a VL of SEQ ID NO: 89 and a VH of SEQ ID NO: 91; or a VL of SEQ ID NO: 93 and a VH of SEQ ID NO: 95; or a VL of SEQ ID NO: 97 and a VH of SEQ ID NO: 99; or a VL of SEQ ID NO: 101 and a VH of SEQ ID NO: 103; or a VL of SEQ ID NO: 105 and a VH of SEQ ID NO: 107; or a VL of SEQ ID NO: 109 and a VH of SEQ ID NO: 111; or a VL of SEQ ID NO: 113 and a VH of SEQ ID NO: 115; or a VL of SEQ ID NO: 117 and a VH of SEQ ID NO: 119; or a VL of SEQ ID NO: 121 and a VH of SEQ ID NO: 123; or a VL of SEQ ID NO: 125 and a VH of SEQ ID NO: 127; or a VL of SEQ ID NO: 129 and a VH of SEQ ID NO: 131; or a VL of SEQ ID NO: 133 and a VH of SEQ ID NO: 135; or a VL of SEQ ID NO: 137 and a VH of SEQ ID NO: 139; or a VL of SEQ ID NO: 141 and a VH of SEQ ID NO: 143; or a VL of SEQ ID NO: 145 and a VH of SEQ ID NO: 147; or a VL of SEQ ID NO: 149 and a VH of SEQ ID NO: 151; or a VL of SEQ ID NO: 153 and a VH of SEQ ID NO: 155; or a VL of SEQ ID NO: 157 and a VH of SEQ ID NO: 159; or a VL of SEQ ID NO: 161 and a VH of SEQ ID NO: 163; or a VL of SEQ ID NO: 165 and a VH of SEQ ID NO: 167; or a VL of SEQ ID NO: 169 and a VH of SEQ ID NO: 171; or a VL of SEQ ID NO: 173 and a VH of SEQ ID NO: 175; or a VL of SEQ ID NO: 177 and a VH of SEQ ID NO: 179; or a VL of SEQ ID NO: 181 and a VH of SEQ ID NO: 183; or a VL of SEQ ID NO: 185 and a VH of SEQ ID NO: 187. In some aspects of the invention the antibody is a chimeric, CDR grafted, humanized or recombinant antibody, or a fragment thereof. In other aspects of the invention the antibody comprising the aforementioned sequences is an internalizing antibody.

In preferred embodiments, the invention provides a humanized antibody that binds to DPEP3 and competes for binding with an antibody comprising three variable light chain CDRs (CDRL) as set forth in SEQ ID NO: 189; and three variable heavy chain CDRs (CDRH) as set forth in SEQ ID NO: 191; or three CDRL as set forth in SEQ ID NO: 193 and three CDRH as set forth in SEQ ID NO: 195; or three CDRL as set forth in SEQ ID NO: 197 and three CDRH as set forth in SEQ ID NO: 199; or three CDRL as set forth in SEQ ID NO: 201 and three CDRH as set forth in SEQ ID NO: 203; or three CDRL as set forth in SEQ ID NO: 205 and three CDRH as set forth in SEQ ID NO: 207; or three CDRL as set forth in SEQ ID NO: 209 and three CDRH as set forth in SEQ ID NO: 211; or three CDRL as set forth in SEQ ID NO: 213 and three CDRH as set forth in SEQ ID NO: 215.

In another aspect of the invention, the humanized antibody comprises a VH and VL, wherein the VL has three CDRL comprising a CDRL1 of SEQ ID NO: 232, a CDRL2 of SEQ ID NO: 233 and a CDRL3 of SEQ ID NO: 234; or a VL having three CDRLs comprising a CDRL1 of SEQ ID NO: 238, a CDRL2 of SEQ ID NO: 239 and a CDRL3 of SEQ ID NO: 240; or a VL having three CDRLs comprising a CDRL1 of SEQ ID NO: 244, a CDRL2 of SEQ ID NO: 245 and a CDRL3 of SEQ ID NO: 246; or a VL having three CDRLs comprising a CDRL1 of SEQ ID NO: 250, a CDRL2 of SEQ ID NO: 251 and a CDRL3 of SEQ ID NO: 252; or a VL having three CDRLs comprising a CDRL1 of SEQ ID NO: 256, a CDRL2 of SEQ ID NO: 257 and a CDRL3 of SEQ ID NO: 258; or a VL having three CDRLs comprising a CDRL1 of SEQ ID NO: 262, a CDRL2 of SEQ ID NO: 263 and a CDRL3 of SEQ ID NO: 264; or a VL having three CDRLs comprising a CDRL1 of SEQ ID NO: 268, a CDRL2 of SEQ ID NO: 269 and a CDRL3 of SEQ ID NO: 270.

In another aspect of the invention, the humanized antibody comprises a VH and VL, wherein the VH has three CDRs (CDRH) comprising a CDRH1 of SEQ ID NO: 235, a CDRH2 of SEQ ID NO: 236 and a CDRH3 of SEQ ID NO: 237; or the VH has three CDRHs comprising a CDRH1 of SEQ ID NO: 241, a CDRH2 of SEQ ID NO: 242 and a CDRH3 of SEQ ID NO: 243; or the VH has three CDRHs comprising a CDRH1 of SEQ ID NO: 247, a CDRH2 of SEQ ID NO: 248 and a CDRH3 of SEQ ID NO: 249; or the VH has three CDRHs comprising a CDRH1 of SEQ ID NO: 253, a CDRH2 of SEQ ID NO: 254 and a CDRH3 of SEQ ID NO: 255; or the VH has three CDRHs comprising a CDRH1 of SEQ ID NO: 259, a CDRH2 of SEQ ID NO: 260 and a CDRH3 of SEQ ID NO: 261; or the VH has three CDRHs comprising a CDRH1 of SEQ ID NO: 265, a CDRH2 of SEQ ID NO: 266 and a CDRH3 of SEQ ID NO: 267; or the VH has three CDRHs comprising a CDRH1 of SEQ ID NO: 271, a CDRH2 of SEQ ID NO: 272 and a CDRH3 of SEQ ID NO: 273.

In a further embodiment of the invention, the humanized antibody comprises a VL and VH wherein the VL has three CDRLs comprising a CDRL1 of SEQ ID NO: 232, a CDRL2 of SEQ ID NO: 233 and a CDRL3 of SEQ ID NO: 234 and the VH has three CDRHs comprising a CDRH1 of SEQ ID NO: 235, a CDRH2 of SEQ ID NO: 236 and a CDRH3 of SEQ ID NO: 237; or an antibody comprising a VL and VH wherein the VL has three CDRLs comprising a CDRL1 of SEQ ID NO: 238, a CDRL2 of SEQ ID NO: 239 and a CDRL3 of SEQ ID NO: 240 and the VH has three CDRHs comprising a CDRH1 of SEQ ID NO: 241, a CDRH2 of SEQ ID NO: 242 and a CDRH3 of SEQ ID NO: 243; or an antibody comprising a VL and VH wherein the VL has three CDRLs comprising a CDRL1 of SEQ ID NO: 244, a CDRL2 of SEQ ID NO: 245 and a CDRL3 of SEQ ID NO: 246 and the VH has three CDRHs comprising a CDRH1 of SEQ ID NO: 247, a CDRH2 of SEQ ID NO: 248 and a CDRH3 of SEQ ID NO: 249; or an antibody comprising a VL and VH wherein the VL has three CDRLs comprising a CDRL1 of SEQ ID NO: 250, a CDRL2 of SEQ ID NO: 251 and a CDRL3 of SEQ ID NO: 252 and the VH has three CDRHs comprising a CDRH1 of SEQ ID NO: 253, a CDRH2 of SEQ ID NO: 254 and a CDRH3 of SEQ ID NO: 255; or an antibody comprising a VL and VH wherein the VL has three CDRLs comprising a CDRL1 of SEQ ID NO: 256, a CDRL2 of SEQ ID NO: 257 and a CDRL3 of SEQ ID NO: 258 and the VH has three CDRHs comprising a CDRH1 of SEQ ID NO: 259, a CDRH2 of SEQ ID NO: 260 and a CDRH3 of SEQ ID NO: 261; or an antibody comprising a VL and VH wherein the VL has three CDRLs comprising a CDRL1 of SEQ ID NO: 262, a CDRL2 of SEQ ID NO: 263 and a CDRL3 of SEQ ID NO: 264 and the VH has three CDRHs comprising a CDRH1 of SEQ ID NO: 265, a CDRH2 of SEQ ID NO: 266 and a CDRH3 of SEQ ID NO: 267; or an antibody comprising a VL and VH wherein the VL has three CDRLs comprising a CDRL1 of SEQ ID NO: 268, a CDRL2 of SEQ ID NO: 269 and a CDRL3 of SEQ ID NO: 270 and the VH has three CDRHs comprising a CDRH1 of SEQ ID NO: 271, a CDRH2 of SEQ ID NO: 272 and a CDRH3 of SEQ ID NO: 273.

In yet another aspect, the invention provides a humanized antibody that binds to DPEP3 comprising a full length light chain set forth as SEQ ID NO: 216 and a full length heavy chain set forth as SEQ ID NO: 217; or a full length light chain set forth as SEQ ID NO: 218 and a full length heavy chain set forth as SEQ ID NO: 219; or a full length light chain set forth as SEQ ID NO: 220 and a full length heavy chain set forth as SEQ ID NO: 221; or a full length light chain set forth as SEQ ID NO: 222 and a full length heavy chain set forth as SEQ ID NO: 223; or a full length light chain set forth as SEQ ID NO: 224 and a full length heavy chain set forth as SEQ ID NO: 225; or a full length light chain set forth as SEQ ID NO: 224 and a full length heavy chain set forth as SEQ ID NO: 226; or a full length light chain set forth as SEQ ID NO: 227 and a full length heavy chain set forth as SEQ ID NO: 228; or a full length light chain set forth as SEQ ID NO: 229 and a full length heavy chain set forth as SEQ ID NO: 230.

The present invention also provides anti-DPEP3 antibody drug conjugates where the antibody disclosed herein, is conjugated to a payload.

In one embodiment, the invention is directed to a nucleic acid encoding the heavy or light chain amino acid sequence of any one of the anti-DPEP3 antibodies disclosed herein. In another embodiment the invention is directed to a vector containing such nucleic acid or a host cell expressing such nucleic acid.

Compatible anti-DPEP3 antibody drug conjugates (ADCs) of the invention generally comprise the formula Ab-[L-D]n, wherein Ab comprises an antibody that binds DPEP3; L is an optional linker; D is a drug; and n is an integer from about 1 to about 20. In particularly preferred embodiments, D comprises a pyrrolobenzodiazepine (PBD). Further provided are pharmaceutical compositions comprising an anti-DPEP3 ADC as disclosed herein.

In another embodiment the present invention provides a method of treating cancer such as ovarian cancer (e.g. ovarian-serous carcinoma or ovarian-papillary serous carcinoma), lung cancer, breast cancer and endometrial cancer, comprising administering a pharmaceutical composition comprising an anti-DPEP3 ADC disclosed herein.

In some embodiments, the invention provides a method of treating cancer comprising administering anti-DPEP3 ADC disclosed herein and further comprising administering to the subject at least one additional therapeutic moiety.

The present invention also provides a method of reducing tumor initiating cells in a tumor cell population, wherein the method comprises contacting (e.g. in vivo or in vivo) a tumor cell population comprising tumor initiating cells and tumor cells other than tumor initiating cells, with an anti-DPEP3 ADC; whereby the frequency of tumor initiating cells is reduced.

Further disclosed herein is a method of delivering a cytotoxin to a cell comprising contacting the cell with an anti-DPEP3 ADC.

BRIEF DESCRIPTION OF THE FIGURES

FIG. 4 is a tabular representation of various characteristics of the anti-DPEP3 antibodies of the invention including isotype, affinity for DPEP3 and cross reactivity to DPEP2 and orthologs of DPEP3;

FIGS. 5A-5D provide amino acid and nucleic acid sequences of mouse and humanized anti-DPEP3 antibodies. FIGS. 5A and 5B show the amino acid sequences of the light chain (FIG. 5A) and heavy chain (FIG. 5B) variable regions (SEQ ID NOS: 21-215, odd numbers) of exemplary murine and humanized anti-DPEP3 antibodies. FIG. 5C shows the nucleic acid sequences of the light and heavy chain variable regions (SEQ ID NOS: 20-214, even numbers) of exemplary mouse and humanized anti-DPEP3 antibodies. FIG. 5D shows the full length amino acid sequences of the light and heavy chains of exemplary humanized anti-DPEP3 antibodies (SEQ ID NOS: 216-230).

DETAILED DESCRIPTION OF THE INVENTION

Figure 1A:
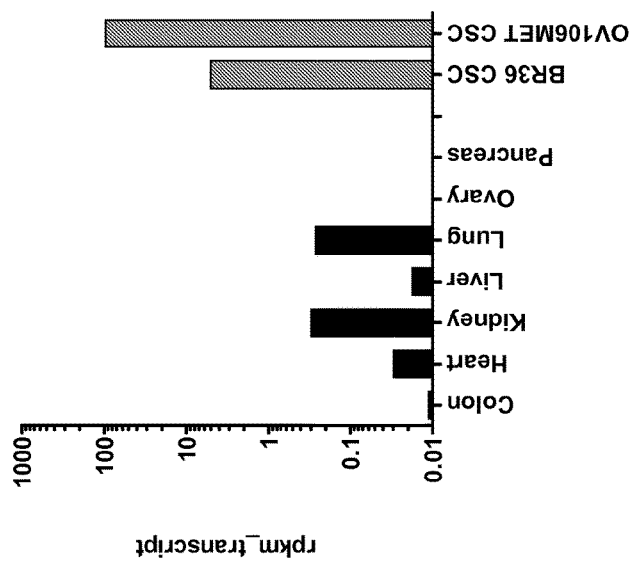
FIGS. 1A and 1B show DPEP3 mRNA expression determined by whole transcriptome sequencing in selected patient-derived xenograft (PDX) tumors analyzed using SOLiD (FIG. 1A) or Illumina platforms (FIG. 1B)

The invention may be embodied in many different forms. Disclosed herein are non-limiting, illustrative embodiments of the invention that exemplify the principles thereof. Any section headings used herein are for organizational purposes only and are not to be construed as limiting the subject matter described. For the purposes of the instant disclosure all identifying sequence accession numbers may be found in the NCBI Reference Sequence (RefSeq) database and/or the NCBI GenBank® archival sequence database unless otherwise noted.

DPEP3 has surprisingly been found to be a biological marker of a number of tumor types and this association may be exploited for the treatment of such tumors. It has also unexpectedly been found that DPEP3 is associated with tumorigenic cells and may be effectively exploited to inhibit or eliminate them. Tumorigenic cells, which will be described in more detail below, are known to exhibit resistance to many conventional treatments. In contrast to the teachings of the prior art, the disclosed compounds, compositions and methods effectively overcome this inherent resistance.

The invention provides anti-DPEP3 antibodies (including antibody drug conjugates) and their use in the prognosis, diagnosis, theragnosis, treatment and/or prevention of a variety of DPEP3-associated cancers regardless of any particular mechanism of action or specifically targeted cellular or molecular component.

I DPEP3 PHYSIOLOGY

Dipeptidase 3 (DPEP3; also known as MBD3) is a glycosylphosphatidylinositol anchored membrane protein from the DPEP family of dipeptidase proteins, which are involved in the hydrolytic metabolism of various dipeptides and some antibiotics containing amide-like linkages (e.g., beta-lactams and penems). Mouse DPEP3 has been shown to cleave cystinyl-bis-glycine, a glutathione cleavage product (Habib et al., PMID: 12738806). Representative DPEP3 protein orthologs include, but are not limited to, human (UniProtKB Q9H4B8.2 [SEQ ID NO: 4], NP_071752.3 [SEQ ID NO: 5]), chimpanzee (NP_001266956), rhesus monkey (NP_00180985), rat (NP_001008384, [SEQ ID NO: 10]), and mouse (NP_082236, [SEQ ID NO: 8]).

In humans, the DPEP3 gene consists of 10 exons spanning approximately 2 kBp on chromosome 16, in a head to tail cluster with the related gene DPEP2, which shares approximately 75% identity at the protein level. Transcription of the DPEP3 locus yields two known RNA transcripts, a longer mature transcript of 1.76 kBp (NM_022357) encoding a 513 amino acid preprotein (NP_071752.3), and an alternatively spliced shorter mature transcript of 1.75 kBp (NM_00129758) encoding a 512 amino acid preprotein (NP_001123230). In addition to the two longer transcripts an alternative version of the DPEP3 preprotein having a shorter leader sequence and comprising 488 amino acids has also been provided (UniProtKB Q9H4B8.2, SEQ ID NO: 4). With respect to the longer 512 and 513 amino acid isoforms the proposed leader sequence comprises approximately 60 amino acid residues while for the shorter 488 amino acid DPEP3 molecule, the leader sequence comprises 35 amino acids. In each case the secretion signal peptide (60 or 35 amino acids) of the preprotein is removed to provide a mature protein of 453 amino acids (UniProtKB Q9H4B8.2, SEQ ID NO: 3) which is then further processed to remove the final 25 amino acids and link the mature protein to the cell membrane via a GPI anchor. The remaining extracellular domain of mature DPEP3 comprises 428 amino acids (A1 to S428 of SEQ ID NO: 3). Unless otherwise indicated all residue numbering of the DPEP3 antigen (e.g., for epitope constituents) will be based on SEQ ID NO: 3.

The DPEP3 protein is a member of the peptidase M19 family, all of which require zinc cofactors for enzymatic function. At least in the mouse testis germ cells, the catalytic complex is formed as a disulfide linked homodimer (Yoshitake et al., 2011: PMID: 21724266). Other than as set forth herein, there is limited information on the function and expression of the human DPEP3 protein. Mouse DPEP3 protein expression has been reported to be limited to the testis and has been shown to cleave cystinyl-bis-glycine, a glutathione cleavage product (Habib et al., PMID: 12738806). There have been no published reports known to the inventors about functional links or associations between DPEP3 and cancer.

II CANCER STEM CELLS

According to the current models, a tumor comprises non-tumorigenic cells and tumorigenic cells. Non-tumorigenic cells do not have the capacity to self-renew and are incapable of reproducibly forming tumors, even when transplanted into immunocompromised mice in excess cell numbers. Tumorigenic cells, also referred to herein as "tumor initiating cells" (TICs), which make up 0.1-40% (more typically 0.1-10%) of a tumor's cell population, have the ability to form tumors. Tumorigenic cells encompass both tumor perpetuating cells (TPCs), referred to interchangeably as cancer stem cells (CSCs) and tumor progenitor cells (TProgs).

CSCs, like normal stem cells that support cellular hierarchies in normal tissue, are able to self-replicate indefinitely while maintaining the capacity for multilineage differentiation. CSCs are able to generate both tumorigenic progeny and non-tumorigenic progeny and are able to completely recapitulate the heterogeneous cellular composition of the parental tumor as demonstrated by serial isolation and transplantation of low numbers of isolated CSCs into immunocompromised mice.

TProgs, like CSCs have the ability to fuel tumor growth in a primary transplant. However, unlike CSCs, they are not able to recapitulate the cellular heterogeneity of the parental tumor and are less efficient at reinitiating tumorigenesis in subsequent transplants because TProgs are typically only capable of a finite number of cell divisions as demonstrated by serial transplantation of low numbers of highly purified TProg into immunocompromised mice. TProgs may further be divided into early TProgs and late TProgs, which may be distinguished by phenotype (e.g., cell surface markers) and their different capacities to recapitulate tumor cell architecture. While neither can recapitulate a tumor to the same extent as CSCs, early TProgs have a greater capacity to recapitulate the parental tumor's characteristics than late TProgs. Notwithstanding the foregoing distinctions, it has been shown that some TProg populations can, on rare occasion, gain self-renewal capabilities normally attributed to CSCs and can themselves become CSCs.

CSCs exhibit higher tumorigenicity and are relatively more quiescent than: (i) TProgs (both early and late TProgs); and (ii) non-tumorigenic cells such as tumor-infiltrating cells, for example, fibroblasts/stroma, endothelial and hematopoietic cells that may be derived from CSCs and typically comprise the bulk of a tumor. Given that conventional therapies and regimens have, in large part, been designed to debulk tumors and attack rapidly proliferating cells, CSCs are more resistant to conventional therapies and regimens than the faster proliferating TProgs and other bulk tumor cell populations such as non-tumorigenic cells. Other characteristics that may make CSCs relatively chemoresistant to conventional therapies are increased expression of multi-drug resistance transporters, enhanced DNA repair mechanisms and anti-apoptotic gene expression. These properties in CSCs constitute a key reason for the failure of standard oncology treatment regimens to ensure long-term benefit for most patients with advanced stage neoplasia because standard chemotherapy does not target the CSCs that actually fuel continued tumor growth and recurrence.

It has surprisingly been discovered that DPEP3 expression is associated with various tumorigenic cell populations. The invention provides anti-DPEP3 antibodies that may be particularly useful for targeting tumorigenic cells and may be used to silence, sensitize, neutralize, reduce the frequency, block, abrogate, interfere with, decrease, hinder, restrain, control, deplete, moderate, mediate, diminish, reprogram, eliminate, or otherwise inhibit (collectively, "inhibit") tumorigenic cells, thereby facilitating the treatment, management and/or prevention of proliferative disorders (e.g. cancer). Advantageously, the novel anti-DPEP3 antibodies of the invention may be selected so they preferably reduce the frequency or tumorigenicity of tumorigenic cells upon administration to a subject regardless of the form of the DPEP3 determinant (e.g., phenotypic or genotypic). The reduction in tumorigenic cell frequency may occur as a result of (i) inhibition or eradication of tumorigenic cells; (ii) controlling the growth, expansion or recurrence of tumorigenic cells; (iii) interrupting the initiation, propagation, maintenance, or proliferation of tumorigenic cells; or (iv) by otherwise hindering the survival, regeneration and/or metastasis of the tumorigenic cells. In some embodiments, the inhibition of tumorigenic cells may occur as a result of a change in one or more physiological pathways. The change in the pathway, whether by inhibition of the tumorigenic cells, modification of their potential (for example, by induced differentiation or niche disruption) or otherwise interfering with the ability of tumorigenic cells to influence the tumor environment or other cells, allows for the more effective treatment of DPEP3 associated disorders by inhibiting tumorigenesis, tumor maintenance and/or metastasis and recurrence.

Methods that can be used to assess the reduction in the frequency of tumorigenic cells, include but are not limited to, cytometric or immunohistochemical analysis, preferably by in vitro or in vivo limiting dilution analysis (Dylla et al. 2008, PMID: PMC2413402 and Hoey et al. 2009, PMID: 19664991).

In vitro limiting dilution analysis may be performed by culturing fractionated or unfractionated tumor cells (e.g. from treated and untreated tumors, respectively) on solid medium that fosters colony formation and counting and characterizing the colonies that grow. Alternatively, the tumor cells can be serially diluted onto plates with wells containing liquid medium and each well can be scored as either positive or negative for colony formation at any time after inoculation but preferably more than 10 days after inoculation.

In vivo limiting dilution is performed by transplanting tumor cells, from either untreated controls or from tumors exposed to selected therapeutic agents, into immunocompromised mice in serial dilutions and subsequently scoring each mouse as either positive or negative for tumor formation. The scoring may occur at any time after the implanted tumors are detectable but is preferably done 60 or more days after the transplant. The analysis of the results of limiting dilution experiments to determine the frequency of tumorigenic cells is preferably done using Poisson distribution statistics or assessing the frequency of predefined definitive events such as the ability to generate tumors in vivo or not (Fazekas et al., 1982, PMID: 7040548).

Flow cytometry and immunohistochemistry may also be used to determine tumorigenic cell frequency. Both techniques employ one or more antibodies or reagents that bind art recognized cell surface proteins or markers known to enrich for tumorigenic cells (see WO 2012/031280). As known in the art, flow cytometry (e.g. florescence activated cell sorting (FACS)) can also be used to characterize, isolate, purify, enrich or sort for various cell populations including tumorigenic cells. Flow cytometry measures tumorigenic cell levels by passing a stream of fluid, in which a mixed population of cells is suspended, through an electronic detection apparatus which is able to measure the physical and/or chemical characteristics of up to thousands of particles per second. Immunohistochemistry provides additional information in that it enables visualization of tumorigenic cells in situ (e.g., in a tissue section) by staining the tissue sample with labeled antibodies or reagents which bind to tumorigenic cell markers.

The antibodies of the invention may be useful for identifying, characterizing, monitoring, isolating, sectioning or enriching populations or subpopulations of tumorigenic cells through methods such as, for example, flow cytometry, magnetic activated cell sorting (MACS), laser mediated sectioning or FACS. FACS is a reliable method used to isolate cell subpopulations at more than 99.5% purity based on specific cell surface markers. Other compatible techniques for the characterization and manipulation of tumorigenic cells including CSCs can be seen, for example, in U.S. patent Ser. Nos. 12/686,359, 12/669,136 and 12/757,649.

Listed below are markers that have been associated with CSC populations and have been used to isolate or characterize CSCs: ABCA1, ABCA3, ABCG2, ADAM9, ADCY9, ADORA2A, AFP, AXIN1, B7H3, BCL9, Bmi-1, BMP-4, C20orf52, C4.4A, carboxypeptidase M, CAV1, CAV2, CD105, CD133, CD14, CD16, CD166, CD16a, CD16b, CD2, CD20, CD24, CD29, CD3, CD31, CD324, CD325, CD34, CD38, CD44, CD45, CD46, CD49b, CD49f, CD56, CD64, CD74, CD9, CD90, CEACAM6, CELSR1, CPD, CRIM1, CX3CL1, CXCR4, DAF, decorin, easyh1, easyh2, EDG3, eed, EGFR, ENPP1, EPCAM, EPHA1, EPHA2, FLJ10052, FLVCR, FZD1, FZD10, FZD2, FZD3, FZD4, FZD6, FZD7, FZD8, FZD9, GD2, GJA1, GLI1, GLI2, GPNMB, GPR54, GPRC5B, IL1R1, IL1RAP, JAM3, Lgr5, Lgr6, LRP3, LY6E, MCP, mf2, mllt3, MPZL1, MUC1, MUC16, MYC, N33, Nanog, NB84, nestin, NID2, NMA, NPC1, oncostatin M, OCT4, OPN3, PCDH7, PCDHA10, PCDHB2, PPAP2C, PTPN3, PTS, RARRES1, SEMA4B, SLC19A2, SLC1A1, SLC39A1, SLC4A11, SLC6A14, SLC7A8, smarcA3, smarcD3, smarcE1, smarcA5, Sox1, STAT3, STEAP, TCF4, TEM8, TGFBR3, TMEPAI, TMPRSS4, transferrin receptor, TrkA, WNT10B, WNT16, WNT2, WNT2B, WNT3, WNT5A, YY1 and β-catenin. See, for example, Schulenburg et al., 2010, PMID: 20185329, U.S. Pat. No. 7,632,678 and U.S.P.N.s. 2007/0292414, 2008/0175870, 2010/0275280, 2010/0162416 and 2011/0020221.

Similarly, non-limiting examples of cell surface phenotypes associated with CSCs of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other CSC surface phenotypes that are known in the art. See, for example, Schulenburg et al., 2010, supra, Visvader et al., 2008, PMID: 18784658 and U.S.P.N. 2008/0138313. Of particular interest with respect to the instant invention are CSC preparations comprising $CD46^{hi}CD324^+$ phenotypes.

"Positive," "low" and "negative" expression levels as they apply to markers or marker phenotypes are defined as follows. Cells with negative expression (i.e. "−") are herein defined as those cells expressing less than, or equal to, the 95th percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the 95th percentile of expression observed with an isotype control antibody using the FMO staining procedure described above are herein defined as "positive" (i.e. "+"). As defined herein there are various populations of cells broadly defined as "positive." A cell is defined as positive if the mean observed expression of the antigen is above the 95th percentile determined using FMO staining with an isotype control antibody as described above. The positive cells may be termed cells with low expression (i.e. "lo") if the mean observed expression is above the $95^{th}$ percentile determined by FMO staining and is within one standard deviation of the $95^{th}$ percentile. Alternatively, the positive cells may be termed cells with high expression (i.e. "hi") if the mean observed expression is above the $95^{th}$ percentile determined by FMO staining and greater than one standard deviation above the $95^{th}$ percentile. In other embodiments the 99th percentile may preferably be used as a demarcation point between negative and positive FMO staining and in particularly preferred embodiments the percentile may be greater than 99%.

The $CD46^{hi}CD324^+$ marker phenotype and those exemplified immediately above may be used in conjunction with standard flow cytometric analysis and cell sorting techniques to characterize, isolate, purify or enrich TIC and/or TPC cells or cell populations for further analysis.

The ability of the antibodies of the current invention to reduce the frequency of tumorigenic cells can therefore be determined using the techniques and markers described above. In some instances, the anti-DPEP3 antibodies may reduce the frequency of tumorigenic cells by 10%, 15%, 20%, 25%, 30% or even by 35%. In other embodiments, the reduction in frequency of tumorigenic cells may be in the order of 40%, 45%, 50%, 55%, 60% or 65%. In certain embodiments, the disclosed compounds my reduce the frequency of tumorigenic cells by 70%, 75%, 80%, 85%, 90% or even 95%. It will be appreciated that any reduction of the frequency of tumorigenic cells is likely to result in a corresponding reduction in the tumorigenicity, persistence, recurrence and aggressiveness of the neoplasia.

III ANTIBODIES

A. Antibody Structure

Antibodies and variants and derivatives thereof, including accepted nomenclature and numbering systems, have been extensively described, for example, in Abbas et al. (2010), *Cellular and Molecular Immunology* ($6^{th}$ Ed.), W.B. Saunders Company; or Murphey et al. (2011), *Janeway's Immunobiology* ($8^{th}$ Ed.), Garland Science.

As used herein an "antibody" or "intact antibody" typically refers to a Y-shaped tetrameric protein comprising two heavy (H) and two light (L) polypeptide chains held together by covalent disulfide bonds and non-covalent interactions. Each light chain is composed of one variable domain (VL) and one constant domain (CL). Each heavy chain comprises one variable domain (VH) and a constant region, which in the case of IgG, IgA, and IgD antibodies, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (from about 10 to about 60 amino acids in various IgG subclasses). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues.

As used herein the term "antibody" includes polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')$_2$, F(ab') fragments, single-chain fragments (e.g. ScFv and ScFvFc); and derivatives thereof including Fc fusions and other modifications, and any other immunoreactive molecule so long as it exhibits preferential association or binding with a determinant. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

The variable domains of antibodies show considerable variation in amino acid composition from one antibody to another and are primarily responsible for antigen recognition and binding. Variable regions of each light/heavy chain pair form the antibody binding site such that an intact IgG antibody has two binding sites (i.e. it is bivalent). VH and VL domains comprise three regions of extreme variability, which are termed hypervariable regions, or more commonly, complementarity-determining regions (CDRs), framed and separated by four less variable regions known as framework regions (FRs). The non-covalent association between the $V_H$ and the $V_L$ region forms the Fv fragment (for "fragment variable") which contains one of the two antigen-binding sites of the antibody. ScFv fragments (for single chain fragment variable), which can be obtained by genetic engineering, associates in a single polypeptide chain, the $V_H$ and the $V_L$ region of an antibody, separated by a peptide linker.

As used herein, the assignment of amino acids to each domain, framework region and CDR may be in accordance with one of the numbering schemes provided by Kabat et al. (1991) *Sequences of Proteins of Immunological Interest* ($5^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, $3^{rd}$ Ed., Wily-VCH Verlag GmbH and Co or AbM (Oxford Molecular/MSI Pharmacopia) unless otherwise noted. The amino acid residues which comprise CDRs as defined by Kabat, Chothia, MacCallum (also known as Contact) and AbM as obtained from the Abysis website database (infra.) are set out below.

TABLE 1

|  | Kabat | Chothia | MacCallum | AbM |
|---|---|---|---|---|
| VH CDR1 | 31-35 | 26-32 | 30-35 | 26-35 |
| VH CDR2 | 50-65 | 52-56 | 47-58 | 50-58 |
| VH CDR3 | 95-102 | 95-102 | 93-101 | 95-102 |
| VL CDR1 | 24-34 | 24-34 | 30-36 | 24-34 |
| VL CDR2 | 50-56 | 50-56 | 46-55 | 50-56 |
| VL CDR3 | 89-97 | 89-97 | 89-96 | 89-97 |

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A.C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably the sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains*. In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. FIGS. 5E to 5K appended hereto show the results of such analysis in the annotation of several exemplary heavy and light chain variable regions. Unless otherwise indicated, all CDRs set forth herein are derived according to the Abysis database website as per Kabat et al.

For heavy chain constant region amino acid positions discussed in the invention, numbering is according to the Eu index first described in Edelman et al., 1969, Proc. Natl. Acad. Sci. USA 63(1): 78-85 describing the amino acid sequence of myeloma protein Eu, which reportedly was the first human IgG1 sequenced. The EU index of Edelman is also set forth in Kabat et al., 1991 (supra.). Thus, the terms "EU index as set forth in Kabat" or "EU index of Kabat" or "EU index" in the context of the heavy chain refers to the residue numbering system based on the human IgG1 Eu antibody of Edelman et al. as set forth in Kabat et al., 1991 (supra.) The numbering system used for the light chain constant region amino acid sequence is similarly set forth in Kabat et al., (supra.) An exemplary kappa light chain constant region amino acid sequence compatible with the present invention is set forth immediately below:

(SEQ ID NO: 1)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC.

Similarly, an exemplary IgG1 heavy chain constant region amino acid sequence compatible with the present invention is set forth immediately below:

(SEQ ID NO: 2)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG.

The disclosed constant region sequences, or variations or derivatives thereof, may be operably associated with the disclosed heavy and light chain variable regions using standard molecular biology techniques to provide full-length antibodies that may be used as such or incorporated in the anti-DPEP3 ADCs of the invention.

More generally the antibodies or immunoglobulins of the invention may be generated from any antibody that specifically recognizes or associates with the relevant determinant. As used herein "determinant" or "target" means any detectable trait, property, marker or factor that is identifiably associated with, or specifically found in or on a particular cell, cell population or tissue. Determinants or targets may be morphological, functional or biochemical in nature and are preferably phenotypic. In certain preferred embodiments a determinant is a protein that is differentially expressed (over- or under-expressed) by specific cell types or by cells under certain conditions (e.g., during specific points of the cell cycle or cells in a particular niche). For the purposes of the instant invention a determinant preferably is differentially expressed on aberrant cancer cells and may comprise a DPEP3 protein, or any of its splice variants, isoforms, homologs or family members, or specific domains, regions or epitopes thereof. An "antigen", "immunogenic determinant", "antigenic determinant" or "immunogen" means any protein or any fragment, region or domain thereof that can stimulate an immune response when introduced into an immunocompetent animal and is recognized by the antibodies produced from the immune response. The presence or absence of the DPEP3 determinants contemplated herein may be used to identify a cell, cell subpopulation or tissue (e.g., tumors, tumorigenic cells or CSCs).

There are two types of disulfide bridges or bonds in immunoglobulin molecules: interchain and intrachain disulfide bonds. As is well known in the art the location and number of interchain disulfide bonds vary according to the immunoglobulin class and species. While the invention is not limited to any particular class or subclass of antibody, the IgG1 immunoglobulin shall be used throughout the instant disclosure for illustrative purposes. In wild-type IgG1 molecules there are twelve intrachain disulfide bonds (four on each heavy chain and two on each light chain) and four interchain disulfide bonds. Intrachain disulfide bonds are generally somewhat protected and relatively less susceptible to reduction than interchain bonds. Conversely, interchain disulfide bonds are located on the surface of the immunoglobulin, are accessible to solvent and are usually relatively easy to reduce. Two interchain disulfide bonds exist between the heavy chains and one from each heavy chain to its respective light chain. It has been demonstrated that interchain disulfide bonds are not essential for chain association. The IgG1 hinge region contain the cysteines in the heavy chain that form the interchain disulfide bonds, which provide structural support along with the flexibility that facilitates Fab movement. The heavy/heavy IgG1 interchain disulfide bonds are located at residues C226 and C229 (Eu numbering) while the IgG1 interchain disulfide bond between the light and heavy chain of IgG1 (heavy/light) are formed between C214 of the kappa or lambda light chain and C220 in the upper hinge region of the heavy chain.

B. Antibody Generation and Production

Antibodies of the invention can be produced using a variety of methods known in the art.

1. Generation of Polyclonal Antibodies in Host Animals

The production of polyclonal antibodies in various host animals is well known in the art (see for example, Harlow and Lane (Eds.) (1988) Antibodies: A Laboratory Manual, CSH Press; and Harlow et al. (1989) Antibodies, NY, Cold Spring Harbor Press). In order to generate polyclonal antibodies, an immunocompetent animal (e.g., mouse, rat, rabbit, goat, non-human primate, etc.) is immunized with an antigenic protein or cells or preparations comprising an antigenic protein. After a period of time, polyclonal antibody-containing serum is obtained by bleeding or sacrificing the animal. The serum may be used in the form obtained from the animal or the antibodies may be partially or fully purified to provide immunoglobulin fractions or isolated antibody preparations.

Any form of antigen, or cells or preparations containing the antigen, can be used to generate an antibody that is specific for a determinant. The term "antigen" is used in a broad sense and may comprise any immunogenic fragment or determinant of the selected target including a single epitope, multiple epitopes, single or multiple domains or the entire extracellular domain (ECD). The antigen may be an isolated full-length protein, a cell surface protein (e.g., immunizing with cells expressing at least a portion of the antigen on their surface), or a soluble protein (e.g., immunizing with only the ECD portion of the protein). The antigen may be produced in a genetically modified cell. Any of the aforementioned antigens may be used alone or in combination with one or more immunogenicity enhancing adjuvants known in the art. The DNA encoding the antigen may be genomic or non-genomic (e.g., cDNA) and may encode at least a portion of the ECD, sufficient to elicit an immunogenic response. Any vectors may be employed to transform the cells in which the antigen is expressed, including but not limited to adenoviral vectors, lentiviral vectors, plasmids, and non-viral vectors, such as cationic lipids.

2. Monoclonal Antibodies

In selected embodiments, the invention contemplates use of monoclonal antibodies. The term "monoclonal antibody" or "mAb" refers to an antibody obtained from a population of substantially homogeneous antibodies, i.e., the individual antibodies comprising the population are identical except for possible mutations (e.g., naturally occurring mutations), that may be present in minor amounts.

Monoclonal antibodies can be prepared using a wide variety of techniques including hybridoma techniques, recombinant techniques, phage display technologies, transgenic animals (e.g., a XenoMouse®) or some combination thereof. For example, in preferred embodiments monoclonal antibodies can be produced using hybridoma and biochemical and genetic engineering techniques such as described in more detail in An, Zhigiang (ed.) *Therapeutic Monoclonal Antibodies: From Bench to Clinic*, John Wiley and Sons, 1$^{st}$ ed. 2009; Shire et. al. (eds.) *Current Trends in Monoclonal Antibody Development and Manufacturing*, Springer Science+Business Media LLC, 1$^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981). Following generation of a number of monoclonal antibodies that bind specifically to a determinant, particularly suitable antibodies may be selected through various screening processes, based on, for example, affinity for the determinant or rate of internalization. In particularly preferred embodiments monoclonal antibodies produced as described herein may be used as "source" antibodies and further modified to, for example, to improve affinity for the target, improve its production in cell culture, reduce immunogenicity in vivo, create multispecific constructs, etc. A more detailed description of monoclonal antibody production and screening is set out below and in the appended Examples.

3. Human Antibodies

The antibodies may comprise fully human antibodies. The term "human antibody" refers to an antibody (preferably a monoclonal antibody) which possesses an amino acid sequence that corresponds to that of an antibody produced by a human and/or has been made using any of the techniques for making human antibodies described below.

In one embodiment, recombinant human antibodies may be isolated by screening a recombinant combinatorial antibody library prepared using phage display. In one embodiment, the library is a scFv phage or yeast display library, generated using human VL and VH cDNAs prepared from mRNA isolated from B-cells.

Human antibodies can also be made by introducing human immunoglobulin loci into transgenic animals, e.g., mice in which the endogenous immunoglobulin genes have been partially or completely inactivated and human immunoglobulin genes have been introduced. Upon challenge antibody generation is observed which closely resembles that seen in humans in all respects, including gene rearrangement, assembly and fully human antibody repertoire. This approach is described, for example, in U.S. Pat. Nos. 5,545,807; 5,545,806; 5,569,825; 5,625,126; 5,633,425; 5,661,016, and U.S. Pat. Nos. 6,075,181 and 6,150,584 regarding XenoMouse® technology; and Lonberg and Huszar, 1995, PMID: 7494109). Alternatively, a human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., 1991, PMID: 2051030; and U.S. Pat. No. 5,750,373. As with other monoclonal antibodies such human antibodies may be used as source antibodies.

4. Derived Antibodies:

Once the source antibodies have been generated, selected and isolated as described above they may be further altered to provide anti-DPEP3 antibodies having improved pharmaceutical characteristics. Preferably the source antibodies are modified or altered using known molecular engineering techniques to provide derived antibodies having the desired therapeutic properties.

4.1 Chimeric and Humanized Antibodies

Selected embodiments of the invention comprise murine monoclonal antibodies that immunospecifically bind to DPEP3 and, for the purposes of the instant disclosure, may be considered "source" antibodies. In selected embodiments, antibodies compatible with the invention can be derived from such source antibodies through optional modification of the constant region and/or the antigen binding amino acid sequences of the source antibody. In certain embodiments an antibody is derived from a source antibody if selected amino acids in the source antibody are altered through deletion, mutation, substitution, integration or combination. In another embodiment, a "derived" antibody is one in which fragments of the source antibody (e.g., one or more CDRs or the entire heavy and light chain variable regions) are combined with or incorporated into an acceptor antibody sequence to provide the derivative antibody (e.g. chimeric or humanized antibodies). These derived antibodies can be generated using standard molecular biological techniques as described below, such as, for example, to improve affinity for the determinant; to improve antibody stability; to improve production and yield in cell culture; to reduce immunogenicity in vivo; to reduce toxicity; to facilitate conjugation of an active moiety; or to create a multispecific antibody. Such antibodies may also be derived from source antibodies through modification of the mature molecule (e.g., glycosylation patterns or pegylation) by chemical means or post-translational modification.

In one embodiment, the chimeric antibodies of the invention comprise chimeric antibodies that are derived from protein segments from at least two different species or class of antibodies that have been covalently joined. The term "chimeric" antibody is directed to constructs in which a portion of the heavy and/or light chain is identical or homologous to corresponding sequences in antibodies from a particular species or belonging to a particular antibody class or subclass, while the remainder of the chain(s) is identical or homologous to corresponding sequences in antibodies from another species or belonging to another antibody class or subclass, as well as fragments of such antibodies (U.S. Pat. No. 4,816,567; Morrison et al., 1984, PMID: 6436822). In some preferred embodiments chimeric antibodies of the instant invention may comprise all or most of the selected murine heavy and light chain variable regions operably linked to human light and heavy chain constant regions. In other particularly preferred embodiments, anti-DPEP3 antibodies may be "derived" from the mouse antibodies disclosed herein.

In other embodiments, the chimeric antibodies of the invention are "CDR grafted" antibodies, where the CDRs (as defined using Kabat, Chothia, McCallum, etc.) are derived from a particular species or belonging to a particular antibody class or subclass, while the remainder of the antibody is derived from an antibody from another species or belonging to another antibody class or subclass. For use in humans, one or more selected rodent CDRs (e.g., mouse CDRs) may be grafted into a human acceptor antibody, replacing one or more of the naturally occurring CDRs of the human antibody. These constructs generally have the advantages of providing full strength human antibody functions, e.g., complement dependent cytotoxicity (CDC) and antibody-dependent cell-mediated cytotoxicity (ADCC) while reducing unwanted immune responses to the antibody by the subject. In particularly preferred embodiments the CDR grafted antibodies will comprise one or more CDRs obtained from a mouse incorporated in a human framework sequence.

Similar to the CDR-grafted antibody is a "humanized" antibody. As used herein, a "humanized" antibody is a human antibody (acceptor antibody) comprising one or more amino acid sequences (e.g. CDR sequences) derived from one or more non-human antibodies (a donor or source antibody). In certain embodiments, "back mutations" can be introduced into the humanized antibody, in which residues in one or more FRs of the variable region of the recipient human antibody are replaced by corresponding residues from the non-human species donor antibody. Such back mutations may help to maintain the appropriate three-dimensional configuration of the grafted CDR(s) and thereby improve affinity and antibody stability. Antibodies from various donor species may be used including, without limitation, mouse, rat, rabbit, or non-human primate. Furthermore, humanized antibodies may comprise new residues that are not found in the recipient antibody or in the donor antibody to, for example, further refine antibody performance. CDR grafted and humanized antibodies compatible with the instant invention are provided as set forth in Example 8 below.

Various art recognized techniques can be used to determine which human sequences to use as acceptor antibodies to provide humanized constructs in accordance with the instant invention. Compilations of compatible human germline sequences and methods of determining their suitability as acceptor sequences are disclosed, for example, in Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638 each of which is incorporated herein in its entirety. The V-BASE directory (VBASE2—Retter et al., Nucleic Acid Res. 33; 671-674, 2005) which provides a comprehensive directory of human immunoglobulin variable region sequences (compiled by Tomlinson, I. A. et al. MRC Centre for Protein Engineering, Cambridge, UK) may also be used to identify compatible acceptor sequences. Additionally, consensus human framework sequences described, for example, in U.S. Pat. No. 6,300,064 may also prove to be compatible acceptor sequences are can be used in accordance with the instant teachings. In general, human framework acceptor sequences are selected based on homology with the murine source framework sequences along with an analysis of the CDR canonical structures of the source and acceptor antibodies. The derived sequences of the heavy and light chain variable regions of the derived antibody may then be synthesized using art recognized techniques.

By way of example CDR grafted and humanized antibodies, and associated methods, are described in U.S. Pat. Nos. 6,180,370 and 5,693,762. For further details, see, e.g., Jones et al., 1986, PMID: 3713831); and U.S. Pat. Nos. 6,982,321 and 7,087,409.

The sequence identity or homology of the CDR grafted or humanized antibody variable region to the human acceptor variable region may be determined as discussed herein and, when measured as such, will preferably share at least 60% or 65% sequence identity, more preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

Figure 5D:
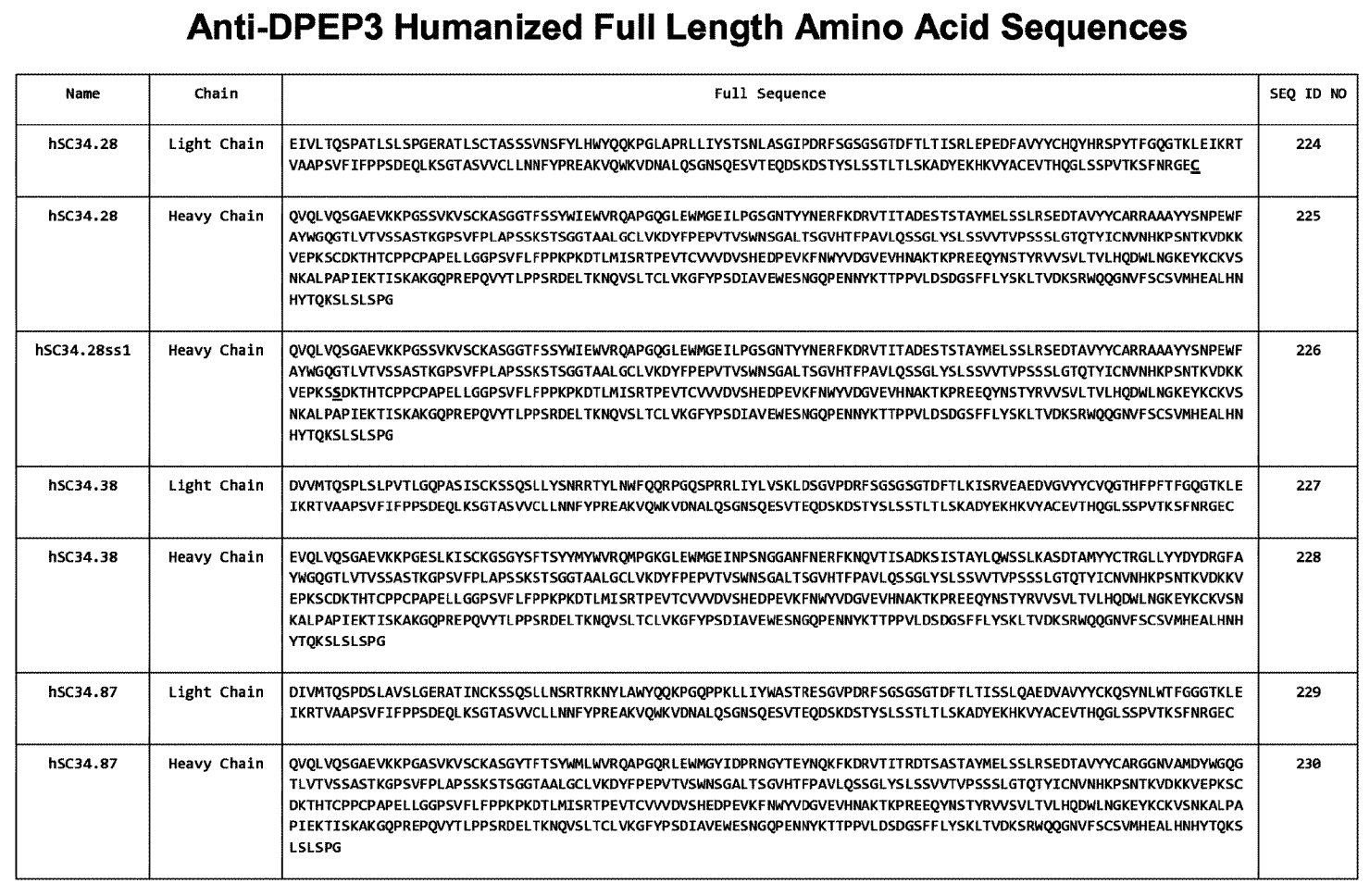
Figure 5E:
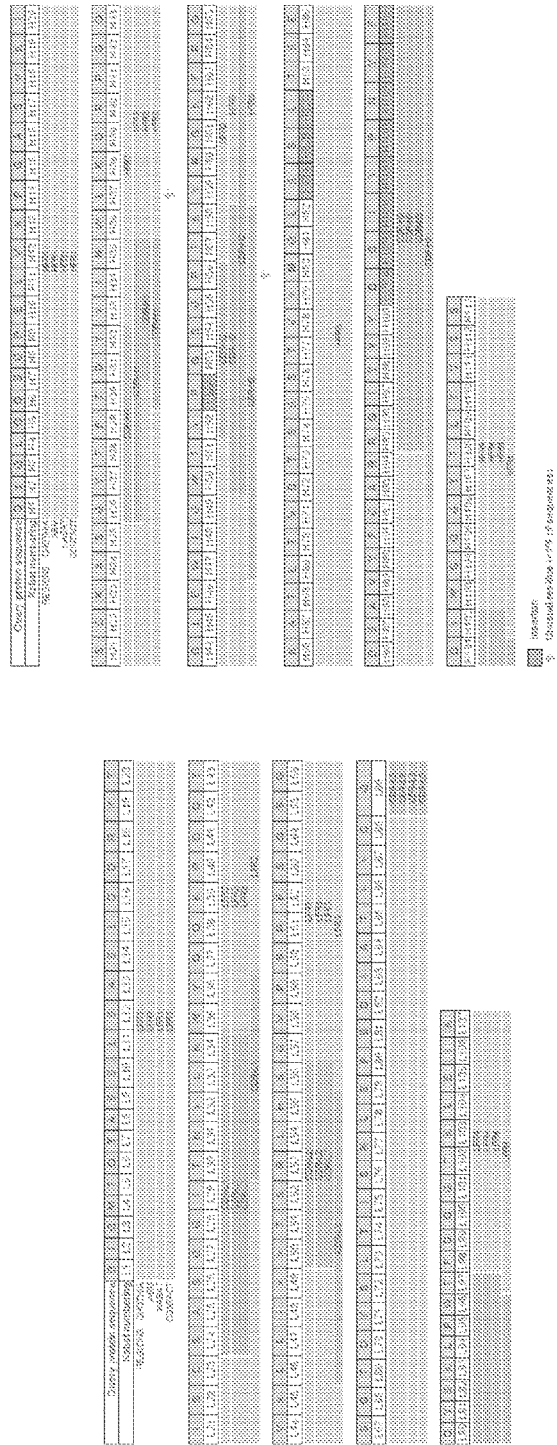
FIGS. 5E-5K show annotated amino acid sequences (numbered as per Kabat et al.) of the light and heavy chain variable regions of the murine anti-DPEP3 antibodies, SC34.2 (FIG. 5E), SC34.11 (FIG. 5F), SC27.14 (FIG. 5G), SC34.25 (FIG. 5H), SC34.28 (FIG. I), SC34.38 (FIG. 5J) and SC34.87 (FIG. 5K), wherein the CDRs are derived using Kabat, Chothia, ABM and Contact (MacCallum) methodology.
Figure 5F:
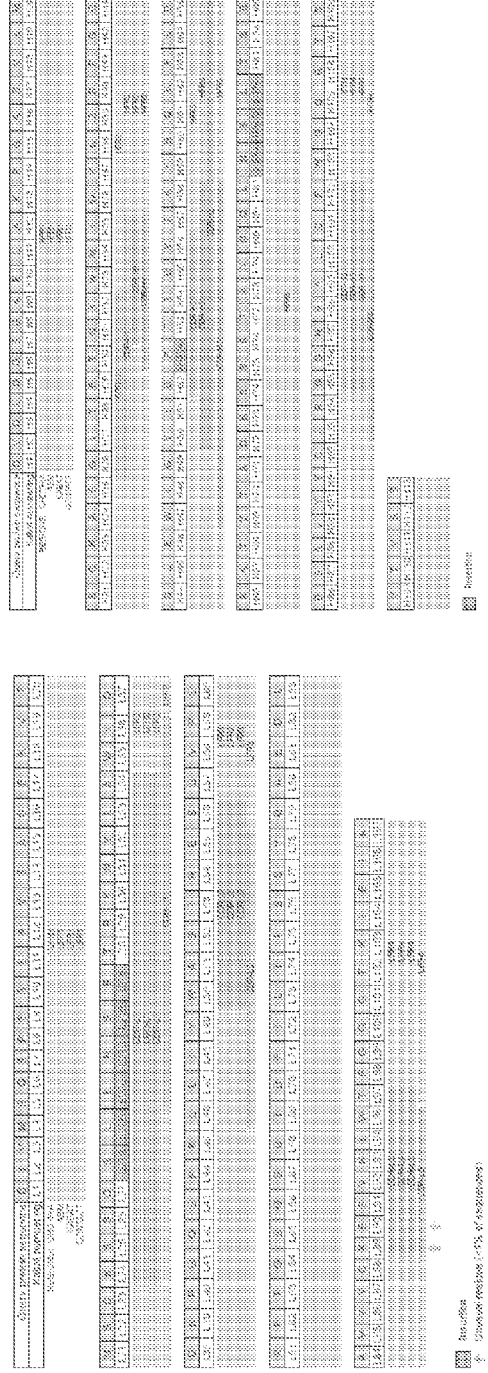
Figure 5G:
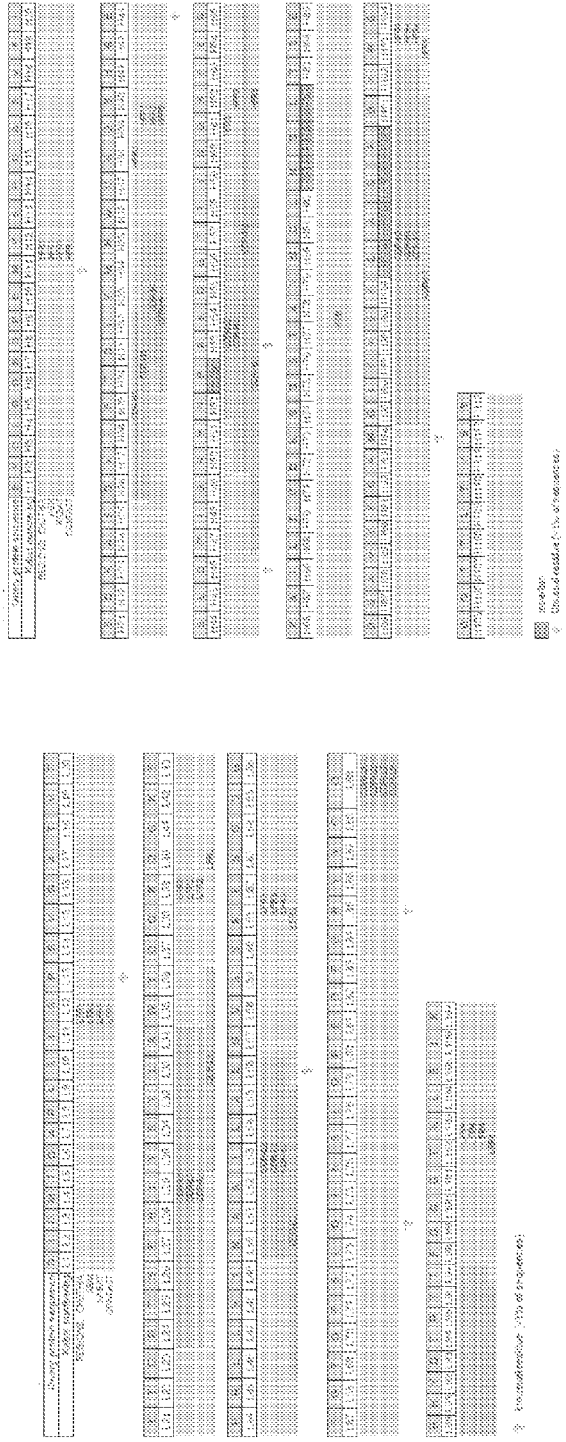
Figure 5H:
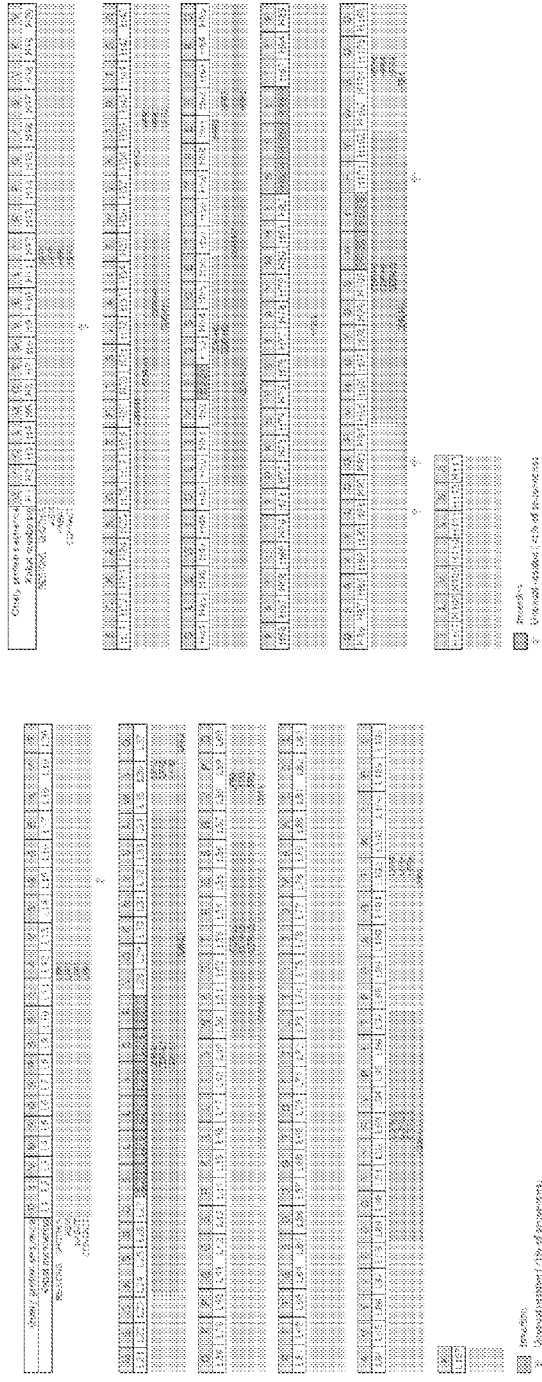
Figure 5I:
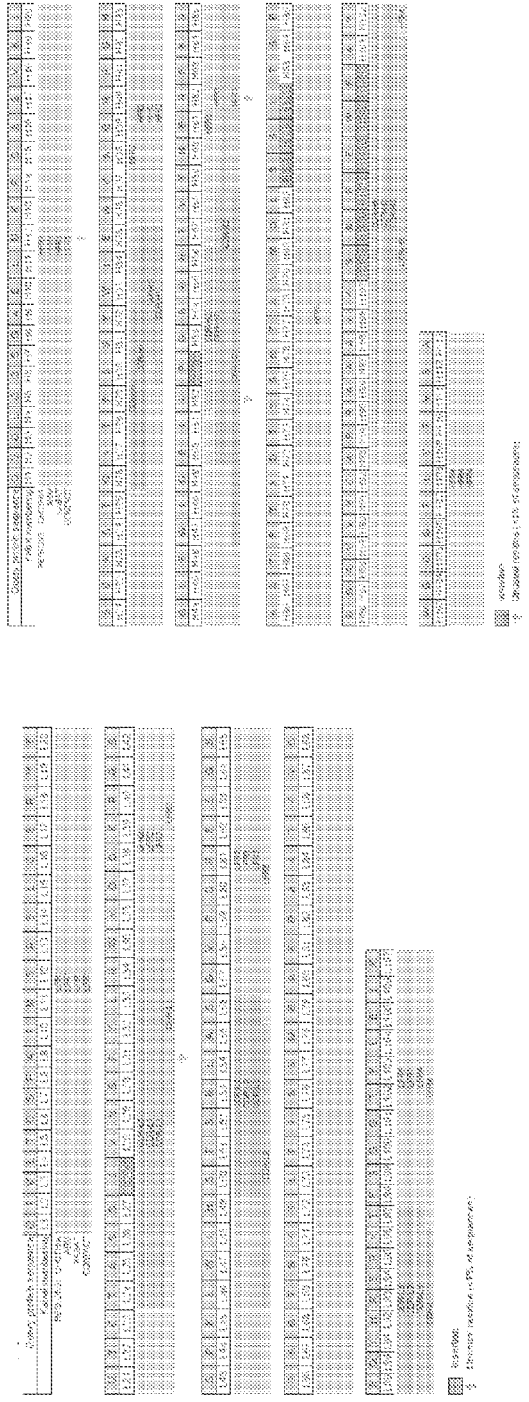
Figure 5J:
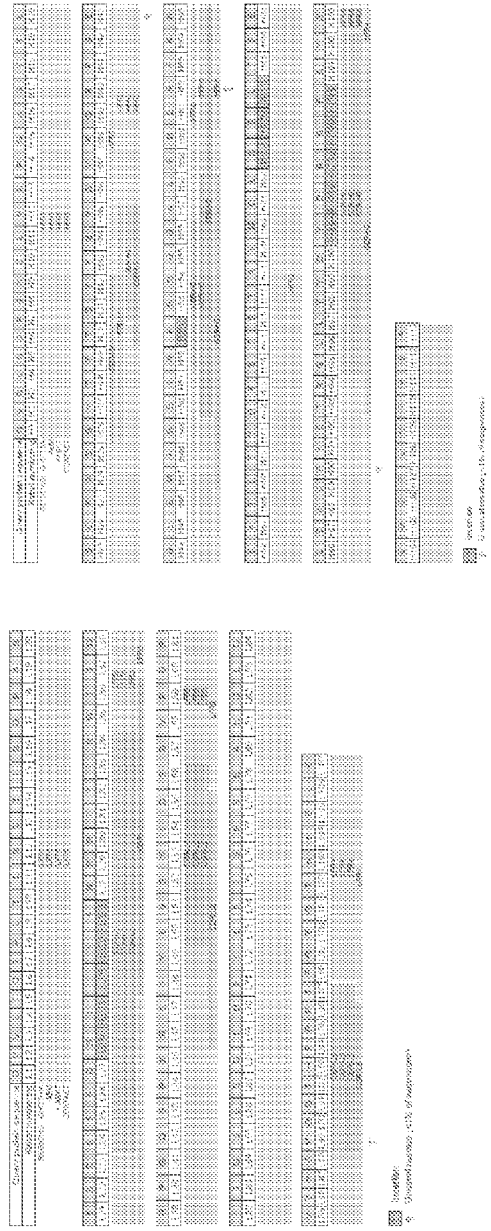
Figure 5K:
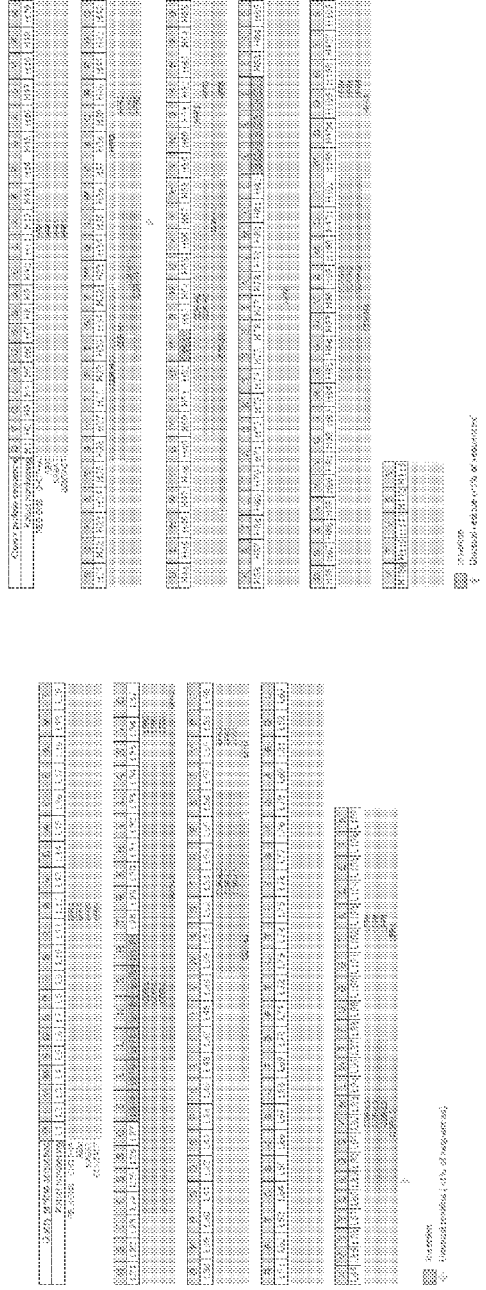

It will be appreciated that the annotated CDRs and framework sequences as provided in the appended FIGS. 5A and 5B are defined as per Kabat et al. using a proprietary Abysis database. However, as discussed herein and shown in FIGS. 5E-5K one skilled in the art could readily identify the CDRs in accordance with definitions provided by Chothia et al., ABM or MacCallum et al as well as Kabat et al. As such, anti-DPEP3 humanized antibodies comprising one or more CDRs derived according to any of the aforementioned systems are explicitly held to be within the scope of the instant invention.

4.2 Site-Specific Antibodies

The antibodies of the instant invention may be engineered to facilitate conjugation to a cytotoxin or other anti-cancer agent (as discussed in more detail below). It is advantageous for the antibody drug conjugate (ADC) preparation to comprise a homogenous population of ADC molecules in terms of the position of the cytotoxin on the antibody and the drug to antibody ratio (DAR). Based on the instant disclosure one skilled in the art could readily fabricate site-specific engineered constructs as described herein. As used herein a "site-specific antibody" or "site-specific construct" means an antibody, or immunoreactive fragment thereof, wherein at least one amino acid in either the heavy or light chain is deleted, altered or substituted (preferably with another amino acid) to provide at least one free cysteine. Similarly, a "site-specific conjugate" shall be held to mean an ADC comprising a site-specific antibody and at least one cytotoxin or other compound conjugated to the unpaired cysteine(s). In certain embodiments the unpaired cysteine residue will comprise an unpaired intrachain residue. In other preferred embodiments the free cysteine residue will comprise an unpaired interchain cysteine residue. The engineered antibody can be of various isotypes, for example, IgG, IgE, IgA or IgD; and within those classes the antibody can be of various subclasses, for example, IgG1, IgG2, IgG3 or IgG4. For IgG constructs the light chain of the antibody can comprise either a kappa or lambda isotype each incorporating a C214 that, in preferred embodiments, may be unpaired due to a lack of a C220 residue in the IgG1 heavy chain.

In one embodiment the engineered antibody comprises at least one amino acid deletion or substitution of an intrachain or interchain cysteine residue. As used herein "interchain cysteine residue" means a cysteine residue that is involved in a native disulfide bond either between the light and heavy chain of an antibody or between the two heavy chains of an antibody while an "intrachain cysteine residue" is one naturally paired with another cysteine in the same heavy or light chain. In one embodiment the deleted or substituted interchain cysteine residue is involved in the formation of a disulfide bond between the light and heavy chain. In another embodiment the deleted or substituted cysteine residue is involved in a disulfide bond between the two heavy chains. In a typical embodiment, due to the complementary structure of an antibody, in which the light chain is paired with the VH and CH1 domains of the heavy chain and wherein the CH2 and CH3 domains of one heavy chain are paired with the CH2 and CH3 domains of the complementary heavy chain, a mutation or deletion of a single cysteine in either the light chain or in the heavy chain would result in two unpaired cysteine residues in the engineered antibody.

In some embodiments an interchain cysteine residue is deleted. In other embodiments an interchain cysteine is substituted for another amino acid (e.g., a naturally occurring amino acid). For example, the amino acid substitution can result in the replacement of an interchain cysteine with a neutral (e.g. serine, threonine or glycine) or hydrophilic (e.g. methionine, alanine, valine, leucine or isoleucine) residue. In one particularly preferred embodiment an interchain cysteine is replaced with a serine.

In some embodiments contemplated by the invention the deleted or substituted cysteine residue is on the light chain (either kappa or lambda) thereby leaving a free cysteine on the heavy chain. In other embodiments the deleted or substituted cysteine residue is on the heavy chain leaving the free cysteine on the light chain constant region. Upon assembly it will be appreciated that deletion or substitution of a single cysteine in either the light or heavy chain of an intact antibody results in a site-specific antibody having two unpaired cysteine residues.

In one particularly preferred embodiment the cysteine at position 214 (C214) of the IgG light chain (kappa or lambda) is deleted or substituted. In another preferred embodiment the cysteine at position 220 (C220) on the IgG heavy chain is deleted or substituted. In further embodiments the cysteine at position 226 or position 229 on the heavy chain is deleted or substituted. In one embodiment C220 on the heavy chain is substituted with serine (C220S) to provide the desired free cysteine in the light chain. In another embodiment C214 in the light chain is substituted with serine (C214S) to provide the desired free cysteine in the heavy chain. Such site-specific constructs provided in Example 15. A summary of these preferred constructs is shown in Table 2 immediately below where all numbering is according to the EU index as set forth in Kabat and WT stands for "wild-type" or native constant region sequences without alterations and delta (Δ) designates the deletion of an amino acid residue (e.g., C214Δ indicates that the cysteine at position 214 has been deleted).

TABLE 2

| Designation | Antibody Component | Alteration |
| --- | --- | --- |
| ss1 | Heavy Chain | C220S |
|  | Light Chain | WT |
| ss2 | Heavy Chain | C220Δ |
|  | Light Chain | WT |
| ss3 | Heavy Chain | WT |
|  | Light Chain | C214Δ |
| ss4 | Heavy Chain | WT |
|  | Light Chain | C214S |

The strategy for generating antibody-drug conjugates with defined sites and stoichiometries of drug loading, as disclosed herein, is broadly applicable to all anti-DPEP3 antibodies as it primarily involves engineering of the conserved constant domains of the antibody. As the amino acid sequences and native disulfide bridges of each class and subclass of antibody are well documented, one skilled in the art could readily fabricate engineered constructs of various antibodies without undue experimentation and, accordingly, such constructs are expressly contemplated as being within the scope of the instant invention.

4.3 Constant Region Modifications and Altered Glycosylation

Selected embodiments of the present invention may also comprise substitutions or modifications of the constant region (i.e. the Fc region), including without limitation, amino acid residue substitutions, mutations and/or modifications, which result in a compound with preferred characteristics including, but not limited to: altered pharmacokinetics, increased serum half-life, increase binding affinity, reduced immunogenicity, increased production, altered Fc ligand binding to an Fc receptor (FcR), enhanced or reduced ADCC or CDC, altered glycosylation and/or disulfide bonds and modified binding specificity.

Compounds with improved Fc effector functions can be generated, for example, through changes in amino acid residues involved in the interaction between the Fc domain and an Fc receptor (e.g., FcγRI, FcγRIIA and B, FcγRIII and FcRn), which may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995).

In selected embodiments, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311). With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

Still other embodiments comprise one or more engineered glycoforms, e.g., a site-specific antibody comprising an altered glycosylation pattern or altered carbohydrate composition that is covalently attached to the protein (e.g., in the Fc domain). See, for example, Shields, R. L. et al. (2002) *J. Biol. Chem.* 277:26733-26740. Engineered glycoforms may be useful for a variety of purposes, including but not limited to enhancing or reducing effector function, increasing the affinity of the antibody for a target or facilitating production of the antibody. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTIII)), by expressing a molecule comprising an Fc region in various organisms or cell lines from various organisms or by modifying carbohydrate(s) after the molecule comprising Fc region has been expressed (see, for example, WO 2012/117002).

4.4 Fragments

Regardless of which form of antibody (e.g. chimeric, humanized, etc.) is selected to practice the invention it will be appreciated that immunoreactive fragments, either by themselves or as part of an antibody drug conjugate, of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody that immunospecifically binds or reacts with a selected antigen or immunogenic determinant thereof or competes with the intact antibody from which the fragments were derived for specific antigen binding.

Exemplary site-specific fragments include: variable light chain fragments (VL), an variable heavy chain fragments (VH), scFv, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active site-specific fragment comprises a portion of the antibody that retains its ability to interact with the antigen/substrates or receptors and modify them in a manner similar to that of an intact antibody (though maybe with somewhat less efficiency). Such antibody fragments may further be engineered to comprise one or more free cysteines.

In other embodiments, an antibody fragment is one that comprises the Fc region and that retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence comprising at least one free cysteine capable of conferring in vivo stability to the fragment.

As would be well recognized by those skilled in the art, fragments can be obtained by molecular engineering or via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragments.

4.5 Multivalent Constructs

In other embodiments, the antibodies and conjugates of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S.P.N. 2009/0130105.

In one embodiment, the antibodies are bispecific antibodies in which the two chains have different specificities, as described in Millstein et al., 1983, *Nature*, 305:537-539. Other embodiments include antibodies with additional specificities such as trispecific antibodies. Other more sophisticated compatible multispecific constructs and methods of their fabrication are set forth in U.S.P.N. 2009/0155255, as well as WO 94/04690; Suresh et al., 1986, *Methods in Enzymology*, 121:210; and WO96/27011.

Multivalent antibodies may immunospecifically bind to different epitopes of the desired target molecule or may immunospecifically bind to both the target molecule as well as a heterologous epitope, such as a heterologous polypeptide or solid support material. While preferred embodiments only bind two antigens (i.e. bispecific antibodies), antibodies with additional specificities such as trispecific antibodies are also encompassed by the instant invention. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

In certain preferred embodiments the antibodies of the invention may be utilized in adoptive immunity gene therapy to treat tumors. In one embodiment the antibodies of the invention (e.g. ScFv fragments) may be used to generate a chimeric antigen receptor (CAR). A "CAR" is a fused protein made up of an ECD comprising the anti-DPEP3 antibodies of the invention or immunoreactive fragments thereof (e.g. ScFv fragments), a transmembrane domain, and at least one intracellular domain. In one embodiment, T-cells, natural killer cells or dendritic cells that have been genetically engineered to express CARs can be introduced into a subject suffering from cancer in order to stimulate the immune system of the subject to specifically target tumor cells expressing DPEP3. In preferred embodiments the CARs of the invention will comprise an intracellular domain that initiates a primary cytoplasmic signaling sequence, that is, a sequence for initiating antigen-dependent primary activation via a T-cell receptor complex, for example, intracellular domains derived from CD3ζ, FcRγ, FcRβ, CD3γ, CD3δ, CD3ε, CD5, CD22, CD79a, CD79b, and CD66d. In other preferred embodiments, the CARs of the invention will comprise an intracellular domain that initiates a secondary or co-stimulating signal, for example, intracellular domains derived from CD2, CD4, CD5, CD8α, CD8β, CD28, CD134, CD137, ICOS, CD154, 4-1BB and glucocorticoid-induced tumor necrosis factor receptor (see U.S.P.N. US/2014/0242701).

In yet other embodiments, antibody variable domains with the desired binding specificities (antibody-antigen combining sites) are fused to immunoglobulin constant domain sequences, such as an immunoglobulin heavy chain constant domain comprising at least part of the hinge, CH2, and/or CH3 regions, using methods well known to those of ordinary skill in the art.

5. Recombinant Production of Antibodies

Antibodies and fragments thereof may be produced or modified using genetic material obtained from antibody producing cells and recombinant technology (see, for example, Berger and Kimmel, Guide to Molecular Cloning Techniques, *Methods in Enzymology* vol. 152 Academic Press, Inc., San Diego, Calif.; Sambrook and Russell (Eds.) (2000) *Molecular Cloning: A Laboratory Manual* (3$^{rd}$ Ed.), NY, Cold Spring Harbor Laboratory Press; Ausubel et al. (2002) *Short Protocols in Molecular Biology: A Compendium of Methods from Current Protocols in Molecular Biology*, Wiley, John & Sons, Inc.; and U.S. Pat. No. 7,709,611).

Another aspect of the invention pertains to nucleic acid molecules that encode the antibodies of the invention. The nucleic acids may be present in whole cells, in a cell lysate, or in a partially purified or substantially pure form. A nucleic acid is "isolated" or rendered substantially pure when separated from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA (e.g. genomic DNA, cDNA), RNA and artificial variants thereof (e.g., peptide nucleic acids), whether single-stranded or double-stranded or RNA, RNA and may or may not contain introns. In a preferred embodiment, the nucleic acid is a cDNA molecule.

Nucleic acids of the invention can be obtained using standard molecular biology techniques. For antibodies expressed by hybridomas (e.g., hybridomas prepared as set forth in the Examples below), cDNAs encoding the light and heavy chains of the antibody can be obtained by standard PCR amplification or cDNA cloning techniques. For antibodies obtained from an immunoglobulin gene library (e.g., using phage display techniques), nucleic acid encoding the antibody can be recovered from the library.

DNA fragments encoding VH and VL segments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, means that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, et al. (1991) (supra)) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. An exemplary IgG1 constant region is set forth in SEQ ID NO: 2. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, et al. (1991) (supra)) and DNA fragments encompassing these regions can be obtained by standard PCR amplification. The light chain constant region can be a kappa or lambda constant region, but most preferably is a kappa constant region. In this respect an exemplary compatible kappa light chain constant region is set forth in SEQ ID NO: 1.

Contemplated herein are certain polypeptides (e.g. antigens or antibodies) that exhibit "sequence identity", sequence similarity" or "sequence homology" to the polypeptides of the invention. A "homologous" polypeptide may exhibit 65%, 70%, 75%, 80%, 85%, or 90% sequence identity. In other embodiments a "homologous" polypeptides may exhibit 93%, 95% or 98% sequence identity. As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

Residue positions which are not identical may differ by conservative amino acid substitutions or by non-conservative amino acid substitutions. A "conservative amino acid substitution" is one in which an amino acid residue is substituted by another amino acid residue having a side chain with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. In cases where there is a substitution with a non-conservative amino acid, in preferred embodiments the polypeptide exhibiting sequence identity will retain the desired function or activity of the polypeptide of the invention (e.g., antibody.)

Also contemplated herein are nucleic acids that that exhibit "sequence identity", sequence similarity" or "sequence homology" to the nucleic acids of the invention. A "homologous sequence" means a sequence of nucleic acid molecules exhibiting at least about 65%, 70%, 75%, 80%, 85%, or 90% sequence identity. In other embodiments, a "homologous sequence" of nucleic acids may exhibit 93%, 95% or 98% sequence identity to the reference nucleic acid.

The instant invention also provides vectors comprising such nucleic acids described above, which may be operably linked to a promoter (see, e.g., WO 86/05807; WO 89/01036; and U.S. Pat. No. 5,122,464); and other transcriptional regulatory and processing control elements of the eukaryotic secretory pathway. The invention also provides host cells harboring those vectors and host-expression systems.

As used herein, the term "host-expression system" includes any kind of cellular system that can be engineered to generate either the nucleic acids or the polypeptides and antibodies of the invention. Such host-expression systems include, but are not limited to microorganisms (e.g., *E. coli* or *B. subtilis*) transformed or transfected with recombinant bacteriophage DNA or plasmid DNA; yeast (e.g., *Saccharomyces*) transfected with recombinant yeast expression vectors; or mammalian cells (e.g., COS, CHO-S, HEK-293T, 3T3 cells) harboring recombinant expression constructs containing promoters derived from the genome of mammalian cells or viruses (e.g., the adenovirus late promoter). The host cell may be co-transfected with two expression vectors, for example, the first vector encoding a heavy chain derived polypeptide and the second vector encoding a light chain derived polypeptide.

Methods of transforming mammalian cells are well known in the art. See, for example, U.S. Pat. Nos. 4,399,216, 4,912,040, 4,740,461, and 4,959,455. The host cell may also be engineered to allow the production of an antigen binding molecule with various characteristics (e.g. modified glycoforms or proteins having GnTIII activity).

For long-term, high-yield production of recombinant proteins stable expression is preferred. Accordingly, cell lines that stably express the selected antibody may be engineered using standard art recognized techniques and form part of the invention. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Any of the selection systems well known in the art may be used, including the glutamine synthetase gene expression system (the GS system) which provides an efficient approach for enhancing expression under certain conditions. The GS system is discussed in whole or part in connection with EP 0 216 846, EP 0 256 055, EP 0 323 997 and EP 0 338 841 and U.S. Pat. Nos. 5,591,639 and 5,879,936. Another preferred expression system for the development of stable cell lines is the Freedom™ CHO-S Kit (Life Technologies).

Once an antibody of the invention has been produced by recombinant expression or any other of the disclosed techniques, it may be purified or isolated by methods known in the art, meaning that it is identified and separated and/or recovered from its natural environment and separated from contaminants that would interfere with diagnostic or therapeutic uses for the antibody. Isolated antibodies include antibodies in situ within recombinant cells.

These isolated preparations may be purified using various art recognized techniques, such as, for example, ion exchange and size exclusion chromatography, dialysis, diafiltration, and affinity chromatography, particularly Protein A or Protein G affinity chromatography.

6. Post-Production Selection

No matter how obtained, antibody-producing cells (e.g., hybridomas, yeast colonies, etc.) may be selected, cloned and further screened for desirable characteristics including, for example, robust growth, high antibody production and desirable antibody characteristics such as high affinity for the antigen of interest. Hybridomas can be expanded in vitro in cell culture or in vivo in syngeneic immunocompromised animals. Methods of selecting, cloning and expanding hybridomas and/or colonies are well known to those of ordinary skill in the art. Once the desired antibodies are identified the relevant genetic material may be isolated, manipulated and expressed using common, art-recognized molecular biology and biochemical techniques.

The antibodies produced by naïve libraries (either natural or synthetic) may be of moderate affinity ($K_a$ of about $10^6$ to $10^7$ $M^{-1}$). To enhance affinity, affinity maturation may be mimicked in vitro by constructing antibody libraries (e.g., by introducing random mutations in vitro by using error-prone polymerase) and reselecting antibodies with high affinity for the antigen from those secondary libraries (e.g. by using phage or yeast display). WO 9607754 describes a method for inducing mutagenesis in a CDR of an immunoglobulin light chain to create a library of light chain genes.

Various techniques can be used to select antibodies, including but not limited to, phage or yeast display in which a library of human combinatorial antibodies or scFv fragments is synthesized on phages or yeast, the library is screened with the antigen of interest or an antibody-binding portion thereof, and the phage or yeast that binds the antigen is isolated, from which one may obtain the antibodies or immunoreactive fragments (Vaughan et al., 1996, PMID: 9630891; Sheets et al., 1998, PMID: 9600934; Boder et al., 1997, PMID: 9181578; Pepper et al., 2008, PMID: 18336206). Kits for generating phage or yeast display libraries are commercially available. There also are other methods and reagents that can be used in generating and screening antibody display libraries (see U.S. Pat. No. 5,223,409; WO 92/18619, WO 91/17271, WO 92/20791, WO 92/15679, WO 93/01288, WO 92/01047, WO 92/09690; and Barbas et al., 1991, PMID: 1896445). Such techniques advantageously allow for the screening of large numbers of candidate antibodies and provide for relatively easy manipulation of sequences (e.g., by recombinant shuffling).

IV CHARACTERISTICS OF ANTIBODIES

In selected embodiments, antibody-producing cells (e.g., hybridomas or yeast colonies) may be selected, cloned and further screened for favorable properties including, for example, robust growth, high antibody production and, as discussed in more detail below, desirable site-specific antibody characteristics. In other cases characteristics of the antibody may be imparted by selecting a particular antigen (e.g., a specific DPEP3 isoform) or immunoreactive fragment of the target antigen for inoculation of the animal. In still other embodiments the selected antibodies may be engineered as described above to enhance or refine immunochemical characteristics such as affinity or pharmacokinetics.

A. Neutralizing Antibodies

In selected embodiments the antibodies of the invention may be "antagonists" or "neutralizing" antibodies, meaning that the antibody may associate with a determinant and block or inhibit the activities of said determinant either directly or by preventing association of the determinant with a binding partner such as a ligand or a receptor, thereby interrupting the biological response that otherwise would result from the interaction of the molecules. A neutralizing or antagonist antibody will substantially inhibit binding of the determinant to its ligand or substrate when an excess of antibody reduces the quantity of binding partner bound to the determinant by at least about 20%, 30%, 40%, 50%, 60%, 70%, 80%, 85%, 90%, 95%, 97%, 99% or more as measured, for example, by target molecule activity or in an in vitro competitive binding assay. It will be appreciated that the modified activity may be measured directly using art recognized techniques or may be measured by the impact the altered activity has downstream (e.g., oncogenesis or cell survival).

B. Internalizing Antibodies

There is evidence that a substantial portion of expressed DPEP3 protein remains associated with the tumorigenic cell surface, thereby allowing for localization and internalization of the disclosed antibodies or ADCs. In preferred embodiments such antibodies will be associated with, or conjugated to, one or more drugs that kill the cell upon internalization. In particularly preferred embodiments the ADCs of the instant invention will comprise an internalizing site-specific ADC.

As used herein, an antibody that "internalizes" is one that is taken up (along with any cytotoxin) by the cell upon binding to an associated antigen or receptor. For therapeutic applications, internalization will preferably occur in vivo in a subject in need thereof. The number of ADCs internalized may be sufficient to kill an antigen-expressing cell, especially an antigen-expressing cancer stem cell. Depending on the potency of the cytotoxin or ADC as a whole, in some instances, the uptake of a single antibody molecule into the cell is sufficient to kill the target cell to which the antibody binds. For example, certain drugs are so highly potent that the internalization of a few molecules of the toxin conjugated to the antibody is sufficient to kill the tumor cell. Whether an antibody internalizes upon binding to a mammalian cell can be determined by various art-recognized assays including those described in the Examples below.

Methods of detecting whether an antibody internalizes into a cell are also described in U.S. Pat. No. 7,619,068.

C. Depleting Antibodies

In other embodiments the antibodies of the invention are depleting antibodies. The term "depleting" antibody refers to an antibody that preferably binds to an antigen on or near the cell surface and induces, promotes or causes the death of the cell (e.g., by CDC, ADCC or introduction of a cytotoxic agent). In preferred embodiments, the selected depleting antibodies will be conjugated to a cytotoxin.

Preferably a depleting antibody will be able to kill at least 20%, 30%, 40%, 50%, 60%, 70%, 80%, 85%, 90%, 95%, 97%, or 99% of DPEP3-expressing cells in a defined cell population. In some embodiments the cell population may comprise enriched, sectioned, purified or isolated tumorigenic cells, including cancer stem cells. In other embodiments the cell population may comprise whole tumor samples or heterogeneous tumor extracts that comprise cancer stem cells. Standard biochemical techniques may be used to monitor and quantify the depletion of tumorigenic cells in accordance with the teachings herein.

D. Binding Affinity

Disclosed herein are antibodies that have a high binding affinity for a specific determinant e.g. DPEP3. The term "$K_D$" refers to the dissociation constant or apparent affinity of a particular antibody-antigen interaction. An antibody of the invention can immunospecifically bind its target antigen when the dissociation constant $K_D$ ($k_{off}/k_{on}$) is $\leq 10^{-7}$ M. The antibody specifically binds antigen with high affinity when the $K_D$ is $\leq 5 \times 10^{-9}$ M, and with very high affinity when the $K_D$ is $\leq 5 \times 10^{-10}$ M. In one embodiment of the invention, the antibody has a $K_D$ of $\leq 10^{-9}$ M and an off-rate of about $1 \times 10^{-4}$/sec. In one embodiment of the invention, the off-rate is $<1 \times 10^{-5}$/sec. In other embodiments of the invention, the antibodies will bind to a determinant with a $K_D$ of between about $10^{-7}$ M and $10^{-10}$ M, and in yet another embodiment it will bind with a $K_D \leq 2 \times 10^{-10}$ M. Still other selected embodiments of the invention comprise antibodies that have a $K_D$ ($k_{off}/k_{on}$) of less than $10^{-6}$M, less than $5 \times 10^{-6}$ M, less than $10^{-7}$ M, less than $5 \times 10^{-7}$ M, less than $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M, less than $5 \times 10^{-14}$ M, less than $10^{15}$ M or less than $5 \times 10^{-15}$ M.

In certain embodiments, an antibody of the invention that immunospecifically binds to a determinant e.g. DPEP3 may have an association rate constant or $k_{on}$ (or $k_a$) rate (antibody+antigen $(Ag)^{k_{on}} \leftarrow$ antibody-Ag) of at least $10^5$ $M^{-1}$ $s^{-1}$, at least $2 \times 10^5$ $M^{-1}$ $s^{-1}$, at least $5 \times 10^5$ $M^{-1}$ $s^{-1}$, at least $10^6$ $M^{-1}$ $s^{-1}$, at least $5 \times 10^6$ $M^{-1}$ $s^{-1}$, at least $10^7$ $M^{-1}$ $s^{-1}$, at least $5 \times 10^7$ $M^{-1}$ $s^{-1}$, or at least $10^8$ $M^{-1}$ $s^{-1}$.

In another embodiment, an antibody of the invention that immunospecifically binds to a determinant e.g. DPEP3 may have a disassociation rate constant or $k_{off}$ (or $k_d$) rate (antibody+antigen $(Ag)^{k_{off}} \leftarrow$ antibody-Ag) of less than $10^{-1}$ $s^{-1}$, less than $5 \times 10^{-1}$ $s^{-1}$, less than $10^{-2}$ $s^{-1}$, less than $5 \times 10^{-2}$ $s^{-1}$, less than $10^{-3}$ $s^{-1}$, less than $5 \times 10^{-3}$ $s^{-1}$, less than $10^{-4}$ $s^{-1}$, less than $5 \times 10^4$ $s^{-1}$, less than $10^{-5}$ $s^{-1}$, less than $5 \times 10^{-5}$ $s^{-1}$, less than $10^{-6}$ $s^{-1}$, less than $5 \times 10^{-6}$ $s^{-1}$ less than $10^{-7}$ $s^{-1}$, less than $5 \times 10^{-7}$ $s^{-1}$, less than $10^{-8}$ $s^{-1}$, less than $5 \times 10^8$ $s^{-1}$, less than $10^{-9}$ $s^{-1}$, less than $5 \times 10^{-9}$ $s^{-1}$ or less than $10^{-10}$ $s^{-1}$.

Binding affinity may be determined using various techniques known in the art, for example, surface plasmon resonance, bio-layer interferometry, dual polarization interferometry, static light scattering, dynamic light scattering, isothermal titration calorimetry, ELISA, analytical ultracentrifugation, and flow cytometry.

E. Binning and Epitope Mapping

As used herein, the term "binning" refers to methods used to group antibodies into "bins" based on their antigen binding characteristics and whether they compete with each other. The initial determination of bins may be further refined and confirmed by epitope mapping and other techniques as described herein. However it will be appreciated that empirical assignment of antibodies to individual bins provides information that may be indicative of the therapeutic potential of the disclosed antibodies.

More specifically, one can determine whether a first reference antibody (or fragment thereof) competes for binding with a second test antibody (i.e., is in the same bin) by using methods known in the art and set forth in the Examples herein. In one embodiment, a reference antibody is associated with DPEP3 antigen under saturating conditions and then the ability of one or more test antibodies to bind to DPEP3 is determined using standard immunochemical techniques. If a test antibody is able to substantially bind to DPEP3 at the same time as the reference anti-DPEP3 antibody, then the test antibody binds to a different epitope than the reference antibody. However, if the test antibody is not able to substantially bind to DPEP3 at the same time, then the test antibody binds to the same epitope, an overlapping epitope, or an epitope that is in close proximity (at least sterically) to the epitope bound by the reference antibody. That is, the test antibody competes for antigen binding and is in the same bin as the reference antibody.

The term "compete" or "competing antibody" when used in the context of the disclosed antibodies means competition between antibodies as determined by an assay in which a test antibody or immunologically functional fragment being tested inhibits specific binding of a reference antibody to a common antigen. Typically, such an assay involves the use of purified antigen (e.g., DPEP3 or a domain or fragment thereof) bound to a solid surface or cells, an unlabeled test antibody and a labeled reference antibody. Competitive inhibition is measured by determining the amount of label bound to the solid surface or cells in the presence of the test antibody. Usually the test antibody is present in excess and/or allowed to bind first. Additional details regarding methods for determining competitive binding are provided in the Examples herein. Usually, when a competing antibody is present in excess, it will inhibit specific binding of a reference antibody to a common antigen by at least 30%, 40%, 45%, 50%, 55%, 60%, 65%, 70% or 75%. In some instance, binding is inhibited by at least 80%, 85%, 90%, 95%, or 97% or more.

Conversely, when the reference antibody is bound it will preferably inhibit binding of a subsequently added test antibody (i.e., a DPEP3 antibody) by at least 30%, 40%, 45%, 50%, 55%, 60%, 65%, 70% or 75%. In some instance, binding of the test antibody is inhibited by at least 80%, 85%, 90%, 95%, or 97% or more.

Generally binning or competitive binding may be determined using various art-recognized techniques, such as, for example, immunoassays such as western blots, radioimmunoassays, enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such immunoassays are routine and well known in the art (see, Ausubel et al, eds, (1994) *Current Protocols in Molecular Biology,*

*Vol. 1, John* Wiley & Sons, Inc., New York). Additionally, cross-blocking assays may be used (see, for example, WO 2003/48731; and Harlow et al. (1988) *Antibodies, A Laboratory Manual*, Cold Spring Harbor Laboratory, Ed Harlow and David Lane).

Other technologies used to determine competitive inhibition (and hence "bins"), include: surface plasmon resonance using, for example, the BIAcore™ 2000 system (GE Healthcare); bio-layer interferometry using, for example, a ForteBio® Octet RED (ForteBio); or flow cytometry bead arrays using, for example, a FACSCanto II (BD Biosciences) or a multiplex LUMINEX™ detection assay (Luminex).

Luminex is a bead-based immunoassay platform that enables large scale multiplexed antibody pairing. The assay compares the simultaneous binding patterns of antibody pairs to the target antigen. One antibody of the pair (capture mAb) is bound to Luminex beads, wherein each capture mAb is bound to a bead of a different color. The other antibody (detector mAb) is bound to a fluorescent signal (e.g. phycoerythrin (PE)). The assay analyzes the simultaneous binding (pairing) of antibodies to an antigen and groups together antibodies with similar pairing profiles. Similar profiles of a detector mAb and a capture mAb indicates that the two antibodies bind to the same or closely related epitopes. In one embodiment, pairing profiles can be determined using Pearson correlation coefficients to identify the antibodies which most closely correlate to any particular antibody on the panel of antibodies that are tested. In preferred embodiments a test/detector mAb will be determined to be in the same bin as a reference/capture mAb if the Pearson's correlation coefficient of the antibody pair is at least 0.9. In other embodiments the Pearson's correlation coefficient is at least 0.8, 0.85, 0.87 or 0.89. In further embodiments, the Pearson's correlation coefficient is at least 0.91, 0.92, 0.93, 0.94, 0.95, 0.96, 0.97, 0.98, 0.99 or 1. Other methods of analyzing the data obtained from the Luminex assay are described in U.S. Pat. No. 8,568,992. The ability of Luminex to analyze 100 different types of beads (or more) simultaneously provides almost unlimited antigen and/or antibody surfaces, resulting in improved throughput and resolution in antibody epitope profiling over a biosensor assay (Miller, et al., 2011, PMID: 21223970).

"Surface plasmon resonance," refers to an optical phenomenon that allows for the analysis of real-time specific interactions by detection of alterations in protein concentrations within a biosensor matrix.

In other embodiments, a technique that can be used to determine whether a test antibody "competes" for binding with a reference antibody is "bio-layer interferometry", an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. Such biolayer interferometry assays may be conducted using a ForteBio® Octet RED machine as follows. A reference antibody (Ab1) is captured onto an anti-mouse capture chip, a high concentration of non-binding antibody is then used to block the chip and a baseline is collected. Monomeric, recombinant target protein is then captured by the specific antibody (Ab1) and the tip is dipped into a well with either the same antibody (Ab1) as a control or into a well with a different test antibody (Ab2). If no further binding occurs, as determined by comparing binding levels with the control Ab1, then Ab1 and Ab2 are determined to be "competing" antibodies. If additional binding is observed with Ab2, then Ab1 and Ab2 are determined not to compete with each other. This process can be expanded to screen large libraries of unique antibodies using a full row of antibodies in a 96-well plate representing unique bins. In preferred embodiments a test antibody will compete with a reference antibody if the reference antibody inhibits specific binding of the test antibody to a common antigen by at least 40%, 45%, 50%, 55%, 60%, 65%, 70% or 75%. In other embodiments, binding is inhibited by at least 80%, 85%, 90%, 95%, or 97% or more.

Once a bin encompassing a group of competing antibodies has been defined, further characterization can be carried out to determine the specific domain or epitope on the antigen to which the antibodies in a bin bind. Domain-level epitope mapping may be performed using a modification of the protocol described by Cochran et al., 2004, PMID: 15099763. Fine epitope mapping is the process of determining the specific amino acids on the antigen that comprise the epitope of a determinant to which the antibody binds. The term "epitope" is used in its common biochemical sense and refers to that portion of the target antigen capable of being recognized and specifically bound by a particular antibody. In certain embodiments, epitopes or immunogenic determinants include chemically active surface groupings of molecules such as amino acids, sugar side chains, phosphoryl groups, or sulfonyl groups, and, in certain embodiments, may have specific three-dimensional structural characteristics, and/or specific charge characteristics. In certain embodiments, an antibody is said to specifically bind an antigen when it preferentially recognizes its target antigen in a complex mixture of proteins and/or macromolecules.

When the antigen is a polypeptide such as DPEP3, epitopes may generally be formed from both contiguous amino acids and noncontiguous amino acids juxtaposed by tertiary folding of a protein ("conformational epitopes"). In such conformational epitopes the points of interaction occur across amino acid residues on the protein that are linearly separated from one another. Epitopes formed from contiguous amino acids (sometimes referred to as "linear" or "continuous" epitopes) are typically retained upon protein denaturing, whereas epitopes formed by tertiary folding are typically lost upon protein denaturing. An antibody epitope typically includes at least 3 amino acids, for example, 4 amino acids, 5 amino acids, 6 amino acids, 7 amino acids, 8 amino acids, 9 amino acids, 10 amino acids, or more, in a unique spatial conformation. Methods of epitope determination or "epitope mapping" are well known in the art and may be used in conjunction with the instant disclosure to identify epitopes on DPEP3 bound by the disclosed antibodies.

Compatible epitope mapping techniques include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496). Other compatible methods comprise yeast display methods such as shown in Example 10 appended hereto. In other embodiments Modification-Assisted Profiling (MAP), also known as Antigen Structure-based Antibody Profiling (ASAP) provides a method that categorizes large numbers of monoclonal antibodies directed against the same antigen according to the similarities of the binding profile of each antibody to chemically or enzymatically modified antigen surfaces (U.S.P.N. 2004/0101920). This technology allows rapid filtering of genetically identical antibodies, such that characterization can be focused on genetically distinct antibodies. It will be appreciated that MAP may be used to sort the DPEP3 antibodies of the invention into groups of antibodies binding different epitopes.

As will be discussed in more detail in Example 10 below the epitopes of three exemplary DPEP3 antibodies (SC34.2, SC34.28 and SC34.10) were determined using the aforementioned methods. The SC34.2 antibody was found to bind to a conformational epitope comprising human DPEP3 amino acid residues selected from the group consisting of E217, R242, Q248, Q372, K375 and E379 (residues numbered as per SEQ ID NO: 3). Moreover, while each of the residues may be involved in defining the epitope to a greater or lesser extent, it will be appreciated that antibodies may associate with a less than intact or partially formed epitope. Accordingly the present invention explicitly encompasses antibodies that bind or associate with an epitope comprising three or more amino acid residues selected from the group consisting of E217, R242, Q248, Q372, K375 and E379 or any antibody that competes with the binding antibody. More specifically the invention encompasses antibodies that bind to an epitope comprising any of the particular residue combinations set forth in Table 3 directly below where X comprises any naturally occurring amino acid with residue numbering according to SEQ ID NO: 3.

TABLE 3

|  |  |  |  |  |  |
|---|---|---|---|---|---|
| 1 | — | R242 | Q248 | Q372 | — | — |
| 2 | — | R242 | Q248 | — | K375 | — |
| 3 | — | R242 | Q248 | — | — | E379 |
| 4 | — | R242 | — | Q372 | K375 | — |
| 5 | — | R242 | — | Q372 | — | E379 |
| 6 | — | R242 | — | — | K375 | E379 |
| 7 | — | — | Q248 | Q372 | K375 | — |
| 8 | — | — | Q248 | Q372 | — | E379 |
| 9 | — | — | Q248 | — | K375 | E379 |
| 10 | — | — | — | Q372 | K375 | E379 |
| 11 | — | R242 | Q248 | Q372 | K375 | — |
| 12 | — | R242 | Q248 | Q372 | — | E379 |
| 13 | — | R242 | Q248 | — | K375 | E379 |
| 14 | — | R242 | — | Q372 | K375 | E379 |
| 15 | — | — | Q248 | Q372 | K375 | E379 |
| 16 | — | R242 | Q248 | Q372 | K375 | E379 |
| 17 | E217 | R242 | Q248 | — | — | — |
| 18 | E217 | R242 | — | Q372 | — | — |
| 19 | E217 | R242 | — | — | K375 | — |
| 20 | E217 | R242 | — | — | — | E379 |
| 21 | E217 | — | Q248 | Q372 | — | — |
| 22 | E217 | — | Q248 | — | K375 | — |
| 23 | E217 | — | Q248 | — | — | E379 |
| 24 | E217 | — | — | Q372 | K375 | — |
| 25 | E217 | — | — | — | K375 | E379 |
| 26 | E217 | — | — | Q372 | — | E379 |
| 27 | E217 | R242 | Q248 | Q372 | — | — |
| 28 | E217 | R242 | Q248 | — | — | E379 |
| 29 | E217 | — | Q248 | Q372 | K375 | — |
| 30 | E217 | R242 | — | Q372 | K375 | — |
| 31 | E217 | R242 | Q248 | — | K375 | — |
| 32 | E217 | — | — | Q372 | K375 | E379 |
| 33 | E217 | — | Q248 | — | K375 | E379 |
| 34 | E217 | — | Q248 | Q372 | — | E379 |
| 35 | E217 | R242 | — | — | K375 | E379 |
| 36 | E217 | R242 | — | Q372 | — | E379 |
| 37 | E217 | — | Q248 | Q372 | K375 | E379 |
| 38 | E217 | R242 | — | Q372 | K375 | E379 |
| 39 | E217 | R242 | Q248 | — | K375 | E379 |
| 40 | E217 | R242 | Q248 | Q372 | — | E379 |
| 41 | E217 | R242 | Q248 | Q372 | K375 | — |
| 42 | E217 | R242 | Q248 | Q372 | K375 | E379 |

The SC34.10 antibody was found to bind to a conformational epitope comprising human DPEP3 amino acid residues selected from the group consisting of R46, R48, R54 and S55 (numbered as per SEQ ID NO: 3). As above, each of the residues may be involved in defining the epitope to a greater or lesser extent, it will be appreciated that an antibody may associate with a less than intact or partially formed epitope. Accordingly the present invention explicitly encompasses antibodies that bind or associate with an epitope comprising three or more amino acid residues selected from the group consisting of R46, R48, R54 and S55 or any antibody that competes with the binding antibody. More specifically the invention encompasses antibodies that bind to any of epitopes 1-5 as set forth in Table 4 directly below where X comprises any naturally occurring amino acid with residue numbering according to SEQ ID NO: 3.

TABLE 4

| 1 | R46 | R48 | R54 | — |
| 2 | R46 | R48 | — | S55 |
| 3 | R46 | — | R54 | S55 |
| 4 | — | R48 | R54 | S55 |
| 5 | R46 | R48 | R54 | S55 |

The SC34.28 antibody was found to bind to a conformational epitope comprising human DPEP3 amino acid residues selected from the group consisting of S380, S384, V386, Q248 (numbered as per SEQ ID NO: 3). In this case a comparative analysis of (i) the amino acid sequences of human DPEP3 and cynomolgus DPEP3; and (ii) differences in affinity of hSC34.28 for each of the two DPEP3 orthologs indicated that V386 and Q248 formed part of the epitope as well as the conventionally mapped residues. Again, each of the residues may be involved in defining the epitope to a greater or lesser extent, it will be appreciated that an antibody may associate with a less than intact or partially formed epitope. Accordingly the present invention explicitly encompasses antibodies that bind or associate with an epitope comprising three or more amino acid residues selected from the group consisting of S380, S384, V386, Q248 or any antibody that competes with the binding antibody. More specifically the invention encompasses antibodies that bind to any of epitopes 1-5 as set forth in Table 5 directly below where X comprises any naturally occurring amino acid with residue numbering according to SEQ ID NO: 3.

TABLE 5

| 1 | Q248 | S380 | S384 | — |
| 2 | Q248 | S380 | — | V386 |
| 3 | Q248 | — | S384 | V386 |
| 4 | — | S380 | S384 | V386 |
| 5 | Q248 | S380 | S384 | V386 |

Once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that compete for binding to the antigen. A high throughput process for binning antibodies based upon their cross-competition is described in WO 03/48731. Other methods of binning or domain level or epitope mapping comprising antibody competition or antigen fragment expression on yeast are well known in the art.

V ANTIBODY CONJUGATES

In certain preferred embodiments the antibodies of the invention may be conjugated with pharmaceutically active or diagnostic moieties to form an "antibody drug conjugate" (ADC) or "antibody conjugate". The term "conjugate" is used broadly and means the covalent or non-covalent association of any pharmaceutically active or diagnostic moiety with an antibody of the instant invention regardless of the method of association. In certain embodiments the association is effected through a lysine or cysteine residue of the antibody. In particularly preferred embodiments the pharmaceutically active or diagnostic moieties may be conjugated to the antibody via one or more site-specific free cysteine(s). The disclosed ADCs may be used for therapeutic and diagnostic purposes.

The ADCs of the instant invention may be used to deliver cytotoxins or other payloads to the target location (e.g., tumorigenic cells and/or cells expressing DPEP3). As used herein the terms "drug" or "warhead" may be used interchangeably and will mean a biologically active or detectable molecule or drug, including anti-cancer agents as described below. A "payload" may comprise a drug or "warhead" in combination with an optional linker compound. The "warhead" on the conjugate may comprise peptides, proteins or prodrugs which are metabolized to an active agent in vivo, polymers, nucleic acid molecules, small molecules, binding agents, mimetic agents, synthetic drugs, inorganic molecules, organic molecules and radioisotopes. In an advantageous embodiment, the disclosed ADCs will direct the bound payload to the target site in a relatively unreactive, non-toxic state before releasing and activating the payload. This targeted release of the payload is preferably achieved through stable conjugation of the payloads (e.g., via one or more cysteines on the antibody) and the relatively homogeneous composition of the ADC preparations which minimize over-conjugated toxic species. Coupled with drug linkers that are designed to largely release the payload once it has been delivered to the tumor site, the conjugates of the instant invention can substantially reduce undesirable non-specific toxicity. This advantageously provides for relatively high levels of the active cytotoxin at the tumor site while minimizing exposure of non-targeted cells and tissue thereby providing an enhanced therapeutic index.

It will be appreciated that, while preferred embodiments of the invention comprise payloads of therapeutic moieties (e.g., cytotoxins), other payloads such as diagnostic agents and biocompatible modifiers may benefit from the targeted release provided by the disclosed conjugates. Accordingly, any disclosure directed to exemplary therapeutic payloads is also applicable to payloads comprising diagnostic agents or biocompatible modifiers as discussed herein unless otherwise dictated by context. The selected payload may be covalently or non-covalently linked to, the antibody and exhibit various stoichiometric molar ratios depending, at least in part, on the method used to effect the conjugation. The conjugates of the instant invention may be represented by the formula:

Ab-[L-D]n or a pharmaceutically acceptable salt thereof wherein
a) Ab comprises an anti-DPEP3 antibody;
b) L comprises an optional linker;
c) D comprises a drug; and
d) n is an integer from about 1 to about 20.

Those of skill in the art will appreciate that conjugates according to the aforementioned formula may be fabricated using a number of different linkers and drugs and that conjugation methodology will vary depending on the selection of components. As such, any drug or drug linker compound that associates with a reactive residue (e.g., cysteine or lysine) of the disclosed antibodies are compatible with the teachings herein. Similarly, any reaction conditions that allow for site-specific conjugation of the selected drug to an antibody are within the scope of the present invention. Notwithstanding the foregoing, particularly preferred embodiments of the instant invention comprise selective conjugation of the drug or drug linker to free cysteines using stabilization agents in combination with mild reducing agents as described herein. Such reaction conditions tend to provide more homogeneous preparations with less non-specific conjugation and contaminants and correspondingly less toxicity.

Exemplary payloads compatible with the teachings herein are listed below:

A. Therapeutic Agents

The antibodies of the invention may be conjugated, linked or fused to or otherwise associated with a pharmaceutically active moiety which is a therapeutic moiety or a drug such as an anti-cancer agent including, but not limited to, cytotoxic agents, cytostatic agents, anti-angiogenic agents, debulking agents, chemotherapeutic agents, radiotherapeutic agents, targeted anti-cancer agents, biological response modifiers, cancer vaccines, cytokines, hormone therapies, anti-metastatic agents and immunotherapeutic agents.

Preferred exemplary anti-cancer agents (including homologs and derivatives thereof) comprise 1-dehydrotestosterone, anthramycins, actinomycin D, bleomycin, calicheamicin, colchicin, cyclophosphamide, cytochalasin B, dactinomycin (formerly actinomycin), dihydroxy anthracin, dione, emetine, epirubicin, ethidium bromide, etoposide, glucocorticoids, gramicidin D, lidocaine, maytansinoids such as DM-1 and DM-4 (Immunogen), mithramycin, mitomycin, mitoxantrone, paclitaxel, procaine, propranolol, puromycin, tenoposide, tetracaine and pharmaceutically acceptable salts or solvates, acids or derivatives of any of the above.

Additional compatible cytotoxins comprise dolastatins and auristatins, including monomethyl auristatin E (MMAE) and monomethyl auristatin F (MMAF) (Seattle Genetics), amanitins such as alpha-amanitin, beta-amanitin, gamma-amanitin or epsilon-amanitin (Heidelberg Pharma), DNA minor groove binding agents such as duocarmycin derivatives (Syntarga), alkylating agents such as modified or dimeric pyrrolobenzodiazepines (PBD), mechlorethamine, thioepa, chlorambucil, melphalan, carmustine (BCNU), lomustine (CCNU), cyclothosphamide, busulfan, dibromomannitol, streptozotocin, mitomycin C and cisdichlorodiamine platinum (II) (DDP) cisplatin, splicing inhibitors such as meayamycin analogs or derivatives (e.g., FR901464 as set forth in U.S. Pat. No. 7,825,267), tubular binding agents such as epothilone analogs and paclitaxel and DNA damaging agents such as calicheamicins and esperamicins, anti-metabolites such as methotrexate, 6-mercaptopurine, 6-thioguanine, cytarabine, and 5-fluorouracil decarbazine, anti-mitotic agents such as vinblastine and vincristine and anthracyclines such as daunorubicin (formerly daunomycin) and doxorubicin and pharmaceutically acceptable salts or solvates, acids or derivatives of any of the above.

In one embodiment the antibodies of the instant invention may be associated with anti-CD3 binding molecules to recruit cytotoxic T-cells and have them target tumorigenic cells (BiTE technology; see e.g., Fuhrmann et. al. (2010) Annual Meeting of AACR Abstract No. 5625).

In further embodiments ADCs of the invention may comprise therapeutic radioisotopes conjugated using appropriate linkers. Exemplary radioisotopes that may be compatible with such embodiments include, but are not limited to, iodine ($^{131}$I, $^{125}$I, $^{123}$I, $^{121}$I), carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In), bismuth ($^{212}$Bi, $^{213}$Bi), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Sn, $^{225}$Ac, $^{76}$Br, and $^{211}$At. Other radionuclides are also available as diagnostic and therapeutic agents, especially those in the energy range of 60 to 4,000 keV.

shown to have potent antitumor properties while exhibiting minimal bone marrow depression. PBDs compatible with the invention may be linked to an antibody using several types of linkers (e.g., a peptidyl linker comprising a maleimido moiety with a free sulfhydryl), and in certain embodiments are dimeric in form (i.e., PBD dimers). Compatible PBDs (and optional linkers) that may be conjugated to the disclosed antibodies are described, for example, in U.S. Pat. Nos. 6,362,331, 7,049,311, 7,189,710, 7,429,658, 7,407,951, 7,741,319, 7,557,099, 8,034,808, 8,163,736, 2011/0256157 and PCT filings WO2011/130613, WO2011/128650, WO2011/130616 and WO2014/057074. Examples of PBD compounds compatible with the instant invention are shown immediately below.

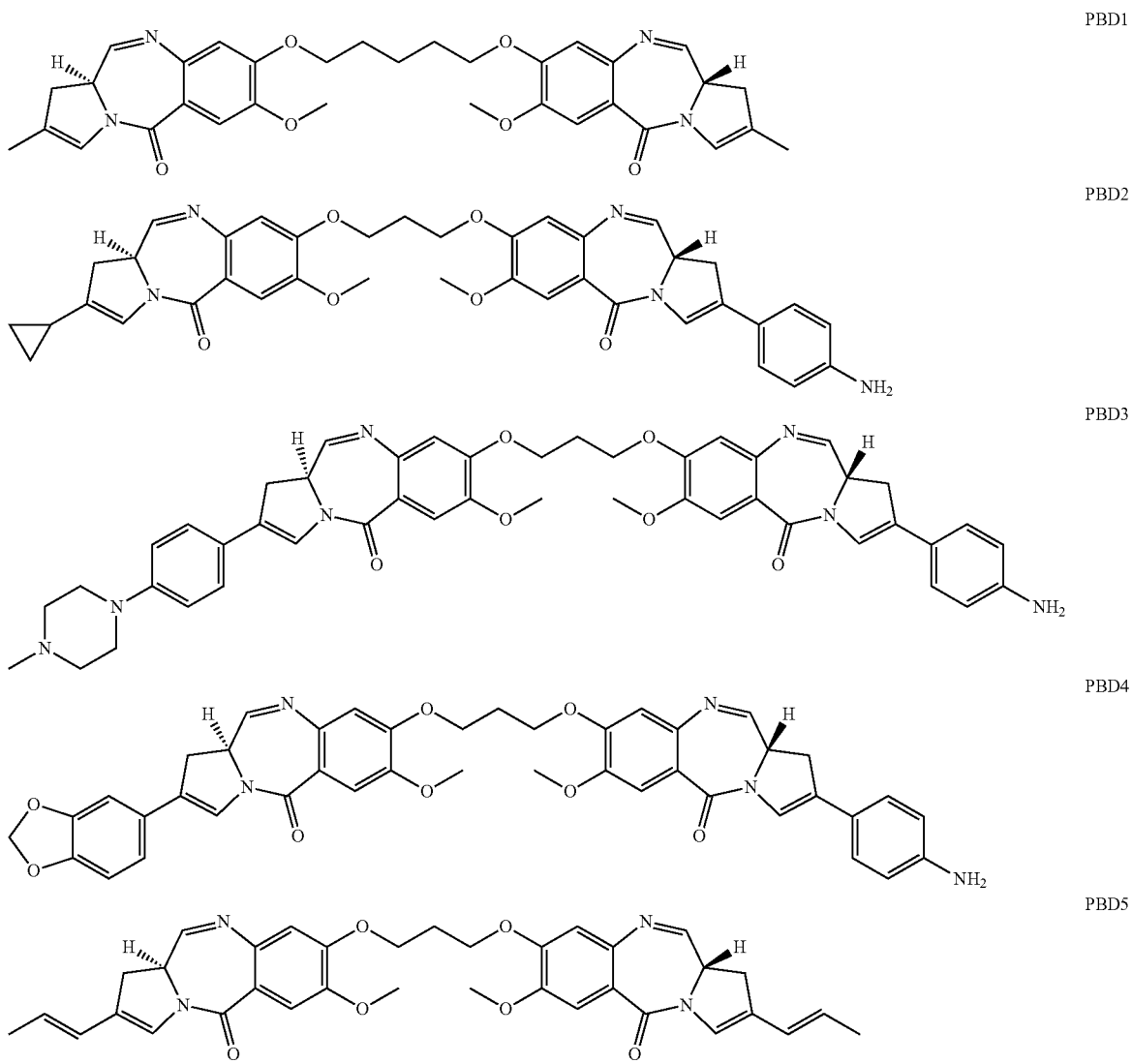

In certain particularly preferred embodiments, the ADCs of the invention may comprise PBDs, and pharmaceutically acceptable salts or solvates, acids or derivatives thereof, as warheads. PBDs are alkylating agents that exert antitumor activity by covalently binding to DNA in the minor groove and inhibiting nucleic acid synthesis. PBDs have been Antibodies of the present invention may also be conjugated to biological response modifiers. For example, in particularly preferred embodiments the drug moiety can be a polypeptide possessing a desired biological activity. Such proteins may include, for example, a toxin such as abrin, ricin A, Onconase (or another cytotoxic RNase), *pseudomo-* nas exotoxin, cholera toxin, diphtheria toxin; an apoptotic agent such as tumor necrosis factor e.g. TNF-α or TNF-β, α-interferon, β-interferon, nerve growth factor, platelet derived growth factor, tissue plasminogen activator, AIM I (WO 97/33899), AIM II (WO 97134911), Fas Ligand (Takahashi et al., 1994, PMID: 7826947), and VEGI (WO 99/23105), a thrombotic agent, an anti-angiogenic agent, e.g., angiostatin or endostatin, a lymphokine, for example, interleukin-1 (IL-1), interleukin-2 (IL-2), interleukin-6 (IL-6), granulocyte macrophage colony stimulating factor (GM-CSF), and granulocyte colony stimulating factor (G-CSF), or a growth factor e.g., growth hormone (GH).

B. Diagnostic or Detection Agents

In other preferred embodiments, the antibodies of the invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled antibodies can be useful for monitoring the development or progression of a hyperproliferative disorder or as part of a clinical testing procedure to determine the efficacy of a particular therapy including the disclosed antibodies (i.e. theragnostics) or to determine a future course of treatment. Such markers or reporters may also be useful in purifying the selected antibody, for use in antibody analytics (e.g., epitope binding or antibody binning), separating or isolating tumorigenic cells or in preclinical procedures or toxicology studies.

Such diagnosis, analysis and/or detection can be accomplished by coupling the antibody to detectable substances including, but not limited to, various enzymes comprising for example horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, non-radioactive paramagnetic metal ions, and molecules that are radiolabeled or conjugated to specific radioisotopes. In such embodiments appropriate detection methodology is well known in the art and readily available from numerous commercial sources.

In other embodiments the antibodies or fragments thereof can be fused or conjugated to marker sequences or compounds, such as a peptide or fluorophore to facilitate purification or diagnostic or analytic procedures such as immunohistochemistry, bio-layer interferometry, surface plasmon resonance, flow cytometry, competitive ELISA, FACs, etc. In preferred embodiments, the marker comprises a histidine tag such as that provided by the pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

C. Biocompatible Modifiers

In selected embodiments the antibodies of the invention may be conjugated with biocompatible modifiers that may be used to adjust, alter, improve or moderate antibody characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weights and molecular configurations that can be selected to impart specific properties to the antibody (e.g. the half-life may be tailored). PEG can be attached to antibodies or antibody fragments or derivatives with or without a multifunctional linker either through conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed antibodies can be conjugated to albumin in order to make the antibody or antibody fragment more stable in vivo or have a longer half-life in vivo. The techniques are well known in the art, see e.g., WO 93/15199, WO 93/15200, and WO 01/77137; and EP 0 413, 622. Other biocompatible conjugates are evident to those of ordinary skill and may readily be identified in accordance with the teachings herein.

D. Linker Compounds

Numerous linker compounds can be used to conjugate the antibodies of the invention to the relevant warhead. The linkers merely need to covalently bind with the reactive residue on the antibody (preferably a cysteine or lysine) and the selected drug compound. Accordingly, any linker that reacts with the selected antibody residue and may be used to provide the relatively stable conjugates (site-specific or otherwise) of the instant invention is compatible with the teachings herein.

Numerous compatible linkers can advantageously bind to reduced cysteines and lysines, which are nucleophilic. Conjugation reactions involving reduced cysteines and lysines include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions. As further discussed herein, thiol-maleimide bioconjugation is one of the most widely used approaches due to its fast reaction rates and mild conjugation conditions. One issue with this approach is the possibility of the retro-Michael reaction and loss or transfer of the maleimido-linked payload from the antibody to other proteins in the plasma, such as, for example, human serum albumin. However, in preferred embodiments the use of selective reduction and site-specific antibodies as set forth herein in Examples 14 and 16 may be used to stabilize the conjugate and reduce this undesired transfer. Thiol-acyl halide reactions provide bioconjugates that cannot undergo retro-Michael reaction and therefore are more stable. However, the thiol-halide reactions in general have slower reaction rates compared to maleimide-based conjugations and are thus not as efficient in providing undesired drug to antibody ratios. Thiol-pyridyl disulfide reaction is another popular bioconjugation route. The pyridyl disulfide undergoes fast exchange with free thiol resulting in the mixed disulfide and release of pyridine-2-thione. Mixed disulfides can be cleaved in the reductive cell environment releasing the payload. Other approaches gaining more attention in bioconjugation are thiol-vinylsulfone and thiol-bisulfone reactions, each of which are compatible with the teachings herein and expressly included within the scope of the invention.

In preferred embodiments compatible linkers will confer stability on the ADCs in the extracellular environment, prevent aggregation of the ADC molecules and keep the ADC freely soluble in aqueous media and in a monomeric state. Before transport or delivery into a cell, the ADC is preferably stable and remains intact, i.e. the antibody remains linked to the drug moiety. While the linkers are stable outside the target cell they are designed to be cleaved or degraded at some efficacious rate inside the cell. Accordingly an effective linker will: (i) maintain the specific binding properties of the antibody; (ii) allow intracellular delivery of the conjugate or drug moiety; (iii) remain stable and intact, i.e. not cleaved or degraded, until the conjugate has been delivered or transported to its targeted site; and (iv) maintain a cytotoxic, cell-killing effect or a cytostatic effect of the drug moiety (including, in some cases, any bystander effects). The stability of the ADC may be measured by standard analytical techniques such as HPLC/UPLC, mass spectroscopy, HPLC, and the separation/analysis techniques LC/MS and LC/MS/MS. As set forth above covalent attachment of the antibody and the drug moiety requires the linker to have two reactive functional groups, i.e. bivalency in a reactive sense. Bivalent linker reagents which are useful to attach two or more functional or biologically active moieties, such as MMAE and site-specific antibodies are known, and methods have been described to provide their resulting conjugates.

Linkers compatible with the present invention may broadly be classified as cleavable and non-cleavable linkers. Cleavable linkers, which may include acid-labile linkers, protease cleavable linkers and disulfide linkers, are internalized into the target cell and are cleaved in the endosomal-lysosomal pathway inside the cell. Release and activation of the cytotoxin relies on endosome/lysosome acidic compartments that facilitate cleavage of acid-labile chemical linkages such as hydrazone or oxime. If a lysosomal-specific protease cleavage site is engineered into the linker the cytotoxins will be released in proximity to their intracellular targets. Alternatively, linkers containing mixed disulfides provide an approach by which cytotoxic payloads are released intracellularly as they are selectively cleaved in the reducing environment of the cell, but not in the oxygen-rich environment in the bloodstream. By way of contrast, compatible non-cleavable linkers containing amide linked polyethyleneglycol or alkyl spacers liberate toxic payloads during lysosomal degradation of the ADC within the target cell. In some respects the selection of linker will depend on the particular drug used in the conjugate, the particular indication and the antibody target.

Accordingly, certain embodiments of the invention comprise a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease Cathepsin-B are peptides comprising Phe-Leu since cathepsin-B has been found to be highly expressed in cancerous tissue. Other examples of such linkers are described, for example, in U.S. Pat. No. 6,214,345. In a specific preferred embodiment, the peptidyl linker cleavable by an intracellular protease is a Val-Cit linker, a Val-Ala linker or a Phe-Lys linker such as is described in U.S. Pat. No. 6,214,345. One advantage of using intracellular proteolytic release of the therapeutic agent is that the agent is typically attenuated when conjugated and the serum stabilities of the conjugates are typically high.

In other embodiments, the cleavable linker is pH-sensitive. Typically, the pH-sensitive linker will be hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable at below pH 5.5 or 5.0, the approximate pH of the lysosome.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(2-pyridyl-dithio) toluene). In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

In particularly preferred embodiments (set forth in U.S.P.N. 2011/0256157) compatible peptidyl linkers will comprise:

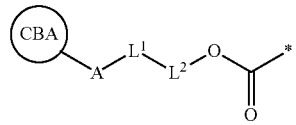

where the asterisk indicates the point of attachment to the drug, CBA is the anti-DPEP3 antibody, $L^1$ is a linker, A is a connecting group (optionally comprising a spacer) connecting $L^1$ to a reactive residue on the antibody, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g.

photolabile) may also be used. Linkers that are cleavable under reducing or oxidizing conditions may also find use in the present invention.

$L^1$ may comprise a contiguous sequence of amino acids. The amino acid sequence may be the target substrate for enzymatic cleavage, thereby allowing release of the drug.

In one embodiment, $L^1$ is cleavable by the action of an enzyme. In one embodiment, the enzyme is an esterase or a peptidase.

In one embodiment, $L^1$ comprises a dipeptide. The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from: -Phe-Lys-, -Val-Ala-, -Val-Lys-, -Ala-Lys-, -Val-Cit-, -Phe-Cit-, -Leu-Cit-, -Ile-Cit-, -Phe-Arg- and -Trp-Cit- where Cit is citrulline.

Preferably, the group —$X_1$—$X_2$— in dipeptide, —NH—$X_1$—$X_2$—CO—, is selected from: -Phe-Lys-, -Val-Ala-, -Val-Lys-, -Ala-Lys-, and -Val-Cit-.

Most preferably, the group —$X_1$—$X_2$— in dipeptide, —NH—$X_1$—$X_2$—CO—, is -Phe-Lys- or -Val-Ala-.

In one embodiment, $L^2$ is present and together with —C(=O)O— forms a self-immolative linker. In one embodiment, $L^2$ is a substrate for enzymatic activity, thereby allowing release of the drug.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and $L^2$ together form the group:

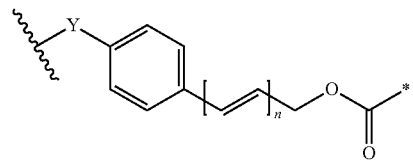

where the asterisk indicates the point of attachment to the drug or cytotoxic agent position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

In another particularly preferred embodiments the linker may include a self-immolative linker and the dipeptide together form the group —NH-Val-Ala-CO—NH-PABC-, which is illustrated below:

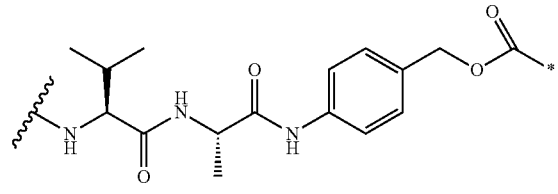 [SMILES: *N[C@H](C(=O)N[C@@H](C)C(=O)Nc1ccc(COC(*)=O)cc1)C(C)C]

where the asterisk indicates the point of attachment to the selected cytotoxic moiety, and the wavy line indicates the point of attachment to the remaining portion of the linker (e.g., the spacer-antibody binding segments) which may be conjugated to the antibody. Upon enzymatic cleavage of the dipeptide the self-immolative linker will allow for clean release of the protected compound (i.e., the cytotoxin) when a remote site is activated, proceeding along the lines shown below:

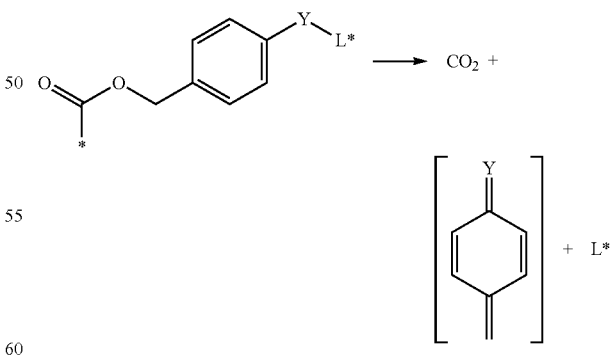

where L* is the activated form of the remaining portion of the linker comprising the now cleaved peptidyl unit. The clean release of the drug ensures they will maintain the desired toxic activity.

In one embodiment, A is a covalent bond. Thus, $L^1$ and the antibody are directly connected. For example, where $L^1$ comprises a contiguous amino acid sequence, the N-terminus of the sequence may connect directly to the antibody residue.

In another embodiment, A is a spacer group. Thus, $L^1$ and the antibody are indirectly connected.

$L^1$ and A may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

As will be discussed in more detail below the drug linkers of the instant invention will preferably be linked to reactive thiol nucleophiles on cysteines, including free cysteines. To this end the cysteines of the antibodies may be made reactive for conjugation with linker reagents by treatment with various reducing agent such as DTT or TCEP or mild reducing agents as set forth herein. In other embodiments the drug linkers of the instant invention will preferably be linked to a lysine.

Preferably, the linker contains an electrophilic functional group for reaction with a nucleophilic functional group on the antibody. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

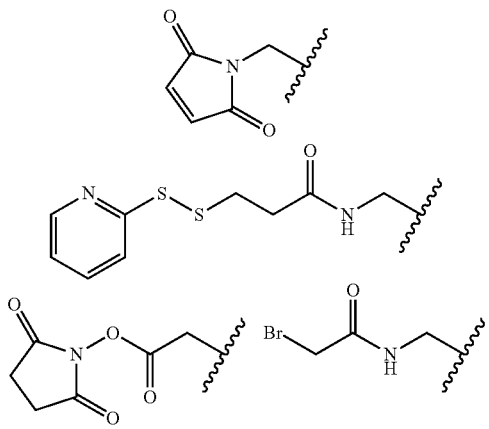

In particularly preferred embodiments the connection between a site-specific antibody and the drug-linker moiety is through a thiol residue of a free cysteine of the site specific antibody and a terminal maleimide group of present on the linker. In such embodiments, the connection between the antibody and the drug-linker is:

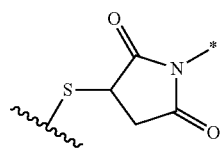 [SMILES: *SC1CC(=O)N(*)C1=O]

where the asterisk indicates the point of attachment to the remaining portion of drug-linker and the wavy line indicates the point of attachment to the remaining portion of the antibody. In this embodiment, the S atom is preferably derived from a site-specific free cysteine. With regard to other compatible linkers the binding moiety comprises a terminal iodoacetamide that may be reacted with activated residues to provide the desired conjugate. In any event one skilled in the art could readily conjugate each of the disclosed drug-linker compounds with a compatible anti-DPEP3 site-specific antibody in view of the instant disclosure.

E. Conjugation

It will be appreciated that a number of well-known different reactions may be used to attach the drug moiety and/or linker to the selected antibody. For example, various reactions exploiting sulfhydryl groups of cysteines may be employed to conjugate the desired moiety. Particularly preferred embodiments will comprise conjugation of antibodies comprising one or more free cysteines as discussed in detail below. In other embodiments ADCs of the instant invention may be generated through conjugation of drugs to solvent-exposed amino groups of lysine residues present in the selected antibody. Still other embodiments comprise activation of the N-terminal threonine and serine residues which may then be used to attach the disclosed payloads to the antibody. The selected conjugation methodology will preferably be tailored to optimize the number of drugs attached to the antibody and provide a relatively high therapeutic index.

Various methods are known in the art for conjugating a therapeutic compound to a cysteine residue and will be apparent to the skilled artisan. Under basic conditions the cysteine residues will be deprotonated to generate a thiolate nucleophile which may be reacted with soft electrophiles, such as maleimides and iodoacetamides. Generally reagents for such conjugations may react directly with a cysteine thiol of a cysteine to form the conjugated protein or with a linker-drug to form a linker-drug intermediate. In the case of a linker, several routes, employing organic chemistry reactions, conditions, and reagents are known to those skilled in the art, including: (1) reaction of a cysteine group of the protein of the invention with a linker reagent, to form a protein-linker intermediate, via a covalent bond, followed by reaction with an activated compound; and (2) reaction of a nucleophilic group of a compound with a linker reagent, to form a drug-linker intermediate, via a covalent bond, followed by reaction with a cysteine group of a protein of the invention. As will be apparent to the skilled artisan from the foregoing, bifunctional linkers are useful in the present invention. For example, the bifunctional linker may comprise a thiol modification group for covalent linkage to the cysteine residue(s) and at least one attachment moiety (e.g., a second thiol modification moiety) for covalent or non-covalent linkage to the compound.

Prior to conjugation, antibodies may be made reactive for conjugation with linker reagents by treatment with a reducing agent such as dithiothreitol (DTT) or (tris(2-carboxyethyl)phosphine (TCEP). In other embodiments additional nucleophilic groups can be introduced into antibodies through the reaction of lysines with reagents, including but not limited to, 2-iminothiolane (Traut's reagent), SATA, SATP or SAT(PEG)4, resulting in conversion of an amine into a thiol.

With regard to such conjugations cysteine thiol or lysine amino groups are nucleophilic and capable of reacting to form covalent bonds with electrophilic groups on linker reagents or compound-linker intermediates or drugs including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a compound or linker include, but are not limited to amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Preferred labeling reagents include maleimide, haloacetyl, iodoacetamide succinimidyl ester, isothiocyanate, sulfonyl chloride, 2,6-dichlorotriazinyl, pentafluorophenyl ester, and phosphoramidite, although other functional groups can also be used. In certain embodiments methods include, for example, the use of maleimides, iodoacetimides or haloacetyl/alkyl halides, aziridne, acryloyl derivatives to react with the thiol of a cysteine to produce a thioether that is reactive with a compound. Disulphide exchange of a free thiol with an activated piridyldisulphide is also useful for producing a conjugate (e.g., use of 5-thio-2-nitrobenzoic (TNB) acid). Preferably, a maleimide is used.

As indicated above, lysine may also be used as a reactive residue to effect conjugation as set forth herein. The nucleophilic lysine residue is commonly targeted through amine-reactive succinimidylesters. To obtain an optimal number of deprotonated lysine residues, the pH of the aqueous solution must be below the pKa of the lysine ammonium group, which is around 10.5, so the typical pH of the reaction is about 8 and 9. The common reagent for the coupling reaction is NHS-ester which reacts with nucleophilic lysine through a lysine acylation mechanism. Other compatible reagents that undergo similar reactions comprise isocyanates and isothiocyanates which also may be used in conjunction with the teachings herein to provide ADCs. Once the lysines have been activated, many of the aforementioned linking groups may be used to covalently bind the warhead to the antibody.

Methods are also known in the art for conjugating a compound to a threonine or serine residue (preferably a N-terminal residue). For example methods have been described in which carbonyl precursors are derived from the 1,2-aminoalcohols of serine or threonine, which can be selectively and rapidly converted to aldehyde form by periodate oxidation. Reaction of the aldehyde with a 1,2-aminothiol of cysteine in a compound to be attached to a protein of the invention forms a stable thiazolidine product. This method is particularly useful for labeling proteins at N-terminal serine or threonine residues.

In particularly preferred embodiments reactive thiol groups may be introduced into the selected antibody (or fragment thereof) by introducing one, two, three, four, or more free cysteine residues (e.g., preparing antibodies comprising one or more free non-native cysteine amino acid residues). Such site-specific antibodies or engineered antibodies, allow for conjugate preparations that exhibit enhanced stability and substantial homogeneity due, at least in part, to the provision of engineered free cysteine site(s) and/or the novel conjugation procedures set forth herein. Unlike conventional conjugation methodology that fully or partially reduces each of the intrachain or interchain antibody disulfide bonds to provide conjugation sites (and is fully compatible with the instant invention), the present invention additionally provides for the selective reduction of certain prepared free cysteine sites and direction of the drug-linker to the same. The conjugation specificity promoted by the engineered sites and the selective reduction allows for a high percentage of site directed conjugation at the desired positions. Significantly some of these conjugation sites, such as those present in the terminal region of the light chain constant region, are typically difficult to conjugate effectively as they tend to cross-react with other free cysteines. However, through molecular engineering and selective reduction of the resulting free cysteines, efficient conjugation rates may be obtained which considerably reduces unwanted high-DAR contaminants and non-specific toxicity. More generally the engineered constructs and disclosed novel conjugation methods comprising selective reduction provide ADC preparations having improved pharmacokinetics and/or pharmacodynamics and, potentially, an improved therapeutic index.

The site-specific constructs present free cysteine(s), which when reduced comprise thiol groups that are nucleophilic and capable of reacting to form covalent bonds with electrophilic groups on linker moieties such as those disclosed above. Preferred antibodies of the instant invention will have reducible unpaired interchain or intrachain cysteines, i.e. cysteines providing such nucleophilic groups. Thus, in certain embodiments the reaction of free sulfhydryl groups of the reduced unpaired cysteines and the terminal maleimido or haloacetamide groups of the disclosed drug-linkers will provide the desired conjugation. In such cases the free cysteines of the antibodies may be made reactive for conjugation with linker reagents by treatment with a reducing agent such as dithiothreitol (DTT) or (tris (2-carboxyethyl)phosphine (TCEP). Each free cysteine will thus present, theoretically, a reactive thiol nucleophile. While such reagents are compatible it will be appreciated that conjugation of the site-specific antibodies may be effected using various reactions, conditions and reagents known to those skilled in the art.

In addition it has been found that the free cysteines of engineered antibodies may be selectively reduced to provide enhanced site-directed conjugation and a reduction in unwanted, potentially toxic contaminants. More specifically "stabilizing agents" such as arginine have been found to modulate intra- and inter-molecular interactions in proteins and may be used, in conjunction with selected reducing agents (preferably relatively mild), to selectively reduce the free cysteines and to facilitate site-specific conjugation as set forth herein. As used herein the terms "selective reduction" or "selectively reducing" may be used interchangeably and shall mean the reduction of free cysteine(s) without substantially disrupting native disulfide bonds present in the engineered antibody. In selected embodiments this may be affected by certain reducing agents. In other preferred embodiments selective reduction of an engineered construct will comprise the use of stabilization agents in combination with reducing agents (including mild reducing agents). It will be appreciated that the term "selective conjugation" shall mean the conjugation of an engineered antibody that has been selectively reduced with a cytotoxin as described herein. In this respect the use of such stabilizing agents in combination with selected reducing agents can markedly improve the efficiency of site-specific conjugation as determined by extent of conjugation on the heavy and light antibody chains and DAR distribution of the preparation.

While not wishing to be bound by any particular theory, such stabilizing agents may act to modulate the electrostatic microenvironment and/or modulate conformational changes at the desired conjugation site, thereby allowing relatively mild reducing agents (which do not materially reduce intact native disulfide bonds) to facilitate conjugation at the desired free cysteine site. Such agents (e.g., certain amino acids) are known to form salt bridges (via hydrogen bonding and electrostatic interactions) and may modulate protein-protein interactions in such a way as to impart a stabilizing effect that may cause favorable conformation changes and/or may reduce unfavorable protein-protein interactions. Moreover, such agents may act to inhibit the formation of undesired intramolecular (and intermolecular) cysteine-cysteine bonds after reduction thus facilitating the desired conjugation reaction wherein the engineered site-specific cysteine is bound to the drug (preferably via a linker). Since selective reduction conditions do not provide for the significant reduction of intact native disulfide bonds, the subsequent conjugation reaction is naturally driven to the relatively few reactive thiols on the free cysteines (e.g., preferably 2 free thiols per antibody). As previously alluded to this considerably reduces the levels of non-specific conjugation and corresponding impurities in conjugate preparations fabricated as set forth herein.

In selected embodiments stabilizing agents compatible with the present invention will generally comprise compounds with at least one moiety having a basic pKa. In certain embodiments the moiety will comprise a primary amine while in other preferred embodiments the amine moiety will comprise a secondary amine. In still other preferred embodiments the amine moiety will comprise a tertiary amine or a guanidinium group. In other selected embodiments the amine moiety will comprise an amino acid while in other compatible embodiments the amine moiety will comprise an amino acid side chain. In yet other embodiments the amine moiety will comprise a proteinogenic amino acid. In still other embodiments the amine moiety comprises a non-proteinogenic amino acid. In particularly preferred embodiments, compatible stabilizing agents may comprise arginine, lysine, proline and cysteine. In addition compatible stabilizing agents may include guanidine and nitrogen containing heterocycles with basic pKa.

In certain embodiments compatible stabilizing agents comprise compounds with at least one amine moiety having a pKa of greater than about 7.5, in other embodiments the subject amine moiety will have a pKa of greater than about 8.0, in yet other embodiments the amine moiety will have a pKa greater than about 8.5 and in still other embodiments the stabilizing agent will comprise an amine moiety having a pKa of greater than about 9.0. Other preferred embodiments will comprise stabilizing agents where the amine moiety will have a pKa of greater than about 9.5 while certain other embodiments will comprise stabilizing agents exhibiting at least one amine moiety having a pKa of greater than about 10.0. In still other preferred embodiments the stabilizing agent will comprise a compound having the amine moiety with a pKa of greater than about 10.5, in other embodiments the stabilizing agent will comprise a compound having a amine moiety with a pKa greater than about 11.0, while in still other embodiments the stabilizing agent will comprise a amine moiety with a pKa greater than about 11.5. In yet other embodiments the stabilizing agent will comprise a compound having an amine moiety with a pKa greater than about 12.0, while in still other embodiments the stabilizing agent will comprise an amine moiety with a pKa greater than about 12.5. Those of skill in the art will understand that relevant pKa's may readily be calculated or determined using standard techniques and used to determine the applicability of using a selected compound as a stabilizing agent.

The disclosed stabilizing agents are shown to be particularly effective at targeting conjugation to free site-specific cysteines when combined with certain reducing agents. For the purposes of the instant invention, compatible reducing agents may include any compound that produces a reduced free site-specific cysteine for conjugation without significantly disrupting the engineered antibody native disulfide bonds. Under such conditions, provided by the combination of selected stabilizing and reducing agents, the activated drug linker is largely limited to binding to the desired free site-specific cysteine site. Relatively mild reducing agents or reducing agents used at relatively low concentrations to provide mild conditions are particularly preferred. As used herein the terms "mild reducing agent" or "mild reducing conditions" shall be held to mean any agent or state brought about by a reducing agent (optionally in the presence of stabilizing agents) that provides thiols at the free cysteine site(s) without substantially disrupting native disulfide bonds present in the engineered antibody. That is, mild reducing agents or conditions are able to effectively reduce free cysteine(s) (provide a thiol) without significantly disrupting the protein's native disulfide bonds. The desired reducing conditions may be provided by a number of sulfhydryl-based compounds that establish the appropriate environment for selective conjugation. In preferred embodiments mild reducing agents may comprise compounds having one or more free thiols while in particularly preferred embodiments mild reducing agents will comprise compounds having a single free thiol. Non-limiting examples of reducing agents compatible with the instant invention comprise glutathione, n-acetyl cysteine, cysteine, 2-aminoethane-1-thiol and 2-hydroxyethane-1-thiol.

It will be appreciated that selective reduction process set forth above is particularly effective at targeted conjugation to the free cysteine. In this respect the extent of conjugation to the desired target site (defined here as "conjugation efficiency") in site-specific antibodies may be determined by various art-accepted techniques. The efficiency of the site-specific conjugation of a drug to an antibody may be determined by assessing the percentage of conjugation on the target conjugation site (in this invention the free cysteine on the c-terminus of the light chain) relative to all other conjugated sites. In certain embodiments, the method herein provides for efficiently conjugating a drug to an antibody comprising free cysteines. In some embodiments, the conjugation efficiency is at least 5%, at least 10%, at least 15%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, at least 98% or more as measured by the percentage of target conjugation relative to all other conjugation sites.

It will further be appreciated that engineered antibodies capable of conjugation may contain free cysteine residues that comprise sulfhydryl groups that are blocked or capped as the antibody is produced or stored. Such caps include small molecules, proteins, peptides, ions and other materials that interact with the sulfhydryl group and prevent or inhibit conjugate formation. In some cases the unconjugated engineered antibody may comprise free cysteines that bind other free cysteines on the same or different antibodies. As discussed herein such cross-reactivity may lead to various contaminants during the fabrication procedure. In some embodiments, the engineered antibodies may require uncapping prior to a conjugation reaction. In specific embodiments, antibodies herein are uncapped and display a free sulfhydryl group capable of conjugation. In specific embodiments, antibodies herein are subjected to an uncapping reaction that does not disturb or rearrange the naturally occurring disulfide bonds. It will be appreciated that in most cases the uncapping reactions will occur during the normal reduction reactions (reduction or selective reduction).

F. DAR Distribution and Purification

One of the advantages of conjugation with site specific antibodies of the present invention is the ability to generate relatively homogeneous ADC preparations comprising a narrow DAR distribution. In this regard the disclosed constructs and/or selective conjugation provides for homogeneity of the ADC species within a sample in terms of the stoichiometric ratio between the drug and the engineered antibody. As briefly discussed above the term "drug to antibody ratio" or "DAR" refers to the molar ratio of drug to antibody. In some embodiments a conjugate preparation may be substantially homogeneous with respect to its DAR distribution, meaning that within the preparation is a predominant species of site-specific ADC with a particular DAR (e.g., a DAR of 2 or 4) that is also uniform with respect to the site of loading (i.e., on the free cysteines). In certain embodiments of the invention it is possible to achieve the desired homogeneity through the use of site-specific antibodies and/or selective reduction and conjugation. In other preferred embodiments the desired homogeneity may be achieved through the use of site-specific constructs in combination with selective reduction. In yet other particularly preferred embodiments the preparations may be further purified using analytical or preparative chromatography techniques. In each of these embodiments the homogeneity of the ADC sample can be analyzed using various techniques known in the art including but not limited to mass spectrometry, HPLC (e.g. size exclusion HPLC, RP-HPLC, HIC-HPLC etc.) or capillary electrophoresis.

With regard to the purification of ADC preparations it will be appreciated that standard pharmaceutical preparative methods may be employed to obtain the desired purity. As discussed herein liquid chromatography methods such as reverse phase (RP) and hydrophobic interaction chromatography (HIC) may separate compounds in the mixture by drug loading value. In some cases, ion-exchange (IEC) or mixed-mode chromatography (MMC) may also be used to isolate species with a specific drug load.

The disclosed ADCs and preparations thereof may comprise drug and antibody moieties in various stoichiometric molar ratios depending on the configuration of the antibody and, at least in part, on the method used to effect conjugation. In certain embodiments the drug loading per ADC may comprise from 1-20 warheads (i.e., n is 1-20). Other selected embodiments may comprise ADCs with a drug loading of from 1 to 15 warheads. In still other embodiments the ADCs may comprise from 1-12 warheads or, more preferably, from 1-10 warheads. In certain preferred embodiments the ADCs will comprise from 1 to 8 warheads.

While theoretical drug loading may be relatively high, practical limitations such as free cysteine cross reactivity and warhead hydrophobicity tend to limit the generation of homogeneous preparations comprising such DAR due to aggregates and other contaminants. That is, higher drug loading, e.g. >6, may cause aggregation, insolubility, toxicity, or loss of cellular permeability of certain antibody-drug conjugates. In view of such concerns practical drug loading provided by the instant invention preferably ranges from 1 to 8 drugs per conjugate, i.e. where 1, 2, 3, 4, 5, 6, 7, or 8 drugs are covalently attached to each antibody (e.g., for IgG1, other antibodies may have different loading capacity depending the number of disulfide bonds). Preferably the DAR of compositions of the instant invention will be approximately 2, 4 or 6 and in particularly preferred embodiments the DAR will comprise approximately 2.

Despite the relatively high level of homogeneity provided by the instant invention the disclosed compositions actually comprise a mixture of conjugates with a range of drugs compounds, from 1 to 8 (in the case of a IgG1). As such, the disclosed ADC compositions include mixtures of conjugates where most of the constituent antibodies are covalently linked to one or more drug moieties and (despite the conjugate specificity of selective reduction) where the drug moieties may be attached to the antibody by various thiol groups. That is, following conjugation ADC compositions of the invention will comprise a mixture of conjugates with different drug loads (e.g., from 1 to 8 drugs per IgG1 antibody) at various concentrations (along with certain reaction contaminants primarily caused by free cysteine cross reactivity). Using selective reduction and post-fabrication purification the conjugate compositions may be driven to the point where they largely contain a single predominant desired ADC species (e.g., with a drug loading of 2) with relatively low levels of other ADC species (e.g., with a drug loading of 1, 4, 6, etc.). The average DAR value represents the weighted average of drug loading for the composition as a whole (i.e., all the ADC species taken together). Due to inherent uncertainty in the quantification methodology employed and the difficulty in completely removing the non-predominant ADC species in a commercial setting, acceptable DAR values or specifications are often presented as an average, a range or distribution (i.e., an average DAR of 2+/−0.5). Preferably compositions comprising a measured average DAR within the range (i.e., 1.5 to 2.5) would be used in a pharmaceutical setting.

Thus, in certain preferred embodiments the present invention will comprise compositions having an average DAR of 1, 2, 3, 4, 5, 6, 7 or 8 each +/−0.5. In other preferred embodiments the present invention will comprise an average DAR of 2, 4, 6 or 8+/−0.5. Finally, in selected preferred embodiments the present invention will comprise an average DAR of 2+/−0.5. It will be appreciated that the range or deviation may be less than 0.4 in certain preferred embodiments. Thus, in other embodiments the compositions will comprise an average DAR of 1, 2, 3, 4, 5, 6, 7 or 8 each +/−0.3, an average DAR of 2, 4, 6 or 8+/−0.3, even more preferably an average DAR of 2 or 4+/−0.3 or even an average DAR of 2+/−0.3. In other embodiments IgG1 conjugate compositions will preferably comprise a composition with an average DAR of 1, 2, 3, 4, 5, 6, 7 or 8 each +/−0.4 and relatively low levels (i.e., less than 30%) of non-predominant ADC species. In other preferred embodiments the ADC composition will comprise an average DAR of 2, 4, 6 or 8 each +/−0.4 with relatively low levels (<30%) of non-predominant ADC species. In particularly preferred embodiments the ADC composition will comprise an average DAR of 2+/−0.4 with relatively low levels (<30%) of non-predominant ADC species. In yet other embodiments the predominant ADC species (e.g., DAR of 2) will be present at a concentration of greater than 65%, at a concentration of greater than 70%, at a concentration of greater than 75%, at a concentration of greater that 80%, at a concentration of greater than 85%, at a concentration of greater than 90%, at a concentration of greater than 93%, at a concentration of greater than 95% or even at a concentration of greater than 97% when measured against other DAR species.

As detailed in the Examples below the distribution of drugs per antibody in preparations of ADC from conjugation reactions may be characterized by conventional means such as UV-Vis spectrophotometry, reverse phase HPLC, HIC, mass spectroscopy, ELISA, and electrophoresis. The quantitative distribution of ADC in terms of drugs per antibody may also be determined. By ELISA, the averaged value of the drugs per antibody in a particular preparation of ADC may be determined. However, the distribution of drug per antibody values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues.

VI DIAGNOSTICS AND SCREENING

A. Diagnostics

The invention provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc.

In a particularly preferred embodiment the antibodies of the instant invention may be used to detect and quantify levels of a particular determinant (e.g., DPEP3) in a patient sample (e.g., plasma or blood) which may, in turn, be used to detect, diagnose or monitor proliferative disorders that are associated with the relevant determinant. In related embodiments the antibodies of the instant invention may be used to detect, monitor and/or quantify circulating tumor cells either in vivo or in vitro (WO 2012/0128801). In still other embodiments the circulating tumor cells may comprise tumorigenic cells.

In certain embodiments of the invention, the tumorigenic cells in a subject or a sample from a subject may be assessed or characterized using the disclosed antibodies prior to therapy or regimen to establish a baseline. In other examples, the tumorigenic cells can be assessed from a sample that is derived from a subject that was treated.

B. Screening

In certain embodiments, the antibodies can be used to screen samples in order to identify compounds or agents (e.g., antibodies or ADCs) that alter a function or activity of tumor cells by interacting with a determinant. In one embodiment, tumor cells are put in contact with an antibody or ADC and the antibody or ADC can be used to screen the tumor for cells expressing a certain target (e.g. DPEP3) in order to identify such cells for purposes, including but not limited to, diagnostic purposes, to monitor such cells to determine treatment efficacy or to enrich a cell population for such target-expressing cells.

In yet another embodiment, a method includes contacting, directly or indirectly, tumor cells with a test agent or compound and determining if the test agent or compound modulates an activity or function of the determinant-associated tumor cells for example, changes in cell morphology or viability, expression of a marker, differentiation or de-differentiation, cell respiration, mitochondrial activity, membrane integrity, maturation, proliferation, viability, apoptosis or cell death. One example of a direct interaction is physical interaction, while an indirect interaction includes, for example, the action of a composition upon an intermediary molecule that, in turn, acts upon the referenced entity (e.g., cell or cell culture).

Screening methods include high throughput screening, which can include arrays of cells (e.g., microarrays) positioned or placed, optionally at pre-determined locations, for example, on a culture dish, tube, flask, roller bottle or plate. High-throughput robotic or manual handling methods can probe chemical interactions and determine levels of expression of many genes in a short period of time. Techniques have been developed that utilize molecular signals, for example via fluorophores or microarrays (Mocellin and Rossi, 2007, PMID: 17265713) and automated analyses that process information at a very rapid rate (see, e.g., Pinhasov et al., 2004, PMID: 15032660). Libraries that can be screened include, for example, small molecule libraries, phage display libraries, fully human antibody yeast display libraries (Adimab), siRNA libraries, and adenoviral transfection vectors.

VII PHARMACEUTICAL PREPARATIONS AND THERAPEUTIC USES

A. Formulations and Routes of Administration

The antibodies or ADCs of the invention can be formulated in various ways using art recognized techniques. In some embodiments, the therapeutic compositions of the invention can be administered neat or with a minimum of additional components while others may optionally be formulated to contain suitable pharmaceutically acceptable carriers. As used herein, "pharmaceutically acceptable carriers" comprise excipients, vehicles, adjuvants and diluents that are well known in the art and can be available from commercial sources for use in pharmaceutical preparation (see, e.g., Gennaro (2003) *Remington: The Science and Practice of Pharmacy with Facts and Comparisons: Drugfacts Plus,* 20th ed., Mack Publishing; Ansel et al. (2004) *Pharmaceutical Dosage Forms and Drug Delivery Systems,* 7$^{th}$ ed., Lippencott Williams and Wilkins; Kibbe et al. (2000) *Handbook of Pharmaceutical Excipients,* 3$^{rd}$ ed., Pharmaceutical Press.)

Suitable pharmaceutically acceptable carriers comprise substances that are relatively inert and can facilitate administration of the antibody or can aid processing of the active compounds into preparations that are pharmaceutically optimized for delivery to the site of action.

Such pharmaceutically acceptable carriers include agents that can alter the form, consistency, viscosity, pH, tonicity, stability, osmolarity, pharmacokinetics, protein aggregation or solubility of the formulation and include buffering agents, wetting agents, emulsifying agents, diluents, encapsulating agents and skin penetration enhancers. Certain non-limiting examples of carriers include saline, buffered saline, dextrose, arginine, sucrose, water, glycerol, ethanol, sorbitol, dextran, sodium carboxymethyl cellulose and combinations thereof. Antibodies for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in *Remington: The Science and Practice of Pharmacy* (2000) 20th Ed. Mack Publishing.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additionally contain other pharmaceutically acceptable carriers, such as anti-oxidants, buffers, preservatives, stabilizers, bacteriostats, suspending agents, thickening agents, and solutes that render the formulation isotonic with the blood (or other relevant bodily fluid) of the intended recipient. Examples of excipients include, for example, water, alcohols, polyols, glycerol, vegetable oils, and the like. Examples of suitable isotonic pharmaceutically acceptable carriers for use in such formulations include Sodium Chloride Injection, Ringer's Solution, or Lactated Ringer's Injection.

Compatible formulations for parenteral administration (e.g., intravenous injection) may comprise ADC or antibody concentrations of from about 10 μg/mL to about 100 mg/mL. In certain selected embodiments antibody or ADC concentrations will comprise 20 μg/mL, 40 μg/mL, 60 μg/mL, 80 μg/mL, 100 μg/mL, 200 μg/mL, 300, μg/mL, 400 μg/mL, 500 μg/mL, 600 μg/mL, 700 μg/mL, 800 μg/mL, 900 μg/mL or 1 mg/mL. In other preferred embodiments ADC concentrations will comprise 2 mg/mL, 3 mg/mL, 4 mg/mL, 5 mg/mL, 6 mg/mL, 8 mg/mL, 10 mg/mL, 12 mg/mL, 14 mg/mL, 16 mg/mL, 18 mg/mL, 20 mg/mL, 25 mg/mL, 30 mg/mL, 35 mg/mL, 40 mg/mL, 45 mg/mL, 50 mg/mL, 60 mg/mL, 70 mg/mL, 80 mg/mL, 90 mg/mL or 100 mg/mL.

The compounds and compositions of the invention may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

B. Dosages

The particular dosage regimen, i.e., dose, timing and repetition, will depend on the particular individual, as well as empirical considerations such as pharmacokinetics (e.g., half-life, clearance rate, etc.). Determination of the frequency of administration may be made by persons skilled in the art, such as an attending physician based on considerations of the condition and severity of the condition being treated, age and general state of health of the subject being treated and the like. Frequency of administration may be adjusted over the course of therapy based on assessment of the efficacy of the selected composition and the dosing regimen. Such assessment can be made on the basis of markers of the specific disease, disorder or condition. In embodiments where the individual has cancer, these include direct measurements of tumor size via palpation or visual observation; indirect measurement of tumor size by x-ray or other imaging techniques; an improvement as assessed by direct tumor biopsy and microscopic examination of a tumor sample; the measurement of an indirect tumor marker (e.g., PSA for prostate cancer) or an antigen identified according to the methods described herein; reduction in the number of proliferative or tumorigenic cells, maintenance of the reduction of such neoplastic cells; reduction of the proliferation of neoplastic cells; or delay in the development of metastasis.

The DPEP3 antibodies or ADCs of the invention may be administered in various ranges. These include about 5 μg/kg body weight to about 100 mg/kg body weight per dose; about 50 μg/kg body weight to about 5 mg/kg body weight per dose; about 100 μg/kg body weight to about 10 mg/kg body weight per dose. Other ranges include about 100 μg/kg body weight to about 20 mg/kg body weight per dose and about 0.5 mg/kg body weight to about 20 mg/kg body weight per dose. In certain embodiments, the dosage is at least about 100 μg/kg body weight, at least about 250 μg/kg body weight, at least about 750 μg/kg body weight, at least about 3 mg/kg body weight, at least about 5 mg/kg body weight, at least about 10 mg/kg body weight.

In selected embodiments the DPEP3 antibodies or ADCs will be administered (preferably intravenously) at approximately 10, 20, 30, 40, 50, 60, 70, 80, 90 or 100 μg/kg body weight per dose. Other embodiments may comprise the administration of ADCs at about 200, 300, 400, 500, 600, 700, 800, 900, 1000, 1100, 1200, 1300, 1400, 1500, 1600, 1700, 1800, 1900 or 2000 μg/kg body weight per dose. In other preferred embodiments the disclosed conjugates will be administered at 2.5, 3, 3.5, 4, 4.5, 5, 5.5, 6, 6.5, 7, 7.5, 8, 9 or 10 mg/kg. In still other embodiments the conjugates may be administered at 12, 14, 16, 18 or 20 mg/kg body weight per dose. In yet other embodiments the conjugates may be administered at 25, 30, 35, 40, 45, 50, 55, 60, 65, 70, 75, 80, 90 or 100 mg/kg body weight per dose. With the teachings herein one of skill in the art could readily determine appropriate dosages for various DPEP3 antibodies or ADCs based on preclinical animal studies, clinical observations and standard medical and biochemical techniques and measurements.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the conjugates may be administered in dosages from 1 mg/m$^2$ to 800 mg/m$^2$, from 50 mg/m$^2$ to 500 mg/m$^2$ and at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$. It will also be appreciated that art recognized and empirical techniques may be used to determine appropriate dosage.

Anti-DPEP3 antibodies or ADCs may be administered on a specific schedule. Generally, an effective dose of the DPEP3 conjugate is administered to a subject one or more times. More particularly, an effective dose of the ADC is administered to the subject once a month, more than once a month, or less than once a month. In certain embodiments, the effective dose of the DPEP3 antibody or ADC may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed antibodies or ADCs.

In certain preferred embodiments the course of treatment involving conjugated antibodies will comprise multiple doses of the selected drug product over a period of weeks or months. More specifically, antibodies or ADCs of the instant invention may administered once every day, every two days, every four days, every week, every ten days, every two weeks, every three weeks, every month, every six weeks, every two months, every ten weeks or every three months. In this regard it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

C. Combination Therapies

Combination therapies may be useful in preventing or treating cancer and in preventing metastasis or recurrence of cancer. "Combination therapy", as used herein, means the administration of a combination comprising at least one anti-DPEP3 antibody or ADC and at least one therapeutic moiety (e.g., anti-cancer agent) wherein the combination preferably has therapeutic synergy or improves the measurable therapeutic effects in the treatment of cancer over (i) the anti-DPEP3 antibody or ADC used alone, or (ii) the therapeutic moiety used alone, or (iii) the use of the therapeutic moiety in combination with another therapeutic moiety without the addition of an anti-DPEP3 antibody or ADC. The term "therapeutic synergy", as used herein, means the combination of an anti-DPEP3 antibody or ADC and one or more therapeutic moiety(ies) having a therapeutic effect greater than the additive effect of the combination of the anti-DPEP3 antibody or ADC and the one or more therapeutic moiety(ies).

Desired outcomes of the disclosed combinations are quantified by comparison to a control or baseline measurement. As used herein, relative terms such as "improve," "increase," or "reduce" indicate values relative to a control, such as a measurement in the same individual prior to initiation of treatment described herein, or a measurement in a control individual (or multiple control individuals) in the absence of the anti-DPEP3 antibodies or ADCs described herein but in the presence of other therapeutic moiety(ies) such as standard of care treatment. A representative control individual is an individual afflicted with the same form of cancer as the individual being treated, who is about the same age as the individual being treated (to ensure that the stages of the disease in the treated individual and the control individual are comparable.) Changes or improvements in response to therapy are generally statistically significant. As used herein, the term "significance" or "significant" relates to a statistical analysis of the probability that there is a non-random association between two or more entities. To determine whether or not a relationship is "significant" or has "significance," a "p-value" can be calculated. P-values that fall below a user-defined cut-off point are regarded as significant. A p-value less than or equal to 0.1, less than 0.05, less than 0.01, less than 0.005, or less than 0.001 may be regarded as significant.

A synergistic therapeutic effect may be an effect of at least about two-fold greater than the therapeutic effect elicited by a single therapeutic moiety or anti-DPEP3 antibody or ADC, or the sum of the therapeutic effects elicited by the anti-DPEP3 antibody or ADC or the single therapeutic moiety(ies) of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single therapeutic moiety or anti-DPEP3 antibody or ADC, or the sum of the therapeutic effects elicited by the anti-DPEP3 antibody or ADC or the single therapeutic moiety(ies) of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

In practicing combination therapy, the anti-DPEP3 antibody or ADC and therapeutic moiety(ies) may be administered to the subject simultaneously, either in a single composition, or as two or more distinct compositions using the same or different administration routes. Alternatively, treatment with the anti-DPEP3 antibody or ADC may precede or follow the therapeutic moiety treatment by, e.g., intervals ranging from minutes to weeks. In one embodiment, both the therapeutic moiety and the antibody or ADC are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the antibody and the therapeutic moiety.

The combination therapy can be administered until the condition is treated, palliated or cured on various schedules such as once, twice or three times daily, once every two days, once every three days, once weekly, once every two weeks, once every month, once every two months, once every three months, once every six months, or may be administered continuously. The antibody and therapeutic moiety(ies) may be administered on alternate days or weeks; or a sequence of anti-DPEP3 antibody or ADC treatments may be given, followed by one or more treatments with the additional therapeutic moiety. In one embodiment an anti-DPEP3 antibody or ADC is administered in combination with one or more therapeutic moiety(ies) for short treatment cycles. In other embodiments the combination treatment is administered for long treatment cycles. The combination therapy can be administered via any route.

In some embodiments the anti-DPEP3 antibodies or ADCs may be used in combination with various first line cancer treatments. In one embodiment the combination therapy comprises the use of an anti-DPEP3 antibody or ADC and a cytotoxic agent such as ifosfamide, mytomycin C, vindesine, vinblastine, etoposide, ironitecan, gemcitabine, taxanes, vinorelbine, methotrexate, and pemetrexed) and optionally one or more other therapeutic moiety(ies).

In another embodiment the combination therapy comprises the use of an anti-DPEP3 antibody or ADC and a platinum-based drug (e.g. carboplatin or cisplatin) and optionally one or more other therapeutic moiety(ies) (e.g. vinorelbine; gemcitabine; a taxane such as, for example, docetaxel or paclitaxel; irinotican; or pemetrexed).

In one embodiment, for example, in the treatment of BR-ERPR, BR-ER or BR-PR cancer, the combination therapy comprises the use of an anti-DPEP3 antibody or ADC and one or more therapeutic moieties described as "hormone therapy". "Hormone therapy" as used herein, refers to, e.g., tamoxifen; gonadotropin or luteinizing releasing hormone (GnRH or LHRH); everolimus and exemestane; toremifene; or aromatase inhibitors (e.g. anastrozole, letrozole, exemestane or fulvestrant).

In another embodiment, for example, in the treatment of BR-HER2, the combination therapy comprises the use of an anti-DPEP3 antibody or ADC and trastuzumab or ado-trastuzumab emtansine and optionally one or more other therapeutic moiety(ies) (e.g. pertuzumab and/or docetaxel).

In some embodiments, for example, in the treatment of metastatic breast cancer, the combination therapy comprises the use of an anti-DPEP3 antibody or ADC and a taxane (e.g. docetaxel or paclitaxel) and optionally an additional therapeutic moiety(ies), for example, an anthracycline (e.g. doxorubicin or epirubicin) and/or eribulin.

In another embodiment, for example, in the treatment of metastatic or recurrent breast cancer or BRCA-mutant breast cancer, the combination therapy comprises the use of an anti-DPEP3 antibody or ADC and megestrol and optionally an additional therapeutic moiety(ies).

In further embodiments, for example, in the treatment of BR-TNBC, the combination therapy comprises the use of an anti-DPEP3 antibody or ADC and a poly ADP ribose polymerase (PARP) inhibitor (e.g. BMN-673, olaparib, rucaparib and veliparib) and optionally an additional therapeutic moiety(ies).

In another embodiment, for example, in the treatment of breast cancer, the combination therapy comprises the use of an anti-DPEP3 antibody or ADC and cyclophosphamide and optionally an additional therapeutic moiety(ies) (e.g. doxorubicin, a taxane, epirubicin, 5-FU and/or methotrexate.

In another embodiment combination therapy for the treatment of EGFR-positive NSCLC comprises the use of an anti-DPEP3 antibody or ADC and afatinib and optionally one or more other therapeutic moiety(ies) (e.g. erlotinib and/or bevacizumab).

In another embodiment combination therapy for the treatment of EGFR-positive NSCLC comprises the use of an anti-DPEP3 antibody or ADC and erlotinib and optionally one or more other therapeutic moiety(ies) (e.g. bevacizumab).

In another embodiment combination therapy for the treatment of ALK-positive NSCLC comprises the use of an anti-DPEP3 antibody or ADC and ceritinib and optionally one or more other therapeutic moiety(ies).

In another embodiment combination therapy for the treatment of ALK-positive NSCLC comprises the use of an anti-DPEP3 antibody or ADC and crizotinib and optionally one or more other therapeutic moiety(ies).

In another embodiment the combination therapy comprises the use of an anti-DPEP3 antibody or ADC and bevacizumab and optionally one or more other therapeutic moiety(ies) (e.g. a taxane such as, for example, docetaxel or paclitaxel; and/or a platinum analog).

In another embodiment the combination therapy comprises the use of an anti-DPEP3 antibody or ADC and bevacizumab and optionally one or more other therapeutic moiety(ies) (e.g. gemcitabine and/or a platinum analog).

In one embodiment the combination therapy comprises the use of an anti-DPEP3 antibody or ADC and a platinum-based drug (e.g. carboplatin or cisplatin) analog and optionally one or more other therapeutic moiety(ies) (e.g. a taxane such as, for example, docetaxel and paclitaxel).

In one embodiment the combination therapy comprises the use of an anti-DPEP3 antibody or ADC and platinum-based drug (e.g. carboplatin or cisplatin) analog and optionally one or more other therapeutic moiety(ies) (e.g. a taxane such, for example, docetaxel and paclitaxel and/or gemcitabine and/or doxorubicin).

In a particular embodiment the combination therapy for the treatment of platinum-resistant tumors comprises the use of an anti-DPEP3 antibody or ADC and doxorubicin and/or etoposide and/or gemcitabine and/or vinorelbine and/or ifosfamide and/or leucovorin-modulated 5-fluoroucil and/or bevacizumab and/or tamoxifen; and optionally one or more other therapeutic moiety(ies).

In another embodiment the combination therapy comprises the use of an anti-DPEP3 antibody or ADC and a PARP inhibitor and optionally one or more other therapeutic moiety(ies).

In another embodiment the combination therapy comprises the use of an anti-DPEP3 antibody or ADC and bevacizumab and optionally cyclophosphamide.

The combination therapy may comprise an anti-DPEP3 antibody or ADC and a chemotherapeutic moiety that is effective on a tumor comprising a mutated or aberrantly expressed gene or protein (e.g. BRCA1).

T lymphocytes (e.g., cytotoxic lymphocytes (CTL)) play an important role in host defense against malignant tumors. CTL are activated by the presentation of tumor associated antigens on antigen presenting cells. Active specific immunotherapy is a method that can be used to augment the T lymphocyte response to cancer by vaccinating a patient with peptides derived from known cancer associated antigens. In one embodiment the combination therapy may comprise an anti-DPEP3 antibody or ADC and a vaccine to a cancer associated antigen (e.g. melanocyte-lineage specific antigen tyrosinase, gp100, Melan-A/MART-1 or gp75.) In other embodiments the combination therapy may comprise administration of an anti-DPEP3 antibody or ADC together with in vitro expansion, activation, and adoptive reintroduction of autologous CTLs or natural killer cells.

CTL activation may also be promoted by strategies that enhance tumor antigen presentation by antigen presenting cells. Granulocyte macrophage colony stimulating factor (GM-CSF) promotes the recruitment of dendritic cells and activation of dendritic cell cross-priming. In one embodiment the combination therapy may comprise the isolation of antigen presenting cells, activation of such cells with stimulatory cytokines (e.g. GM-CSF), priming with tumor-associated antigens, and then adoptive reintroduction of the antigen presenting cells into patients in combination with the use of anti-DPEP3 antibodies or ADCs and optionally one or more different therapeutic moiety(ies).

The invention also provides for the combination of anti-DPEP3 antibodies or ADCs with radiotherapy. The term "radiotherapy", as used herein, means, any mechanism for inducing DNA damage locally within tumor cells such as gamma-irradiation, X-rays, UV-irradiation, microwaves, electronic emissions and the like. Combination therapy using the directed delivery of radioisotopes to tumor cells is also contemplated, and may be used in combination or as a conjugate of the anti-DPEP3 antibodies disclosed herein. Typically, radiation therapy is administered in pulses over a period of time from about 1 to about 2 weeks. Optionally, the radiation therapy may be administered as a single dose or as multiple, sequential doses.

In other embodiments an anti-DPEP3 antibody or ADC may be used in combination with one or more of the anti-cancer agents described below.

D. Anti-Cancer Agents

The term "anti-cancer agent" or "chemotherapeutic agent" as used herein is one subset of "therapeutic moieties", which in turn is a subset of the agents described as "pharmaceutically active moieties". More particularly "anti-cancer agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, biological response modifiers, therapeutic antibodies, cancer vaccines, cytokines, hormone therapy, anti-metastatic agents and immunotherapeutic agents. It will be appreciated that in selected embodiments as discussed above, such anti-cancer agents may comprise conjugates and may be associated with antibodies prior to administration. In certain embodiments the disclosed anti-cancer agent will be linked to an antibody to provide an ADC as disclosed herein.

The term "cytotoxic agent", which can also be an anti-cancer agent means a substance that is toxic to the cells and decreases or inhibits the function of cells and/or causes destruction of cells. Typically, the substance is a naturally occurring molecule derived from a living organism (or a synthetically prepared natural product). Examples of cytotoxic agents include, but are not limited to, small molecule toxins or enzymatically active toxins of bacteria (e.g., Diphtheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *saponaria officinalis* inhibitor, mitegellin, restrictocin, phenomycin, neomycin, and the tricothecenes) or animals, (e.g., cytotoxic RNases, such as extracellular pancreatic RNases; DNase I, including fragments and/or variants thereof).

An anti-cancer agent can include any chemical agent that inhibits, or is designed to inhibit, a cancerous cell or a cell likely to become cancerous or generate tumorigenic progeny (e.g., tumorigenic cells). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. Such agents are often administered, and are often most effective, in combination, e.g., in the formulation CHOP. Again, in selected embodiments such anti-cancer agents may be conjugated to the disclosed antibodies.

Examples of anti-cancer agents that may be used in combination with (or conjugated to) the antibodies of the invention include, but are not limited to, alkylating agents, alkyl sulfonates, anastrozole, amanitins, aziridines, ethylenimines and methylamelamines, acetogenins, a camptothecin, BEZ-235, bortezomib, bryostatin, callystatin, CC-1065, ceritinib, crizotinib, cryptophycins, dolastatin, duocarmycin, eleutherobin, erlotinib, pancratistatin, a sarcodictyin, spongistatin, nitrogen mustards, antibiotics, enediyne dynemicin, bisphosphonates, esperamicin, chromoprotein enediyne antiobiotic chromophores, aclacinomysins, actinomycin, authramycin, azaserine, bleomycins, cactinomycin, canfosfamide, carabicin, carminomycin, carzinophilin, chromomycinis, cyclosphosphamide, dactinomycin, daunorubicin, detorubicin, 6-diazo-5-oxo-L-norleucine, doxorubicin, epirubicin, esorubicin, exemestane, fluorouracil, fulvestrant, gefitinib, idarubicin, lapatinib, letrozole, lonafarnib, marcellomycin, megestrol acetate, mitomycins, mycophenolic acid, nogalamycin, olivomycins, pazopanib, peplomycin, potfiromycin, puromycin, quelamycin, rapamycin, rodorubicin, sorafenib, streptonigrin, streptozocin, tamoxifen, tamoxifen citrate, temozolomide, tepodina, tipifarnib, tubercidin, ubenimex, vandetanib, vorozole, XL-147, zinostatin, zorubicin; anti-metabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, polysaccharide complex, razoxane; rhizoxin; SF-1126, sizofiran; spirogermanium; tenuazonic acid; triaziquone; 2,2',2''-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside; cyclophosphamide; thiotepa; taxoids, chloranbucil; gemcitabine; 6-thioguanine; mercaptopurine; methotrexate; platinum analogs, vinblastine; platinum; etoposide; ifosfamide; mitoxantrone; vincristine; vinorelbine; novantrone; teniposide; edatrexate; daunomycin; aminopterin; xeloda; ibandronate; irinotecan, topoisomerase inhibitor RFS 2000; difluorometlhylornithine; retinoids; capecitabine; combretastatin; leucovorin; oxaliplatin; XL518, inhibitors of PKC-alpha, Raf, H-Ras, EGFR and VEGF-A that reduce cell proliferation and pharmaceutically acceptable salts or solvates, acids or derivatives of any of the above. Also included in this definition are anti-hormonal agents that act to regulate or inhibit hormone action on tumors such as anti-estrogens and selective estrogen receptor antibodies, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts or solvates, acids or derivatives of any of the above.

Particularly preferred anti-cancer agents comprise commercially or clinically available compounds such as erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®). Additional commercially or clinically available anti-cancer agents comprise oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL@, Wyeth), pazopanib (GlaxoSmithKline), canfosfamide (TELCYTA®, Telik), thiotepa and cyclosphosphamide (CYTOXAN®, NEOSAR®); vinorelbine (NAVELBINE®); capecitabine (XELODA®, Roche), tamoxifen (including NOLVADEX®; tamoxifen citrate, FARESTON® (toremifine citrate) MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca).

The term "pharmaceutically acceptable salt" or "salt" means organic or inorganic salts of a molecule or macromolecule. Acid addition salts can be formed with amino groups. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1' methylene bis-(2-hydroxy 3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Where multiple charged atoms are part of the pharmaceutically acceptable salt, the salt can have multiple counter ions. Hence, a pharmaceutically acceptable salt can have one or more charged atoms and/or one or more counterion.

"Pharmaceutically acceptable solvate" or "solvate" refers to an association of one or more solvent molecules and a molecule or macromolecule. Examples of solvents that form pharmaceutically acceptable solvates include, but are not limited to, water, isopropanol, ethanol, methanol, DMSO, ethyl acetate, acetic acid, and ethanolamine.

In other embodiments the antibodies or ADCs of the instant invention may be used in combination with any one of a number of antibodies (or immunotherapeutic agents) presently in clinical trials or commercially available. The disclosed antibodies may be used in combination with an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lambrolizumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nivolumab, nofetumomabn, obinutuzumab, ocaratuzumab, ofatumumab, olaratumab, olaparib, onartuzumab, oportuzumab, oregovomab, panitumumab, parsatuzumab, patritumab, pemtumomab, pertuzumab, pidilizumab, pintumomab, pritumumab, racotumomab, radretumab, ramucirumab, rilotumumab, rituximab, robatumumab, satumomab, selumetinib, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, 3F8, MDX-1105 and MEDI4736 and combinations thereof.

Other particularly preferred embodiments comprise the use of antibodies approved for cancer therapy including, but not limited to, rituximab, gemtuzumab ozogamcin, alemtuzumab, ibritumomab tiuxetan, tositumomab, bevacizumab, cetuximab, patitumumab, ofatumumab, ipilimumab and brentuximab vedotin. Those skilled in the art will be able to readily identify additional anti-cancer agents that are compatible with the teachings herein.

E. Radiotherapy

The present invention also provides for the combination of antibodies or ADCs with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed antibodies or ADCs may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

VIII INDICATIONS

The invention provides for the use of antibodies and ADCs of the invention for the diagnosis, theragnosis, treatment and/or prophylaxis of various disorders including neoplastic, inflammatory, angiogenic and immunologic disorders and disorders caused by pathogens. Particularly, key targets for treatment are neoplastic conditions comprising solid tumors, although hematologic malignancies are within the scope of the invention. In certain embodiments the antibodies of the invention will be used to treat tumors or tumorigenic cells expressing a particular determinant (e.g. DPEP3). Preferably the "subject" or "patient" to be treated will be human although, as used herein, the terms are expressly held to comprise any mammalian species.

Neoplastic conditions subject to treatment in accordance with the instant invention may be benign or malignant; solid tumors or other blood neoplasia; and may be selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In other preferred embodiments, the disclosed antibodies and ADCs are especially effective at treating lung cancer, including the following subtypes: small cell lung cancer and non-small cell lung cancer (e.g. squamous cell non-small cell lung cancer or squamous cell small cell lung cancer). In selected embodiments the antibodies and ADCs can be administered to patients exhibiting limited stage disease or extensive stage disease. In other preferred embodiments the disclosed conjugated antibodies will be administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g. carboplatin, cisplatin, oxaliplatin) and/or a taxane (e.g. docetaxel, paclitaxel, larotaxel or cabazitaxel).

In a particularly preferred embodiment the disclosed antibodies and ADCs are effective at treating ovarian cancer, including ovarian-serous carcinoma and ovarian-papillary serous carcinoma.

The invention also provides for a preventative or prophylactic treatment of subjects who present with benign or precancerous tumors. No particular type of tumor or proliferative disorder is excluded from treatment using the antibodies of the invention.

IX ARTICLES OF MANUFACTURE

The invention includes pharmaceutical packs and kits comprising one or more containers, wherein a container can comprise one or more doses of an antibody or ADC of the invention. In certain embodiments, the pack or kit contains a unit dosage, meaning a predetermined amount of a composition comprising, for example, an antibody or ADC of the invention, with or without one or more additional agents and optionally, one or more anti-cancer agents.

The kit of the invention will generally contain in a suitable container a pharmaceutically acceptable formulation of the antibody or ADC of the invention and, optionally, one or more anti-cancer agents in the same or different containers. The kits may also contain other pharmaceutically acceptable formulations or devices, either for diagnosis or combination therapy. Examples of diagnostic devices or instruments include those that can be used to detect, monitor, quantify or profile cells or markers associated with proliferative disorders (for a full list of such markers, see above). In particularly preferred embodiments the devices may be used to detect, monitor and/or quantify circulating tumor cells either in vivo or in vitro (see, for example, WO 2012/0128801). In still other preferred embodiments the circulating tumor cells may comprise tumorigenic cells. The kits contemplated by the invention can also contain appropriate reagents to combine the antibody or ADC of the invention with an anti-cancer agent or diagnostic agent (e.g., see U.S. Pat. No. 7,422,739).

When the components of the kit are provided in one or more liquid solutions, the liquid solution can be non-aqueous, however, an aqueous solution is preferred, with a sterile aqueous solution being particularly preferred. The formulation in the kit can also be provided as dried powder(s) or in lyophilized form that can be reconstituted upon addition of an appropriate liquid. The liquid used for reconstitution can be contained in a separate container. Such liquids can comprise sterile, pharmaceutically acceptable buffer(s) or other diluent(s) such as bacteriostatic water for injection, phosphate-buffered saline, Ringer's solution or dextrose solution. Where the kit comprises the antibody or ADC of the invention in combination with additional therapeutics or agents, the solution may be pre-mixed, either in a molar equivalent combination, or with one component in excess of the other. Alternatively, the antibody or ADC of the invention and any optional anti-cancer agent or other agent can be maintained separately within distinct containers prior to administration to a patient.

The kit can comprise one or multiple containers and a label or package insert in, on or associated with the container(s), indicating that the enclosed composition is used for diagnosing or treating the disease condition of choice. Suitable containers include, for example, bottles, vials, syringes, etc. The containers can be formed from a variety of materials such as glass or plastic. The container(s) can comprise a sterile access port, for example, the container may be an intravenous solution bag or a vial having a stopper that can be pierced by a hypodermic injection needle.

In some embodiments the kit can contain a means by which to administer the antibody and any optional components to a patient, e.g., one or more needles or syringes (pre-filled or empty), an eye dropper, pipette, or other such like apparatus, from which the formulation may be injected or introduced into the subject or applied to a diseased area of the body. The kits of the invention will also typically include a means for containing the vials, or such like, and other components in close confinement for commercial sale, such as, e.g., blow-molded plastic containers into which the desired vials and other apparatus are placed and retained.

X MISCELLANEOUS

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular. In addition, ranges provided in the specification and appended claims include both end points and all points between the end points. Therefore, a range of 2.0 to 3.0 includes 2.0, 3.0, and all points between 2.0 and 3.0.

Generally, techniques of cell and tissue culture, molecular biology, immunology, microbiology, genetics and chemistry described herein are those well known and commonly used in the art. The nomenclature used herein, in association with such techniques, is also commonly used in the art. The methods and techniques of the invention are generally performed according to conventional methods well known in the art and as described in various references that are cited throughout the present specification unless otherwise indicated.

XI REFERENCES

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PBD, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding only. No unnecessary limitations are to be understood therefrom. The invention is not limited to the exact details shown and described. Variations obvious to one skilled in the art are included in the invention defined by the claims. Any section headings used herein are for organizational purposes only and are not to be construed as limiting the subject matter described.

XII SEQUENCE LISTING SUMMARY

Appended to the instant application is a sequence listing comprising a number of nucleic acid and amino acid sequences. The following Table 6 provides a summary of the included sequences.

TABLE 6

| SEQ ID NO | Description |
|---|---|
| 1 | Kappa light chain constant region protein |
| 2 | IgG1 heavy chain constant region protein |
| 3 | Human DPEP3 isoform a mature protein (UniProtKB/Swiss-Prot. Q9H4B8.2; residues 36-488) |
| 4 | Human DPEP3 isoform a precursor protein (UniProtKB/Swiss-Prot. Q9H4B8.2; residues 1-488) |
| 5 | Human DPEP3 isoform a precursor protein (GenBank Accession No. NP_071752.3) |
| 6 | Human DPEP3 cDNA clone (GenBank Accession No. BC037243) |
| 7 | Human DPEP2 protein (GenBank Accession No. NP_071750) |
| 8 | Mouse DPEP3 protein (GenBank Accession No. NP_082236) |
| 9 | Mouse DPEP3 cDNA clone (GenBank Accession No. BC051148) |
| 10 | Rat DPEP3 protein (GenBank Accession No. NP_001008384) |
| 11 | Rat DPEP3 cDNA (GenBank Accession No. BC085826) |
| 12-19 | Reserved |
| 20 | SC34.2 VL DNA |
| 21 | SC34.2 VL protein |
| 22 | SC34.2 VH DNA |
| 23 | SC34.2 VH protein |
| 24-187 | Additional mouse clones as in SEQ ID NOs: 20-23 |
| 188 | hSC34.2 humanized clone VL DNA |
| 189 | hSC34.2 humanized clone VL protein |
| 190 | hSC34.2 humanized clone VH DNA |
| 191 | hSC34.2 humanized clone VH protein |
| 192-215 | Additional humanized clones as in SEQ ID NOs: 188-191 |
| 216 | hSC34.2 full length light chain (LC) protein |
| 217 | hSC34.2 full length heavy chain (HC) protein |
| 218-230 | Additional full length LC and HC proteins as in SEQ ID NOs: 216-217 |
| 231 | Reserved |
| 232, 233, 234 | hSC34.2 CDRL1, CDRL2, CDRL3 |
| 235, 236, 237 | hSC34.2 CDRH1, CDRH2, CDRH3 |
| 238, 239, 240 | hSC34.11 CDRL1, CDRL2, CDRL3 |
| 241, 242, 243 | hSC34.11 CDRH1, CDRH2, CDRH3 |
| 244, 245, 246 | hSC34.14 CDRL1, CDRL2, CDRL3 |
| 247, 248, 249 | hSC34.14 CDRH1, CDRH2, CDRH3 |

TABLE 6-continued

| SEQ ID NO | Description |
|---|---|
| 250, 251, 252 | hSC34.25 CDRL1, CDRL2, CDRL3 |
| 253, 254, 255 | hSC34.25 CDRH1, CDRH2, CDRH3 |
| 256, 257, 258 | hSC34.28 and hSC34.28ss1 CDRL1, CDRL2, CDRL3 |
| 259, 260, 261 | hSC34.28 and hSC34.28ss1 CDRH1, CDRH2, CDRH3 |
| 262, 263, 264 | hSC34.38 CDRL1, CDRL2, CDRL3 |
| 265, 266, 267 | hSC34.38 CDRH1, CDRH2, CDRH3 |
| 268, 269, 270 | hSC34.87 CDRL1, CDRL2, CDRL3 |
| 271, 272, 273 | hSC34.87 CDRH1, CDRH2, CDRH3 |

Table 6 above may further be used to identify SEQ ID NOS associated with exemplary CDRs delineated in FIGS. 5A and 5B. FIGS. 5A and 5B denote the three Kabat CDRs of each heavy (CDRH) and light (CDRL) chain variable region sequence and Table 3 above provides, for selected humanized antibodies, a SEQ ID designation that may be applied to each CDRL1, CDRL2 and CDRL3 of the light chain and each CDRH1, CDRH2 and CDRH3 of the heavy chain. For example the hSC34.2 light chain (SEQ ID NO: 189) comprises CDRL1 (SEQ ID NO: 232) as set forth in FIG. 5A (i.e., SASQGITNYLN). Similarly, CDRL2 (SEQ ID NO: 233) of the hSC34.2 light chain would also be as set forth in FIG. 5A (i.e., YTSRLHS). The same CDR sequences are also provided in the appended sequence listing.

XIII EXAMPLES

The invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

PDX tumor cell types are denoted by an abbreviation followed by a number, which indicates the particular tumor cell line. The passage number of the tested sample is indicated by p0-p# appended to the sample designation where p0 is indicative of an unpassaged sample obtained directly from a patient tumor and p# is indicative of the number of times the tumor has been passaged through a mouse prior to testing. As used herein, the abbreviations of the tumor types and subtypes are shown in Table 7 as follows:

TABLE 7

| Tumor Type | Abbreviation | Tumor subtype | Abbreviation |
|---|---|---|---|
| Breast | BR | estrogen receptor positive and/or progesterone receptor positive | BR-ERPR |
|  |  | ERBB2/Neu positive | BR-ERBB2/Neu |
|  |  | HER2 positive | BR-HER2 |
|  |  | triple-negative | TNBC |
|  |  | claudin subtype of triple-negative | TNBC-CLDN |
| colorectal | CR |  |  |
| endometrial | EN |  |  |
| gastric | GA | diffuse adenocarcinoma | GA-Ad-Dif/Muc |
|  |  | intestinal adenocarcinoma | GA-Ad-Int |
|  |  | stromal tumors | GA-GIST |
| glioblastoma | GB |  |  |
| head and neck | HN |  |  |
| kidney | KDY | clear renal cell carcinoma | KDY-CC |
|  |  | papillary renal cell carcinoma | KDY-PAP |
|  |  | transitional cell or urothelial carcinoma | KDY-URO |
|  |  | unknown | KDY-UNK |
| liver | LIV | hepatocellular carcinoma | LIV-HCC |
|  |  | cholangiocarcinoma | LIV-CHOL |
| lymphoma | LN |  |  |
| lung | LU | adenocarcinoma | LU-Ad |
|  |  | carcinoid | LU-CAR |
|  |  | large cell neuroendocrine | LU-LCC |
|  |  | non-small cell | NSCLC |
|  |  | squamous cell | LU-SCC |
|  |  | small cell | SCLC |
|  |  | spindle cell | LU-SPC |
| melanoma | MEL |  |  |
| ovarian | OV | clear cell | OV-CC |
|  |  | endometroid | OV-END |
|  |  | mixed subtype | OV-MIX |
|  |  | malignant mixed mesodermal | OV-MMMT |
|  |  | mucinous | OV-MUC |
|  |  | neuroendocrine | OV-NET |
|  |  | papillary serous | OV-PS |
|  |  | serous | OV-S |

TABLE 7-continued

| Tumor Type | Abbreviation | Tumor subtype | Abbreviation |
|---|---|---|---|
| | | small cell | OV-SC |
| | | transitional cell carcinoma | OV-TCC |
| pancreatic | PA | acinar cell carcinoma | PA-ACC |
| | | duodenal carcinoma | PA-DC |
| | | mucinous adenocarcinoma | PA-MAD |
| | | neuroendocrine | PA-NET |
| | | adenocarcinoma | PA-PAC |
| | | adenocarcinoma exocrine type | PA-PACe |
| | | ductal adenocarcinoma | PA-PDAC |
| | | ampullary adenocarcinoma | PA-AAC |
| prostate | PR | | |
| skin | SK | melanoma | MEL |
| | | squamous cell carcinomas | SK-SCC |

Example 1

Identification of Differential DPEP3 Expression Using Whole Transcriptome Sequencing To characterize the cellular heterogeneity of solid tumors as they exist in cancer patients, aid in the identification of TICs using particular phenotypic markers and identify clinically relevant therapeutic targets, a large PDX tumor bank was developed and maintained using art recognized techniques. The PDX tumor bank, comprising a large number of discrete tumor cell lines, was propagated in immunocompromised mice through multiple passages of tumor cells originally obtained from cancer patients afflicted by a variety of solid tumor malignancies. Early passage PDX tumors are representative of tumors in their native environments and respond to therapeutic agents such as irinotecan (i.e. Camptosar®), providing clinically relevant insight into underlying mechanisms driving tumor growth and resistance to current therapies.

To generate RNA from the PDX tumor cell lines, tumors were resected from mice after they reached 800-2,000 mm³ and the tumors were dissociated into single cell suspensions using art-recognized enzymatic digestion techniques (see, for example, U.S.P.N. 2007/0292414). Select dissociated PDX tumor cell preparations were depleted of mouse cells and sorted based on their expression of $CD46^{hi}$ and $CD324^+$, markers of TIC subpopulations (see U.S.P.N.s 2013/0260385, 2013/0061340 and 2013/0061342). Cells that expressed human EpCAM, with a $CD46^{hi}/CD324^+$ phenotype (i.e. TIC); or EpCAM, with a $CD46^{lo/-}/CD324^+$ phenotype (i.e. NTG cells), were isolated by FACS using a FACSAria cell sorter (BD Biosciences) and lysed in RLT-plus RNA lysis buffer per the manufacturer's instructions. The lysates were then stored at −80° C. and thawed for RNA extraction. Upon thawing, total RNA was extracted using an RNeasy isolation kit (Qiagen) following the vendor's instructions and then quantified using a Nanodrop spectrophotometer (Thermo Scientific) and/or a Bioanalyzer 2100 (Agilent Technologies), again using the manufacturer's protocols and recommended instrument settings. The resulting total RNA preparations were assessed by genetic sequencing and gene expression analyses.

Whole transcriptome sequencing of qualified, high quality RNA was performed using two different systems. Some samples were analyzed using the Applied Biosystems (ABI) Sequencing by Oligo Ligation/Detection (SOLiD) 4.5 or SOLID 5500xl next generation sequencing system (Life Technologies). Other samples were analyzed using the Illumina HiSeq 2000 or 2500 next generation sequencing system (Illumina).

SOLiD whole transcriptome analysis was performed with cDNA that was generated from 1 ng total RNA samples using either a modified whole transcriptome protocol from ABI designed for low input total RNA or an Ovation RNA-Seq System V2™ (NuGEN Technologies). The resulting cDNA library was fragmented, and barcode adapters added to allow pooling of fragment libraries from different samples during sequencing runs. Data generated by the SOLiD platform mapped to 34,609 genes (as annotated by RefSeq version 47 using NCBI version hg19.2 of the published human genome) and provided verifiable measurements of RNA levels in most samples.

Sequencing data from the SOLiD platform is nominally represented as a transcript expression value using the metrics RPM (reads per million) or RPKM (read per kilobase per million) mapped to exon regions of genes, enabling basic gene expression analysis to be normalized and enumerated as RPM_Transcript or RPKM_Transcript.

Illumina whole transcriptome analysis was performed with cDNA that was generated using 5 ng total RNA with the TruSeq RNA Sample Preparation Kit v2 (Illumina). The resulting cDNA was fragmented and barcoded. Sequencing data from the Illumina platform were nominally represented as a fragment expression value using the metrics FPM (fragment per million) or FPKM (fragment per kilobase per million) mapped to exon regions of genes, enabling basic gene expression analysis to be normalized and enumerated as FPM_Transcript or FPKM_Transcript.

Figure 1B:
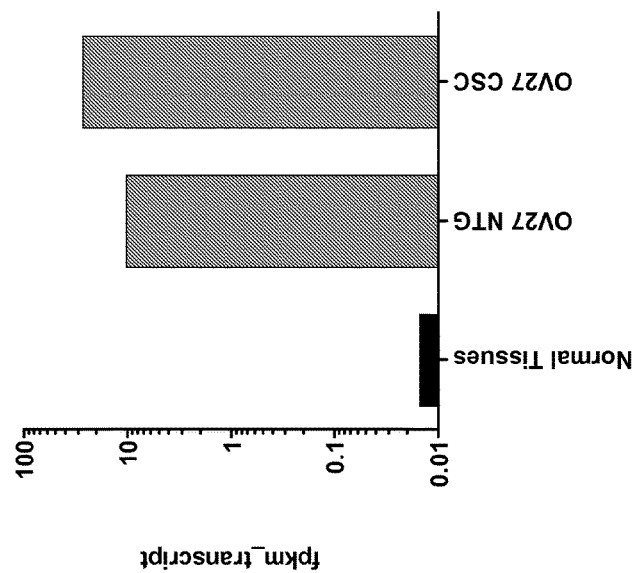

The results of SOLiD whole transcriptome sequencing showed elevated expression of DPEP3 mRNA in the TIC tumor cell subpopulations of BR36 and OV106MET PDX cell lines compared to normal major vital organ tissues, including colon, heart, kidney, liver, lung, ovary and pancreas tissue (FIG. 1A). Similarly, Illumina whole transcriptome sequencing showed elevated expression of DPEP3 mRNA in the TIC tumor cell subpopulation of OV27 compared to the NTG population as well as normal tissues, including colon, heart, kidney, liver, lung, ovary, pancreas, skin, spleen, stomach and trachea (FIG. 1B). The identification of elevated DPEP3 mRNA expression in breast and ovarian human tumors indicated that this antigen merited further evaluation as a potential diagnostic and/or immunotherapeutic target.

Example 2

Expression of DPEP3 mRNA in Tumors Using qRT-PCR

To confirm expression of DPEP3 in tumor cells qRT-PCR was performed on various PDX cell lines using the Fluidigm BioMark™ HD System according to industry standard protocols. 1 ng of RNA, prepared as described in Example 1, was converted to cDNA using the High Capacity cDNA Archive kit (Life Technologies) according to the manufacturer's instructions. cDNA material, pre-amplified using a DPEP3-specific Taqman assay, was then used for subsequent qRT-PCR experiments.

Figure 2A:
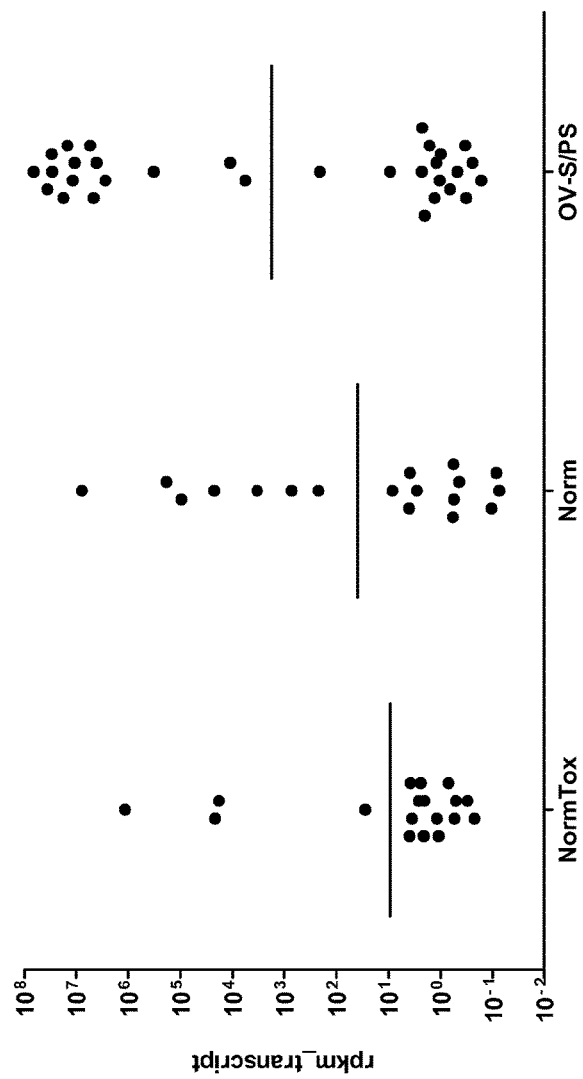
FIG. 2A shows DPEP3 mRNA expression determined by qRT-PCR in ovarian PDX tumor subtypes.

Expression in normal tissues (NormTox or Norm) was compared to expression in OV-S/PS PDX cell lines (FIG. 2A; each dot represents the average relative expression of each individual tissue or PDX tumor cell line, with a horizontal line representing the geometric mean). High expression of DPEP3 was observed in a subpopulation of OV-S/PS tumors, as discussed in more detail below. Normal tissues expressing DPEP3 include testes, dorsal root ganglion, stomach, small intestine, melanocytes, brain, B cells, adipose tissue, neutrophils and monocytes. "NormTox" represents the following samples of normal tissue of organs having more of a toxicity risk in the context of antibody drug conjugate therapeutics: artery, vein, dorsal root ganglion, vascular smooth muscle cells, spleen, trachea, skin, kidney, stomach, liver, lung, esophagus, small intestine, adrenal gland, skeletal muscle, pancreas, heart and colon. Another set of normal tissues designated "Norm" represents the following samples of normal tissue having a lower risk in the context of antibody drug conjugate therapeutics: ovary, breast, testes, uterus, thyroid, peripheral blood mononuclear cells, NK cells, B cells, T cells, monocytes, neutrophils, normal bone marrow, thymus, adipose, salivary gland, brain, prostate and melanocytes.

Figure 2B:
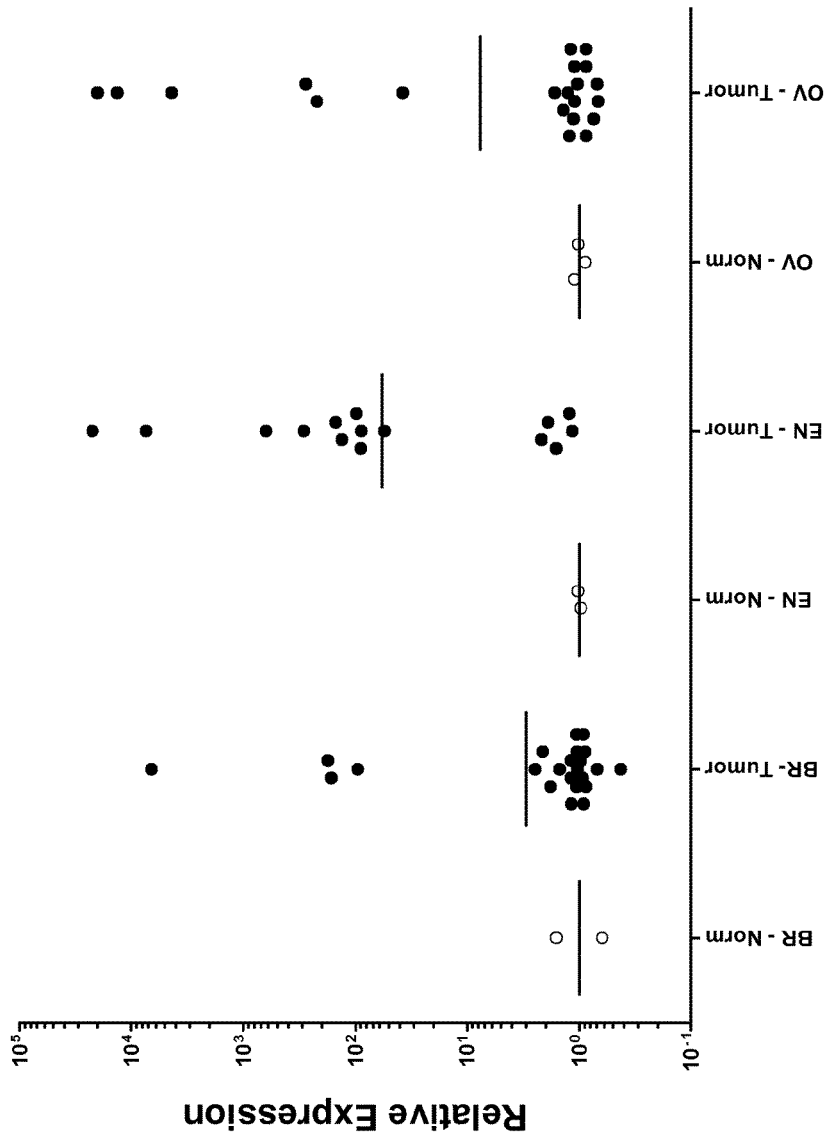
FIG. 2B shows DPEP3 mRNA expression in whole tumor specimens (black dots) or normal tissue (white dots) from patients with various tumor types as determined by qRT-PCR Origene array.

To further expand the analysis to a larger group of primary human tumor samples as well as normal tissue samples, the same Taqman qRT-PCR assay was performed as described above using a TissueScan™ qPCR (Origene Technologies) 384-well array. This array enables comparison of gene expression across 18 different solid tumor types, with multiple patient derived samples for each tumor type. Expression levels of DPEP3 mRNA in various whole tumor specimens (black dots) were normalized against 1-actin and plotted relative to expression in the normal tissue (white dots) for each tumor type analyzed. Specimens not amplified were assigned a cycle count value (Ct) of 45, which represents the last cycle of amplification in the experimental protocol. Each dot represents a single tissue specimen, with the mean geometric value represented as a black line. Overexpression of DPEP3 relative to matched normal tissue was seen in BR, EN and OV tumors (FIG. 2B). Other normal samples lacked expression of DPEP3, including adrenal, cervix, colon, esophagus, kidney, liver, lymph node, pancreas, prostate, thyroid, bladder and uterus (data not shown).

These data demonstrate that DPEP3 is expressed in BR, EN and OV tumors and may be a good target for the development of an antibody-based therapeutic in these indications.

Example 3

DPEP3 Expression in Tumors from the Cancer Genome Atlas

Figure 3:
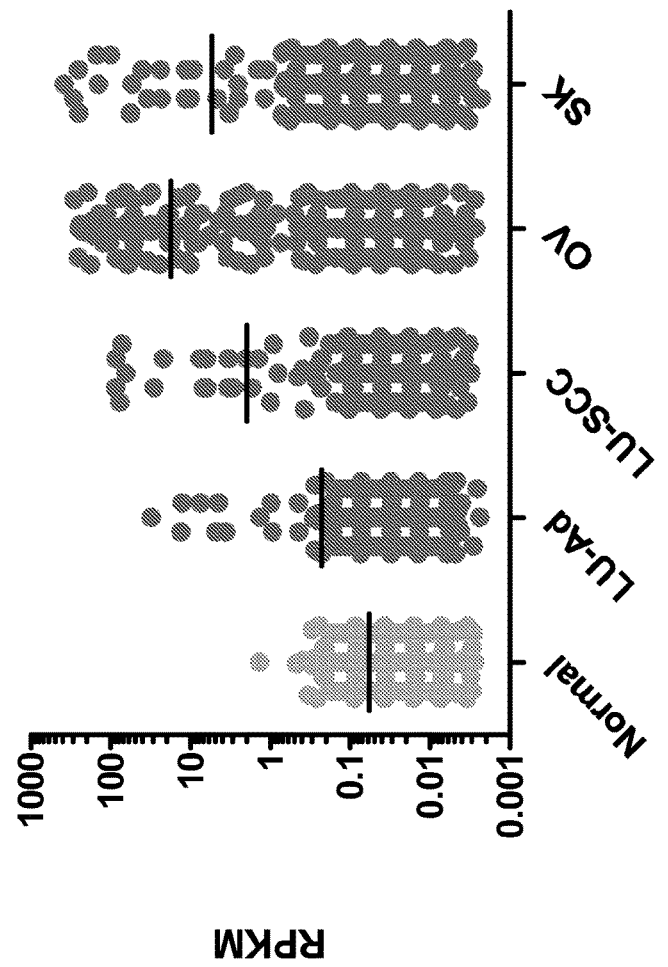
FIG. 3 shows mRNA expression of DPEP3 in ovarian, lung and skin tumors and normal tissues derived from The Cancer Genome Atlas database.

Overexpression of DPEP3 mRNA was confirmed in various tumors using a large, publically available dataset of tumors and normal samples known as The Cancer Genome Atlas (TCGA, National Cancer Institute). Exon level 3 expression data from the IlluminaHiSeq_RNASeqV2 platform was downloaded from the TCGA Data Portal (https://tcga-data.nci.nih.gov/tcga/tcgaDownload.jspl and parsed to aggregate the reads from the individual exons of each gene to generate a single value read per kilobase of exon per million mapped reads (RPKM). FIG. 3 shows that DPEP3 expression is elevated in subsets of OV, SK, LU-SCC, and LU-Ad tumor types compared to normal tissue samples in TCGA. These data confirm the previous observations from whole transcriptome and qRT-PCR analysis in Examples 1 and 2, that elevated DPEP3 mRNA can be found in OV, SK and LU tumors indicating that anti-DPEP3 antibodies may be useful therapeutics for these tumors.

Example 4

Cloning of Recombinant DPEP2 and DPEP3 Proteins

DNA Fragments Encoding Human DPEP3 and DPEP2 Proteins.

To generate all molecular and cellular materials required in the invention pertaining to the human DPEP3 (hDPEP3) protein (UniProtKB I/Swiss-Prot. Q9H4B8.2), a cDNA clone encoding the full length hDPEP3 open reading frame (GenBank accession BC037243, [SEQ ID NO: 6]) was purchased (ThermoFisher). This cDNA clone was used for all subsequent engineering of constructs expressing the mature hDPEP3 protein or fragments thereof.

To generate immunoreactive or immunospecific antibodies to the hDPEP3 protein, a chimeric fusion gene was generated in which the extracellular domain (ECD) of the hDPEP3 protein, comprising residues A61-S488 from accession NP_071752, was fused in-frame with either a histidine tag or human IgG2 Fc tag. This was done as follows: a DNA fragment encoding the ECD of hDPEP3 protein was PCR amplified from the hDPEP3 cDNA clone and subcloned into a CMV driven expression vector in frame and downstream of an IgK signal peptide sequence and upstream of either a histidine tag or a human IgG2 Fc cDNA, using standard molecular techniques. The CMV-driven hDPEP3 expression vector permits high level transient expression in HEK-293T and/or CHO-S cells. Suspension or adherent cultures of HEK-293T cells, or suspension CHO-S cells were transfected with expression constructs encoding either the hDPEP3-ECD-His or hDPEP3-ECD-Fc proteins using polyethylenimine polymer as the transfecting reagent. Three to five days after transfection the hDPEP3-ECD-His or hDPEP3-ECD-Fc proteins were purified from clarified cell-supernatants using an AKTA explorer and either Nickel-EDTA (Qiagen) or MabSelect SuRe™ Protein A (GE Healthcare Life Sciences) columns, respectively.

To generate hDPEP2 protein for cross-reactivity studies, a cDNA clone encoding a major portion of the human DPEP2 (hDPEP2) protein was purchased from Origene, although sequence analysis of the translation product of this clone versus the RefSeq accession for hDPEP2 (NP_071750, [SEQ ID NO: 7]) showed that a portion of the amino terminal sequence of the RefSeq protein was missing from the Origene clone. Therefore, a 0.62 kBp synthetic DNA was manufactured (GeneWiz) to encode the desired front end of the hDPEP2 ORF corresponding to the sequence in the RefSeq protein. An in vitro seamless cloning technique (In Fusion, Clontech) was used according to manufacturer's instructions to assemble a full length ORF encoding a protein corresponding to the hDPEP2 RefSeq. This assembled cDNA clone was used for all subsequent engineering of constructs expressing the mature hDPEP2 protein or fragments thereof.

Human DPEP2 protein was made by generating a chimeric fusion gene in which the ECD of the hDPEP2 protein, comprising residues A33-S463 from accession NP_071750, was fused in-frame with either a histidine tag or human IgG2 Fc tag in the same manner as described for the chimeric gene constructs with hDPEP3 above. Similarly, histidine-tagged or human IgG2-tagged recombinant hDPEP2 was produced in HEK-293T and/or CHO-S cells using the methods described above for hDPEP3.

DNA Fragments Encoding Mouse, Human and Cynomolgus DPEP3 Proteins.

The molecular and cellular materials pertaining to the mouse, rat and cynomolgus DPEP3 proteins were generated as follows.

For mouse DPEP3 protein (mDPEP3) a cDNA clone (GenBank accession BC051148, [SEQ ID NO: 9]) encoding a protein identical to the mouse RefSeq DPEP3 protein (GenBank accession NP_082236) was purchased (ThermoFisher). For rat DPEP3 protein (rDPEP3) a cDNA clone (GenBank accession BC085826, [SEQ ID NO: 11]) encoding a protein identical to the rat RefSeq DPEP3 protein (GenBank accession NP_001008384) was purchased (ThermoFisher). For cynomolgus monkey (*Macaca fascicularis*) DPEP3 protein (cDPEP3), the cynomolgus monkey DPEP3 sequence was first deduced by BLASTing the DNA sequence encoding the hDPEP3 protein versus the cynomolgus whole genome shotgun contigs sequence database at the NCBI, and filling any gaps within the cynomolgus genome sequences with those deduced from the Rhesus monkey (*Macaca mulatta*) genome. The predicted cynomolgus DPEP3 ORF sequence was then synthesized as a codon-optimized DNA fragment (GeneWiz).

These DNA clones were used as templates for various PCR reactions to generate chimeric fusion genes for the mouse, rat or cynomolgus DPEP3 ECDs with a histidine tag or human IgG2 Fc tag. These constructs were produced in HEK-293T and/or CHO-S cells using the methods described above for hDPEP3.

Cell Line Engineering

Using molecular biological techniques well known in the art, engineered cell lines overexpressing the various DPEP3 proteins listed above were constructed using lentiviral vectors to transduce HEK-293T cell lines. First, PCR was used to amplify the DNA fragments encoding the protein of interest (e.g., hDPEP3, mDPEP3, rDPEP3 or cDPEP3) using the specific DNA fragments described above as templates. Then, the individual PCR products were subcloned into the multiple cloning site (MCS) of the lentiviral expression vector, pCDH-EF1-MCS-IRES-GFP (System Biosciences), to generate a suite of lentiviral vectors. The internal ribosome entry site (IRES) sequence in the resultant pCDH-EF1-DPEP3-IRES-GFP vectors permits cap-independent initiation of a second protein from a single mRNA transcript. High level expression of the DPEP3 protein encoded upstream of the IRES correlates with co-expression of the GFP marker protein encoded downstream of the IRES element. This suite of lentiviral vectors was used to create separate stable HEK-293T cell lines overexpressing individual DPEP3 proteins. DPEP3-positive cells were selected using FACS of high-expressing HEK-293T subclones based on their positive GFP signal.

Example 5

Generation of Anti-DPEP3 Antibodies

Anti-DPEP3 mouse antibodies were produced as follows. Six mice (two each of the following strains: Balb/c, CD-1, FVB) were inoculated with 10 µg hDPEP3-His protein emulsified with an equal volume of TiterMax® adjuvant. Following the initial inoculation the mice were injected twice weekly for 4 weeks with 5 µg hDPEP3-His protein emulsified with an equal volume of alum adjuvant plus CpG.

Mice were sacrificed and draining lymph nodes (popliteal, inguinal, and medial iliac) were dissected and used as a source for antibody producing cells. A single cell suspension of B cells ($430 \times 10^6$ cells) were fused with non-secreting P3-63Ag8.653 myeloma cells (ATCC # CRL-1580) at a ratio of 1:1 by electro cell fusion using a model BTX Hybrimmune System (BTX Harvard Apparatus). Cells were re-suspended in hybridoma selection medium consisting of DMEM medium supplemented with azaserine, 15% fetal clone I serum, 10% BM condimed, 1 mM nonessential amino acids, 1 mM HEPES, 100 IU penicillin-streptomycin, and 50 µM 2-mercaptoethanol, and were cultured in four T225 flasks in 100 mL selection medium per flask. The flasks were placed in a humidified 37° C. incubator containing 5% $CO_2$ and 95% air for 6 days.

Following fusion, the hybridoma library cells were collected from the flasks and plated at one cell per well (using the FACSAria I cell sorter) in 90 µL of supplemented hybridoma selection medium (as described above) into 12 Falcon 384-well plates. The rest of the library was stored in liquid nitrogen.

The hybridomas were cultured for 10 days and the supernatants were screened for antibodies specific to hDPEP3 using flow cytometry performed as follows. $1 \times 10^5$ per well of HEK-293T cells stably transduced with hDPEP3 were incubated for 30 mins. with 25 µL hybridoma supernatent. Cells were washed with PBS/2% FCS and then incubated with 25 µL per sample DyeLight 649-labeled goat anti-mouse IgG, Fc fragment-specific secondary antibody diluted 1:300 in PBS/2% FCS. After a 15 min. incubation cells were washed twice with PBS/2% FCS and re-suspended in PBS/2% FCS with DAPI and analyzed by flow cytometry for fluorescence exceeding that of cells stained with an isotype control antibody. Remaining unused hybridoma library cells were frozen in liquid nitrogen for future library testing and screening.

The hDPEP3-His immunization campaign yielded numerous mouse antibodies that bound to the surface of hDPEP3-expressing HEK-293T cells.

Example 6

Characteristics of Anti-DPEP3 Antibodies

Various methods were used to characterize the anti-DPEP3 antibodies generated (Example 5) in terms of isotype, affinity for hDPEP3, cross reactivity to hDPEP1, hDEP2, mDPEP3, rDPEP3 and cDPEP3, kinetics of binding and establishing unique epitope bins occupied by the respective antibodies.

The isotype of a representative number of antibodies was determined using the Milliplex mouse immunoglobulin isotyping kit (Millipore) according to the manufacturer's protocols. Results for the unique DPEP3-specific antibodies can be seen in FIG. 4.

The anti-DPEP3 antibodies were screened by ELISA for cross-reactivity with mouse, rat and cynomolgus DPEP3 and for cross reactivity to hDPEP2, the closest DPEP3 family member. ELISA was conducted as follows. Plates were coated with purified mouse, rat or cynomolgus DPEP3-His or hDPEP2-His at 0.3 µg/mL in 0.2 M carbonate-bicarbonate buffer, pH 9.4 overnight at 4° C. The protein solution was removed and the wells were blocked with 1% (w/v) BSA in PBS (PBSA), 100 μL/well for 1 hour at 37° C. Anti-DPEP3 antibody or a mouse isotype control antibody was then added at 1 μg/mL in 50 μL PBSA for 1 hour at room temperature. After washing with water, 50 μL/well HRP-labeled goat anti-mouse IgG antibody diluted 1:10,000 in PBSA was added for 30 min at room temperature. The plates were washed and developed by the addition of 40 μL/well of the TMB substrate solution (Thermo Scientific) at room temperature. An equal volume of 0.2 M $H_2SO_4$ was added to stop substrate development. The samples were then analyzed by spectrophotometer at OD 450. Samples that had an OD 450 greater than 1.5 times the background were considered to be cross-reactive. The cross reactivity results for exemplary DPEP3-specific antibodies can be seen in FIG. 4.

The affinity of the antibodies for hDPEP3-His was qualitatively determined from kinetics curves generated with a ForteBio RED as follows. Anti-DPEP3 antibodies were immobilized onto anti-mouse Fc capture biosensors with a contact time of 3 mins. and a flow rate of 1000 rpm. The captured antibody loading from baseline was constant at 0.3-1 units. Following antibody capture and 30 second baseline, the biosensors were dipped into a 200 nM solution of hDPEP3-His for a 4 min. association phase followed by a 3 min. dissociation phase at a shaking rate of 1000 rpm. The biosensors were regenerated by dipping into 10 mM glycine, pH 1.7 following each cycle. The data was processed by subtracting a control mouse IgG surface response from the specific antibody response and data was truncated to the association and dissociation phase. The association and dissociation curves were used to qualitatively estimate the affinities of selected antibodies. FIG. 4 shows the affinities of a selection of antibodies where antibodies with an estimated apparent affinity ($K_D$) for hDPEP3-His of less than 5 nM are denoted with "+++", those with an estimated $K_D$ of 5-10 nM are denoted with "++" and those with an estimated $K_D$ of greater than 10 nM are denoted with "+". A designation of "ND" means that the estimated $K_D$ was not determined.

The affinity of a number of anti-DPEP3 antibodies was confirmed by surface plasmon resonance using a BIAcore 2000 instrument (GE Healthcare). An anti-mouse antibody capture kit was used to immobilize mouse anti-DPEP3 antibodies on a CM5 biosensor chip. Prior to each antigen injection cycle, mouse antibodies at a concentration of 0.1-2 μg/mL were captured on the surface with a contact time of 2 min. and a flow rate of 5 μL/min. Following antibody capture and baseline, monomeric hDPEP3-His antigen, generated as described in Example 4, was flowed over the surface at various concentrations for a 2-4 min. association phase followed by a 4-15 min. dissociation phase at a flow rate of 5 μL/min. The data was processed by subtracting a control non-binding antibody surface response from the specific antibody surface response and data was truncated to the association and dissociation phase. The resulting response curves were used to fit a 1:1 Langmuir binding model and to generate an apparent affinity using the calculated $k_{on}$ and $k_{off}$ kinetics constants using BiaEvaluation Software 3.1 (GE Healthcare) (data not shown). Using an anti-human antibody capture kit, a similar protocol was used to measure the affinity of humanized antibodies (hSC34.2, hSC34.11, hSC34.14, hSC34.25, hSC34.28, hSC34.38, hSC34.87—see Example 8) to confirm cross reactivity with hDPEP3-His, rDPEP3-His, hDPEP1-His, and hDPEP2-proteins. None of the antibodies tested were found to be cross reactive with ratDPEP3-His or hDPEP1-His. Of those tested in the BIAcore assay only hSC34.14 was found to be cross-reactive with hDPEP2-His.

Antibody binning was determined for various anti-DPEP3 antibodies. A ForteBio RED was used per manufacturer's instructions to identify competing antibodies that bound to the same or different epitope bins. A reference anti-DPEP3 antibody (Ab1) was captured onto an anti-mouse capture chip, a high concentration of non-binding antibody was then used to block the chip and a baseline was collected. Monomeric, recombinant hDPEP3-His (from Example 4) was then captured by the specific antibody (Ab1) and the tip was dipped into a well with either the same antibody (Ab1) as a control or into a well with a different test antibody (Ab2). If additional binding was observed with a new antibody, then Ab1 and Ab2 were determined to be in a different bin. If no further binding occurred, as determined by comparing binding levels with the control Ab1, then Ab2 was determined to be in the same bin. This process can be expanded to screen large libraries of unique antibodies using a full row of antibodies in a 96-well plate representing unique bins. The results of the competition assay shown in FIG. 4 demonstrate that the antibodies that were screened can be grouped into at least four unique bins (A-D) on the hDPEP3 protein, wherein the members of each group or bin compete with each other for binding to the hDPEP3 protein. A fifth bin, designated "Bin U", contains antibodies that do not compete with the antibodies in bins A-D, but may compete for binding with each other.

Example 7

Sequencing of Anti-DPEP3 Antibodies

Anti-DPEP3 antibodies were generated as described above and then sequenced. Selected hybridoma cells were lysed in Trizol® reagent (Trizol® Plus RNA Purification System, Life Technologies) to prepare the RNA. Between $10^4$ and $10^5$ cells were re-suspended in 1 mL Trizol and shaken vigorously after addition of 200 μL chloroform. Samples were then centrifuged at 4° C. for 10 mins. and the aqueous phase was transferred to a fresh microfuge tube and an equal volume of 70% ethanol was added. The sample was loaded on an RNeasy Mini spin column, placed in a 2 mL collection tube and processed according to the manufacturer's instructions. Total RNA was extracted by elution, directly to the spin column membrane with 100 μL RNase-free water. The quality of the RNA preparations was determined by fractionating 3 μL in a 1% agarose gel before being stored at −80° C. until used.

The variable region of the Ig heavy chain of each hybridoma was amplified using a 5' primer mix comprising 32 mouse specific leader sequence primers designed to target the complete mouse VH repertoire in combination with a 3' mouse Cγ primer specific for all mouse Ig isotypes. Similarly, a primer mix containing thirty two 5' VK leader sequences designed to amplify each of the VK mouse families was used in combination with a single reverse primer specific to the mouse kappa constant region in order to amplify and sequence the kappa light chain. The VH and VL transcripts were amplified from 100 ng total RNA using the Qiagen One Step RT-PCR RT-PCR kit as follows. A total of eight RT-PCR reactions were run for each hybridoma, four for the VK light chain and four for the Vγ heavy chain. PCR reaction mixtures included 3 μL of RNA, 0.5 μL of 100 μM of either heavy chain or kappa light chain primers (custom synthesized by IDT), 5 μL of 5× RT-PCR buffer, 1 μL dNTPs, 1 μL of enzyme mix containing reverse transcriptase and DNA polymerase, and 0.4 µL of ribonuclease inhibitor RNasin (1 unit). The thermal cycler program was RT step 50° C. for 30 mins., 95° C. for 15 mins. followed by 30 cycles of (95° C. for 30 seconds, 48° C. for 30 seconds, 72° C. for 1 min.) There was then a final incubation at 72° C. for 10 mins.

The extracted PCR products were sequenced using the same specific variable region primers as described above for the amplification of the variable regions. Nucleotide sequences were analyzed using the IMGT sequence analysis tool (http://www.imgt.org/IMGTmedical/sequence_analysis.html) to identify germline V, D and J gene members with the highest sequence homology. FIG. 5A depicts the contiguous amino acid sequences of the VL chains of 42 novel mouse anti-DPEP3 antibodies (SEQ ID NOS: 21-185, odd numbers) and FIG. 5B depicts the contiguous amino acid sequences of the VH chains of the same 42 novel mouse anti-DPEP3 antibodies (SEQ ID NOS 23-187, odd numbers). The designated CDRs and framework regions in FIGS. 5A and 5B were parsed as per Kabat et al. (supra) and were determined using a proprietary version of the Abysis database. Taken together, FIGS. 5A and 5B provide the annotated variable region sequences of 42 mouse anti-DPEP3 antibodies termed: SC34.2, SC34.4, SC34.5, SC34.6 (duplicate of SC34.21), SC34.7, SC34.11, SC34.13, SC34.14, SC34.16, SC34.18, SC34.19, SC34.20, SC34.23, SC34.24, SC34.25, SC34.26, SC34.27, SC34.28, SC34.33, SC34.36, SC34.38, SC34.39, SC34.40, SC34.41 (duplicate of SC34.61), SC34.46, SC34.48, SC34.49, SC34.50, SC34.53, SC34.58, SC34.63, SC34.67, SC34.71, SC34.76, SC34.78, SC34.83, SC34.86, SC34.87, SC34.89, SC34.90, SC34.91 and SC34.95. FIG. 5C shows the corresponding nucleic acid sequences for each amino acid sequence in FIGS. 5A and 5B (SEQ ID NOS 20-186, even numbers).

Example 8

Generation of Chimeric and Humanized Anti-DPEP3 Antibodies

Chimeric anti-DPEP3 antibodies (comprising a murine VH and VL and a human constant region) were generated using art-recognized techniques as follows. Total RNA was extracted from the anti-DPEP3 antibody-producing hybridomas using the method described in Example 1 and the RNA was PCR amplified. Data regarding V, D and J gene segments of the VH and VL chains of the mouse antibodies were obtained from the nucleic acid sequences of the anti-DPEP3 antibodies of the invention (see FIG. 5C for nucleic acid sequences). Primer sets specific to the framework sequence of the VH and VL chain of the antibodies were designed using the following restriction sites: AgeI and XhoI for the VH fragments, and XmaI and DraIII for the VL fragments. PCR products were purified with a Qiaquick PCR purification kit (Qiagen), followed by digestion with restriction enzymes AgeI and XhoI for the VH fragments and XmaI and DraIII for the VL fragments. The VH and VL digested PCR products were purified and ligated into IgH or IgK expression vectors, respectively. Ligation reactions were performed in a total volume of 10 µL with 200 U T4-DNA Ligase (New England Biolabs), 7.5 µL of digested and purified gene-specific PCR product and 25 ng linearized vector DNA. Competent E. coli DH10B bacteria (Life Technologies) were transformed via heat shock at 42° C. with 3 µL ligation product and plated onto ampicillin plates at a concentration of 100 µg/mL. Following purification and digestion of the amplified ligation products, the VH fragment was cloned into the AgeI-XhoI restriction sites of the pEE6.4 expression vector (Lonza) comprising HuIgG1 (pEE6.4HuIgG1) and the VL fragment was cloned into the XmaI-DraIII restriction sites of the pEE12.4 expression vector (Lonza) comprising a human kappa light constant region (pEE12.4Hu-Kappa).

The selected chimeric antibodies were expressed by co-transfection of HEK-293T cells with pEE6.4HuIgG1 and pEE12.4Hu-Kappa expression vectors. Prior to transfection the HEK-293T cells were cultured in 150 mm plates under standard conditions in Dulbecco's Modified Eagle's Medium (DMEM) supplemented with 10% heat inactivated FCS, 100 µg/mL streptomycin and 100 U/mL penicillin G. For transient transfections cells were grown to 80% confluency. 12.5 µg each of pEE6.4HuIgG1 and pEE12.4Hu-Kappa vector DNA were added to 50 µL HEK-293T transfection reagent in 1.5 mL Opti-MEM. The mix was incubated for 30 min. at room temperature and added to cells. Supernatants were harvested three to six days after transfection. Culture supernatants containing recombinant chimeric antibodies were cleared from cell debris by centrifugation at 800×g for 10 min. and stored at 4° C. Recombinant chimeric antibodies were purified with Protein A beads.

Mouse anti-DPEP3 antibodies (the same used to generate the chimeric antibodies) were humanized using a proprietary computer-aided CDR-grafting method (Abysis Database, UCL Business) and standard molecular engineering techniques as follows. Human framework regions of the variable regions were designed based on the highest homology between the framework sequences and CDR canonical structures of human germline antibody sequences and the framework sequences and CDRs of the relevant mouse antibodies. For the purpose of the analysis the assignment of amino acids to each of the CDR domains was done in accordance with Kabat et al. numbering. Once the variable regions were selected, they were generated from synthetic gene segments (Integrated DNA Technologies). Humanized antibodies were cloned and expressed using the molecular methods described above for chimeric antibodies.

The VL and VH amino acid sequences of the humanized antibodies hSC34.2, hSC34.11, hSC34.14, hSC34.25, hSC34.28, hSC34.38 and hSC34.87 (FIGS. 5A and 5B; SEQ ID NOS: 189-215, odd numbers) were derived from the VL and VH amino acid sequences of the corresponding mouse antibodies (e.g. hSC34.2 was derived from SC34.2). The corresponding nucleic acid sequences of the VL and VH of the humanized anti-DPEP3 antibodies are set forth in FIG. 5C (SEQ ID NOS: 188-214, even numbers). FIG. 5D shows the full length amino acid sequences of the light and heavy chains of exemplary humanized anti-DPEP3 antibodies hSC34.2, hSC34.11, hSC34.14, hSC34.25, hSC34.28, hSC34.38 and hSC34.87 (SEQ ID NOS: 216-230) while FIGS. 5E-5K show the CDRs of the light and heavy chain variable regions of the murine source antibodies (i.e., SC34.2, SC34.11, SC34.14, SC34.25, SC34.28, SC34.38 and SC34.87), as determined by Kabat, Chothia, ABM and Contact methods.

In order to maintain the favorable properties of the selected antibodies only a single framework modification was undertaken in the VH of hSC34.14 and hSC34.38 at positions 94 and 93, respectively (see Table 8 below).

TABLE 8

| mAb | human VH | human JH | FW changes | human VK | human JK | FW changes |
|---|---|---|---|---|---|---|
| hSC34.2 | IGHV5-51*01 | JH6 | None | IGKV1-39*01 | JK1 | None |
| hSC34.11 | IGHV5-51*01 | JH1 | None | IGKV1-27*01 | JK4 | None |
| hSC34.14 | IGHV1-3*01 | JH6 | R94M | IGKV1-39*01 | JK2 | None |
| hSC34.25 | IGHV1-3*01 | JH1 | None | IGKV4-1*01 | JK2 | None |
| hSC34.28 | IGHV1-69*01 | JH1 | None | IGKV3D-20*01 | JK2 | None |
| hSC34.38 | IGHV5-51*01 | JH1 | A93T | IGKV2D-30*01 | JK2 | None |
| hSC34.87 | IGHV1-3*01 | JH1 | None | IGKV4-1*01 | JK2 | None |

Example 9

DPEP3 Protein Expression in Tumors

Given the elevated DPEP3 mRNA transcript levels associated with various tumors described in Examples 1 and 2, work was undertaken to test whether DPEP3 protein expression was also elevated in PDX tumors. To detect and quantify DPEP3 protein expression, an electrochemiluminscence DPEP3 sandwich ELISA assay was developed using the MSD Discovery Platform (Meso Scale Discovery).

PDX tumors were excised from mice and flash frozen on dry ice/ethanol. Protein Extraction Buffer (Biochain Institute) was added to the thawed tumor pieces and tumors were pulverized using a TissueLyser system (Qiagen). Lysates were cleared by centrifugation (20,000 g, 20 mins., 4° C.) and the total protein concentration in each lysate was quantified using bicinchoninic acid. The protein lysates were then normalized to 5 mg/mL and stored at −80° C. until assayed. Normal tissue lysates were purchased from a commercial source.

DPEP3 protein concentrations from the lysate samples were determined by interpolating the values from a standard protein concentration curve that was generated using purified recombinant DPEP3 protein with a histidine tag (from Example 4). The DPEP3 protein standard curve and protein quantification assay were conducted as follows:

MSD standard plates were coated overnight at 4° C. with 15 µL of SC34.14 antibody at 1 µg/mL in PBS. Plates were washed in PBST and blocked in 35 µL MSD 3% Blocker A solution for one hour while shaking. Plates were again washed in PBST. 10 µL of 10× diluted lysate (or serially diluted recombinant DPEP3 standard) in MSD 1% Blocker A containing 10% Protein Extraction Buffer was also added to the wells and incubated for two hours while shaking. Plates were again washed in PBST. The SC34.96 antibody was then sulfo-tagged and 10 µL of the tagged SC34.96 was added to the washed plates at 0.5 µg/mL in MSD 1% Blocker A for 1 hour at room temperature while shaking. Plates were washed in PBST. MSD Read Buffer T with surfactant was diluted to 1× in water and 35 µL was added to each well. Plates were read on an MSD Sector Imager 2400 using an integrated software analysis program to derive DPEP3 concentrations in PDX samples via interpolation from the standard curve. Values were then divided by total protein concentration to yield nanograms of DPEP3 per milligram of total lysate protein. The resulting concentrations are set forth in FIG. 6 wherein each spot represents DPEP3 protein concentrations derived from a single PDX tumor line. While each spot is derived from a single PDX line, in most cases multiple biological samples were tested from the same PDX line and values were averaged to provide the data point.

Figure 6:
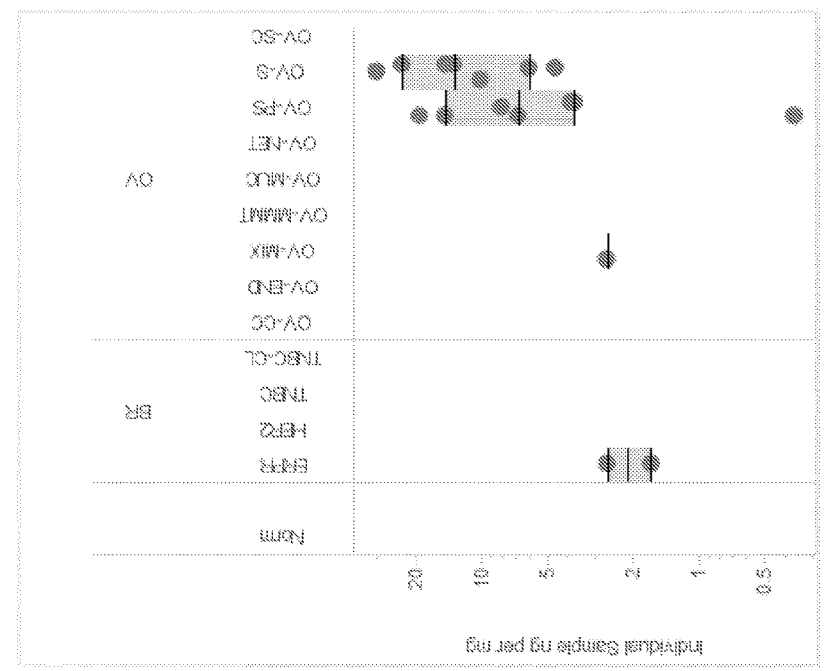
FIG. 6 shows DPEP3 protein expression in various BR and OV PDX tumor subpopulations.

FIG. 6 shows that representative samples of ovarian tumors have high DPEP3 protein expression. OV27MET showed high expression of DPEP3 (35 ng/ml), whereas OV87MET did not show expression of DPEP3 (0 ng/ml). In addition, a subset of breast tumors demonstrated moderate expression of DPEP3. The normal tissue lysates ("Norm") showed no DPEP3 protein expression. These data, combined with the mRNA transcription data for DPEP3 expression in the preceding examples reinforce the proposition that DPEP3 provides an attractive target for therapeutic intervention.

Example 10

Epitope Mapping of Anti-DPEP3 Antibodies

Epitope mapping was performed on selected anti-DPEP3 antibodies using a modification of a yeast display method described previously (Chao et al., Nat Protoc. 1(2): 755-768, 2007).

Two methods were used to identify a subset of residues on the extracellular domain (ECD) for further screening to identify the epitopes of selected anti-DPEP3 antibodies. The first method involved homology modeling of DPEP3 using SWISS-MODEL and the structure of DPEP1 (Protein Data Bank (PDB): 1 ITU) in order to identify the surface exposed residues of DPEP3. Based on these results, individual mutations to alanine on DPEP3 were constructed using the Quikchange Site Directed Mutagenesis kit (Agilent), and expressed in a yeast display format. The resulting library was screened as set forth below.

The second method involved the generation of mutant libraries of DPEP3 screened for loss of binding to selected anti-DPEP3 antibodies. Briefly, libraries of DPEP3 mutants were generated with error prone PCR using nucleotide analogues 8-oxo-2'deoxyguanosine 5'-triphosphate and 2'-deoxy-p-nucleoside-5'triphosphate (TriLink Bio) for a target mutagenesis rate of one amino acid mutation per clone. The DPEP3 mutants were transformed into a yeast display format. The library was stained with chicken anti c-myc (Life Technologies) at 1:250 dilution and either 10 or 20 nM murine or humanized anti DPEP3 antibody, followed by Alexa 488-conjugated goat anti-chicken antibody and either Alexa 647-conjugated goat anti-mouse IgG antibody or goat anti-human IgG antibody. Clones that exhibited a loss of binding compared to wild type DPEP3 ECD were selected by FACS using a FACS Aria (BD Biosciences). The selected clones were re-grown, and re-screened by FACS for loss of binding to the target antibody. Using the Zymoprep Yeast Plasmid Miniprep kit (Zymo Research), individual ECD clones were isolated and sequenced. Where necessary, mutations were reformatted as single-mutant ECD clones or as point mutants to alanine using the Quikchange site directed mutagenesis kit (Agilent).

Individual ECD mutant clones identified by both methods were then screened by flow cytometry to determine whether there was loss of binding relative to the wild type ECD across a panel of conformationally specific antibodies. Mutations from the yeast library method that involved cysteine, proline, or stop codons were automatically discarded due to the high likelihood of a mutation that caused misfolding. Individual ECD mutant clones and wild type ECD were stained with antibodies as described above, except that the anti-DPEP3 antibodies of interest were stained at a range of 100 pM to 33 nM. When compared across the panel, any point mutations that resulted in loss of binding to both the antibody of interest and a non-competing antibody were concluded to cause misfolding of DPEP3. Any point mutations that resulted in loss of binding by only the antibody of interest but not by other antibodies in the panel were concluded to not affect folding of the ECD. These residues were concluded to be part of the epitope of the antibody of interest.

Results of the mapping for three exemplary antibodies are shown below in Table 9 where specific mutations are indicated along with the ability of the subject antibody to bind the mutated DPEP3 homolog. In Table 9 those residues implicated as epitope constituents are indicated by a # in front of the subject mutated residue. Mutations found to result in DPEP3 misfolding are indicated by an * and were not considered when determining epitope constituents.

TABLE 9

| hDPEP3 mutant | Loss of binding with SC34.2 | Loss of binding with SC34.28 | Loss of binding with SC34.10 |
| --- | --- | --- | --- |
| #R46A | None | None | Complete |
| #R48A | None | None | Partial |
| #R54A | None | None | Complete |
| #S55D | None | None | Partial |
| Q71A | None | None | None |
| K74A | None | None | None |
| L77A* | Not clear | Partial | Partial |
| Q78A | None | None | None |
| D79A | None | None | None |
| N84A | None | None | Not clear |
| S86A | None | None | None |
| H87A | None | None | None |
| R96A | None | None | None |
| D97A | None | None | None |
| Q112A | None | None | None |
| Q116A | None | None | None |
| S135A | None | None | None |
| S137A | None | None | None |
| L141A* | Partial | Partial | Partial |
| E146A | None | None | None |
| N149A | None | None | None |
| S150A | None | None | None |
| Q152A | None | None | None |
| F201A | None | None | None |
| R202T | None | None | None |
| R202A | None | None | None |
| H203A | None | None | None |
| H204A | None | None | None |
| Y206A | None | None | None |
| N208A | None | None | None |
| #E217A | Partial | None | None |
| R241A | None | None | None |
| #R242A | Partial | None | None |
| #Q248T | Partial | None | None |
| Q248A | None | None | None |
| D263A | None | None | Not clear |
| Q274A | None | None | None |
| K277A | None | None | None |
| K278A | None | None | None |
| G329A | None | None | None |
| R330A | None | None | None |
| Q333A | None | None | None |
| E336A | None | None | None |
| S350A | None | None | None |
| S352A | Not clear | None | None |
| E355A | None | None | None |
| E356A | None | None | None |
| E356K | None | None | None |
| #Q372A | Complete | None | None |
| E374K* | Complete | Complete | Complete |
| #K375A | Complete | None | None |
| #K375E | Complete | None | None |

TABLE 9-continued

| hDPEP3 mutant | Loss of binding with SC34.2 | Loss of binding with SC34.28 | Loss of binding with SC34.10 |
| --- | --- | --- | --- |
| #K375M | Complete | None | None |
| #E379A | Partial | None | None |
| S380A | None | None | None |
| #S380R | None | Partial | None |
| #S384A | None | Partial | None |
| E387A* | Partial | Partial | Partial |
| E389A | None | None | None |
| Y392A | None | None | None |
| G393A | None | None | None |
| S398A | None | None | None |
| S401A | None | None | None |
| H402A | None | None | None |
| L403A | None | None | None |
| WT DPEP3 | None | None | None | implicated as an epitope component
*apparent misfolding mutation

Based on data derived from the mutated homologs potential epitope constituents for each of the tested antibodies are set forth in Table 10 immediately below.

TABLE 10

| Antibody Clone | Epitope Associated Residues |
| --- | --- |
| SC34.2 | E217, R242, Q248, Q372, K375, E379 |
| SC34.10 | R46, R48, R54, S55 |
| SC34.28 | Q248, S380, S384, V386 |

Example 11

Detection of DPEP3 Surface Expression in Tumor Populations by Flow Cytometry

Flow cytometry was used to assess the ability of the anti-DPEP3 antibodies of the invention to specifically detect the presence of hDPEP3 protein on the surface of HEK-293T cell lines overexpressing hDPEP3 and on the surface of various PDX tumor cell lines.

Figure 7A:
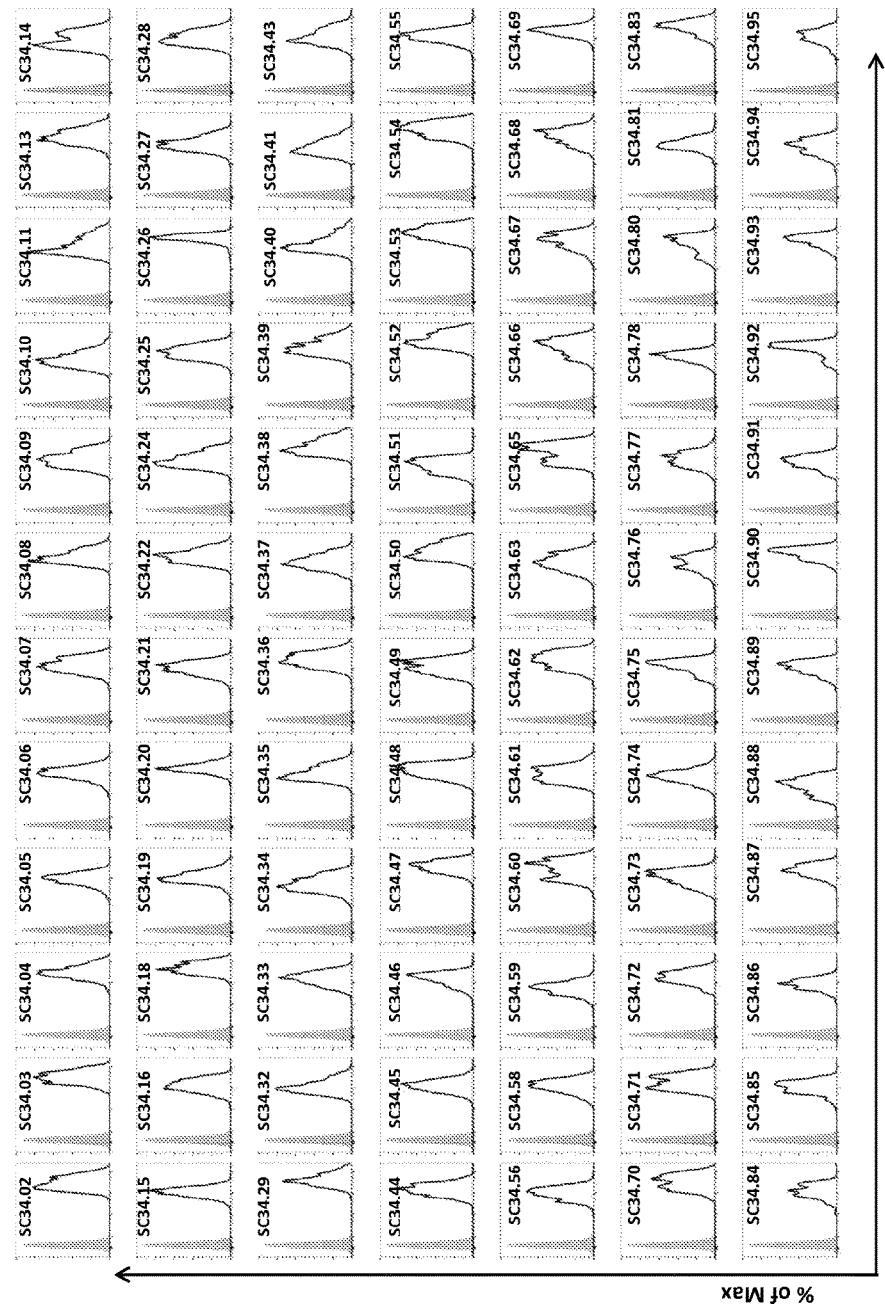
FIG. 7A shows the ability of numerous anti-DPEP3 antibodies to bind HEK-293T cells overexpressing DPEP3 using flow cytometry where results are shown as a histogram, with the solid black line indicating the binding to cells overexpressing DPEP3 of the indicated antibody compared to isotype-control (gray-fill)

HEK-293T parental cells or HEK-293T cells overexpressing hDPEP3 were harvested and isolated into single cell suspensions with Versene (Life Technologies). The isolated cells were incubated for 30 mins. with anti-DPEP3 antibodies and washed twice in PBS/2% FCS. The cells were incubated for 15 mins. with 50 µL per sample AlexaFluor-647 labeled goat-anti-mouse IgG, Fc fragment specific secondary antibody diluted 1:200 in PBS/2% FCS, washed twice with PBS/2% FCS and re-suspended in PBS/2% FCS with DAPI (to detect living cells). The cells were analyzed on a BD FACS Canto II flow cytometer with anti-DPEP3 antibodies. FIG. 7A shows that multiple exemplary anti-DPEP3 antibodies of the invention were able to specifically bind to HEK-293T cells overexpressing hDPEP3 but did not bind to parental HEK-293T control cells.

The ability of the antibodies of the invention to bind ovarian PDX tumor cell lines, including ovarian tumor initiating cells (TICs), was also assessed using flow cytometry. Ovarian PDX tumors were harvested and dissociated using art-recognized enzymatic tissue digestion techniques to obtain single cell suspensions of PDX tumor cells (see, for example, U.S.P.N. 2007/0292414). PDX tumor single cell suspensions were incubated with 4',6-diamidino-2-phenylindole (DAPI) to exclude dead cells, anti-mouse CD45 and H-2K$^d$ antibodies to identify mouse cells, and anti-human EPCAM antibody to identify human cells. In addition the tumor cells were incubated with anti-human CD46 and/or CD324 and ESA in order to isolate TICs (see U.S.P.N.s 2013/0260385, 2013/0061340 and 2013/0061342 and Example 1 above). Mouse cells that stained positive for CD45 and H-2K$^d$ were excluded from the analysis. The tumor cells were then analyzed by flow cytometry using a BD FACS Canto II flow cytometer with anti-DPEP3 antibodies.

Figure 7B:
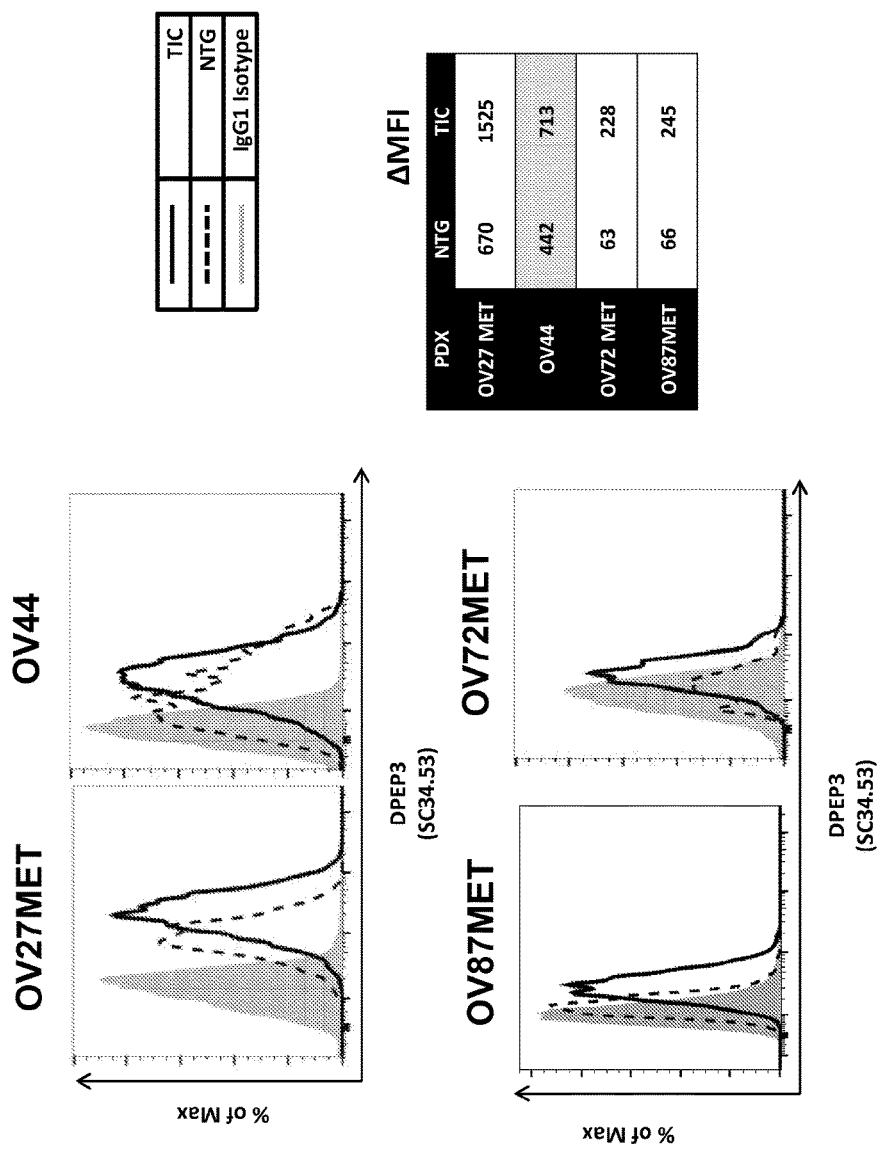
FIGS. 7B-7D show expression of DPEP3 protein on the surface of tumor initiating cells (solid black line) compared to non-tumorigenic cells (dashed line) in three subtypes of ovarian tumor cell populations as determined by flow cytometry with a specific anti-DPEP3 antibody, compared to staining using an isotype control (gray-fill)
Figure 7C:
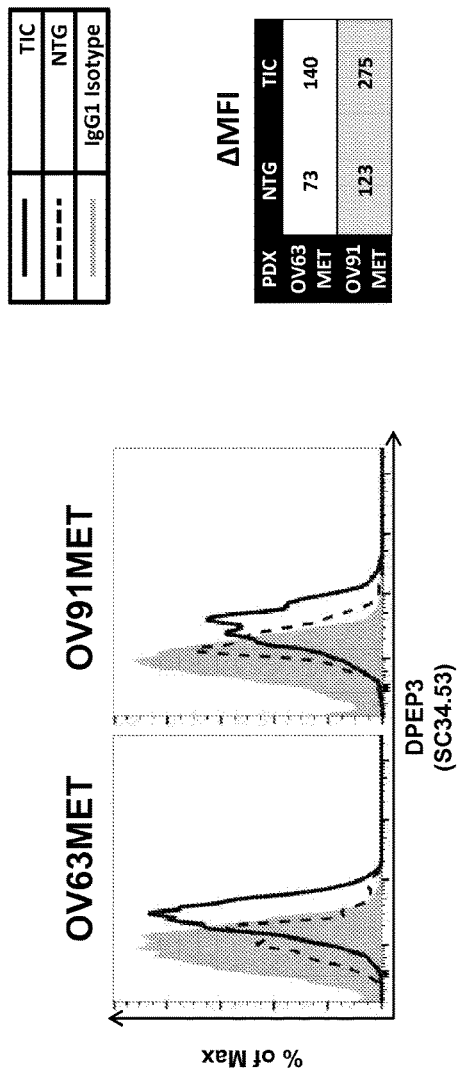
Figure 7D:
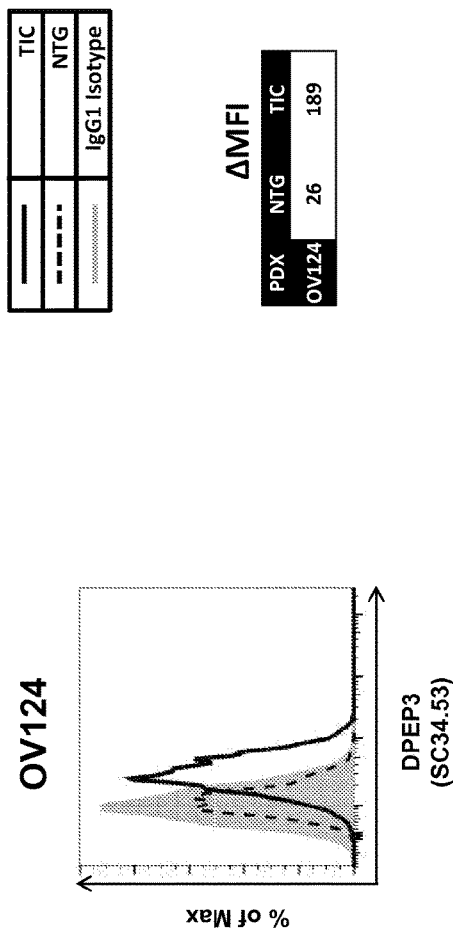

FIGS. 7B-7D show that the anti-hDPEP3 antibody SC34.53 detected expression of the DPEP3 protein on live human TIC subpopulations (solid black line) of some OV-S PDX lines (e.g., OV27MET, OV44) and to a lesser extent in other OV-S PDX lines (e.g. OV72MET and OV87MET) (FIG. 7B) whereas NTG cells (not expressing CD324, or ESA) (dashed line) demonstrated significantly less staining with anti-DPEP3 antibodies. The anti-hDPEP3 antibody SC34.53 also detected expression of the DPEP3 protein on live human TIC subpopulations in OV-PS (e.g. OV63MET, OV91 MET, OV119MET) (FIG. 7C) and OV-MMMT (e.g. OV124) (FIG. 7D) compared to NTG cells. Isotype control antibodies were employed to confirm staining specificity (gray-filled). A table summarizing the differential staining of anti-DPEP3 antibodies observed on the surface of TIC and NTG cells is shown as an inset in FIGS. 7B-7D, with expression enumerated as the change in geometric mean fluorescence intensity (ΔMFI) between the indicated anti-DPEP3 antibody and the isotype control for the respective tumor cell subpopulations.

Example 12

Detection of DPEP3 on the Surface of Tumors Using Immunohistochemistry and In Situ Hybridization Immunohistochemistry (IHC) was performed on PDX tumor tissue sections to assess the expression and location of DPEP3 in tumor cells.

In order to identify an IHC-compatible anti-DPEP3 antibody, IHC was performed on HEK-293T parental cell pellets or DPEP3-expressing HEK-293T cell pellets using numerous anti-DPEP3 antibodies of the invention. IHC was performed, as described below, on HEK-293T cells pellets that were formalin fixed and paraffin embedded (FFPE) as is standard in the art. Planar sections of cell pellet blocks were cut and mounted on glass microscope slides. After xylene de-paraffinization 5 μm sections were pre-treated with Antigen Retrieval Solution (Dako) for 20 mins. at 99° C., cooled to 75° C. and then treated with 0.3% hydrogen peroxide in PBS followed by Avidin/Biotin Blocking Solution (Vector Laboratories). FFPE slides were then blocked with 10% horse serum in 3% BSA in PBS buffer and incubated with a primary anti-DPEP3 antibody of the invention, diluted to 10 μg/ml in 3% BSA/PBS, for 30 mins. at room temperature. FFPE slides were incubated with biotin-conjugated horse anti-mouse antibody (Vector Laboratories), diluted to 2.5 μg/ml in 3% BSA/PBS, for 30 mins. at room temperature followed by incubation in streptavidin-HRP (ABC Elite Kit; Vector Laboratories). Chromogenic detection was developed with 3,3'-diaminobenzidine (Thermo Scientific) for 5 mins. at room temperature and tissues were counterstained with Meyer's hematoxylin (IHC World), washed with alcohol and immersed in xylene. Anti-DPEP3 antibody SC34.58 was able to specifically detect DPEP3-overexpressing HEK-293T cell pellets more effectively than other anti-DPEP3 antibodies of the invention that were tested (data not shown). The ability of the SC34.58 antibody to specifically detect DPEP3 was confirmed by a competition experiment in which the SC34.58 antibody was mixed with a 5× molar ratio excess of hDPEP3-His protein and then incubated with DPEP3-expressing HEK-293T FFPE sections. The absence of positive staining demonstrated that the hDPEP3-His protein interfered with the binding of the anti-DPEP3 SC34.58 antibody to the DPEP3-overexpressing HEK-293T cells (data not shown).

Figure 8A:
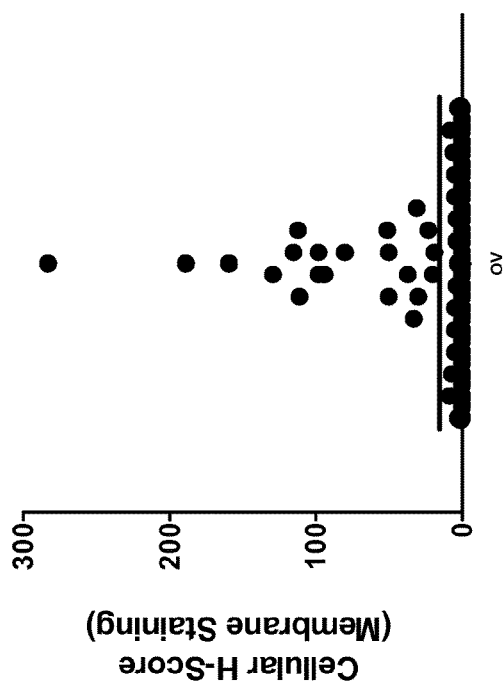
FIGS. 8A and 8B show expression of DPEP3 in a tissue microarray of high grade serous ovarian carcinoma as measured by immunohistochemistry (FIG. 8A) and by in situ hybridization (FIG. 8B)

FIG. 8A shows expression of hDPEP3 in 125 primary patient ovarian tumor samples analyzed on a tissue microarray (TMA) (University of Oklahoma). Expression was detected with the anti-DPEP3 SC34.58 antibody using IHC. Membrane expression was analyzed with an automated image analysis software package (Leica Biosystems) that quantifies the intensity of cell surface staining and provides a final "H-Score", which reflects the percentage of tumor cells stained at each intensity level (0 for no staining and 3 for intense staining). The H-Score is calculated as follows: (% at 0)*0+(% at 1+)*1+(% at 2+)*2+(% at 3+)*3. Thus, the H-Score produces a continuous variable that ranges from 0 to 300. FIG. 8A shows that 17% of the tumors on the TMA expressed hDPEP3. DPEP3 expression was also determined for a number of PDX tumor cell lines, including OV27MET, which had high expression of DPEP3 (H-Score=113), and OV87MET, which had very low expression of DPEP3 (H-Score=3).

Figure 8B:
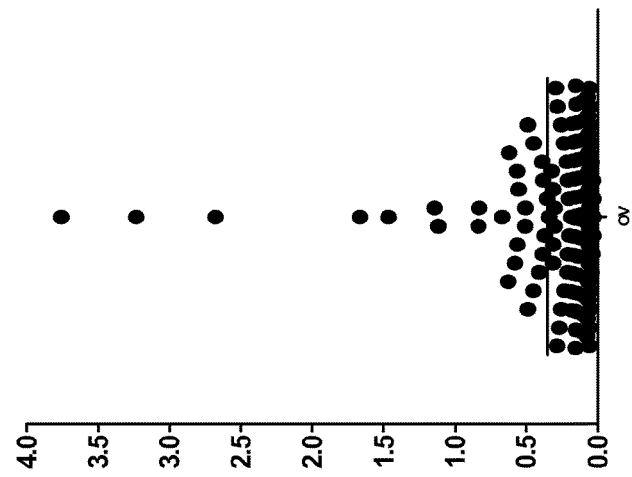

RNA in situ hybridization for DPEP3 mRNA was performed using an RNAscope® 2.0 Reagent Kit (Advanced Cell Diagnostics; Wang et al, 2012, PMID: 22166544). The RNAscope probe used for DPEP3 was designed between nucleotides 187-1696. Each sample was quality controlled for RNA integrity with an RNAscope probe specific to Peptidylprolyl Isomerase B (PPIB), a cyclosporine-binding protein located within the endoplasmic reticulum of all cells. Background staining was determined using a probe specific to DiAminoPimelate (dapB) RNA. Briefly, a TMA comprising 125 samples of primary patient ovarian tumors (University of Oklahoma) was pretreated with heat and protease prior to hybridization with the target oligo probes. Preamplifier, amplifier and HRP-labeled oligos were then hybridized sequentially, followed by chromogenic precipitate development with 3,3'-diaminobenzidine. Specific RNA staining signal was identified as brown, punctate dots. The TMA was counterstained with Gill's Hematoxylin. HALO™ image analysis software (Indica Labs) was used to analyze the data. Specifically, individual in situ hybridization dots were counted in the tumor region of each tissue microarray core and an "average dot per cell" score was generated. All cores that had an "average dot per cell score" of less than 0.20 were considered negative. FIG. 8B shows that 40% of the tumors represented on the TMA that was tested expressed hDPEP3. The horizontal lines represents the average score for all of the cores that were tested, which was 0.4. The in situ hybridization results in FIG. 8B shows an overall greater percentage of tumors expressing the DPEP3 gene compared to the IHC results shown in FIG. 8A, which detects expression of DPEP3 protein. This is due to the increased sensitivity of the in situ hybridization assay over the IHC assay.

The data demonstrate that a significant portion of the ovarian tumors tested express DPEP3 and that anti-DPEP3 antibodies have diagnostic utility in ovarian cancer.

Example 13

Anti-DPEP3 Antibodies Facilitate Delivery of Cytotoxic Agents In Vitro

To determine whether anti-DPEP3 antibodies of the invention are able to internalize in order to mediate the delivery of cytotoxic agents to live tumor cells, an in vitro cell killing assay was performed using selected anti-DPEP3 antibodies and saporin linked to a secondary anti-mouse antibody FAB fragment. Saporin is a plant toxin that deactivates ribosomes, thereby inhibiting protein synthesis and resulting in the death of the cell. Saporin is only cytotoxic inside the cell where it has access to ribosomes, but is unable to internalize on its own. Therefore, saporin-mediated cellular cytotoxicity in these assays is indicative of the ability of the anti-mouse FAB-saporin conjugate to internalize into the target cell only upon binding and internalization of mouse anti-DPEP3 antibodies.

Figure 9:
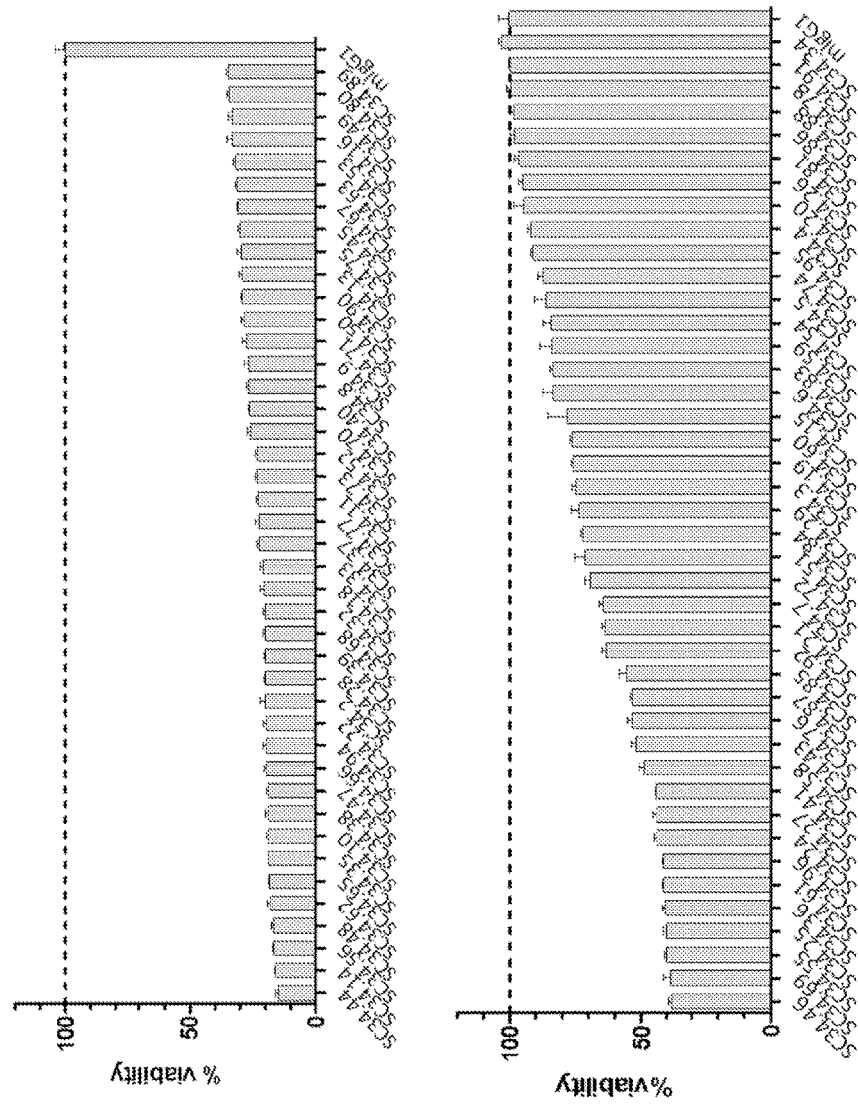
FIG. 9 shows the ability of multiple anti-DPEP3-saporin antibody drug conjugates to internalize into HEK-293T cells overexpressing DPEP3 and kill the cells by mediating the delivery of the saporin cytotoxin in vitro.

Single cell suspensions of HEK-293T cells overexpressing hDPEP3 were plated at 500 cells per well into BD Tissue Culture plates (BD Biosciences). One day later, various concentrations of purified anti-DPEP3 antibodies were added to the culture together with a fixed concentration of 2 nM anti-Mouse IgG FAB-saporin conjugates (Advanced Targeting Systems). HEK-293T cells overexpressing DPEP3 were incubated for 72 hours. After the incubation viable cells were enumerated using CellTiter-Glo® (Promega) as per the manufacturer's instructions. Raw luminescence counts using cultures containing cells incubated only with the secondary FAB-saporin conjugate were set as 100% reference values and all other counts were calculated as a percentage of the reference value. A large subset of anti-DPEP3 antibodies at a concentration of 20 pM effectively killed HEK-293T cells overexpressing hDPEP3 with varying efficacy (FIG. 9), whereas the mouse IgG1 isotype control antibody (mIgG1) at the same concentration did not.

The above results demonstrate the ability of anti-DPEP3 antibodies to mediate internalization and their ability to deliver cytotoxic payloads, supporting the hypothesis that anti-DPEP3 antibodies may have therapeutic utility as the targeting moiety for antibody drug conjugates.

Example 14

Preparation of Anti-DPEP3 Antibody-Drug Conjugates

Anti-DPEP3 antibody drug conjugates (ADCs) were prepared having the Ab-[L-D] structure as described above. Each ADC comprised an anti-DPEP3 antibody covalently linked to a linker-drug comprising a terminal maleimido moiety with a free sulfhydryl group and a pyrrolobenzodiazepine (PBD) dimer. In all cases PBD1, the structure of which is provided above, was used.

Anti-DPEP3 ADCs were synthesized and purified using art recognized techniques as follows. The cysteine bonds of selected anti-DPEP3 murine antibodies (SC34.25, SC34.83, SC34.97 and SC34.95) and humanized antibodies (hSC34.2, hSC34.11, hSC34.14, hSC34.25, hSC34.28 and hSC34.38) were partially reduced with a pre-determined molar addition of tris (2-carboxyethyl)-phosphine (TCEP) per mol antibody for 90 min. at 20° C. in phosphate buffered saline (PBS) with 5 mM EDTA. The maleimido linker payload, dissolved in dimethyl acetamide (DMA), was added at a ratio of 3.0 mol/mol anti-DPEP3 antibody. The reaction was allowed to proceed for 30 min. The reaction was then quenched with the addition of an excess amount of N-acetyl cysteine (NAC) compared to linker-drug using a 10 mM stock solution prepared in water. After a minimum quench time of 20 mins., the pH was adjusted to 6.0 with the addition of 0.5 M acetic acid and buffer exchanged into diafiltration buffer by diafiltration using a 30 kDa membrane. The diafiltered anti-DPEP3 ADC was then formulated with sucrose and polysorbate-20 to the target final concentration. The final ADC "HIC purified DAR=2" preparation was analyzed using RP-HPLC to determine the percent conjugation on the HCs and LCs and the DAR distribution. The samples were also analyzed using analytical HIC to determine the amount of DAR=2 species relative to the unwanted DAR>2 and DAR<2 species (see Example 16).

The resulting anti-DPEP3 ADCs were termed SC34.25-PBD1, SC34.83-PBD1, SC34.97-PBD1, SC34.95-PBD1, hSC34.2-PBD1, hSC34.11-PBD1, hSC34.14-PBD1, hSC34.25-PBD1, hSC34.28-PBD1 and hSC34.38-PBD1.

Example 15

Generation of Site-Specific Anti-DPEP3 Antibodies

An engineered human IgG1/kappa anti-DPEP3 site-specific antibody was constructed comprising a native light chain (LC) constant region and heavy chain (HC) constant region, wherein cysteine 220 (C220) in the upper hinge region of the HC, which forms an interchain disulfide bond with cysteine 214 (C214) in the LC, was substituted with serine (C220S). When assembled the HCs and LCs form an antibody comprising two free cysteines that are suitable for conjugation to a therapeutic agent. Unless otherwise noted, all numbering of constant region residues is in accordance with the EU numbering scheme as set forth in Kabat et al.

The engineered antibody was generated as follows. An expression vector encoding the humanized anti-DPEP3 antibody hSC34.28 HC (SEQ ID NO: 207), was used as a template for PCR amplification and site directed mutagenesis. Site directed mutagenesis was performed using the Quick-Change® system (Agilent Technologies) according to the manufacturer's instructions.

The vector encoding the mutant C220S HC of hSC34.28 was co-transfected with the native IgG1 kappa LC of hSC34.28 (SEQ ID NO: 205) in CHO-S cells and expressed using a mammalian transient expression system. The engineered anti-DPEP3 site-specific antibody containing the C220S mutant was termed hSC34.28ss1. Amino acid sequences of the full length LC and HC of the hSC34.28ss1 site specific antibody are shown in FIG. 5D (SEQ ID NOS: 224 and 226). The reactive cysteine in the LC is underlined as is the mutated residue at position 220 in the HC. The engineered anti-DPEP3 antibodies were characterized by SDS-PAGE to confirm that the correct mutants had been generated. SDS-PAGE was conducted on a pre-cast 10% Tris-Glycine mini gel from life technologies in the presence and absence of a reducing agent such as DTT (dithiothreitol). Following electrophoresis, the gels were stained with a colloidal coomassie solution. Under reducing conditions, two bands corresponding to the free LCs and free HCs, were observed. This pattern is typical of IgG molecules in reducing conditions. Under non-reducing conditions, the band patterns were different from native IgG molecules, indicative of the absence of a disulfide bond between the HC and LC. A band around 98 kD corresponding to the HC-HC dimer was observed. In addition, a faint band corresponding to the free LC and a predominant band around 48 kD that corresponded to a LC-LC dimer was observed. The formation of some amount of LC-LC species is expected due to the free cysteines on the C-terminus of each LC.

Example 16

Conjugation of Site Specific Anti-DPEP3 Antibodies Using a Selective Reduction Process The site specific antibody hSC34.28ss1, generated as set forth in Example 15 above, was conjugated to PBD1 via a terminal maleimido moiety with a free sulfhydryl group. The desired product is an ADC that is maximally conjugated on the unpaired cysteine (C214) on each LC constant region and that minimizes ADCs having a drug to antibody ratio (DAR) which is greater than 2 (DAR>2) while maximizing ADCs having a DAR of 2 (DAR=2).

In order to further improve the specificity of the conjugation and homogeneity of the final site-specific ADC, the hSC34.28ss1 antibody was selectively reduced using a process comprising a stabilizing agent (e.g. L-arginine) and a mild reducing agent (e.g. glutathione) prior to conjugation with the linker-drug, followed by preparative hydrophobic interaction chromatography (HIC) that was used to separate the different DAR species. The above procedures were conducted as described below.

A preparation of hSC34.28ss1 was partially reduced in a buffer containing 1M L-arginine/5 mM glutathione, reduced (GSH)/5 mM EDTA, pH 8.0 for a minimum of one hour at room temperature. All preparations were then buffer exchanged into a 20 mM Tris/3.2 mM EDTA, pH 8.2 buffer using a 30 kDa membrane (Millipore Amicon Ultra) to remove the reducing buffer. The resulting partially reduced preparations were then conjugated to PBD1 via a maleimide linker for a minimum of 30 mins. at room temperature. The reaction was then quenched with the addition of excess NAC compared to linker-drug using a 10 mM stock solution prepared in water. After a minimum quench time of 20 mins., the pH was adjusted to 6.0 with the addition of 0.5 M acetic acid. The conjugated preparation of hSC34.28ss1-PBD1 was buffer exchanged into diafiltration buffer using a 30 kDa membrane, diluted with a high salt buffer to increase the conductivity to promote binding onto the resin, and then loaded on a Butyl HP resin chromatography column (GE Life Sciences). A decreasing salt gradient was employed to separate the different DAR species based on hydrophobicity, where DAR=0 species eluted first, followed by DAR=1, DAR=2, and then higher DAR species.

Figure 10A:
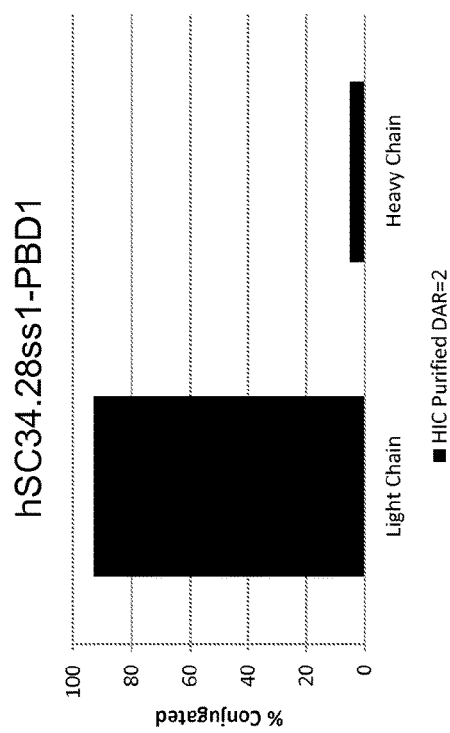
FIGS. 10A and 10B show reverse phase high performance liquid chromatography (RP-HPLC) analysis (FIG. 10A) and analytical hydrophobic interaction chromatography (FIG. 10B) of site specific anti-DPEP3 antibody drug conjugates.
Figure 10B:
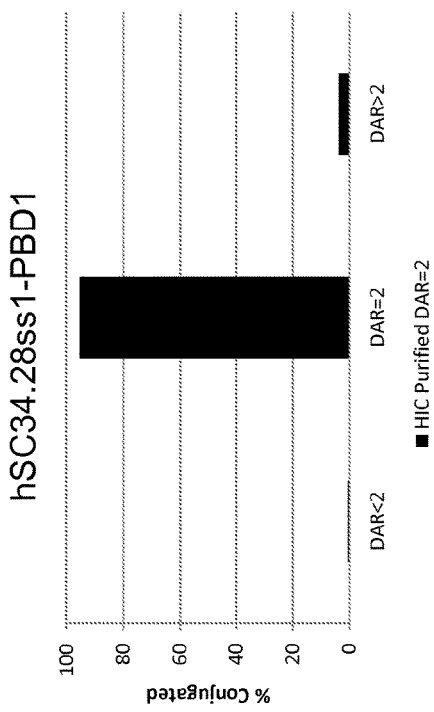

The final antibody-drug "HIC purified DAR=2" preparation was analyzed using RP-HPLC to determine the percent conjugation on the HCs and LCs and the DAR distribution. Results showed that 93% of the drug was conjugated to the LC and 5% of the drug was conjugated to the HC (FIG. 10A). The sample was also analyzed using analytical HIC to determine the amount of DAR=2 species relative to the unwanted DAR>2 and DAR<2 species. Results showed that 96% of the sample was DAR=2 species (FIG. 10B). The selective conjugation method in combination with the engineered constructs and HIC purification process resulted in DAR=2 levels greater than 95%, as well as light chain conjugation levels greater than 90%, indicating a high degree of homogeneity in the final sample with conjugation substantially limited to the desired free cysteine residues on the C-terminus of the light chain constant region.

Example 17

Anti-DPEP3 ADCs Facilitate Delivery of Cytotoxic Agents In Vitro

To determine whether anti-DPEP3 ADCs of the invention were able to internalize in order to mediate the delivery of cytotoxic agents to live tumor cells, an in vitro cell killing assay was performed using the anti-DPEP3 ADC, hSC34.28-PBD1.

Figure 11:
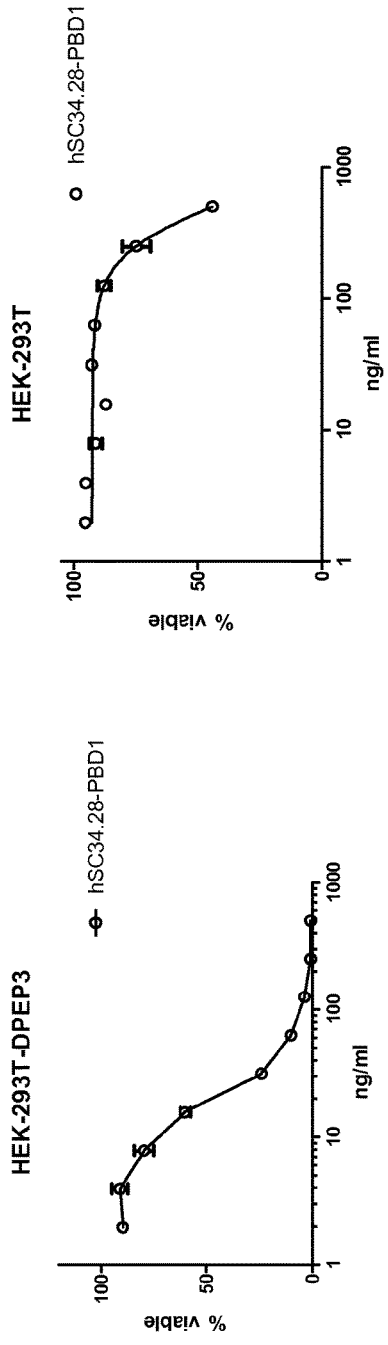
FIG. 11 shows the ability of multiple anti-DPEP3-PBD1 antibody drug conjugates to internalize into HEK-293T cells overexpressing DPEP3 and kill the cells by mediating the delivery of the PBD cytotoxin in vitro.

Single cell suspensions of HEK-293T cells overexpressing hDPEP3 or naïve HEK293T cells were plated at 500 cells per well into BD Tissue Culture plates (BD Biosciences). One day later, various concentrations of purified hSC34.28-PBD1 were added to the cultures. The cells were incubated for 96 hours. After the incubation viable cells were enumerated using CellTiter-Glo® (Promega) as per the manufacturer's instructions. Raw luminescence counts using cultures containing non-treated cells were set as 100% reference values and all other counts were calculated as a percentage of the reference value. FIG. 11 shows that the HEK-293T cell lines overexpressing DPEP3 were much more sensitive to the hSC34.28-PBD1 ADC compared to the naive HEK-293T cells.

The above results demonstrate the ability of anti-DPEP3 ADCs to specifically mediate internalization and delivery of cytotoxic payloads to cells expressing DPEP3.

Example 18

Humanized Anti-DPEP3 Antibody Drug Conjugates Suppress Tumor Growth In Vivo

The anti-DPEP3 ADCs, generated as described in Example 14 above, were tested to demonstrate their ability to suppress ovarian tumor growth in immunodeficient mice.

Figure 12:
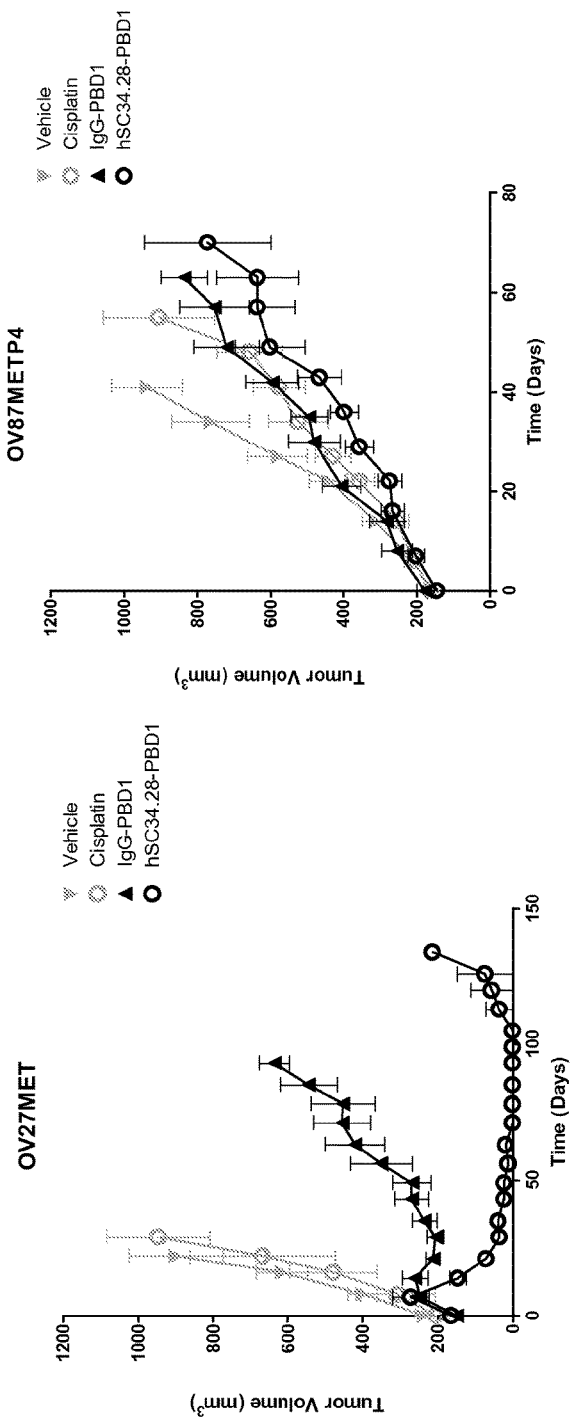
FIG. 12 shows the ability of an anti-DPEP3-PBD1 antibody drug conjugate to reduce, in vivo, the volume of an ovarian PDX tumor that expresses DPEP3 (OV27MET) compared to an ovarian tumor that does not express DPEP3 (OV87MET).

An OV-S PDX tumor line expressing DPEP3 (OV27MET) and an OV-S tumor lines exhibiting lower levels of DPEP3 expression (OV87MET), were grown subcutaneously in the flanks of female NOD/SCID mice using art-recognized techniques. Tumor volumes and mouse weights were monitored once or twice per week. When tumor volumes reached 150-250 mm$^3$, mice were randomly assigned to treatment groups and injected intraperitoneally with either 2 doses of 5 mg/kg cisplatin (the standard of care), a single dose of 1 or 2 mg/kg hSC34.28-PBD1, a single dose of 2 mg/kg anti-hapten control human IgG-PBD1 or vehicle control (0.9% saline or 5% glucose). Following treatment, tumor volumes and mouse weights were monitored until tumors exceeded 800 mm$^3$ or mice became sick. Mice treated with hSC34.28-PBD1 did not exhibit any adverse health effects beyond those typically seen in immunodeficient, tumor-bearing NOD/SCID mice. FIG. 12 shows that in an ovarian PDX tumor that expressed DPEP3 (OV27MET), the administration of the anti-DPEP3 ADC, hSC34.28-PBD1, resulted in tumor suppression lasting over 100 days whereas the administration of the standard of care, cisplatin, and the control antibody IgG-PBD1 did not result in any tumor volume reduction. Conversely, the anti-DPEP3 ADC had no effect compared to cisplatin or the other controls in OV87MET tumors, an ovarian PDX cell line that had much lower expression levels of DPEP3 as measured by IHC (Example 12), a chemiluminescent assay (Example 9) and flow cytometry (Example 11).

The ability of hSC34.28-PBD1 to specifically kill DPEP3-expressing ovarian tumor cells and dramatically suppress tumor growth in vivo for extended periods further validates the use of anti-DPEP3 ADCs in the therapeutic treatment of ovarian cancer and in particular in OV-S subtypes of ovarian cancer.

Example 19

Reduction of Tumor Initiating Cell Frequency by Anti-DPEP3 Antibody-Drug Conjugates As demonstrated in Example 11 DPEP3 expression is associated with tumorigenic cells. Accordingly, to demonstrate that treatment with anti-DPEP3 ADCs reduces the frequency of TICs that are known to be drug resistant and to fuel tumor recurrence and metastasis, in vivo limiting dilution assays (LDA) are performed, for example, essentially as described below.

PDX tumors (e.g. melanoma or ovarian) are grown subcutaneously in immunodeficient mice. When tumor volumes average 150 mm$^3$-250 mm$^3$ in size, the mice are randomly segregated into two groups. One group is injected intraperitoneally with a human IgG1 conjugated to a drug as a negative control; and the other group is injected intraperitoneally with an anti-DPEP3 ADC (e.g., as prepared in Examples 14 and 16). One week following dosing, two representative mice from each group are euthanized and their tumors are harvested and dispersed to single-cell suspensions. The tumor cells from each treatment group are then harvested, pooled and disaggregated as previously described in Example 1. The cells are labeled with FITC conjugated anti-mouse H2kD and anti-mouse CD45 antibodies to detect mouse cells; EpCAM to detect human cells; and DAPI to detect dead cells. The resulting suspension is then sorted by FACS using a BD FACS Canto II flow cytometer and live human tumor cells are isolated and collected.

Four cohorts of mice are injected with either 1250, 375, 115 or 35 sorted live, human cells from tumors treated with anti-DPEP3 ADC. As a negative control four cohorts of mice are transplanted with either 1000, 300, 100 or 30 sorted live, human cells from tumors treated with the control IgG1 ADC. Tumors in recipient mice are measured weekly, and individual mice are euthanized before tumors reach 1500 mm$^3$. Recipient mice are scored as having positive or negative tumor growth. Positive tumor growth is defined as growth of a tumor exceeding 100 mm$^3$. Poisson distribution statistics (L-Calc software, Stemcell Technologies) is used to calculate the frequency of TICs in each population.

---

The invention claimed is:

1. An antibody drug conjugate comprising a monoclonal antibody conjugated, linked, or otherwise associated with a cytotoxic agent,
   wherein the monoclonal antibody binds human DPEP3 and comprises three complementarity determining regions of a light chain variable region set forth as SEQ ID NO: 205 and three complementarity determining regions of a heavy chain variable region set forth as SEQ ID NO: 207.

2. The antibody drug conjugate of claim 1, wherein mutating at least one of amino acids E217, R242, Q248, Q372, K375, and E379 of SEQ ID NO: 3 results in loss of binding of the antibody to DPEP3.

3. The antibody drug conjugate of claim 1, wherein the monoclonal antibody binds to an epitope on human DPEP3 that comprises residues E217, R242, Q248, Q372, K375, and E379.

4. The antibody drug conjugate of claim 1, wherein the monoclonal antibody is a chimeric, CDR grafted, or humanized antibody.

5. The antibody drug conjugate of claim 1, comprising the formula Ab-[L-D]n, wherein:
   a) Ab comprises the antibody;
   b) L comprises an optional linker;
   c) D comprises a drug, which is the cytotoxic agent; and
   d) n is an integer from about 1 to about 20.

6. The antibody drug conjugate of claim 1, wherein the cytotoxic agent is a pyrrolobenzodiazepine (PBD).

7. A pharmaceutical composition comprising (i) the antibody drug conjugate of claim 1 and (ii) a pharmaceutically acceptable carrier.

8. The antibody drug conjugate of claim 1, wherein the antibody comprises residues 24-34 of SEQ ID NO: 205 for CDRL1, residues 50-56 of SEQ ID NO: 205 for CDRL2, residues 89-97 of SEQ ID NO: 205 for CDRL3, residues 31-35 of SEQ ID NO: 207 for CDRH1, residues 50-65 of SEQ ID NO: 207 for CDRH2 and residues 95-102 of SEQ ID NO: 207 for CDRH3, wherein the CDR residues are numbered according to Kabat.

9. The antibody drug conjugate of claim 1, wherein the antibody comprises residues 24-34 of SEQ ID NO: 205 for CDRL1, residues 50-56 of SEQ ID NO: 205 for CDRL2, residues 89-97 of SEQ ID NO: 205 for CDRL3, residues 26-32 of SEQ ID NO: 207 for CDRH1, residues 52-56 of SEQ ID NO: 207 for CDRH2 and residues 95-102 of SEQ ID NO: 207 for CDRH3, wherein the CDR residues are numbered according to Chothia.

10. The antibody drug conjugate of claim 1, wherein the antibody comprises residues 30-36 of SEQ ID NO: 205 for CDRL1, residues 46-55 of SEQ ID NO: 205 for CDRL2, residues 89-96 of SEQ ID NO: 205 for CDRL3, residues 30-35 of SEQ ID NO: 207 for CDRH1, residues 47-58 of SEQ ID NO: 207 for CDRH2 and residues 93-101 of SEQ ID NO: 207 for CDRH3, wherein the CDR residues are numbered according to MacCallum.

11. The antibody drug conjugate of claim 1, wherein the antibody comprises residues 24-34 of SEQ ID NO: 205 for CDRL1, residues 50-56 of SEQ ID NO: 205 for CDRL2, residues 89-97 of SEQ ID NO: 205 for CDRL3, residues 26-35 of SEQ ID NO: 207 for CDRH1, residues 50-58 of SEQ ID NO: 207 for CDRH2 and residues 95-102 of SEQ ID NO: 207 for CDRH3, wherein the CDR residues are numbered according to AbM.

12. The antibody drug conjugate of claim 1, wherein the antibody comprises a light chain variable region set forth as SEQ ID NO: 205 and a heavy chain variable region set forth as SEQ ID NO: 207.

13. The antibody drug conjugate of claim 1, wherein the antibody comprises two light chains and two heavy chains, wherein each of the two light chains comprises a sequence set forth as SEQ ID NO: 224 and each of the two heavy chains comprises a sequence set forth as SEQ ID NO: 225.

14. The antibody drug conjugate of claim 1, wherein the antibody comprises two light chains, two heavy chains, and two unpaired cysteine residues.

15. The antibody drug conjugate of claim 14, wherein each of the two light chains comprises an unpaired cysteine residue.

16. The antibody drug conjugate of claim 15, wherein the two light chains each comprise an unpaired cysteine residue at position C214.

17. The antibody drug conjugate of claim 14, wherein each of the two heavy chains comprises an unpaired cysteine residue.

18. The antibody drug conjugate of claim 17, wherein each of the two heavy chains comprise IgG1 comprising an unpaired cysteine residue at position C220.

19. The antibody drug conjugate of claim 14, wherein the antibody comprises an IgG1 monoclonal antibody comprising (i) a cysteine residue at heavy chain position 220 and a deletion of a cysteine residue at light chain position 214; (ii) a cysteine residue at heavy chain position 220 and a substitution of a cysteine residue at light chain position 214; (iii) a cysteine residue at light chain position 214 and a deletion of a cysteine residue at heavy chain position 220; or (iv) a cysteine residue at light chain position 214 and a substitution of a cysteine residue at heavy chain position 220; and wherein the antibody comprises native cysteine residues at heavy chain positions 226 and 229.

20. The antibody drug conjugate of claim 14, wherein each of the two light chains comprises a sequence set forth as SEQ ID NO: 224 and each of the two heavy chains comprises a sequence set forth as SEQ ID NO: 226.

21. The antibody drug conjugate of claim 1, wherein the antibody is conjugated to the cytotoxic agent.

22. The antibody drug conjugate of claim 1, wherein the cytotoxic agent is a pyrrolobenzodiazepine having the structure:

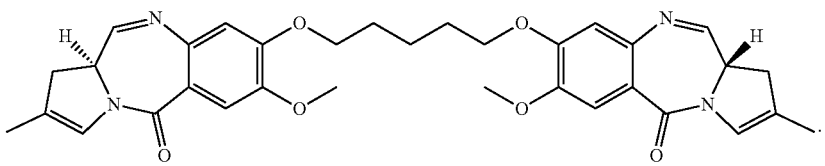

23. The antibody drug conjugate of claim 1, wherein the antibody comprises a light chain variable region set forth as SEQ ID NO: 205 and a heavy chain variable region set forth as SEQ ID NO: 207 and wherein the cytotoxic agent is a pyrrolobenzodiazepine having the structure:

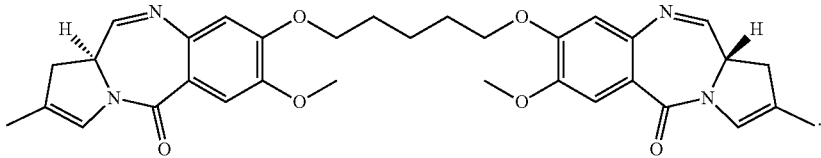

24. The antibody drug conjugate of claim 1, wherein the antibody comprises two light chains and two heavy chains, wherein each of the two light chains comprises a sequence set forth as SEQ ID NO: 224 and each of the two heavy chains comprises a sequence set forth as SEQ ID NO: 226, and wherein the cytotoxic agent is a pyrrolobenzodiazepine having the structure:

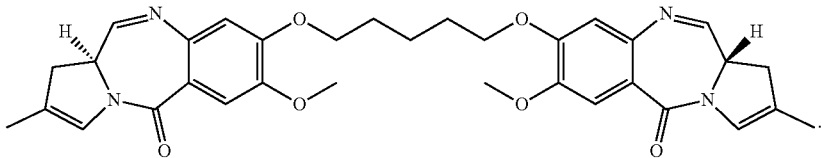

25. The antibody drug conjugate of claim 1, wherein the antibody drug conjugate has a drug loading of 2.

26. The antibody drug conjugate of claim 25, comprising a linker.

27. The antibody drug conjugate of claim 26, wherein the linker is a cleavable linker.

28. The antibody drug conjugate of claim 27, wherein the linker comprises a maleimide linker.

29. The pharmaceutical composition of claim 7, comprising a drug to antibody ratio (DAR) of 1, 2, 3, 4, 5, 6, 7 or 8 each ±0.4.

30. The pharmaceutical composition of claim 7, comprising a drug to antibody ratio (DAR) of 2±0.4.

31. The pharmaceutical composition of claim 30, comprising less than 30% of non-predominant antibody drug conjugate species.

32. The pharmaceutical formulation of claim 7, wherein the antibody drug conjugate further comprises a linker and wherein:
  (a) the antibody comprises a light chain variable region set forth as SEQ ID NO: 205 and a heavy chain variable region set forth as SEQ ID NO: 207; and
  (b) the cytotoxic agent is a pyrrolobenzodiazepine having the structure:

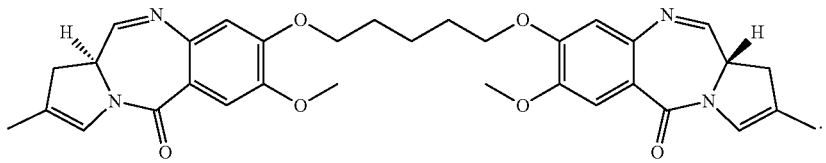

33. The pharmaceutical composition of claim 7, wherein the antibody drug conjugate further comprises a linker and wherein:
  (a) the antibody comprises two light chains and two heavy chains, wherein the two light chains each comprise a sequence set forth as SEQ ID NO: 224 and the two heavy chains each comprise a sequence set forth as SEQ ID NO: 226; and
  (b) the cytotoxic agent is a pyrrolobenzodiazepine having the structure:

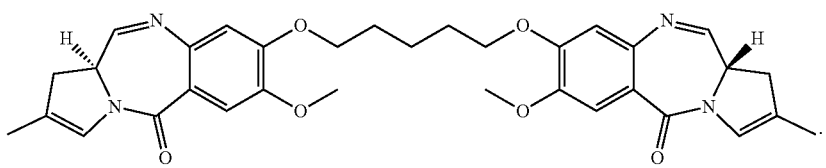

34. The pharmaceutical composition of claim 32, comprising a drug to antibody ratio (DAR) of 1, 2, 3, 4, 5, 6, 7 or 8 each ±0.4.

35. The pharmaceutical composition of claim 32, comprising a drug to antibody ratio (DAR) of 2±0.4.

36. The pharmaceutical composition of claim 32, comprising less than 30% of non-predominant antibody drug conjugate species.

37. The pharmaceutical composition of claim 33, comprising a drug to antibody ratio (DAR) of 2±0.4.

38. The pharmaceutical composition of claim 33, comprising less than 30% of non-predominant antibody drug conjugate species.

* * * * *